US012753413B2

(12) United States Patent
Wang et al.

(10) Patent No.: US 12,753,413 B2
(45) Date of Patent: Oct. 6, 2026

(54) RNA GUIDE GENOME EDITING IN CITRUS USING CRISPR-RIBONUCLEOPROTEIN COMPLEXES

(71) Applicant: UNIVERSITY OF FLORIDA RESEARCH FOUNDATION, INCORPORATED, Gainesville, FL (US)

(72) Inventors: Nian Wang, Auburndale, FL (US); Xiaoen Huang, Lake Alfred, FL (US); Tirtha Lamichhane, Winter Haven, FL (US); Ali Parsaeimehr, Winter Haven, FL (US); Su Hang, Winter Haven, FL (US); Shumig Wang, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 625 days.

(21) Appl. No.: 17/632,371

(22) PCT Filed: Aug. 3, 2020

(86) PCT No.: PCT/US2020/044766
§ 371 (c)(1),
(2) Date: Feb. 2, 2022

(87) PCT Pub. No.: WO2021/026081
PCT Pub. Date: Feb. 11, 2021

(65) Prior Publication Data

US 2022/0282266 A1 Sep. 8, 2022

Related U.S. Application Data

(60) Provisional application No. 62/882,375, filed on Aug. 2, 2019.

(51) Int. Cl.

| | |
|---|---|
| ***C12N 15/82*** | (2006.01) |
| ***C12N 5/00*** | (2006.01) |
| ***C12N 9/22*** | (2006.01) |
| ***C12N 15/11*** | (2006.01) |

(52) U.S. Cl.
CPC ....... *C12N 15/8213* (2013.01); *C12N 5/0025* (2013.01); *C12N 9/22* (2013.01); *C12N 15/11* (2013.01); *C12N 15/8205* (2013.01); *C12N 15/8281* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2018/0245096 A1* 8/2018 Wang ................. C12N 15/8239

FOREIGN PATENT DOCUMENTS

WO WO-2018102816 A1 * 6/2018 ............... A01H 1/08
WO 2021026081 A2 2/2021

OTHER PUBLICATIONS

Zhang et al. (Plant cell Re., 36: 1883-1887, Published 2017).*
Xu et al. (Evolutionary Bioinformatics, 9:215-228, Published 228).*
Genbank (Sequence accession No. XM_024189816, published Feb. 26, 2018).*
PCT/US2020/044766, PCT Search Report & Written Opinion mailed Feb. 12, 2021, 16 pages.
Adli, Mazhar, "The CRISPR tool kit for genome editing and beyond" Nature Communications, 2018, vol. 9, No. 1911, 13 pages.
Andersson, Mariette et al., "Genome editing in potato via CRISPR-Cas9 ribonucleoprotein delivery", Physiologia Plantarum, 2018, vol. 164, pp. 378-384.
Bae, Sangsu et al., "Cas-OFFinder: a fast and versatile algorithm that searches for potential off-target site of Cas9 RNA-guided endonucleases", Bioinformatics Application Note, 2014, vol. 30, No. 10, pp. 1473-1475.
Begemann, Matthew B. et al., "Precise insertion and guided editing of higher plant genomes using Cpf1 CRISPR nucleases", Scientific Reports, 2017, vol. 7, No. 11606, 6 pages.
Berges, Thierry et al., "Heat Shock at an Elevated Temperature Improves Transformation Efficiency of Protoplasts from Podospora anserina", Journal of General Microbiology, 1989, vol. 135, pp. 601-604.
Chen, Longzheng et al., "A method for the production and expedient screening of CRISPR/Cas9-mediated non-trangenic mutant plants", Horticulture Research, 2018, vol. 5, No. 13, 12 pages.
Clark, Kelley et al., "An effector from the Huanglongbing-associated pathogen targets citrus proteases", Nature Communications, 2018, vol. 9, No. 1718, 11 pages.
Duan, Shuo et al., "Functional characterization of the citrus canker susceptibility gene CsLOB1", Molecular Plant Pathology, 2018, vol. 19, No. 8, pp. 1908-1916.
Endo, Akira et al., "Efficient targeted mutagenesis of rice and tobacco genomes using Cpf1 from Francisella novicida", Scientific Reports, 2016, vol. 6, No. 38169, 9 pages.
Fan, Di et al., "Efficient CRISPR/Cas9-mediated Targeted Mutagenesis in Populus in the First Generation", Scientific Reports, 2015, vol. 5, No. 12217, 7 pages.
Fang, Yujie et al., "Conserved miR164-targeted NAC genes negatively regulate drought resistance in rice", Journal of Experimental Botany, 2014, vol. 65, No. 8, pp. 2119-2135.

(Continued)

*Primary Examiner* — Vinod Kumar
(74) *Attorney, Agent, or Firm* — Timothy H. Van Dyke; Wolter Van Dyke Davis, PLLC

(57) ABSTRACT

Disclosed herein are methods and materials for editing genes in citrus cells. Specifically exemplified is the implementation of an optimized Cas9 and the CRISPR type II class nuclease. Also exemplified is the use of a U6-1 promoter for driving expressing of editing constructs in citrus cells. Various protocols and sequences for editing genes are disclosed as well.

3 Claims, 47 Drawing Sheets

Specification includes a Sequence Listing.

(56) References Cited

OTHER PUBLICATIONS

Ference, Christopher M. et al., "Recent advances in the understanding of *Xanthomonas citri* ssp. citri pathogenesis and citrus canker disease management", Molecular Plant Pathology, 2018, vol. 19, No. 6, pp. 1302-1318.
Ferenczi, Aron et al., "Efficient targeted DNA editing and replacement in Chlamydomonas reinhardtii using Cpf1 fibonucleoproteins and single-stranded DND", Nov. 3, 2017, PNAS, 6 pages.
Fu, Yanfang et al., "High frequency off-target mutagenesis induced by CRISPR-Cas nucleases in humans", Nat. Biotechnol., Sep. 2013, vol. 31, No. 9, pp. 822-826.
GenBank, "mth2-14616RM1 BAC end, cultivar Jemalong A17 of Medicago truncatula, genomic survey sequence", GenBank: CR482498.1, Downloaded from Internet Jan. 4, 2021, 1 page.
Hu, Yang et al., "Latral organ boundaries 1 is a disease susceptibility gene for citrus bacterial canker disease", Plant Biology,PNAS, Dec. 18, 2013, 9 pages.
Hu, Liu et al., "Comparing successful gene knock-in efficiencies of CRISPR/Cas9 with ZFNs and TALENs gene editing systems in bovine and dairy goat fetal fibroblasts", Journal of Integrative Agriculture, 2018, vol. 17, No. 2, pp. 406-414.
Jia, Hongge et al., "Targeted Genome Editing of Sweet Orange Using Cas9/sgRNA", PLOS One, Apr. 7, 2014, vol. 9, No. 4, 6 pages.
Jia, Hongge et al, "Editing Citrus Genome via SaCas9/sgRNA System", Frontiers in Plant Science, Dec. 12, 2017, vol. 8,No. 2135, 9 pages.
Jia, Hongge et al., "Modification of the PthA4 effector binding elements in Type 1 CsLoB1 promoter using Cas9/sgRNA to produce transgenic Duncan grapefruit alleviating XccApthA4:dCsLOB1.3 infection", Plant Biotechnology Journal, 2016, vol. 14, pp. 1291-1301.
Jia Hongge et al., "Genome editing of the disease susceptibility gene CsLOB1 in citrus confers resistance to citrus canker", Plant Biotechnology Journal, 2017, vol. 15, pp. 817-823.
Kim, Hyeran et al., "CRISPR/Cpf1-mediated DNA-free plant genome editing", Nature Communications, Aug. 10, 2016, vol. 8, No. 14406, 7 pages.
Kleinstiver, Benjamin P. et al., "Genome-wide specificities of CRISPR-Cas Cpf1 nucleases in human cells", Nat Biotechnol., Aug. 2016, vol. 34, No. 8, pp. 869-874.
Kleter, Gijs et al., "Gene-Edited Crops: Towards a Harmonized Safety Assessment", Trends in Biotechnology, 2017, 5 pages.
LeBlance, Chantal et al., "Increased efficiency of targeted mutagenesis by CRISPR/Ca9 in plants using heat stress", The Journal, 2018, vol. 93, pp. 377-386.
Liang, Zhen et al., "Efficient DNA-free genome editing of bread wheat using CRISPR/Cas9 ribonucleoprotein complexes", Nature Communications, 2017, vol. 8, No. 14261, 5 pages.
Lin, Li et al., "Engineering the Direct Repeat Sequence of crRNA for Optimization of FnCpf1-Mediated Genome Editing in Human Cells", Molecular Therapy, Nov. 2018, vol. 26, No. 11, pp. 2650-2657.
Lin, Choun-Sea et al., "Application of protoplast technology to CRISPR/Cas9 mutagenesis: from single-cell mutation detection to mutant plant regeneration", Plant Biotechnology Journal, 2018, vol. 16, pp. 1295-1310.
Martin-Pizarro, Carmen et al., "Genome Editing as a Tool for Fruit Ripening Manipulation", Frontiers in Plant Science, Sep. 25, 2018, vol. 9, No. 1415, 8 pages.
Moreno-Mateos, Miguel A. et al., "CRISPR-Cpf1 mediates efficient homology-directed repair and temperature-controlled genome editing", 2017, Nature Communications, vol. 8, No. 2024, 9 pages.
Park, Jong Jin et al., "DNA-Free Genome Editing via Ribonucleoprotein (RNP) Delivery of CRISPR/Cas in Lettuce", Methods and Protocols, Methods in Molecular Biology, 2019, vol. 1917, pp. 337-354.
Peng, Aihong et al., "Engineering canker-resistant plants through CRISPR/ Cas9-targeted editing of the susceptibility gene CsLOB1 promoter in citrus", Plant Biotechnology Journal, 2017, vol. 15, pp. 1509-1519.
Port, Filip et al., "Augmenting CRISPR applications in *Drosophila* with tRNAflanked Cas9 and Cpf1 sgRNAs", Nat Methods. Oct. 2016, vol. 13, No. 10, pp. 852-854.
Safari, Fatemeh et al., "CRISPR Cpf1 proteins: structure, function and implications for genome editing", Cell Biosci, 2019, vol. 9, No. 36, 21 pages.
Shankar, Sumitra et al., "Genome editing of oncogenes with ZFNs and TALENs: caveats in nuclease design", Cancer Cell Int, 2018, vol. 18, No. 169, 11 pages.
Stella, Stefano et al., "Structure of the Cpf1 endonuclease R-loop complex after target DNA cleavage", bioRxiv, Apr. 29, 2017, 30 pages.
Swart, Dean C. et al., "Structural basis for guide RNA processing and seed-dependent DNA targeting and cleavage by CRISPR-Cas12a", Mol Cell. Apr. 2, 20170; vol. 66, No., pp. 221-233.
Tang, Xu et al., "Single transcript unit CRISPR 2.0 systems for robust Cas9 and Cas 12a mediated plant genome editing", Plant Biotechnology Journal, 2019, vol. 17, pp. 1431-1445.
Tu, Mengjun et al., "A 'new lease of life': FnCpf1 possesses DNA cleavage activity for genome editing in human cells", Nucleic Acids Research, 2017, vol. 45, No. 19 11295-11304.
Wang et al., "Multiplex gene editing in rice with simplified CRISPR-Cpf1 and CRISPR-Cas9 systems", Simplified single transcriptional unit CRISPR systems, JIPB, Aug. 2018, vol. 60, issue 8, pp. 626-631.
Wang, Mugui et al., "Multiplex Gene Editing in Rice Using the CRISPR-Cpf1 System" Molecular Plant, Jul. 2017, vol. 10, pp. 1011-1013.
Wu, G. Albert et al., "Sequencing of diverse mandarin, pummelo and orange genomes reveals complex history of admixture during citrus domestication", Nature Biotechnology, vol. 32, No. 7, Jul. 2014, pp. 656-662.
Xu, Qiang et al., "The draft genome of sweet orange (*Citrus sinensis*)", Nature America, 2013, 10 pages.
Xu, Rongfang et al., "Generation of targeted mutant rice using a CRISPR-Cpf1 system", Plant Biotechnology Journal, 2017, vol. 15, pp. 713-717.
Xu, Rongfang et al., "Enhanced genome editing in rice using single transcript unit CRISPR-LbCpf1 systems", Plant Biotechnology Journal, 2019, vol. 17, pp. 553-555.
Yan, Liujua et al., "High-Efficiency Genome Editing in *Arabidopsis* Using YAO Promoter-Driven CRISPR/Cas9 System", Molecular Plant, Dec. 2015, vol. 8, pp. 1820-1823.
Yin, X. et al., "CRISPR-Cas9 and CRISPR-Cpf1 mediated 1 targeting of a stomotal developmental gene EPFL9 in fice", Plant Cell Reports, 2017, vol. 35, No. 5, pp. 745-757.
Zeng, Yan et al., "The initiation, propagation and dynamics of CRISPR-SpyCas9 R-loop complex", Nucleic Acids Research, 2018, vol. 46, No. 1, pp. 350-361.
Zetsche, Bernd et al., "Cpf1 Is a Single RNA-Guided Endonuclease of a Class 2 CRISPR-Cas System", Cell, 2015, vol. 163, pp. 759-771.

* cited by examiner

FIG. 1

SEQ ID NO: 1 Optimized Cas9 sequence

ATGGACAAGAAGTACAGCATCGGTCTTGATATTGGTACTAACTCTGTGGGTTGGGCTGTTATTACTGAT
GAGTATAAGGTGCCTAGCAAGAAGTTTAAGGTGCTTGGTAATACCGACAGACATTCTATTAAGAAGAA
TCTTATTGGTGCTCTTCTTTTTGATTCTGGCGAGACTGCTGAGGCTACTAGACTTAAGAGAACTGCTAG
AAGAAGGTACACTAGAAGAAAGAACAGGATCTGCTACCTTCAAGAGATTTTCTCTAATGAGATGGCCA
AGGTTGACGATTCTTTTTTTCACAGACTCGAGGAGTCTTTCCTTGTTGAGGAGGATAAGAAGCATGAG
AGACATCCTATTTTCGGTAACATCGTTGACGAGGTTGCTTATCATGAGAAGTATCCTACTATCTACCAC
CTTAGAAAGAAGCTTGTGGATTCTACTGACAAGGCTGATCTTAGACTTATCTACCTTGCTCTTGCTCAT
ATGATCAAGTTCAGAGGTCATTTCCTCATCGAGGGTGATCTTAATCCTGATAATAGCGATGTGGACAA
GCTTTTTATCCAGCTTGTTCAAACCTACAACCAGCTTTTTGAGGAGAATCCTATCAACGCTTCTGGTGT
TGATGCTAAGGCTATTCTTTCTGCTAGACTTTCTAAGAGCAGGAGACTTGAGAATCTTATCGCTCAACT
TCCTGGTGAGAAGAAGAATGGTCTTTTTGGTAACCTCATCGCTCTTTCTCTTGGTCTTACTCCTAATTTC
AAGAGCAACTTCGACCTTGCTGAGGATGCTAAGCTTCAACTTTCTAAGGATACCTACGACGATGATCT
TGATAACCTTCTTGCTCAAATCGGTGATCAATACGCTGATCTTTTCCTTGCTGCTAAGAATCTTAGCGA
TGCTATTCTTCTCAGCGATATTCTTAGGGTTAACACTGAGATCACCAAGGCTCCTCTTTCTGCTTCTATG
ATTAAGAGATACGACGAGCATCACCAAGATCTTACTCTTCTTAAGGCTCTTGTGAGACAACAACTTCCT
GAGAAGTATAAGGAGATCTTCTTCGATCAGAGCAAGAATGGTTACGCTGGTTATATTGACGGTGGTGC
TTCTCAAGAGGAGTTTTATAAGTTCATCAAGCCCATCCTCGAGAAGATGGATGGTACTGAGGAGCTTC
TTGTTAAGCTTAATAGGGAGGATCTCCTTAGAAAGCAAAGAACTTTCGACAACGGTTCTATCCCTCATC
AAATTCATCTCGGTGAGCTTCATGCTATTCTTAGAAGACAAGAGGACTTCTACCCTTTTCTTAAGGATA
ACAGGGAGAAGATCGAGAAGATTCTTACTTTCAGGATTCCTTACTACGTGGGTCCTCTTGCTAGAGGT
AATTCTAGATTTGCTTGGATGACCAGAAAGTCTGAGGAGACTATTACTCCTTGGAATTTCGAGGAGGT
TGTTGATAAGGGTGCTTCTGCTCAATCTTTTATCGAGAGAATGACCAACTTCGACAAGAATCTTCCTAA
CGAGAAGGTTCTTCCTAAGCATTCTCTTCTTTACGAGTACTTCACCGTTTACAACGAGCTTACTAAGGT
TAAGTACGTGACTGAGGGTATGAGAAAGCCTGCTTTTCTTTCTGGTGAGCAAAAGAAGGCTATCGTTG
ATCTTCTTTTCAAGACCAACAGGAAGGTTACTGTTAAGCAACTTAAGGAGGACTACTTCAAGAAGATC
GAGTGCTTTGATAGCGTTGAGATTTCTGGTGTTGAGGATAGATTCAACGCTTCTCTTGGTACTTACCAT
GATCTTCTTAAGATCATCAAGGACAAGGACTTCCTTGATAACGAGGAGAATGAGGATATCCTTGAGGA
TATTGTGCTCACTCTTACTCTTTTCGAGGATAGAGAGATGATCGAGGAGAGACTTAAGACTTATGCTCA
TCTTTTCGACGACAAGGTTATGAAGCAACTTAAGAGAAGGAGGTACACTGGTTGGGGTAGACTTTCTA
GAAAGCTTATTAACGGCATCAGGGATAAGCAATCTGGTAAGACTATCCTTGACTTCCTTAAGTCTGAC
GGTTTTGCTAATAGGAACTTCATGCAACTCATCCATGACGATTCTCTTACTTTCAAGGAGGATATCCAG
AAGGCTCAAGTTTCTGGTCAAGGTGATTCTCTTCATGAGCATATTGCTAACCTCGCTGGTTCTCCTGCT
ATTAAGAAGGGTATTCTTCAGACTGTGAAGGTTGTTGATGAGCTTGTTAAGGTTATGGGTAGACATAA
GCCTGAGAATATCGTTATCGAGATGGCTAGAGAGAACCAAACTACTCAAAAGGGTCAAAAGAACAGC
AGAGAGAGAATGAAGAGAATCGAGGAGGGTATTAAGGAGCTTGGTTCTCAAATTCTCAAGGAGCATC
CTGTTGAGAATACTCAACTTCAAAACGAGAAGCTCTACCTTTACTACCTTCAAAACGGTAGAGACATG
TACGTTGATCAAGAGCTTGATATCAACAGGCTTTCTGATTACGACGTTGATCATATCGTGCCTCAATCT
TTTCTCAAGGATGATTCTATCGACAACAAGGTTCTCACTAGATCTGATAAGAACAGGGGTAAGTCTGA
TAACGTTCCTTCTGAGGAGGTTGTTAAGAAGATGAAGAACTACTGGAGGCAACTTCTTAACGCTAAGC
TTATTACCCAGAGAAAGTTCGATAACCTCACTAAGGCTGAGAGAGGTGGTCTTTCTGAGCTTGATAAG
GCTGGTTTTATCAAGAGACAGCTTGTTGAGACTAGGCAAATTACTAAGCACGTTGCTCAAATCCTCGA
TTCTAGAATGAACACTAAGTACGACGAGAACGATAAGCTTATCAGAGAGGTTAAGGTGATCACTCTTA
AGTCTAAGCTCGTTTCTGACTTCAGAAAGGATTTCCAATTCTACAAGGTGAGGGAGATTAACAACTAC
CATCATGCTCATGACGCTTATCTTAACGCTGTTGTTGGTACTGCTCTTATTAAGAAGTACCCTAAGCTC
GAGTCTGAGTTTGTTTATGGTGATTACAAGGTGTACGACGTTAGAAAGATGATCGCTAAGTCTGAGCA
AGAGATTGGTAAGGCTACTGCTAAGTATTTCTTCTACAGCAACATCATGAACTTCTTCAAGACCGAGA
TCACTCTTGCTAATGGTGAGATTAGAAAGAGGCCTCTTATCGAGACTAACGGTGAGACTGGTGAGATT
GTTTGGGATAAGGGTAGAGATTTCGCTACTGTTAGAAAGGTTCTCTCTATGCCTCAAGTTAACATCGTT
AAGAAGACCGAGGTTCAAACTGGTGGTTTTTCTAAGGAGTCTATCCTTCCTAAGAGGAATAGCGATAA
GCTTATCGCTAGAAAGAAGGATTGGGACCCTAAGAAGTATGGTGGTTTTGATTCTCCTACCGTTGCTTA
TTCTGTGCTTGTTGTTGCTAAGGTTGAGAAGGGTAAGTCTAAGAAGCTTAAGTCTGTGAAGGAGCTTCT

FIG. 1(Cont.)

TGGTATTACTATCATGGAGAGAAGCTCTTTCGAGAAGAATCCTATTGACTTCCTCGAGGCTAAGGGTT
ATAAGGAGGTTAAGAAGGATCTCATCATCAAGCTTCCTAAGTACTCTCTTTTCGAGCTTGAGAATGGT
AGAAAGAGAATGCTTGCTTCTGCTGGTGAGCTTCAAAAGGGTAATGAGCTTGCTCTTCCTTCTAAGTAT
GTGAATTTCCTCTACCTCGCTTCTCATTATGAGAAGCTTAAGGGTTCTCCTGAGGATAATGAGCAAAAG
CAACTTTTCGTGGAGCAACATAAGCATTACCTTGATGAGATCATCGAGCAAATCTCTGAGTTTTCTAAG
AGGGTTATCCTCGCTGATGCTAATCTTGATAAGGTTCTTAGCGCTTACAACAAGCATAGAGATAAGCC
TATCAGGGAGCAAGCTGAGAATATTATTCACCTTTTCACCCTCACCAACCTTGGTGCTCCTGCTGCTTT
TAAGTATTTTGATACCACCATCGACAGGAAGAGATATACTTCTACTAAGGAGGTGCTCGATGCTACTC
TTATTCATCAATCTATCACCGGTCTCTACGAGACTAGAATTGATCTTTCTCAGCTCGGTGGTGATTAA

FIG. 2

ATGGCCCCCAAGAAGAAGAGAAAGGTTGGCATTCACGGCGTTCCCGCAGCAAGCAAGTTAGAGAAGTTTACGAAT
TGTTACTCACTGTCAAAGACGCTGCGTTTTAAGGCTATCCCTGTCGGGAAGACGCAAGAGAATATCGACAATAAGC
GACTGTTAGTCGAGGACGAGAAGCGCGCCGAGGACTACAAGGGCGTCAAGAAGCTGTTAGACCGCTATTACCTGA
GCTTTATCAATGACGTCTTACACTCAATCAAGCTGAAGAATCTGAATAACTACATCTCACTGTTTCGTAAGAAGAC
GAGAACGGAGAAGGAGAATAAGGAGCTGGAGAATCTGGAGATCAATCTGCGTAAGGAGATCGCGAAGGCTTTTA
AGGGAAATGAGGGGTACAAGTCACTGTTTAAGAAGGACATCATCGAGACGATCCTGCCTGAGTTTTTAGACGACA
AGGACGAGATCGCCCTGGTCAATAGCTTTAATGGCTTTACGACGGCGTTTACGGGCTTTTTCGACAATCGGGAGAA
TATGTTTTCAGAGGAAGCGAAGTCAACGTCAATCGCTTTTCGTTGCATCAATGAGAATCTGACGCGGTATATCTCA
AATATGGACATCTTTGAGAAGGTCGACGCTATCTTTGACAAGCACGAGGTCCAAGAGATCAAGGAGAAGATCCTG
AATTCAGACTACGACGTCGAGGACTTTTTCGAGGGAGAGTTTTTCAATTTTGTCTTAACGCAAGAGGGGATCGACG
TCTATAATGCCATCATCGGCGGTTTTGTCACGGAGTCAGGAGAGAAGATCAAGGGGCTGAATGAGTATATCAATCT
GTACAATCAAAAGACGAAGCAAAAGCTGCCTAAGTTTAAGCCTCTGTACAAGCAAGTCTTATCAGACAGGGAGTC
ATTATCATTTTATGGCGAGGGTTACACGTCAGACGAGGAAGTCCTGGAGGTCTTTAGAAATACGCTGAATAAGAAT
TCAGAGATCTTTTCATCAATCAAGAAGCTGGAGAAGCTGTTTAAGAATTTTGACGAGTATTCATCAGCTGGAATCT
TTGTCAAGAATGGGCCTGCCATCTCAACGATCTCAAAGGACATCTTTGGCGAGTGGAATGTCATCCGTGACAAGTG
GAATGCTGAGTACGACGACATCCACCTGAAGAAGAAGGCCGTCGTCACGGAGAAGTATGAGGACGACCGTCGTAA
GAGCTTTAAGAAGATCGGGTCATTTTCACTGGAGCAATTACAAGAGTACGCCGACGCGGACCTGTCAGTCGTCGA
GAAGTTAAAGGAGATCATCATCCAAAAGGTCGACGAGATCTATAAGGTCTACGGCTCATCAGAGAAGTTATTTGA
CGCCGACTTTGTCCTGGAGAAGTCATTAAAGAAGAATGACGCGGTCGTCGCTATCATGAAGGACCTGTTAGACTCA
GTCAAGTCATTTGAGAATTATATCAAGGCGTTTTTCGGAGAGGGGAAGGAGACGAATAGGGACGAGTCATTTTAC
GGTGACTTTGTCCTGGCCTATGACATCCTGTTAAAGGTCGACCACATCTATGACGCGATCAGAAATTACGTCACGC
AAAAGCCTTACTCAAAGGACAAGTTTAAGCTGTACTTTCAAAATCCTCAGTTTATGGGCGGCTGGGACAAGGACA
AGGAGACGGACTACCGTGCGACGATCCTGCGGTATGGATCAAAGTATTACTTAGCCATCATGGACAAGAAGTATG
CGAAGTGCCTGCAAAAGATCGACAAGGACGACGTCAATGGCAATTACGAGAAGATCAATTACAAGCTGCTGCCTG
GTCCTAATAAGATGTTACCTAAGGTCTTTTTCTCAAAGAAGTGGATGGCTTATTACAATCCTTCAGAGGACATCCA
AAAGATCTATAAGAATGGCACGTTTAAGAAGGGTGACATGTTTAATCTGAATGACTGTCACAAGTTAATCGACTTT
TTCAAGGACTCAATCTCACGATACCCTAAGTGGTCAAATGCTTACGACTTTAATTTTTCAGAGACGGAGAAGTACA
AGGACATCGCCGGCTTTTATCGCGAGGTCGAGGAGCAAGGTTATAAGGTCAGCTTTGAGTCAGCGTCAAAGAAGG
AAGTCGACAAGCTGGTCGAGGAAGGCAAGCTGTACATGTTTCAAATCTACAATAAGGACTTTTCAGACAAGTCAC
ACGGGACGCCTAATCTGCACACGATGTACTTTAAGCTGCTGTTTGACGAGAATAACCACGGGCAAATCAGGCTGTC
AGGCGGTGCTGAGCTGTTTATGAGGAGAGCCTCACTGAAGAAGGAAGAGTTAGTCGTCCACCCTGCTAATTCACCT
ATCGCCAATAAGAATCCCGACAATCCTAAGAAGACGACGACGCTGTCATATGACGTCTACAAGGACAAGCGTTTT
TCAGAGGACCAATATGAGTTACACATCCCTATCGCGATCAATAAGTGTCCTAAGAATATCTTTAAGATCAATACGG
AGGTCCGGGTCCTGTTAAAGCACGACGACAATCCTTACGTCATCGGCATCGACCGTGGTGAGCGGAATCTGTTATA
TATCGTCGTCGTCGACGGCAAGGGTAATATCGTCGAGCAATACTCACTGAATGAGATCATCAATAACTTTAATGGT
ATCAGAATCAAGACGGACTATCACTCACTGTTAGACAAGAAGGAGAAGGAGCGATTTGAGGCGCGCCAAAATTGG
ACGTCAATCGAGAATATCAAGGAGCTGAAGGCTGGTTACATCTCACAAGTCGTCCACAAGATCTGCGAGTTAGTC
GAGAAGTATGACGCCGTCATCGCGCTGGAGGACTTAAATTCAGGCTTTAAGAATTCACGAGTCAAGGTCGAGAAG
CAAGTCTACCAAAAGTTTGAGAAGATGCTGATCGACAAGCTGAATTACATGGTCGACAAGAAGTCAAATCCTTGT
GCTACGGGAGGGGCCCTGAAGGGCTACCAAATCACGAATAAGTTTGAGAGCTTTAAGTCAATGTCAACGCAAAAT
GGTTTTATCTTTTATATCCCTGCGTGGTTAACGTCAAAGATCGACCCTTCAACGGGATTTGTCAATCTGTTAAAGAC
GAAGTACACGTCAATCGCTGACTCAAAGAAGTTTATCTCATCATTTGACCGAATCATGTATGTCCCTGAGGAAGAC
CTGTTTGAGTTTGCGTTAGACTACAAGAATTTTTCACGCACGGACGCTGACTATATCAAGAAGTGGAAGCTGTATT
CATACGGCAATCGAATCCGCATCTTTAGGAATCCTAAGAAGAATAACGTCTTTGACTGGGAGGAAGTCTGCCTGAC
GTCAGCCTACAAGGAGCTGTTTAATAAGTACGGCATCAATTACCAACAAGGTGACATCAGAGCGCTGTTATGTGA
GCAATCAGACAAGGCGTTTTATTCAAGCTTTATGGCTCTGATGTCACTGATGTTACAAATGAGGAATTCAATCACG
GGCAGAACGGACGTCGACTTTTTAATCTCACCTGTCAAGAATTCAGACGGTATCTTTTATGACTCACGTAATTACG
AGGCGCAAGAGAATGCTATCCTGCCTAAGAATGCTGACGCCAATGGCGCCTACAATATCGCGCGGAAGGTCTTAT
GGGCCATCGGGCAGTTTAAGAAGGCGGAGGACGAGAAGCTGGACAAGGTCAAGATCGCGATCTCAAATAAGGAG
TGGTTAGAGTATGCTCAAACGTCAGTGAAGCACAAGCGACCCGCAGCAACCAAGAAGGCAGGGCAGGCGAAGAA
GAAGAAGTAAGACGACTAGTG (SEQ ID NO:2)

FIG. 3A

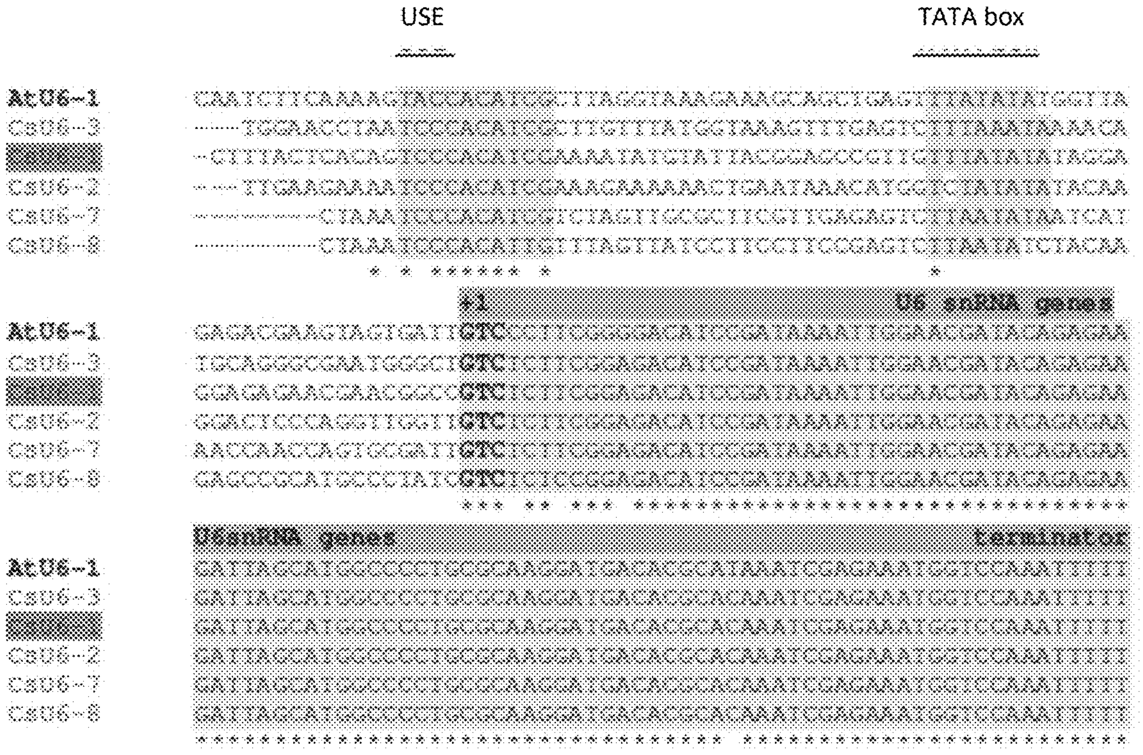

SEQ ID NOs: 3, 4, 5, 6, 7, and 8.

FIG. 3B

TATGATAATAAAACTCCCAGAGGGGTCACATTTATTTGAGGAGAATTTAAAAAAAAA
AAAATCACCAGAAAGAGGTGCCGATGAATGCAATAAGGGATGCAAATTATTTATTTA
CCTTTACAGGCATTTAGTATTTAATTTTATTTTCAGTTATTGTTCACTGATAATCGAAT
TTTAATGGAGTCGGTCATGGAAGGCATGCACATAAAATATGAGGATGCAGGTAAG
GTTTGCGCGGTCTGAAATTTCAATGACGGCGTACCTCTCTCTATCACAAGAAATAT
GTAATAATATGTTTGTAATTTAGAATTTTTTTCTGTAATTGACAGTATTTTGTAGATAA
GGAATGCCACTCTATAGGTACTGCTAAAAGATGGGCCAATATAGGTGCGGCCCAT
GAGCCCATTGTATTTAAAGAATCTTTACTCACAGTCCCACATCGAAAATATGTATTA
CGGAGCCGTTGTTTATATATAGGAGGAGAGAACGAACGGCCGTCTCTTCGGAGAC
ATCCGATAAAATTGGAACGATACAGAGAAGATTAGCATGGCCCCTGCGCAAGGAT
GACACGCACAAATCGAGAAATGGTCCAAA*TTTTTTT*CTTCCCCCTCATTCGGGCTT

FIG. 3B (Cont.)

GTTTAATCAGTCGGCAGTTTGACGATGTTAGCTTCTGCAGTTTGATTCCATCGTTAA
CCATATAAATTTTTTT (SEQ ID NO:9)

FIG. 4

CsU6-2 promoter: from Chromosome 2 of Valencia

TCAGGAGCCGGTTGAATTTGATTGTTGTTTGATGTTTAGGTATGCTTACAATTTTTTA
CTAAATAAGGTAATAATTGTTCCTTTTATTTTATTCATTTAGCTTGGTACTTGTCGTA
ATCTATCTCCGTCAATGTCAGCTTCTTCTGTGTCGGAAGAAGCTGAAAAATGTTGTT
GAAGGCCCTTTCATTTATTATTATCATTATTATGTTTAATTTTGTTCGGCAAATGTGT
ACTAATTTGGTTCGAATCGTTCGATCTCATAATACAAACATGTAATGAGTTATTTATG
ACGTCATGGATGCGGTTAGTTTGCGTGGTCTGAAATTTCAACCAAATTATTCAATCA
TGGTGGTGGCCGGCTGGTGCCTATCCCTTGATTGAAATATGCAATTAAAATTCTCG
TAATAATGTTGATTTGTTCTATATACTTGAATTGATGGTATTAATTATTGTTATAAAAG
CACTAACTTGTTTGAGAAAGGGGATAACTAAAAGGTAATAATAATAATAATAAAATA
AAGAAAAGGCCCAACACATGGGCGCCCTATCTGTTGGGCCAAATGCCATAAGAGG
ATCCAGCTAGCCCGTTGAAGAAAATCCCACATCGAAAGAAAAAACTGAATAAACAT
GGTCTATATATACAAGGACTCCCAGGTTGGTTG (SEQ ID NO:10)

FIG. 5

CsU6-7 promoter: from Chromosome 7 of Valencia

TGTTGTGCGGGATCTTTTAAGTAGGAACTGACAAGTTTCCCTCACCCACATCTTTC
GTGAAGCGAATTCAGCTACAGATTTCATGGCTAATATGGCTCATTCAATCTCTCATG
GGTTACATTTATTTACTAGCCTACATGTGTGTATTTATTCAAGTTTATTGCAAGACAT
GTTTGGGGTTGCTAAACTCCGTATTGTTCCGGTTTAGCTCGCTTTATTGAGCCCAT
CTTAATAAAAAAAAAAAAAAGACTTCCTTCTATGATTTTAGGGAAAATTACTATAATA
TTATCCATAAGAGTAAATTTTGGACCTACGCGTGCAGATATGTACATATATTTTTTAA
TAAAAACAATTACTGCATGGACTGGACTTCGTAGCATCTTTTTTGGGCTCAGGAAG
GGCCTAAAGTTATGATAGCCAGACAGACGTCATGTGGTTCGGTTCAAATTGAACTA
AATCCCACATCGTCTAGTTGCGCTTCGTTGAGAGTCTTAATATAATCATAACCAACC

AGTGCGATTG (SEQ ID NO:11)

FIG. 13

GAATTCCCTGCAGGTAATTAAATAAGCTTCAAATAAAACGAAAGGCTCAGTCGAAAGACTG
GGCCTTTCGTTTTATCTGTTGTTTGTCGGTGAACGCTCTCCTGAGTAGGACAAATCCGCCGGG
AGCGGATTTGAACGTTGCGAAGCAACGGCCCGGAGGGTGGCGGGCAGGACGCCCGCCATAA
ACTGCCAGGCATCAAATTAAGCAGAAGGCCATCCTGACGGATGGCCTTTTTGCGTTTCTACA
AACTCTTTCGGTCCGTTGTTTATTTTTCTAAATACATTCAAATATGTATCCGCTCATGAGACA
ATAACCCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAAACGCT
GGTGAAAGTAAAAGATGCTGAAGATCAGTTGGGTGCACGAGTGGGTTACATCGAACTGGAT
CTCAACAGCGGTAAGATCCTTGAGAGTTTTCGCCCCGAAGAACGTTTCCCAATGATGAGCAC
TTTTAAAGTTCTGCTATGTGGCGCGGTATTATCCCGTGTTGACGCCGGGCAAGAGCAACTCG
GTCGCCGCATACACTATTCTCAGAATGACTTGGTTGAGTACTCACCAGTCACAGAAAAGCAT
CTTACGGATGGCATGACAGTAAGAGAATTATGCAGTGCTGCCATAACCATGAGTGATAACA
CTGCGGCCAACTTACTTCTGACAACGATCGGAGGACCGAAGGAGCTAACCGCTTTTTTGCAC
AACATGGGGGATCATGTAACTCGCCTTGATCGTTGGGAACCGGAGCTGAATGAAGCCATAC
CAAACGACGAGCGTGACACCACGATGCCTGTAGCAATGGCAACAACGTTGCGCAAACTATT
AACTGGCGAACTACTTACTCTAGCTTCCCGGCAACAATTAATAGACTGGATGGAGGCGGATA
AAGTTGCAGGACCACTTCTGCGCTCGGCCCTTCCGGCTGGCTGGTTTATTGCTGATAAATCTG
GAGCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAGA
TCGCTGAGATAGGTGCCTCACTGATTAAGCATTGGTAACTGTCAGACCAAGTTTACTCATAT
ATACTTTAGATTGATTTCCTTAGGACTGAGCGTCAACCCCGTAGAAAAGATCAAAGGATCTT
CTTGAGATCCTTTTTTTCTGCGCGTAATCTGCTGCTTGCAAACAAAAAAACCACCGCTACCAG
CGGTGGTTTGTTTGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCACCACTTCAAGAA
CTCTGTAGCACCGCCTACATACCTCGCTCTGCTAATCCTGTTACCAGTGGCTGCTGCCAGTGG
CGATAAGTCGTGTCTTACCGGGTTGGACTCAAGACGATAGTTACCGGATAAGGCGCAGCGGT
CGGGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGA
AACGCCTGGTATCTTTATAGTCCTGTCGGGTTTCGCCACCTCTGACTTGAGCGTCGATTTTTG
TGATGCTCGTCAGGGGGGCGGAGCCTATGGAAAAACGCCAGCAACGCGGCCTTTTTACGGTT
CCTGGCCTTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACCGAGCGCAG
CGAGTCAGTGAGCGAGGAAGCGGAAGAGCGCCTGATGCGGTATTTTCTCCTTACGCATCTGT
GCGGTATTTCACACCGCATATAAGGTGCACTGTGACTGGGTCATGGCTGCGCCCCGACACCC
GCCAACACCCGCTGACGCGCCCTGACGGGCTTGTCTGCTCCCGGCATCCGCTTACAGACAAG
CTGTGACCGTCTCCGGGAGCTGCATGTGTCAGAGGTTTTCACCGTCATCACCGAAACGCGCG
AGGCAGCTGCGGTAAAGCTCATCAGCGTGGTCGTGCAGCGATTCACAGATGTCTGCCTGTTC
ATCCGCGTCCAGCTCGTTGAGTTTCTCCAGAAGCGTTAATGTCTGGCTTCTGATAAAGCGGG
CCATGTTAAGGGCGGTTTTTTCCTGTTTGGTCACTGATGCCTCCGTGTAAGGGGGATTTCTGT
TCATGGGGGTAATGATACCGATGAAACGAGAGAGGATGCTCACGATACGGGTTACTGATGA
TGAACATGCCCGGTTACTGGAACGTTGTGAGGGTAAACAACTGGCGGTATGGATGCGGCGG

FIG. 13 (cont.)

GACCAGAGAAAAATCACTCAGGGTCAATGCCAGCGCTTCGTTAATACAGATGTAGGTGTTCC
ACAGGGTAGCCAGCAGCATCCTGCGATGCAGATCCGGAACATAATGGTGCAGGGCGCTGAC
TTCCGCGTTTCCAGACTTTACGAAACACGGAAACCGAAGACCATTCATGTTGTTGCTCAGGT
CGCAGACGTTTTGCAGCAGCAGTCGCTTCACGTTCGCTCGCGTATCGGTGATTCATTCTGCTA
ACCAGTAAGGCAACCCCGCCAGCCTAGCCGGGTCCTCAACGACAGGAGCACGATCATGCGC
ACCCGTGGCCAGGACCCAACGCTGCCCGAAATTCCGACACCATCGAATGGTGCAAAACCTTT
CGCGGTATGGCATGATAGCGCCCGGAAGAGAGTCAATTCAGGGTGGTGAATGTGAAACCAG
TAACGTTATACGATGTCGCAGAGTATGCCGGTGTCTCTTATCAGACCGTTTCCCGCGTGGTG
AACCAGGCCAGCCACGTTTCTGCGAAAACGCGGGAAAAAGTGGAAGCGGCGATGGCGGAG
CTGAATTACATTCCCAACCGCGTGGCACAACAACTGGCGGGCAAACAGTCGTTGCTGATTGG
CGTTGCCACCTCCAGTCTGGCCCTGCACGCGCCGTCGCAAATTGTCGCGGCGATTAAATCTC
GCGCCGATCAACTGGGTGCCAGCGTGGTGGTGTCGATGGTAGAACGAAGCGGCGTCGAAGC
CTGTAAAGCGGCGGTGCACAATCTTCTCGCGCAACGCGTCAGTGGGCTGATCATTAACTATC
CGCTGGATGACCAGGATGCCATTGCTGTGGAAGCTGCCTGCACTAATGTTCCGGCGTTATTT
CTTGATGTCTCTGACCAGACACCCATCAACAGTATTATTTTCTCCCATGAAGACGGTACGCG
ACTGGGCGTGGAGCATCTGGTCGCATTGGGTCACCAGCAAATCGCGCTGTTAGCGGGCCCAT
TAAGTTCTGTCTCGGCGCGTCTGCGTCTGGCTGGCTGGCATAAATATCTCACTCGCAATCAA
ATTCAGCCGATAGCGGAACGGGAAGGCGACTGGAGTGCCATGTCCGGTTTTCAACAAACCA
TGCAAATGCTGAATGAGGGCATCGTTCCCACTGCGATGCTGGTTGCCAACGATCAGATGGCG
CTGGGCGCAATGCGCGCCATTACCGAGTCCGGGCTGCGCGTTGGTGCGGATATTTCGGTAGT
GGGATACGACGATACCGAAGACAGCTCATGTTATATCCCGCCGTTAACCACCATCAAACAG
GATTTTCGCCTGCTGGGGCAAACCAGCGTGGACCGCTTGCTGCAACTCTCTCAGGGCCAGGC
GGTGAAGGGCAATCAGCTGTTGCCCGTCTCACTGGTGAAAAGAAAAACCACCCTGGCGCCC
AATACGCAAACCGCCTCTCCCCGCGCGTTGGCCGATTCATTAATGCAGCTGGCACGACAGGT
TTCCCGACTGGAAAGCGGGCAGTGAGCGCAACGCAATTAATGTAAGTTAGCTCACTCATTAG
GCACAATTCTCATGTTTGACAGCTTATCATCGACTGCACGGTGCACCAATGCTTCTGGCGTCA
GGCAGCCATCGGAAGCTGTGGTATGGCTGTGCAGGTCGTAAATCACTGCATAATTCGTGTCG
CTCAAGGCGCACTCCCGTTCTGGATAATGTTTTTTGCGCCGACATCATAACGGTTCTGGCAA
ATATTCTGAAATGAGCTGTTGACAATTAATCATCGGCTCGTATAATGTGTGGAATTGTGAGC
GGATAACAATTTCACACAGGAAACAGCCAGTCCGTTTAGGTGTTTTCACGAGCAATTGACCA
ACAAGGACCATAGATTATGAAAATCGAAGAAGGTAAACTGGTAATCTGGATTAACGGCGAT
AAAGGCTATAACGGTCTCGCTGAAGTCGGTAAGAAATTCGAGAAAGATACCGGAATTAAAG
TCACCGTTGAGCATCCGGATAAACTGGAAGAGAAATTCCCACAGGTTGCGGCAACTGGCGA
TGGCCCTGACATTATCTTCTGGGCACACGACCGCTTTGGTGGCTACGCTCAATCTGGCCTGTT
GGCTGAAATCACCCCGGACAAAGCGTTCCAGGACAAGCTGTATCCGTTTACCTGGGATGCCG
TACGTTACAACGGCAAGCTGATTGCTTACCCGATCGCTGTTGAAGCGTTATCGCTGATTTATA
ACAAAGATCTGCTGCCGAACCCGCCAAAAACCTGGGAAGAGATCCCGGCGCTGGATAAAGA
ACTGAAAGCGAAAGGTAAGAGCGCGCTGATGTTCAACCTGCAAGAACCGTACTTCACCTGG
CCGCTGATTGCTGCTGACGGGGGTTATGCGTTCAAGTATGAAAACGGCAAGTACGACATTAA
AGACGTGGGCGTGGATAACGCTGGCGCGAAAGCGGGTCTGACCTTCCTGGTTGACCTGATTA
AAAACAAACACATGAATGCAGACACCGATTACTCCATCGCAGAAGCTGCCTTTAATAAAGG
CGAAACAGCGATGACCATCAACGGCCCGTGGGCATGGTCCAACATCGACACCAGCAAAGTG
AATTATGGTGTAACGGTACTGCCGACCTTCAAGGGTCAACCATCCAAACCGTTCGTTGGCGT
GCTGAGCGCAGGTATTAACGCCGCCAGTCCGAACAAAGAGCTGGCAAAAGAGTTCCTCGAA

FIG. 13 (cont.)

AACTATCTGCTGACTGATGAAGGTCTGGAAGCGGTTAATAAAGACAAACCGCTGGGTGCCG
TAGCGCTGAAGTCTTACGAGGAAGAGTTGGTGAAAGATCCGCGTATTGCCGCCACTATGGA
AAACGCCCAGAAAGGTGAAATCATGCCGAACATCCCGCAGATGTCCGCTTTCTGGTATGCCG
TGCGTACTGCGGTGATCAACGCCGCCAGCGGTCGTCAGACTGTCGATGAAGCCCTGAAAGA
CGCGCAGACTAATTCGAGCTCGAACAACAACAACAATAACAATAACAACAACCTCGGGATC
GAGGGAAGGATTTCACATATGTCCATGGGCGGCCGCGATATCGTCGACATGACACAGTTCG
AGGGCTTTACCAACCTGTATCAGGTGAGCAAGACACTGCGGTTTGAGCTGATCCCACAGGGC
AAGACCCTGAAGCACATCCAGGAGCAGGGCTTCATCGAGGAGGACAAGGCCCGCAATGATC
ACTACAAGGAGCTGAAGCCCATCATCGATCGGATCTACAAGACCTATGCCGACCAGTGCCTG
CAGCTGGTGCAGCTGGATTGGGAGAACCTGAGCGCCGCCATCGACTCCTATAGAAAGGAGA
AAACCGAGGAGACAAGGAACGCCCTGATCGAGGAGCAGGCCACATATCGCAATGCCATCCA
CGACTACTTCATCGGCCGGACAGACAACCTGACCGATGCCATCAATAAGAGACACGCCGAG
ATCTACAAGGGCCTGTTCAAGGCCGAGCTGTTTAATGGCAAGGTGCTGAAGCAGCTGGGCA
CCGTGACCACAACCGAGCACGAGAACGCCCTGCTGCGGAGCTTCGACAAGTTTACAACCTA
CTTCTCCGGCTTTTATGAGAACAGGAAGAACGTGTTCAGCGCCGAGGATATCAGCACAGCCA
TCCCACACCGCATCGTGCAGGACAACTTCCCCAAGTTTAAGGAGAATTGTCACATCTTCACA
CGCCTGATCACCGCCGTGCCCAGCCTGCGGGAGCACTTTGAGAACGTGAAGAAGGCCATCG
GCATCTTCGTGAGCACCTCCATCGAGGAGGTGTTTTCCTTCCCTTTTTATAACCAGCTGCTGA
CACAGACCCAGATCGACCTGTATAACCAGCTGCTGGGAGGAATCTCTCGGGAGGCAGGCAC
CGAGAAGATCAAGGGCCTGAACGAGGTGCTGAATCTGGCCATCCAGAAGAATGATGAGACA
GCCCACATCATCGCCTCCCTGCCACACAGATTCATCCCCCTGTTTAAGCAGATCCTGTCCGAT
AGGAACACCCTGTCTTTCATCCTGGAGGAGTTTAAGAGCGACGAGGAAGTGATCCAGTCCTT
CTGCAAGTACAAGACACTGCTGAGAAACGAGAACGTGCTGGAGACAGCCGAGGCCCTGTTT
AACGAGCTGAACAGCATCGACCTGACACACATCTTCATCAGCCACAAGAAGCTGGAGACAA
TCAGCAGCGCCCTGTGCGACCACTGGGATACACTGAGGAATGCCCTGTATGAGCGGAGAAT
CTCCGAGCTGACAGGCAAGATCACCAAGTCTGCCAAGGAGAAGGTGCAGCGCAGCCTGAAG
CACGAGGATATCAACCTGCAGGAGATCATCTCTGCCGCAGGCAAGGAGCTGAGCGAGGCCT
TCAAGCAGAAAACCAGCGAGATCCTGTCCCACGCACACGCCGCCCTGGATCAGCCACTGCCT
ACAACCCTGAAGAAGCAGGAGGAGAAGGAGATCCTGAAGTCTCAGCTGGACAGCCTGCTGG
GCCTGTACCACCTGCTGGACTGGTTTGCCGTGGATGAGTCCAACGAGGTGGACCCCGAGTTC
TCTGCCCGGCTGACCGGCATCAAGCTGGAGATGGAGCCTTCTCTGAGCTTCTACAACAAGGC
CAGAAATTATGCCACCAAGAAGCCCTACTCCGTGGAGAAGTTCAAGCTGAACTTTCAGATGC
CTACACTGGCCTCTGGCTGGGACGTGAATAAGGAGAAGAACAATGGCGCCATCCTGTTTGTG
AAGAACGGCCTGTACTATCTGGGCATCATGCCAAAGCAGAAGGGCAGGTATAAGGCCCTGA
GCTTCGAGCCCACAGAGAAAACCAGCGAGGGCTTTGATAAGATGTACTATGACTACTTCCCT
GATGCCGCCAAGATGATCCCAAAGTGCAGCACCCAGCTGAAGGCCGTGACAGCCCACTTTC
AGACCCACACAACCCCCATCCTGCTGTCCAACAATTTCATCGAGCCTCTGGAGATCACAAAG
GAGATCTACGACCTGAACAATCCTGAGAAGGAGCCAAAGAAGTTTCAGACAGCCTACGCCA
AGAAAACCGGCGACCAGAAGGGCTACAGAGAGGCCCTGTGCAAGTGGATCGACTTCACAAG
GGATTTTCTGTCCAAGTATACCAAGACAACCTCTATCGATCTGTCTAGCCTGCGGCCATCCTC
TCAGTATAAGGACCTGGGCGAGTACTATGCCGAGCTGAATCCCCTGCTGTACCACATCAGCT
TCCAGAGAATCGCCGAGAAGGAGATCATGGATGCCGTGGAGACAGGCAAGCTGTACCTGTT
CCAGATCTATAACAAGGACTTTGCCAAGGGCCACCACGGCAAGCCTAATCTGCACACACTGT
ATTGGACCGGCCTGTTTTCTCCAGAGAACCTGGCCAAGACAAGCATCAAGCTGAATGGCCAG

FIG. 13 (cont.)

GCCGAGCTGTTCTACCGCCCTAAGTCCAGGATGAAGAGGATGGCACACCGGCTGGGAGAGA
AGATGCTGAACAAGAAGCTGAAGGATCAGAAAACCCCAATCCCCGACACCCTGTACCAGGA
GCTGTACGACTATGTGAATCACAGACTGTCCCACGACCTGTCTGATGAGGCCAGGGCCCTGC
TGCCCAACGTGATCACCAAGGAGGTGTCTCACGAGATCATCAAGGATAGGCGCTTTACCAGC
GACAAGTTCTTTTTCCACGTGCCTATCACACTGAACTATCAGGCCGCCAATTCCCCATCTAAG
TTCAACCAGAGGGTGAATGCCTACCTGAAGGAGCACCCCGAGACACCTATCATCGGCATCG
ATCGGGGCGAGAGAAACCTGATCTATATCACAGTGATCGACTCCACCGGCAAGATCCTGGA
GCAGCGGAGCCTGAACACCATCCAGCAGTTTGATTACCAGAAGAAGCTGGACAACAGGGAG
AAGGAGAGGGTGGCAGCAAGGCAGGCCTGGTCTGTGGTGGGCACAATCAAGGATCTGAAGC
AGGGCTATCTGAGCCAGGTCATCCACGAGATCGTGGACCTGATGATCCACTACCAGGCCGTG
GTGGTGCTGGAGAACCTGAATTTCGGCTTTAAGAGCAAGAGGACCGGCATCGCCGAGAAGG
CCGTGTACCAGCAGTTCGAGAAGATGCTGATCGATAAGCTGAATTGCCTGGTGCTGAAGGAC
TATCCAGCAGAGAAAGTGGGAGGCGTGCTGAACCCATACCAGCTGACAGACCAGTTCACCT
CCTTTGCCAAGATGGGCACCCAGTCTGGCTTCCTGTTTTACGTGCCTGCCCCATATACATCTA
AGATCGATCCCCTGACCGGCTTCGTGGACCCCTTCGTGTGGAAAACCATCAAGAATCACGAG
AGCCGCAAGCACTTCCTGGAGGGCTTCGACTTTCTGCACTACGACGTGAAAACCGGCGACTT
CATCCTGCACTTTAAGATGAACAGAAATCTGTCCTTCCAGAGGGGCCTGCCCGGCTTTATGC
CTGCATGGGATATCGTGTTCGAGAAGAACGAGACACAGTTTGACGCCAAGGGCACCCCTTTC
ATCGCCGGCAAGAGAATCGTGCCAGTGATCGAGAATCACAGATTCACCGGCAGATACCGGG
ACCTGTATCCTGCCAACGAGCTGATCGCCCTGCTGGAGGAGAAGGGCATCGTGTTCAGGGAT
GGCTCCAACATCCTGCCAAAGCTGCTGGAGAATGACGATTCTCACGCCATCGACACCATGGT
GGCCCTGATCCGCAGCGTGCTGCAGATGCGGAACTCCAATGCCGCCACAGGCGAGGACTAT
ATCAACAGCCCCGTGCGCGATCTGAATGGCGTGTGCTTCGACTCCCGGTTTCAGAACCCAGA
GTGGCCCATGGACGCCGATGCCAATGGCGCCTACCACATCGCCCTGAAGGGCCAGCTGCTGC
TGAATCACCTGAAGGAGAGCAAGGATCTGAAGCTGCAGAACGGCATCTCCAATCAGGACTG
GCTGGCCTACATCCAGGAGCTGCGCAACAAAAGGCCGGCGGCCACGAAAAAGGCCGGCCAG
GCAAAAAAGAAAAAG (SEQ ID NO:3331)

FIG. 14

GAATTCCCTGCAGGTAATTAAATAAGCTTCAAATAAAACGAAAGGCTCAGTCGAAAGACTG
GGCCTTTCGTTTTATCTGTTGTTTGTCGGTGAACGCTCTCCTGAGTAGGACAAATCCGCCGGG
AGCGGATTTGAACGTTGCGAAGCAACGGCCCGGAGGGTGGCGGGCAGGACGCCCGCCATAA
ACTGCCAGGCATCAAATTAAGCAGAAGGCCATCCTGACGGATGGCCTTTTTGCGTTTCTACA
AACTCTTTCGGTCCGTTGTTTATTTTTCTAAATACATTCAAATATGTATCCGCTCATGAGACA
ATAACCCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAAACGCT
GGTGAAAGTAAAAGATGCTGAAGATCAGTTGGGTGCACGAGTGGGTTACATCGAACTGGAT
CTCAACAGCGGTAAGATCCTTGAGAGTTTTCGCCCCGAAGAACGTTTCCCAATGATGAGCAC
TTTTAAAGTTCTGCTATGTGGCGCGGTATTATCCCGTGTTGACGCCGGGCAAGAGCAACTCG
GTCGCCGCATACACTATTCTCAGAATGACTTGGTTGAGTACTCACCAGTCACAGAAAAGCAT
CTTACGGATGGCATGACAGTAAGAGAATTATGCAGTGCTGCCATAACCATGAGTGATAACA
CTGCGGCCAACTTACTTCTGACAACGATCGGAGGACCGAAGGAGCTAACCGCTTTTTTGCAC
AACATGGGGGATCATGTAACTCGCCTTGATCGTTGGGAACCGGAGCTGAATGAAGCCATAC
CAAACGACGAGCGTGACACCACGATGCCTGTAGCAATGGCAACAACGTTGCGCAAACTATT
AACTGGCGAACTACTTACTCTAGCTTCCCGGCAACAATTAATAGACTGGATGGAGGCGGATA
AAGTTGCAGGACCACTTCTGCGCTCGGCCCTTCCGGCTGGCTGGTTTATTGCTGATAAATCTG
GAGCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAGA
TCGCTGAGATAGGTGCCTCACTGATTAAGCATTGGTAACTGTCAGACCAAGTTTACTCATAT
ATACTTTAGATTGATTTCCTTAGGACTGAGCGTCAACCCCGTAGAAAAGATCAAAGGATCTT
CTTGAGATCCTTTTTTTCTGCGCGTAATCTGCTGCTTGCAAACAAAAAAACCACCGCTACCAG
CGGTGGTTTGTTTGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCACCACTTCAAGAA
CTCTGTAGCACCGCCTACATACCTCGCTCTGCTAATCCTGTTACCAGTGGCTGCTGCCAGTGG
CGATAAGTCGTGTCTTACCGGGTTGGACTCAAGACGATAGTTACCGGATAAGGCGCAGCGGT
CGGGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGA
AACGCCTGGTATCTTTATAGTCCTGTCGGGTTTCGCCACCTCTGACTTGAGCGTCGATTTTTG
TGATGCTCGTCAGGGGGGCGGAGCCTATGGAAAAACGCCAGCAACGCGGCCTTTTTACGGTT
CCTGGCCTTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACCGAGCGCAG
CGAGTCAGTGAGCGAGGAAGCGGAAGAGCGCCTGATGCGGTATTTTCTCCTTACGCATCTGT
GCGGTATTTCACACCGCATATAAGGTGCACTGTGACTGGGTCATGGCTGCGCCCCGACACCC
GCCAACACCCGCTGACGCGCCCTGACGGGCTTGTCTGCTCCCGGCATCCGCTTACAGACAAG
CTGTGACCGTCTCCGGGAGCTGCATGTGTCAGAGGTTTTCACCGTCATCACCGAAACGCGCG
AGGCAGCTGCGGTAAAGCTCATCAGCGTGGTCGTGCAGCGATTCACAGATGTCTGCCTGTTC
ATCCGCGTCCAGCTCGTTGAGTTTCTCCAGAAGCGTTAATGTCTGGCTTCTGATAAAGCGGG
CCATGTTAAGGGCGGTTTTTTCCTGTTTGGTCACTGATGCCTCCGTGTAAGGGGGATTTCTGT
TCATGGGGGTAATGATACCGATGAAACGAGAGAGGATGCTCACGATACGGGTTACTGATGA
TGAACATGCCCGGTTACTGGAACGTTGTGAGGGTAAACAACTGGCGGTATGGATGCGGCGG

FIG. 14(cont.)

GACCAGAGAAAAATCACTCAGGGTCAATGCCAGCGCTTCGTTAATACAGATGTAGGTGTTCC
ACAGGGTAGCCAGCAGCATCCTGCGATGCAGATCCGGAACATAATGGTGCAGGGCGCTGAC
TTCCGCGTTTCCAGACTTTACGAAACACGGAAACCGAAGACCATTCATGTTGTTGCTCAGGT
CGCAGACGTTTTGCAGCAGCAGTCGCTTCACGTTCGCTCGCGTATCGGTGATTCATTCTGCTA
ACCAGTAAGGCAACCCCGCCAGCCTAGCCGGGTCCTCAACGACAGGAGCACGATCATGCGC
ACCCGTGGCCAGGACCCAACGCTGCCCGAAATTCCGACACCATCGAATGGTGCAAAACCTTT
CGCGGTATGGCATGATAGCGCCCGGAAGAGAGTCAATTCAGGGTGGTGAATGTGAAACCAG
TAACGTTATACGATGTCGCAGAGTATGCCGGTGTCTCTTATCAGACCGTTTCCCGCGTGGTG
AACCAGGCCAGCCACGTTTCTGCGAAAACGCGGGAAAAAGTGGAAGCGGCGATGGCGGAG
CTGAATTACATTCCCAACCGCGTGGCACAACAACTGGCGGGCAAACAGTCGTTGCTGATTGG
CGTTGCCACCTCCAGTCTGGCCCTGCACGCGCCGTCGCAAATTGTCGCGGCGATTAAATCTC
GCGCCGATCAACTGGGTGCCAGCGTGGTGGTGTCGATGGTAGAACGAAGCGGCGTCGAAGC
CTGTAAAGCGGCGGTGCACAATCTTCTCGCGCAACGCGTCAGTGGGCTGATCATTAACTATC
CGCTGGATGACCAGGATGCCATTGCTGTGGAAGCTGCCTGCACTAATGTTCCGGCGTTATTT
CTTGATGTCTCTGACCAGACACCCATCAACAGTATTATTTTCTCCCATGAAGACGGTACGCG
ACTGGGCGTGGAGCATCTGGTCGCATTGGGTCACCAGCAAATCGCGCTGTTAGCGGGCCCAT
TAAGTTCTGTCTCGGCGCGTCTGCGTCTGGCTGGCTGGCATAAATATCTCACTCGCAATCAA
ATTCAGCCGATAGCGGAACGGGAAGGCGACTGGAGTGCCATGTCCGGTTTTCAACAAACCA
TGCAAATGCTGAATGAGGGCATCGTTCCCACTGCGATGCTGGTTGCCAACGATCAGATGGCG
CTGGGCGCAATGCGCGCCATTACCGAGTCCGGGCTGCGCGTTGGTGCGGATATTTCGGTAGT
GGGATACGACGATACCGAAGACAGCTCATGTTATATCCCGCCGTTAACCACCATCAAACAG
GATTTTCGCCTGCTGGGGCAAACCAGCGTGGACCGCTTGCTGCAACTCTCTCAGGGCCAGGC
GGTGAAGGGCAATCAGCTGTTGCCCGTCTCACTGGTGAAAAGAAAAACCACCCTGGCGCCC
AATACGCAAACCGCCTCTCCCCGCGCGTTGGCCGATTCATTAATGCAGCTGGCACGACAGGT
TTCCCGACTGGAAAGCGGGCAGTGAGCGCAACGCAATTAATGTAAGTTAGCTCACTCATTAG
GCACAATTCTCATGTTTGACAGCTTATCATCGACTGCACGGTGCACCAATGCTTCTGGCGTCA
GGCAGCCATCGGAAGCTGTGGTATGGCTGTGCAGGTCGTAAATCACTGCATAATTCGTGTCG
CTCAAGGCGCACTCCCGTTCTGGATAATGTTTTTTGCGCCGACATCATAACGGTTCTGGCAA
ATATTCTGAAATGAGCTGTTGACAATTAATCATCGGCTCGTATAATGTGTGGAATTGTGAGC
GGATAACAATTTCACACAGGAAACAGCCAGTCCGTTTAGGTGTTTTCACGAGCAATTGACCA
ACAAGGACCATAGATTATGAAAATCGAAGAAGGTAAACTGGTAATCTGGATTAACGGCGAT
AAAGGCTATAACGGTCTCGCTGAAGTCGGTAAGAAATTCGAGAAAGATACCGGAATTAAAG
TCACCGTTGAGCATCCGGATAAACTGGAAGAGAAATTCCCACAGGTTGCGGCAACTGGCGA
TGGCCCTGACATTATCTTCTGGGCACACGACCGCTTTGGTGGCTACGCTCAATCTGGCCTGTT
GGCTGAAATCACCCCGGACAAAGCGTTCCAGGACAAGCTGTATCCGTTTACCTGGGATGCCG
TACGTTACAACGGCAAGCTGATTGCTTACCCGATCGCTGTTGAAGCGTTATCGCTGATTTATA
ACAAAGATCTGCTGCCGAACCCGCCAAAAACCTGGGAAGAGATCCCGGCGCTGGATAAAGA
ACTGAAAGCGAAAGGTAAGAGCGCGCTGATGTTCAACCTGCAAGAACCGTACTTCACCTGG
CCGCTGATTGCTGCTGACGGGGGTTATGCGTTCAAGTATGAAAACGGCAAGTACGACATTAA
AGACGTGGGCGTGGATAACGCTGGCGCGAAAGCGGGTCTGACCTTCCTGGTTGACCTGATTA
AAAACAAACACATGAATGCAGACACCGATTACTCCATCGCAGAAGCTGCCTTTAATAAAGG
CGAAACAGCGATGACCATCAACGGCCCGTGGGCATGGTCCAACATCGACACCAGCAAAGTG
AATTATGGTGTAACGGTACTGCCGACCTTCAAGGGTCAACCATCCAAACCGTTCGTTGGCGT
GCTGAGCGCAGGTATTAACGCCGCCAGTCCGAACAAAGAGCTGGCAAAAGAGTTCCTCGAA

FIG. 14(cont.)

AACTATCTGCTGACTGATGAAGGTCTGGAAGCGGTTAATAAAGACAAACCGCTGGGTGCCG
TAGCGCTGAAGTCTTACGAGGAAGAGTTGGTGAAAGATCCGCGTATTGCCGCCACTATGGA
AAACGCCCAGAAAGGTGAAATCATGCCGAACATCCCGCAGATGTCCGCTTTCTGGTATGCCG
TGCGTACTGCGGTGATCAACGCCGCCAGCGGTCGTCAGACTGTCGATGAAGCCCTGAAAGA
CGCGCAGACTAATTCGAGCTCGAACAACAACAACAATAACAATAACAACAACCTCGGGATC
GAGGGAAGGATTTCACATATGTCCATGGGCGGCCGCGATATCGTCGACATGAGCAAGCTGG
AGAAGTTTACAAACTGCTACTCCCTGTCTAAGACCCTGAGGTTCAAGGCCATCCCTGTGGGC
AAGACCCAGGAGAACATCGACAATAAGCGGCTGCTGGTGGAGGACGAGAAGAGAGCCGAG
GATTATAAGGGCGTGAAGAAGCTGCTGGATCGCTACTATCTGTCTTTTATCAACGACGTGCT
GCACAGCATCAAGCTGAAGAATCTGAACAATTACATCAGCCTGTTCCGGAAGAAAACCAGA
ACCGAGAAGGAGAATAAGGAGCTGGAGAACCTGGAGATCAATCTGCGGAAGGAGATCGCC
AAGGCCTTCAAGGGCAACGAGGGCTACAAGTCCCTGTTTAAGAAGGATATCATCGAGACAA
TCCTGCCAGAGTTCCTGGACGATAAGGACGAGATCGCCCTGGTGAACAGCTTCAATGGCTTT
ACCACAGCCTTCACCGGCTTCTTTGATAACAGAGAGAATATGTTTTCCGAGGAGGCCAAGAG
CACATCCATCGCCTTCAGGTGTATCAACGAGAATCTGACCCGCTACATCTCTAATATGGACA
TCTTCGAGAAGGTGGACGCCATCTTTGATAAGCACGAGGTGCAGGAGATCAAGGAGAAGAT
CCTGAACAGCGACTATGATGTGGAGGATTTCTTTGAGGGCGAGTTCTTTAACTTTGTGCTGA
CACAGGAGGGCATCGACGTGTATAACGCCATCATCGGCGGCTTCGTGACCGAGAGCGGCGA
GAAGATCAAGGGCCTGAACGAGTACATCAACCTGTATAATCAGAAAACCAAGCAGAAGCTG
CCTAAGTTTAAGCCACTGTATAAGCAGGTGCTGAGCGATCGGGAGTCTCTGAGCTTCTACGG
CGAGGGCTATACATCCGATGAGGAGGTGCTGGAGGTGTTTAGAAACACCCTGAACAAGAAC
AGCGAGATCTTCAGCTCCATCAAGAAGCTGGAGAAGCTGTTCAAGAATTTTGACGAGTACTC
TAGCGCCGGCATCTTTGTGAAGAACGGCCCCGCCATCAGCACAATCTCCAAGGATATCTTCG
GCGAGTGGAACGTGATCCGGGACAAGTGGAATGCCGAGTATGACGATATCCACCTGAAGAA
GAAGGCCGTGGTGACCGAGAAGTACGAGGACGATCGGAGAAAGTCCTTCAAGAAGATCGGC
TCCTTTTCTCTGGAGCAGCTGCAGGAGTACGCCGACGCCGATCTGTCTGTGGTGGAGAAGCT
GAAGGAGATCATCATCCAGAAGGTGGATGAGATCTACAAGGTGTATGGCTCCTCTGAGAAG
CTGTTCGACGCCGATTTTGTGCTGGAGAAGAGCCTGAAGAAGAACGACGCCGTGGTGGCCA
TCATGAAGGACCTGCTGGATTCTGTGAAGAGCTTCGAGAATTACATCAAGGCCTTCTTTGGC
GAGGGCAAGGAGACAAACAGGGACGAGTCCTTCTATGGCGATTTTGTGCTGGCCTACGACA
TCCTGCTGAAGGTGGACCACATCTACGATGCCATCCGCAATTATGTGACCCAGAAGCCCTAC
TCTAAGGATAAGTTCAAGCTGTATTTTCAGAACCCTCAGTTCATGGGCGGCTGGGACAAGGA
TAAGGAGACAGACTATCGGGCCACCATCCTGAGATACGGCTCCAAGTACTATCTGGCCATCA
TGGATAAGAAGTACGCCAAGTGCCTGCAGAAGATCGACAAGGACGATGTGAACGGCAATTA
CGAGAAGATCAACTATAAGCTGCTGCCCGGCCCTAATAAGATGCTGCCAAAGGTGTTCTTTT
CTAAGAAGTGGATGGCCTACTATAACCCCAGCGAGGACATCCAGAAGATCTACAAGAATGG
CACATTCAAGAAGGGCGATATGTTTAACCTGAATGACTGTCACAAGCTGATCGACTTCTTTA
AGGATAGCATCTCCCGGTATCCAAAGTGGTCCAATGCCTACGATTTCAACTTTTCTGAGACA
GAGAAGTATAAGGACATCGCCGGCTTTTACAGAGAGGTGGAGGAGCAGGGCTATAAGGTGA
GCTTCGAGTCTGCCAGCAAGAAGGAGGTGGATAAGCTGGTGGAGGAGGGCAAGCTGTATAT
GTTCCAGATCTATAACAAGGACTTTTCCGATAAGTCTCACGGCACACCCAATCTGCACACCA
TGTACTTCAAGCTGCTGTTTGACGAGAACAATCACGGACAGATCAGGCTGAGCGGAGGAGC
AGAGCTGTTCATGAGGCGCGCCTCCCTGAAGAAGGAGGAGCTGGTGGTGCACCCAGCCAAC

FIG. 14(cont.)

TCCCCTATCGCCAACAAGAATCCAGATAATCCCAAGAAAACCACAACCCTGTCCTACGACGT
GTATAAGGATAAGAGGTTTTCTGAGGACCAGTACGAGCTGCACATCCCAATCGCCATCAATA
AGTGCCCCAAGAACATCTTCAAGATCAATACAGAGGTGCGCGTGCTGCTGAAGCACGACGA
TAACCCCTATGTGATCGGCATCGATAGGGGCGAGCGCAATCTGCTGTATATCGTGGTGGTGG
ACGGCAAGGGCAACATCGTGGAGCAGTATTCCCTGAACGAGATCATCAACAACTTCAACGG
CATCAGGATCAAGACAGATTACCACTCTCTGCTGGACAAGAAGGAGAAGGAGAGGTTCGAG
GCCCGCCAGAACTGGACCTCCATCGAGAATATCAAGGAGCTGAAGGCCGGCTATATCTCTCA
GGTGGTGCACAAGATCTGCGAGCTGGTGGAGAAGTACGATGCCGTGATCGCCCTGGAGGAC
CTGAACTCTGGCTTTAAGAATAGCCGCGTGAAGGTGGAGAAGCAGGTGTATCAGAAGTTCG
AGAAGATGCTGATCGATAAGCTGAACTACATGGTGGACAAGAAGTCTAATCCTTGTGCAAC
AGGCGGCGCCCTGAAGGGCTATCAGATCACCAATAAGTTCGAGAGCTTTAAGTCCATGTCTA
CCCAGAACGGCTTCATCTTTTACATCCCTGCCTGGCTGACATCCAAGATCGATCCATCTACCG
GCTTTGTGAACCTGCTGAAAACCAAGTATACCAGCATCGCCGATTCCAAGAAGTTCATCAGC
TCCTTTGACAGGATCATGTACGTGCCCGAGGAGGATCTGTTCGAGTTTGCCCTGGACTATAA
GAACTTCTCTCGCACAGACGCCGATTACATCAAGAAGTGGAAGCTGTACTCCTACGGCAACC
GGATCAGAATCTTCCGGAATCCTAAGAAGAACAACGTGTTCGACTGGGAGGAGGTGTGCCT
GACCAGCGCCTATAAGGAGCTGTTCAACAAGTACGGCATCAATTATCAGCAGGGCGATATC
AGAGCCCTGCTGTGCGAGCAGTCCGACAAGGCCTTCTACTCTAGCTTTATGGCCCTGATGAG
CCTGATGCTGCAGATGCGGAACAGCATCACAGGCCGCACCGACGTGGATTTTCTGATCAGCC
CTGTGAAGAACTCCGACGGCATCTTCTACGATAGCCGGAACTATGAGGCCCAGGAGAATGC
CATCCTGCCAAAGAACGCCGACGCCAATGGCGCCTATAACATCGCCAGAAAGGTGCTGTGG
GCCATCGGCCAGTTCAAGAAGGCCGAGGACGAGAAGCTGGATAAGGTGAAGATCGCCATCT
CTAACAAGGAGTGGCTGGAGTACGCCCAGACCAGCGTGAAGCACAAAAGGCCGGCGGCCAC
GAAAAAGGCCGGCCAGGCAAAAAAGAAAAAG (SEQ ID NO:~~34~~32)

FIG. 15

GAATTCCCTGCAGGTAATTAAATAAGCTTCAAATAAAACGAAAGGCTCAGTCGAAAGACTG
GGCCTTTCGTTTTATCTGTTGTTTGTCGGTGAACGCTCTCCTGAGTAGGACAAATCCGCCGGG
AGCGGATTTGAACGTTGCGAAGCAACGGCCCGGAGGGTGGCGGGCAGGACGCCCGCCATAA
ACTGCCAGGCATCAAATTAAGCAGAAGGCCATCCTGACGGATGGCCTTTTTGCGTTTCTACA
AACTCTTTCGGTCCGTTGTTTATTTTTCTAAATACATTCAAATATGTATCCGCTCATGAGACA
ATAACCCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAAACGCT
GGTGAAAGTAAAAGATGCTGAAGATCAGTTGGGTGCACGAGTGGGTTACATCGAACTGGAT
CTCAACAGCGGTAAGATCCTTGAGAGTTTTCGCCCCGAAGAACGTTTCCCAATGATGAGCAC
TTTTAAAGTTCTGCTATGTGGCGCGGTATTATCCCGTGTTGACGCCGGGCAAGAGCAACTCG
GTCGCCGCATACACTATTCTCAGAATGACTTGGTTGAGTACTCACCAGTCACAGAAAAGCAT
CTTACGGATGGCATGACAGTAAGAGAATTATGCAGTGCTGCCATAACCATGAGTGATAACA
CTGCGGCCAACTTACTTCTGACAACGATCGGAGGACCGAAGGAGCTAACCGCTTTTTTGCAC
AACATGGGGGATCATGTAACTCGCCTTGATCGTTGGGAACCGGAGCTGAATGAAGCCATAC
CAAACGACGAGCGTGACACCACGATGCCTGTAGCAATGGCAACAACGTTGCGCAAACTATT
AACTGGCGAACTACTTACTCTAGCTTCCCGGCAACAATTAATAGACTGGATGGAGGCGGATA
AAGTTGCAGGACCACTTCTGCGCTCGGCCCTTCCGGCTGGCTGGTTTATTGCTGATAAATCTG
GAGCCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAGA
TCGCTGAGATAGGTGCCTCACTGATTAAGCATTGGTAACTGTCAGACCAAGTTTACTCATAT
ATACTTTAGATTGATTTCCTTAGGACTGAGCGTCAACCCCGTAGAAAAGATCAAAGGATCTT
CTTGAGATCCTTTTTTTCTGCGCGTAATCTGCTGCTTGCAAACAAAAAAACCACCGCTACCAG
CGGTGGTTTGTTTGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCACCACTTCAAGAA
CTCTGTAGCACCGCCTACATACCTCGCTCTGCTAATCCTGTTACCAGTGGCTGCTGCCAGTGG
CGATAAGTCGTGTCTTACCGGGTTGGACTCAAGACGATAGTTACCGGATAAGGCGCAGCGGT
CGGGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGGAC
AGGTATCCGGTAAGCGGCAGGGTCGGAACAGGAGAGCGCACGAGGGAGCTTCCAGGGGGA
AACGCCTGGTATCTTTATAGTCCTGTCGGGTTTCGCCACCTCTGACTTGAGCGTCGATTTTTG
TGATGCTCGTCAGGGGGGCGGAGCCTATGGAAAAACGCCAGCAACGCGGCCTTTTTACGGTT
CCTGGCCTTTTGCTGGCCTTTTGCTCACATGTTCTTTCCTGCGTTATCCCCTGATTCTGTGGAT
AACCGTATTACCGCCTTTGAGTGAGCTGATACCGCTCGCCGCAGCCGAACGACCGAGCGCAG
CGAGTCAGTGAGCGAGGAAGCGGAAGAGCGCCTGATGCGGTATTTTCTCCTTACGCATCTGT
GCGGTATTTCACACCGCATATAAGGTGCACTGTGACTGGGTCATGGCTGCGCCCCGACACCC
GCCAACACCCGCTGACGCGCCCTGACGGGCTTGTCTGCTCCCGGCATCCGCTTACAGACAAG
CTGTGACCGTCTCCGGGAGCTGCATGTGTCAGAGGTTTTCACCGTCATCACCGAAACGCGCG
AGGCAGCTGCGGTAAAGCTCATCAGCGTGGTCGTGCAGCGATTCACAGATGTCTGCCTGTTC
ATCCGCGTCCAGCTCGTTGAGTTTCTCCAGAAGCGTTAATGTCTGGCTTCTGATAAAGCGGG
CCATGTTAAGGGCGGTTTTTTCCTGTTTGGTCACTGATGCCTCCGTGTAAGGGGGATTTCTGT
TCATGGGGGTAATGATACCGATGAAACGAGAGAGGATGCTCACGATACGGGTTACTGATGA
TGAACATGCCCGGTTACTGGAACGTTGTGAGGGTAAACAACTGGCGGTATGGATGCGGCGG
GACCAGAGAAAAATCACTCAGGGTCAATGCCAGCGCTTCGTTAATACAGATGTAGGTGTTCC

FIG. 15(cont.)

ACAGGGTAGCCAGCAGCATCCTGCGATGCAGATCCGGAACATAATGGTGCAGGGCGCTGAC
TTCCGCGTTTCCAGACTTTACGAAACACGGAAACCGAAGACCATTCATGTTGTTGCTCAGGT
CGCAGACGTTTTGCAGCAGCAGTCGCTTCACGTTCGCTCGCGTATCGGTGATTCATTCTGCTA
ACCAGTAAGGCAACCCCGCCAGCCTAGCCGGGTCCTCAACGACAGGAGCACGATCATGCGC
ACCCGTGGCCAGGACCCAACGCTGCCCGAAATTCCGACACCATCGAATGGTGCAAAACCTTT
CGCGGTATGGCATGATAGCGCCCGGAAGAGAGTCAATTCAGGGTGGTGAATGTGAAACCAG
TAACGTTATACGATGTCGCAGAGTATGCCGGTGTCTCTTATCAGACCGTTTCCCGCGTGGTG
AACCAGGCCAGCCACGTTTCTGCGAAAACGCGGGAAAAAGTGGAAGCGGCGATGGCGGAG
CTGAATTACATTCCCAACCGCGTGGCACAACAACTGGCGGGCAAACAGTCGTTGCTGATTGG
CGTTGCCACCTCCAGTCTGGCCCTGCACGCGCCGTCGCAAATTGTCGCGGCGATTAAATCTC
GCGCCGATCAACTGGGTGCCAGCGTGGTGGTGTCGATGGTAGAACGAAGCGGCGTCGAAGC
CTGTAAAGCGGCGGTGCACAATCTTCTCGCGCAACGCGTCAGTGGGCTGATCATTAACTATC
CGCTGGATGACCAGGATGCCATTGCTGTGGAAGCTGCCTGCACTAATGTTCCGGCGTTATTT
CTTGATGTCTCTGACCAGACACCCATCAACAGTATTATTTTCTCCCATGAAGACGGTACGCG
ACTGGGCGTGGAGCATCTGGTCGCATTGGGTCACCAGCAAATCGCGCTGTTAGCGGGCCCAT
TAAGTTCTGTCTCGGCGCGTCTGCGTCTGGCTGGCTGGCATAAATATCTCACTCGCAATCAA
ATTCAGCCGATAGCGGAACGGGAAGGCGACTGGAGTGCCATGTCCGGTTTTCAACAAACCA
TGCAAATGCTGAATGAGGGCATCGTTCCCACTGCGATGCTGGTTGCCAACGATCAGATGGCG
CTGGGCGCAATGCGCGCCATTACCGAGTCCGGGCTGCGCGTTGGTGCGGATATTTCGGTAGT
GGGATACGACGATACCGAAGACAGCTCATGTTATATCCCGCCGTTAACCACCATCAAACAG
GATTTTCGCCTGCTGGGGCAAACCAGCGTGGACCGCTTGCTGCAACTCTCTCAGGGCCAGGC
GGTGAAGGGCAATCAGCTGTTGCCCGTCTCACTGGTGAAAAGAAAAACCACCCTGGCGCCC
AATACGCAAACCGCCTCTCCCCGCGCGTTGGCCGATTCATTAATGCAGCTGGCACGACAGGT
TTCCCGACTGGAAAGCGGGCAGTGAGCGCAACGCAATTAATGTAAGTTAGCTCACTCATTAG
GCACAATTCTCATGTTTGACAGCTTATCATCGACTGCACGGTGCACCAATGCTTCTGGCGTCA
GGCAGCCATCGGAAGCTGTGGTATGGCTGTGCAGGTCGTAAATCACTGCATAATTCGTGTCG
CTCAAGGCGCACTCCCGTTCTGGATAATGTTTTTTGCGCCGACATCATAACGGTTCTGGCAA
ATATTCTGAAATGAGCTGTTGACAATTAATCATCGGCTCGTATAATGTGTGGAATTGTGAGC
GGATAACAATTTCACACAGGAAACAGCCAGTCCGTTTAGGTGTTTTCACGAGCAATTGACCA
ACAAGGACCATAGATTATGAAAATCGAAGAAGGTAAACTGGTAATCTGGATTAACGGCGAT
AAAGGCTATAACGGTCTCGCTGAAGTCGGTAAGAAATTCGAGAAAGATACCGGAATTAAAG
TCACCGTTGAGCATCCGGATAAACTGGAAGAGAAATTCCCACAGGTTGCGGCAACTGGCGA
TGGCCCTGACATTATCTTCTGGGCACACGACCGCTTTGGTGGCTACGCTCAATCTGGCCTGTT
GGCTGAAATCACCCCGGACAAAGCGTTCCAGGACAAGCTGTATCCGTTTACCTGGGATGCCG
TACGTTACAACGGCAAGCTGATTGCTTACCCGATCGCTGTTGAAGCGTTATCGCTGATTTATA
ACAAAGATCTGCTGCCGAACCCGCCAAAAACCTGGGAAGAGATCCCGGCGCTGGATAAAGA
ACTGAAAGCGAAAGGTAAGAGCGCGCTGATGTTCAACCTGCAAGAACCGTACTTCACCTGG
CCGCTGATTGCTGCTGACGGGGGTTATGCGTTCAAGTATGAAAACGGCAAGTACGACATTAA
AGACGTGGGCGTGGATAACGCTGGCGCGAAAGCGGGTCTGACCTTCCTGGTTGACCTGATTA
AAAACAAACACATGAATGCAGACACCGATTACTCCATCGCAGAAGCTGCCTTTAATAAAGG
CGAAACAGCGATGACCATCAACGGCCCGTGGGCATGGTCCAACATCGACACCAGCAAAGTG
AATTATGGTGTAACGGTACTGCCGACCTTCAAGGGTCAACCATCCAAACCGTTCGTTGGCGT

FIG. 15(cont.)

GCTGAGCGCAGGTATTAACGCCGCCAGTCCGAACAAAGAGCTGGCAAAAGAGTTCCTCGAA
AACTATCTGCTGACTGATGAAGGTCTGGAAGCGGTTAATAAAGACAAACCGCTGGGTGCCG
TAGCGCTGAAGTCTTACGAGGAAGAGTTGGTGAAAGATCCGCGTATTGCCGCCACTATGGA
AAACGCCCAGAAAGGTGAAATCATGCCGAACATCCCGCAGATGTCCGCTTTCTGGTATGCCG
TGCGTACTGCGGTGATCAACGCCGCCAGCGGTCGTCAGACTGTCGATGAAGCCCTGAAAGA
CGCGCAGACTAATTCGAGCTCGAACAACAACAACAATAACAATAACAACAACCTCGGGATC
GAGGGAAGGATTTCACATATGTCCATGGGCGGCCGCGATATCGTCGACATGAGCATCTACCA
GGAGTTCGTCAACAAGTATTCACTGAGTAAGACACTGCGGTTCGAGCTGATCCCACAGGGCA
AGACACTGGAGAACATCAAGGCCCGAGGCCTGATTCTGGACGATGAGAAGCGGGCAAAAG
ACTATAAGAAAGCCAAGCAGATCATTGATAAATACCACCAGTTCTTTATCGAGGAAATTCTG
AGCTCCGTGTGCATCAGTGAGGATCTGCTGCAGAATTACTCAGACGTGTACTTCAAGCTGAA
GAAGAGCGACGATGACAACCTGCAGAAGGACTTCAAGTCCGCCAAGGACACCATCAAGAAA
CAGATTAGCGAGTACATCAAGGACTCCGAAAAGTTTAAAAATCTGTTCAACCAGAATCTGAT
CGATGCTAAGAAAGGCCAGGAGTCCGACCTGATCCTGTGGCTGAAACAGTCTAAGGACAAT
GGGATTGAACTGTTCAAGGCTAACTCCGATATCACTGATATTGACGAGGCACTGGAAATCAT
CAAGAGCTTCAAGGGATGGACCACATACTTTAAAGGCTTCCACGAGAACCGCAAGAACGTG
TACTCCAGCAACGACATTCCTACCTCCATCATCTACCGAATCGTCGATGACAATCTGCCAAA
GTTCCTGGAGAACAAGGCCAAATATGAATCTCTGAAGGACAAAGCTCCCGAGGCAATTAAT
TACGAACAGATCAAGAAAGATCTGGCTGAGGAACTGACATTCGATATCGACTATAAGACTA
GCGAGGTGAACCAGAGGGTCTTTTCCCTGGACGAGGTGTTTGAAATCGCCAATTTCAACAAT
TACCTGAACCAGTCCGGCATTACTAAATTCAATACCATCATTGGCGGGAAGTTTGTGAACGG
GGAGAATACCAAGCGCAAGGGAATTAACGAATACATCAATCTGTATAGCCAGCAGATCAAC
GACAAAACTCTGAAGAAATACAAGATGTCTGTGCTGTTCAAACAGATCCTGAGTGATACCG
AGTCCAAGTCTTTTGTCATTGATAAACTGGAAGATGACTCAGACGTGGTCACTACCATGCAG
AGCTTTTATGAGCAGATCGCCGCTTTCAAGACAGTGGAGGAAAAATCTATTAAGGAAACTCT
GAGTCTGCTGTTCGATGACCTGAAAGCCCAGAAGCTGGACCTGAGTAAGATCTACTTCAAAA
ACGATAAGAGTCTGACAGACCTGTCACAGCAGGTGTTTGATGACTATTCCGTGATTGGGACC
GCCGTCCTGGAGTACATTACACAGCAGATCGCTCCAAAGAACCTGGATAATCCCTCTAAGAA
AGAGCAGGAACTGATCGCTAAGAAAACCGAGAAGGCAAAATATCTGAGTCTGGAAACAATT
AAGCTGGCACTGGAGGAGTTCAACAAGCACAGGGATATTGACAAACAGTGCCGCTTTGAGG
AAATCCTGGCCAACTTCGCAGCCATCCCCATGATTTTTGATGAGATCGCCCAGAACAAAGAC
AATCTGGCTCAGATCAGTATTAAGTACCAGAACCAGGGCAAGAAAGACCTGCTGCAGGCTT
CAGCAGAAGATGACGTGAAAGCCATCAAGGATCTGCTGGACCAGACCAACAATCTGCTGCA
CAAGCTGAAAATCTTCCATATTAGTCAGTCAGAGGATAAGGCTAATATCCTGGATAAAGACG
AACACTTCTACCTGGTGTTCGAGGAATGTTACTTCGAGCTGGCAAACATTGTCCCCCTGTATA
ACAAGATTAGGAACTACATCACACAGAAGCCTTACTCTGACGAGAAGTTTAAACTGAACTTC
GAAAATAGTACCCTGGCCAACGGGTGGGATAAGAACAAGGAGCCTGACAACACAGCTATCC
TGTTCATCAAGGATGACAAGTACTATCTGGGAGTGATGAATAAGAAAAACAATAAGATCTT
CGATGACAAAGCCATTAAGGAGAACAAAGGGGAAGGATACAAGAAAATCGTGTATAAGCT
GCTGCCCGGCGCAAATAAGATGCTGCCTAAGGTGTTCTTCAGCGCCAAGAGTATCAAATTCT
ACAACCCATCCGAGGACATCCTGCGGATTAGAAATCACTCAACACATACTAAGAACGGGAG

FIG. 15(cont.)

CCCCCAGAAGGGATATGAGAAATTTGAGTTCAACATCGAGGATTGCAGGAAGTTTATTGACT
TCTACAAGCAGAGCATCTCCAAACACCCTGAATGGAAGGATTTTGGCTTCCGGTTTTCCGAC
ACACAGAGATATAACTCTATCGACGAGTTCTACCGCGAGGTGGAAAATCAGGGGTATAAGC
TGACTTTTGAGAACATTTCTGAAAGTTACATCGACAGCGTGGTCAATCAGGGAAAGCTGTAC
CTGTTCCAGATCTATAACAAAGATTTTTCAGCATACAGCAAGGGCAGACCAAACCTGCATAC
ACTGTACTGGAAGGCCCTGTTCGATGAGAGGAATCTGCAGGACGTGGTCTATAAACTGAAC
GGAGAGGCCGAACTGTTTTACCGGAAGCAGTCTATTCCTAAGAAAATCACTCACCCAGCTAA
GGAGGCCATCGCTAACAAGAACAAGGACAATCCTAAGAAAGAGAGCGTGTTCGAATACGAT
CTGATTAAGGACAAGCGGTTCACCGAAGATAAGTTCTTTTTCCATTGTCCAATCACCATTAA
CTTCAAGTCAAGCGGCGCTAACAAGTTCAACGACGAGATCAATCTGCTGCTGAAGGAAAAA
GCAAACGATGTGCACATCCTGAGCATTGACCGAGGAGAGCGGCATCTGGCCTACTATACCCT
GGTGGATGGCAAAGGGAATATCATTAAGCAGGATACATTCAACATCATTGGCAATGACCGG
ATGAAAACCAACTACCACGATAAACTGGCTGCAATCGAGAAGGATAGAGACTCAGCTAGGA
AGGACTGGAAGAAAATCAACAACATTAAGGAGATGAAGGAAGGCTATCTGAGCCAGGTGGT
CCATGAGATTGCAAAGCTGGTCATCGAATACAATGCCATTGTGGTGTTCGAGGATCTGAACT
TCGGCTTTAAGAGGGGGCGCTTTAAGGTGGAAAAACAGGTCTATCAGAAGCTGGAGAAAAT
GCTGATCGAAAAGCTGAATTACCTGGTGTTTAAAGATAACGAGTTCGACAAGACCGGAGGC
GTCCTGAGAGCCTACCAGCTGACAGCTCCCTTTGAAACTTTCAAGAAAATGGGAAAACAGA
CAGGCATCATCTACTATGTGCCAGCCGGATTCACTTCCAAGATCTGCCCCGTGACCGGCTTT
GTCAACCAGCTGTACCCTAAATATGAGTCAGTGAGCAAGTCCCAGGAATTTTTCAGCAAGTT
CGATAAGATCTGTTATAATCTGGACAAGGGGTACTTCGAGTTTTCCTTCGATTACAAGAACT
TCGGCGACAAGGCCGCTAAGGGGAAATGGACCATTGCCTCCTTCGGATCTCGCCTGATCAAC
TTTCGAAATTCCGATAAAAACCACAATTGGGACACTAGGGAGGTGTACCCAACCAAGGAGC
TGGAAAAGCTGCTGAAAGACTACTCTATCGAGTATGGACATGGCGAATGCATCAAGGCAGC
CATCTGTGGCGAGAGTGATAAGAAATTTTTCGCCAAGCTGACCTCAGTGCTGAATACAATCC
TGCAGATGCGGAACTCAAAGACCGGGACAGAACTGGACTATCTGATTAGCCCCGTGGCTGA
TGTCAACGGAAACTTCTTCGACAGCAGACAGGCACCCAAAAATATGCCTCAGGATGCAGAC
GCCAACGGGGCCTACCACATCGGGCTGAAGGGACTGATGCTGCTGGGCCGGATCAAGAACA
ATCAGGAGGGGAAGAAGCTGAACCTGGTCATTAAGAACGAGGAATACTTCGAGTTTGTCCA
GAATAGAAATAACAAAAGGCCGGCGGCCACGAAAAAGGCCGGCCAGGCAAAAAAGAAAAA
G (SEQ ID NO:~~35~~33)

FIG. 16

TCCTCATCCCTTACTGTCTTTGCTTTCTCACTAACTACTACAACCCAACAGTTTTCTTCTCTCA
AAAATGGAATGCAAACACAAAATTAATGTAGCAATCCCAATCACTAATATGAAGAACACTC
AATTCTCATCTCCATCTACTTTCTCTACTTCTCCTCCTTCTCAATCTTCTCCACGCTTCCCTTCT
CCTAATCATCAACAATTGTCTTCTCCAGAATCTTCTCCAAGCTTTAAAGCTTCTCCTTCACAA
TCCTCTCCAAATCTTGCAGCTCCCCTCTCTCCGCCGCCTATAGTTCTTAGCCCTTGTGCTGCTT
GCAAAATCCTCCGCCGCAGATGCGTCGAGAAATGTGTTTTAGCTCCATATTTTCCACCAACC
GAACCATACAAGTTCACCATTGCTCATAGAGTCTTCGGTGCTAGCAATATCATCAAGTTCTT
GCAGGAACTGCCAGAATCTCAACGAGCAGATGCAGTGAGCAGCATGGTCTATGAAGCAAGT
GCCAGAATCCGGGATCCTGTTTACGGCTGCGCCGGGGCTATTTGCCATCTCCAGAAACAAGT
CAGTGAGCTTCAGGCTCAGTTAGCCAAGGCACAGGCTGAGCTTGTCACCATGGAAAGCCAG
CAACGCAATTTAATAACTCTAATTTGCATGGAAATGGCACAATCTCAAGAACAAGTCTTGCA
GCAGCAGCAGCAGCAGCAGCAACAGTTCATGGATACTAGCTGTTTTTTGGATGACAATGGTA
TTGGATCAGCTTGGGAGCCTCTGTGGACATGATCAAGAGAAATTAAAGCAAGATTGTTGAA
ATTTTAACCTTTTAAGAGATTATTTACATAAAGCTAAACATACTTAATTATAAAGTTTCTGA
TCAATAATTAAAGTTATTTGCTGCGCGGTAGATGGGAGTGATTATTATGTGCTTTAATTTTCA
TTAGTCTTGTTGACAAAAAGGAATCTTTGAACCATCTGGAGAAGTCCTTTGTTAACGGTTCG
AGATTAATTATTAGTTTATCTTTATTTACATTTAGTGAAATTTTGTTTTTAACTAATTTTATAG
ACATAAATAACCCAACCAAGATGGGAATTCAGTGCTGA (SEQ ID NO:36)

a b

FIG. 20C, FIG. 20D and FIG. 20E
c
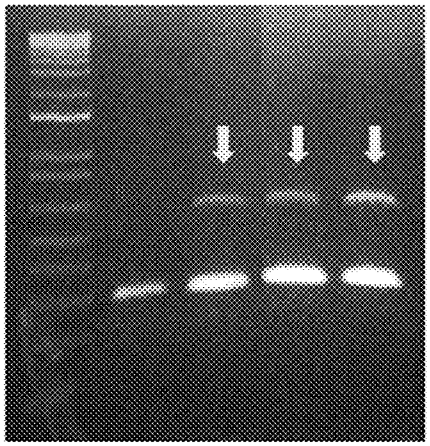
d
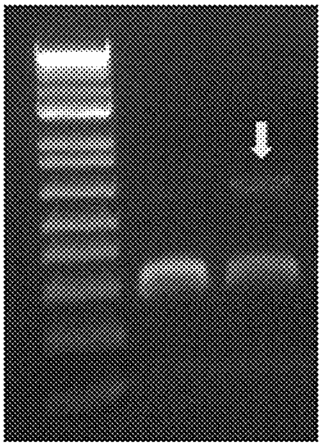
e
CsLOB1
WT: GCACAAGGGCTAAGAAC TATAGG
M1: GCACAAGGGCTAAGAACATATAGG +1A
M2: GCACAAGGGCTAAGA – – TATAGG -2
M3: GCAC – – – – – – – – – – – – – – – – – AGG -16
M4: GCACAAGGGCTAAGAA – TATAGG -1
M5: GCACAAGGGCTAA – – – – TATAGG -4

FIG. 22

WT

GCACAAGGGCTAAGAACTATAGGCGGCG

Type I insertion

GCACAAGGGCTAAGAACGTATAGGCGGCG +1 G (1)
GCACAAGGGCTAAGAACTTATAGGCGGCG +1 T (5)
GCACAAGGGCTAAGAACATATAGGCGGCG +1 A (2)

Type II deletion

GCACAAGGGCTAAGAAC – ATAGGCGGCG -1 T (14)
GCACAAGGGCTAAGAA – TATAGGCGGCG -1 C (7)
GCACAAGGGCTAAGAA – – ATAGGCGGCG -2 CT (3)
GCACAAGGGCTAAGA – – TATAGGCGGCG -2 AC (6)
GCACAAGGGCTAAGAACTA – – GGCGGCG -2 TA (2)
GCACAAGGGCTAAGA – – – ATAGGCGGCG -3 ACT (2)
GCACAAGGGCTAA – – – ATATAGGCGGCG -3 GAA, C A (1)
GCACAAGGGCTAAGAA – – – TAGGCGGCG -3 CTA (2)
GCACAAGGGCTAAG – – – TATAGGCGGCG -3 AAC (1)
GCACAAGGGCTAA – – – – TATAGGCGGCG -4 GACC (2)
GCACAAGGGCTA – – – – – TATAGGCGGCG -5 AGAAC (1)
GCACAAGGGCTAA – – – – – ATAGGCGGCG -5 GAACT (1)
GCACAAGGGCTA – – – – – – ATAGGCGGCG -6 AGAACT (1)
GCACAAGGGCT – – – – – – TATAGGCGGCG -6 AAGAAC (2)
GCACAAGGGC – – – – – – – – ATAGGCGGCG -8 TAAGAACT (1)
GCACA– – – – – – – – – – – – – – – – GGCGGCG -16 AGGGCTAAGAACTATA (1)

Type III change

GCACAAGGGCTAAGAACTGTAGGCGGCG A G (1)
GCACAAGGGCTAAGAACTACAGGCGGCG T C (1)

(a) LbCas12a-crRNA-cspds-mediated indels

| | |
|---|---|
| Wild type (X98) | TCTTTCCAGTTTTCAGGTAACTGAAGCTTGAGGATATCAACTGAAGG |
| -TTGAGGAT (x1) | TCTTTCCAGTTTTCAGGTAACTGAAGC--------ATCAACTGAAGG |
| -TTGAGGATA (x1) | TCTTTCCAGTTTTCAGGTAACTGAAGC---------TCAACTGAAGG |

(b) The chromatograms of LbCas12a-crRNA-cspds-mediated indels

FIG. 27

```
Type I     CGTCATTCAATTAAAATTAATGACGTCATCTAGTGGCTCGGTGACATACGCTTTAGATAC  60
           |||||||||||||||||||||||||||||||||||||| |||||||||||||||||||||
Type II    CGTCATTCAATTAAAATTAATGACGTCATCTAGTGGCTTGGTGACATACGCTTTAGATAC  60

Type I     AATTGTCATTCTTGCCTTTTCCTTTCTCTATATAAACCCCTTTTGCCTTCAACTTTGTTT  120
           ||||||||||||||||||||||||||||||||||||||||||||||||| ||||||||||
Type II    AATTGTCATTCTTGCCTTTTCCTTTCTCTATATAAACCCCTTTTGCCTT-AACTTTGTTT  119

Type I     CAACTAAAGCAGCTCCTCCTCATCCCTTACTGTCTTTGCTTTCTCACTAACTACTACAAC  180
           |||||||||||||||||||||||||||||||||||| |||||||||||||||||||||||
Type II    CAACTAAAGCAGCTCCTCCTCATCCCTTACTGTCTTCGCTTTCTCACTAACTACTACAAC  179

Type I     CCAACAGTTTTCTTCTCTCAAAAATGGAATGCAAACACAAAATTAATGTAGCAATCCCAA  240
           ||||||||||||||||||||||||||||||||| ||||||||||||||||||||||||||
Type II    CCAACAGTTTTCTTCTCTCAAAAATGGAATGCAGACACAAAATTAATGTAGCAATCCCAA  239

Type I     TCACTAATATGAAGAACACTCAATTCTCATCTCCATCTACTTTCTCTA  288
           |||||||||||||||| |||||||||||||||||||||||||||||||
Type II    TCACTAATATGAAGAATACTCAATTCTCATCTCCATCTACTTTCTCTA  287
```

FIG. 32A, FIG. 32B and FIG. 32C

A

```
                                                                                   +1
                    USE motif                              TATA Box                 .
AtU6-26  CAATCTTCAAAAGTCCCACATCGCTTAGATAAGAAAACGAAGCTGAGTTTATATACAGCTAGAGTCGAAGTAGTGATTG
CsU6-2   CCGTTGAAGAAAATCCCACATCGAAAGAAAAAACTGAATAAACATGGTCTATATATACAAGGACTCCCAGG-TTGGTTG
CsU6-7   AAATTGAACTAAATCCCACATCGTCTAGTTGCGCTTCGTTGAGAGTCTTAATATAATCATAACCAACCAGT-GCGATTG

AtU6-26  TCCCTTAGGGGACATCCGATAAAATTGGAACGATACAGAGAAGATTAGCATGGCCCCTGCGCAAGGATGACACGCATAA
CsU6-2   TCTCTTCGGAGACATCCGATAAAATTGGAACGATACAGAGAAGATTAGCATGGCCCCTGCGCAAGGATGACACGCACAA
CsU6-7   TCTCTTCGGAGACATCCGATAAAATTGGAACGATACAGAGAAGATTAGCATGGCCCCTGCGCAAGGATGACACGCACAA
                                              U6 snRNA

AtU6-26  ATCGAGAAATGGTCCAAATTTTTTTT
CsU6-2   ATCGAGAAATGGTCCAAATTTTTTTT
CsU6-7   ATCGAGAAATGGTCCAAATTTTTTTT
              U6 snRNA
```

B

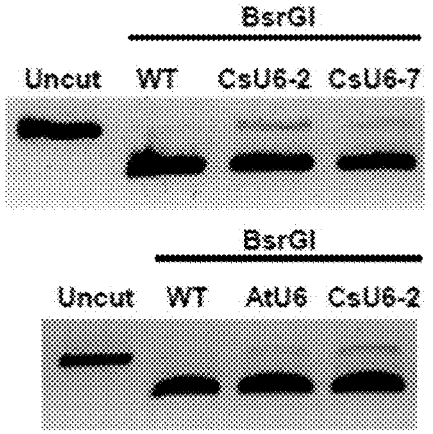

C

RNA GUIDE GENOME EDITING IN CITRUS USING CRISPR-RIBONUCLEOPROTEIN COMPLEXES

STATEMENT REGARDING FEDERALLY SPONSORED RESEARCH OR DEVELOPMENT

This invention was made with government support under 2017-67013-26527 and 2018-70016-27412 awarded by The United States Department of Agriculture, National Institutes of Food & Agriculture. The government has certain rights in the invention.

This invention was made in whole or in part with funds provided by The Citrus Research and Development Foundation, Inc

REFERENCE TO ELECTRONIC SEQUENCE LISTING

The application contains a Sequence Listing which has been submitted electronically in ASCII text format and is hereby incorporated by reference in its entirety. Said text copy, created on Sep. 20, 2020, is named "10457434US1.txt" and is 84,555 bytes in size. The sequence listing contained in this .txt file is part of the specification and is hereby incorporated by reference herein in its entirety.

BACKGROUND

1. Field

The invention relates to methods for gene editing in crops, including citrus crops. In particular, the invention relates to optimized CRISPR-Cas9 sequences for in vivo expression and gene editing in citrus, useful for reduction of bacterial disease in citrus crops.

2. Background

Citrus (Rutaceae) is a woody plant, and the genus includes a range of 5 high value crops, such as oranges, lemons, grapefruits, pomelos, and limes (El-Otmani et al., 2011). Citrus is one of the top three fruit crops grown in tropical and sub-tropical regions of the world. In recent years, citrus industry has been under immense pressure to develop new germplasm to overcome barriers to production resulting from diseases, insects and abiotic stresses. Especially, citrus canker and citrus Huanglongbing caused by Candidatus Liberibacter presents an unprecedented challenge to citrus production worldwide (Wang et al. 2017). Genetic improvement of citrus using conventional breeding is a lengthy and challenging process due to the complex reproductive biology of citrus including sexual incompatibility, highly heterozygous nature, nucellar seedlings, male or female sterility and the long juvenile phase (Omura and Shimada 2016).

Unfortunately, citrus plants are susceptible to the canker, a devastating disease caused by *Xanthomonas citri* ssp. *citri* (Xcc) bacteria. Xcc has currently burdened significant financial loss to the citrus industry. Xcc forms necrosis and lesions on leaves, and induces severe defoliation, twig dieback, blemished fruit and premature fruit drop (Lanza et al., 2018). Recent findings show that, the *Citrus sinensis* lateral organ boundary 1 (CsLOB1) a member of the lateral organ boundary domain functions as a disease susceptibility gene in citrus bacterial canker (Duan et al., 2018).

Genome editing is a powerful tool for increasing plant yields, improving food quality, enhancing crop disease resistance, and developing new cultivars to meet market needs (Begemann et al., 2017). At present, several strategies are being exploited to edit plant genomes, including CRISPR-Cas, meganucleases, TALENs and zinc finger nucleases (Martín-Pizarro and Posé, 2018). Among them, Clustered Regularly Interspaced Short Palindromic Repeat (CRISPR)-mediated genome editing is the most attractive, owing to its comparatively casier and less expensive implementation (Islam, 2018). To date, CRISPR-SpCas9, which is derived from *Streptococcus pyogenes*, has been widely used to modify the genomes of a variety of organisms. However, one major drawback associated with the CRISPR-SpCas9 system is its off-target effects (Fu et al., 2013), which has raised concerns and limited its adoption. Recently, CRISPR-Cas12a from *Prevotella* and *Francisella*, a class II/type V CRISPR nuclease, has been employed as an alternative system for genome editing, and notably, it is reported to have fewer off-targets in comparison with Cas9 (Kim et al., 2016; Kleinstiver et al., 2016).

CRISPR-Cas 12a has several unique features distinct from those of CRISP-SpCas9 (Zetsche et al., 2015; Zetsche et al., 2017), as follows: 1) The canonical protospacer adjacent motif (PAM) of CRISPR-Cas 12a is TTTV (V=A, C, and G), which is located at the 5' end of the target site, whereas the CRISPR-SpCas9 PAM is NGG, which is located at the 3' end of the target site; 2) CRISPR-Cas 12a requires a 43 nt crRNA, and CRISPR-SpCas9 requires ~ 100 nt gRNA; 3) CRISPR-Cas 12a generates 5' staggered ends distal from the PAM, while CRISPR-SpCas9 generates blunt ends 3 bp upstream of the PAM; 4) Cas12a has both DNase activity and RNase activity, which is useful for multiplexed genome editing (Zetsche et al., 2017). These complementary properties make the CRISPR-Cas 12a an important genome-editing tool. CRISPR-Cas 12a was first successfully employed to edit the mammalian genome (Zetsche et al., 2015). Since then, CRISPR-Cas 12a has been successfully used to modify other organisms, such as plants, *Drosophila*, and zebrafish (Endo et al., 2016; Moreno-Mateos et al., 2017; Port and Bullock, 2016). To date, Acidaminococcus sp. BV3L6 Cas 12a (AsCas12a), *Francisella novicida* Cas 12a (FnCas12a) and Lachnospiraceae bacterium ND2006 Cas12a (LbCas 12a) have been used to edit the genomes of crop and model plants, including green alga, rice, soybeans and tobacco (Begemann et al., 2017; Endo et al., 2016; Ferenczi et al., 2017; Hu et al., 2017; Kim et al., 2017; Tang et al., 2017; Wang et al., 2017; Xu et al., 2016; Yin et al., 2017), but not citrus. In addition, the performances of the three Cas 12a homologs are different. LbCas 12a reportedly performs better than AsCas 12a in rice (Tang et al., 2017).

A potential long term solution to citrus Huanglongbing (HLB) or other diseases of citrus is genome modification/gene editing of citrus. To overcome the susceptibility of citrus to Xcc, genome editing as a precise method for modification of genome sequences can play vital roles. In the past decades it was discovered by generating a double-strand breaks (DSBs) at the target sequence, the DNA repaired by the error prone non-homologous end-joining and homology-directed repair mechanisms often cause mismatches at the target site (Adli, 2018; Wu et al., 2018). This finding offered a valuable venue to generate knockout and loss-of-function mutants, thus a number of technologies, such as TAL effectors nucleases (TALENs), zinc finger nucleases (ZFNs), and clustered regularly interspaced short palindromic repeats (CRISPR) capable of generating DSBs were introduced by the scientists (Liu et al., 2018; Shankar et al., 2018).

CRISPR has rapidly turned out to be an important technology for genome editing applications due to its simplicity, effectiveness and flexibility. In most of the studies, the CRISPR constructs and the selectable markers have been successfully employed in plant genome editing using either *Agrobacterium tumefaciens* infection or particle bombardment (Anand and Jones, 2018). In both scenarios, the delivered DNA mostly integrates into the genome causing a range of side effects (i.e. off-site cutting, gene inactivation, and mosaicism), thus these approaches could be incompatible in plants if safety approval is necessary (Chen et al., 2018; Kleter et al., 2019). To cope with these undesired effects CRISPR-Cas Ribonucleoprotein complexes (CRISPR-Cas 30 RNPs) is considered as a potent approach.

Citrus genome modification has been conducted via transgenically express Cas9/sgRNA in planta. Genetically modified plants generated via transgenic expression of Cas9/sgRNA contain foreign DNA sequences, requiring rigorous deregulation process before commercialization. Additionally, constant expression of Cas9/sgRNA in transgenic plants may lead to accumulation of off-target effects. Cas9/sgRNA in genetically edited crop plants can be removed by backcrossing them to wild type plants. However, the approach for tree species is laborious and time-consuming, and impractical particularly considering the long juvenile period for citrus. In addition, backcrossing of citrus will lead to loss of traits of the parental cultivars. Transient expression of either Cas9-sgRNA ribonucleoproteins, Cas9/sgRNA DNA or RNA has been used successfully to generate non-transgenic genome-modified plants including *Arabidopsis thaliana*, tobacco, lettuce, rice, wheat, and maize (Woo et al., 2015; Svitashev et al., 2016; Zhang et al., 2016; Liang et al., 2017). However, non-transgenic genome modified citrus has not been reported previously, thus limiting the application of genome editing technology to solve many urgent issues of citrus industry.

CRISPR-Cas RNPs can be produced fast and delivered directly to the cells as completely functional complexes. Indeed, they are instantaneously active after transfection, and rapidly breakdown inside the cell. This rapid breakdown kinetics permits CRISPR-Cas RNPs to modify the target genes with lower off-target effects (Andersson et al., 2018; Liang et al., 2017). However a successful editing using CRISPR-Cas RNPs always rely on an efficient CRISPR RNA (crRNA) and a solid delivery method which can avoid the influence of cell wall as a major barrier. In this regard, plant protoplasts generated by the removal of cell wall using enzymatic digestion provides a promising strategy to improve the efficiency of CRISPR-Cas RNP systems, since the lack of the cell wall makes it possible to employ transfection or electroporation for RNPs and/or nucleic acid deliveries. Moreover, the protoplast can be used to analyze target site mutagenesis efficiency and can be regenerated into plant (C. Lin et al., 2018; Park et al., 2019).

CRISPR-Cas RNPs can be produced fast and delivered directly to the cells as completely functional complexes. Indeed, they are instantaneously active after transfection, and rapidly breakdown inside the cell. This rapid breakdown kinetics permits CRISPR-Cas RNPs to modify the target genes with lower off-target effects (Andersson et al., 2018; Liang et al., 2017). However a successful editing using CRISPR-Cas RNPs always rely on an efficient CRISPR RNA (crRNA) and a solid delivery method which can avoid the influence of cell wall as a major barrier. In this regard, plant protoplasts generated by the removal of cell wall using enzymatic digestion provides a promising strategy to improve the efficiency of CRISPR-Cas RNP systems, since the lack of the cell wall makes it possible to employ transfection or electroporation for RNPs and/or nucleic acid deliveries. Moreover, the protoplast can be used to analyze target site mutagenesis efficiency and can be regenerated into plant (C. Lin et al., 2018; Park et al., 2019).

Among the CRISPR systems, Cpf1 as the effector of the CRISPR locus is identified as a class two CRISPR which recognizes the target DNA region via protospacer adjacent motif (PAM) scanning (PAM in Cpf1 is highly specific to the 5'-TTTV-3') (Zetsche et al., 2015). CRISPR-Cpf1 systems create 5' staggered ends, which potentially can facilitate precise gene replacement using non-homologous end joining (NHEJ), moreover it cleaves DNA at sites distal to the PAM. Such distal cleavage allows previously mutated sequences to be severed repeatedly, promoting homology-dependent repair (HDR) (Safari et al., 2019; Tang et al., 2017). To date three homologs of Cpf1, including *Francisella novicida* (FnCpf1), Acidaminococcus spp. (AsCpf1), and Lachnospiraceae bacterium (LbCpf1) have been applied to genome engineering of different organisms, however, literatures show that, the editing efficiency of CRISPR-Cas systems in woody plants is quite low (Fan et al., 2015; Kim et al., 2016).

CRISPR-Cas RNPs can be produced fast and delivered directly to the cells as completely functional complexes. Indeed, they are instantaneously active after transfection, and rapidly breakdown inside the cell. This rapid breakdown kinetics permits CRISPR-Cas RNPs to modify the target genes with lower off-target effects (Andersson et al., 2018; Liang et al., 2017). However a successful editing using CRISPR-Cas RNPs always rely on an efficient CRISPR RNA (crRNA) and a solid delivery method which can avoid the influence of cell wall as a major barrier. In this regard, plant protoplasts generated by the removal of cell wall using enzymatic digestion provides a promising strategy to improve the efficiency of CRISPR-Cas RNP systems, since the lack of the cell wall makes it possible to employ transfection or electroporation for RNPs and/or nucleic acid deliveries. Moreover, the protoplast can be used to analyze target site mutagenesis efficiency and can be regenerated into plant (C. Lin et al., 2018; Park et al., 2019).

Duncan grapefruit is a hybrid between the pummelo (*C. maxima*) and the sweet orange (*C. sinensis*) (Velasco and Licciardello, 2014). Type I CsLOBP originates from sweet orange (Xu et al., 2013), and Type II CsLOBP comes from the pummelo (Wu et al., 2014). Therefore, one of the challenges of SpCas9-mediated EBEPthA4-CsLOBP modification is the fact that two types of CsLOBPs in Duncan grapefruits make a single sgRNA targeting infeasible for modifying two alleles. An alternative genome editing system that can be employed to edit two alleles of EBEPthA4-CsLOBPs using a single sgRNA/crRNA would be helpful. CRISPR-Cas 12a recognizes a thymidine-rich PAM site, TTTV, which commonly occurs in the promoter regions and the 5' and 3' UTRs (Moreno-Mateos et al., 2017; Zetsche et al., 2015).

There remains a need in the art for progress in making non-transgenic genome editing of citrus via transient expression of Cas9-sgRNA DNA into protoplasts by PEG-mediated transfection.

SUMMARY

In this study, LbCas 12a was employed to edit the Duncan grapefruit gene CsPDS via Xcc-facilitated agroinfiltration.

The results verified that LbCas 12a could be harnessed to edit the citrus genome. Subsequently, using a single crRNA, EBEPthA4-CsLOBP was successfully modified by LbCas 12a in transgenic Duncan plants. Notably, one transgenic Duncan line could alleviate XccΔpthA4: dCsLOB1.4-induced canker symptoms.

The invention relates to efficient CRISPR-Cas9 sequences for in vivo expression and gene editing in citrus, and methods for achieving optimized expression of certain genes in citrus crops, useful to combat bacterial disease in plants. Specifically, the invention relates to In an embodiment, provided is a CsCas9 citrus codon-optimized Cas9 gene of SEQ ID NO: 1. Another embodiment relates to a Cas9 gene linked to a CsU6 promoter. In a specific embodiment, provided is a gene construct comprising CsCas9 (SEQ ID NO:1) and CsU6-1 (SEQ ID NO: 5 or SEQ ID NO:9), which are operably linked.

According to another embodiment, provided is a method of altering expression of at least one gene product comprising introducing into a citrus plant cell an engineered, non-naturally occurring gene editing system comprising one or more vectors, said citrus plant cell containing and expressing a DNA molecule having a target sequence and encoding the gene. The gene editing system of the method includes: (a) a first regulatory element operable in a plant cell operably linked to at least one nucleotide sequence encoding a CRISPR-Cas system guide RNA (gRNA) that hybridizes with the target sequence, and (b) a second regulatory element operable in a plant cell operably linked to a nucleotide sequence encoding a Type-II CRISPR-associated nuclease, wherein components (a) and (b) are located on same or different vectors of the system, whereby the guide RNA targets the target sequence and the CRISPR-associated nuclease cleaves the DNA molecule, whereby expression of the at least one gene product is altered; and, wherein the CRISPR-associated nucleas and the guide RNA do not naturally occur together. In a specific embodiment, the sequence encoding a gRNA and said sequence encoding a Type-II CRISPR-associated nuclease are operably linked to a terminator sequence functional in a plant cell. In one example, the type II CRISPR-associated nuclease is Cas9, which may be codon-optimized for citrus. A specific example of a codon-optimized Cas9 is SEQ ID NO: 1, or a nucleotide sequence having at least 90%, 95%, 97% or 98% identity therewith. In an alternate embodiment, the type II CRISPR-associated nuclease is cfp1. In an example the first regulatory element comprises a DNA-dependent RNA polymerase III (Pol III) promoter sequence. In a specific example, the Pol III promoter sequence comprises a citrus U6 promoter nucleotide sequence. In even more specific examples, the citrus U6 promoter nucleotide sequence is SEQ ID NO:4, SEQ ID NO: 5, SEQ ID NO:6, SEQ ID NO:7, SEQ ID NO:8, SEQ ID NO:9, SEQ ID NO: 149 or SEQ ID NO: 150, or a nucleotide sequence having at least 90%, 95%, 97% or 98% identity therewith.

A further embodiment disclosed herein pertains to a method of altering expression of at least one gene product comprising introducing into a citrus plant cell a CRISPR-Cas-ribonucleoprotein complex (CRISPR-Cas-RNP). The citrus plant cell contains and expresses a DNA molecule having a target sequence and encoding the gene, wherein the CRISPR-Cas-RNP comprises a CRISPR-Cas system guide RNA (gRNA) that hybridizes with the target sequence, and a class-II CRISPR-associated nuclease. The class II CRISPR-associated nuclease may comprise cfp1. Examples of the cfp1 include at least one selected from the group consisting of FnCpf1 from *Francisella novicida*, AsCpf1 from Acidaminococcus sp, and LbCpf1 from Lachnospiraceae bacterium. According to another example of this method, the class II CRISPR-associated nuclease comprises Cas9. In a specific example, the gene comprises CsLOB1. In an alternate embodiment, the citrus plant cell is an embryogenic cell.

Also disclosed are plant cells and plants or seeds thereof harboring such plant cells that are edited according to the embodiments described herein.

The method of gene editing described herein may serve to enhance or engender the plant with one or more of the following traits: herbicide tolerance, drought tolerance, male sterility, insect resistance, abiotic stress tolerance, modified fatty acid metabolism, modified carbohydrate metabolism, modified seed yield, modified oil percent, modified protein percent, and resistance to bacterial disease, fungal disease or viral disease.

Also provided are compositions comprising the nucleic acids described herein and a carrier. These and other aspects are described in further detail below.

BRIEF DESCRIPTION OF THE DRAWINGS

FIG. 1 provide the sequence of SpCas9 optimized sequence: CsCas9 (SEQ ID NO:1).

FIG. 2 provides the sequence of Cas 12a optimized sequence (LbCpf1) (SEQ ID NO:2).

FIG. 3A shows sequences of the identified U6 promoters AtU6-1 SEQ ID NO: 3), CsU6-1 (SEQ ID NO. 5), CsU6-3 (SEQ ID NO: 4), CsU6-2 (SEQ ID NO: 6), CsU6-7 (SEQ ID NO: 7) and CsU6-8 (SEQ ID NO:8). FIG. 3B provides the sequence of the CsU6-1 promoter (496 bp); SEQ ID NO:9. The promoter is shown with the USE and TATA promoter elements in bold, the U6 snRNA (noncoding) genes in underline, and the terminator sequence in italics.

FIG. 4 provides the sequence of the CsU6-2 promoter from chromosome 2 of Valencia (SEQ ID NO:10).

FIG. 5 provides the sequence of the CsU6-7 promoter from chromosome 7 of Valencia (SEQ ID NO:11).

FIG. 13 provides the sequence of pMAL-C5X/AsCpf1 vector (SEQ ID NO:31).

FIG. 14 provide the sequence of pMAL-C5X/LbCpf1 vector (SEQ ID NO:32).

FIG. 15 provide the sequence of pMAL-C5X/FnCpf1 vector (SEQ ID NO:33).

FIG. 16 provides the sequence of Citrus canker susceptibility gene CsLOB1 sequence (SEQ ID NO:34).

FIG. 20C and FIG. 20D show results of the first and second digestions, respectively. FIG. 20E and FIG. 20F show the part mutant sequencing and the chromatogram, respectively. Sequences related to Wt, M1+1A, M2-2, M3-16, M4-1 and M5-4 relate SEQ ID NOs 44, 45, 46, 47, 48, and 49, respectively. The red letters indicate PAM, the letters with underline indicate the sgRNA sequence, the blue letters indicate inserted bases, the '-' symbols indicate deleted bases and the bases with yellow highlighting are PAM in FIG. 20F.

FIG. 22 Summarization of the mutations resulting from CRISPR/Cas9 mediated genome editing. SEQ ID NO: 50 (WT), SEQ ID NO: 51 (Type I insertion, +1 G (1)), SEQ ID NO: 52 (Type I insertion, +1T (5)), SEQ ID NO: 53 (Type I insertion, +1 A (2)), SEQ ID NO:54 (Type II deletion, −1 T (14)), SEQ ID NO:55 (Type II deletion, −1 C (7)), SEQ ID NO:56 (Type II deletion, −2 CT (3)); SEQ ID NO:57 (Type II deletion, −2 AC (6)), SEQ ID NO:58 (Type II deletion, −2 TA (2)), SEQ ID NO:59 (Type II deletion, −3 ACT (2)), SEQ ID NO:60 (Type II deletion, −3 GAA, CA (1)), SEQ ID NO:61 (Type II deletion, −3 CTA (2)), SEQ ID NO:62 (Type II deletion, −3 AAC (1)), SEQ ID NO:63 (Type II deletion, −4 GACC (2)), SEQ ID NO:64 (Type II deletion, −5 AGAAC (1)), SEQ ID NO:65 (Type II deletion, −5 GAACT (1)), SEQ ID NO: 66 (Type II deletion, −6 AGAACT (1)), SEQ ID NO:67 (Type II deletion, −6 AAGAAC (2)), SEQ ID NO:68 (Type II deletion, −8 TAAGAACT (1)), SEQ ID NO:69 (Type II deletion, −16 AGGGCTAAGAACTATA (1)), SEQ ID NO:70 (Type III change, A G (1)), SEQ ID NO:71 (Type III change, T C (1))

FIG. 27 is a sequence alignment of two alleles of CsLOB1, Type I and Type II (SEQ ID NOs: 77 and 78). The crRNA-targeting site is indicated in blue. PAM is indicated in red. The translation start site is indicated in green. The difference in the two alleles is shown in purple. The EBEPthA4-CsLOBP is highlighted by a red rectangle, which is overlapped with artificial dTALE dCsLOB1.1. The dCsLOB1.2-binding site is indicated with a blue rectangle, the dCsLOB1.3-binding site is noted by an orange rectangle, and the artificial dTALE dCsLOB1.4 binding site is highlighted by a green rectangle.

FIG. 34C shows CRISPR-LbCas 12a-mediated indel chromatograms in CsLOBP.

FIG. 31A shows the artificial dTALE dCsLOB1.4, developed to activate Type II CsLOBP specifically. SEQ ID NO:94 is shown (Type II CsLOBP). RVDs 519 of the artificial dTALE dCsLOB1.4 bind to AAACCCCTTTTGCCTTAACTT (SEQ ID NO:95), 2 bp downstream 520 of EBEpthA4-TII CsLOBP, which is underlined. MTII CsLOBP, mutant Type II CsLOBP; GUSin, the intron-containing β-522 glucuronidase; and HptII, the coding sequence of hygromycin phosphotransferase II. FIG. 31B is a schematic diagram of p1380-MTII 521 CsLOBP-GUSin. MTII CsLOBP, mutant Type II CsLOBP; GUSin, the intron-containing β-522 glucuronidase; and HptII, the coding sequence of hygromycin phosphotransferase II. FIG. 31C shows data from a GUS assay. FIG. 31D shows leaves from the indicated plants.

FIG. 32 shows an alignment of selected CsU6 promoters with the *Arabidopsis* U6-26 promoter (FIG. 32A). AtU6-26, CsU6-2, CsU6-7, as shown, relate to SEQ ID NO: 148, SEQ ID NO: 149 and SEQ ID NO:150, respectively. FIG. 32B shows, a mutation analysis as measured by the loss of the BsrGI restriction enzyme site due to targeted mutagenesis at the selected BsrGI site. The BsrGI-resistant band shows edited alleles. FIG. 32C shows a comparison of editing efficiency between CsU6-2 and AtU6-26.

DETAILED DESCRIPTION

Figure 6A:
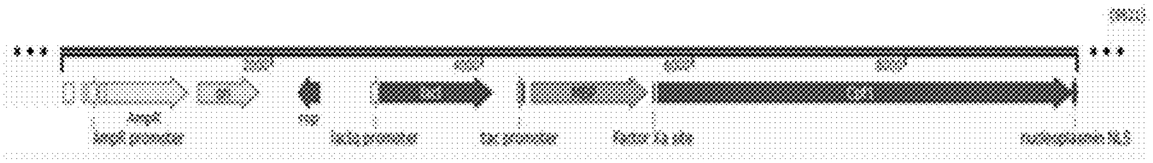
FIG. 6A shows the relative location of three types of Cpf1 (AsCpf1, LbCpf1, and FnCpf1), as cloned inside the pMAL-c5X vector containing a tac promoter with malE translation initiation signals.

To overcome above noted limitations with using CRISPR in citrus, an approach to deliver Cpf1-RNPs into the plant cells using a protoplast based system to target the susceptibility gene CsLOB1 is herein reported. Based on this system, the CsLOB1 gene was disrupted using Cpf1-RNPs. The data provided herein confirms CRISPR-Cpf1 system as a potent tool for genome modifications in Citrus.

In addition, also disclosed herein are improved methods for citrus genome editing using a CRISPR-Cas9 approach. Genome editing in citrus has been reported (Jia H. & Wang, N (2014) PLOS one vol9, issue 4, e93806), however, low genome editing efficiency and biallelic homozygous mutation is still an existing challenge (Jia et al. Plant Biotechnol J. 2017 July; 15 (7): 817-823). Certain promoters have been identified that result in high genome editing efficacy in citrus.

To overcome above noted limitations with using CRISPR in citrus, an approach to deliver Cpf1-RNPs into the plant cells using a protoplast based system to target the susceptibility gene CsLOB1 is herein reported. Based on this system, the CsLOB1 gene was disrupted using Cpf1-RNPs. The data provided herein confirms CRISPR-Cpf1 system as a potent tool for genome modifications in Citrus and other crops.

In addition, also disclosed herein are improved methods for citrus genome editing using a CRISPR-Cas9 approach. Genome editing in citrus has been reported (Jia H. & Wang, N (2014) PLOS one vol. 9, issue 4, e93806), however, low genome editing efficiency and biallelic homozygous mutation is still an existing challenge (Jia et al. Plant Biotechnol J. 2017 July; 15 (7): 817-823). Certain promoters have been identified that result in high genome editing efficacy in citrus. Some sequences of interest are provided in FIG. 1 (SpCas9 optimized sequence, CsCas9); FIG. 2 (Cas12a optimized sequence (LbCpf1); FIG. 3A and FIG. 3B (showing the identified citrus U6 promoter (CsU6-1)); FIGS. 4-5 (CsU6-2 and CsU6-7 promoters).

1. Definitions

Unless defined otherwise, all technical and scientific terms used herein have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, e.g., Sambrook et al. MOLECULAR CLONING: A LABORATORY MANUAL, 2d ed., Cold Spring Harbor Laboratory Press, 1989; 3d ed., 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

The term "about," as used herein, means plus or minus 20 percent of the recited value, so that, for example, "about 0.125" means 0.125±0.025, and "about 1.0" means 1.0±0.2.

The term "citrus" refers to any known citrus variety. Citrus varieties contemplated by this disclosure include, but are not limited to, cultivated citrus types such as sweet orange, bitter orange, blood orange, grapefruit, pomelo, citron, Clementine, naval orange, lemon, lime, mandarin, tangerine, tangelo, or the like.

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

The term "sequence" refers to a nucleotide sequence of any length, which can be DNA or RNA; can be linear, circular or branched and can be either single-stranded or double stranded.

The term "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination there between, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

2. Embodiments of the Invention

Plant Protoplast transformation

Plant protoplast transformation has been widely adopted in several crop species for practical applications, since they are totipotent and have the ability to go from single cell to dedifferentiation, proliferation and regeneration into different organs. Currently, CRISPR/Cas systems have been successfully test and adopted mainly in vegetative plants (i.e. rice, *Arabidopsis*, maize, wheat, lettuce, and tobacco), nevertheless there is no reports on using CRISPR-Cas RNP systems for editing woody plants, and citrus in particular.

To establish a platform for editing the citrus cells, protoplast from suspension culture of embryogenic calli of *C. sinensis* were isolated. Several factors including the enzyme concentration, enzyme incubation time, osmotic condition and the age of suspension culture influence the yield, viability and transfection efficiency. As disclosed herein, these various factors were studied to obtain a high quality of protoplast for better transfection efficiency. Evidence points to this fact that the CRISPR/Cas systems compared to the other editing tools like TALENs and ZFNs are easy to construct and inexpensive, nevertheless, the applications of CRISPR/Cas systems are narrowed because of their off-target effects, and integration of unwanted foreign DNA into the genome, which can raise GMO regulation concerns. In line to overcome these limitations, data is presented herein demonstrating delivery of CRISPR/Cpf1-RNPs rather than delivery of the plasmid into the protoplast cells to avoid unwanted integration of plasmid DNA into the citrus genome.

Successful expression and isolation of three homologs of Cpf1 (FnCpf1, AsCpf1, LbCpf1) was conducted to identify the most efficient one for targeting the CsLOB1gene in *C. sinensis*. Indeed, five crRNAs were designed and synthesized for each homologs of Cpf1. By employing in vitro cleavage assay, active crRNA was identified for targeting CsLOB1gene for each Cpf1 homologs, and it was determined whether the structural characteristics like thermodynamic properties of crRNA plays central roles in target cleavage. It was discovered that the most efficient crRNAs (23nt) had the higher GC-content and the lowest minimum free energy, supporting the in vivo stability of identified crRNAs. Significantly, by increasing the free energy, the gene editing activity decreases. It has been observed that RNA with higher GC-content have more stable secondary structures than RNA strands with lower GC-content. Indeed, the speed at which polymerase travels alongside of an associated RNA strand is correlated to the secondary structure that the polymerase attaches, and that polymerase works at a slower rate when face to more secondary structures, these parameters should be considered during in vitro synthesizing of crRNA for a good quality and effective RNP complex.

In addition, a set of PEG concentration (w/v) under different incubation times were used to identify the best concentration and the incubation time for an optimum transfection. The delivery of Cpf1 proteins (60 μg) mixed with their corresponding crRNA (60 μg) labeled with sulfo-cyanine 5 nhs ester showed the highest transfection at the 40% (w/v) with 20 minute incubation time. PEG-transfection is known to be concentration dependent and higher concentrations have reverse influences as PEG became poisonous for the cells. It was found that among the Cpf1-RNPs homologous sequences of the FnCpf1 (using crRNA with the spacer sequence of 5'-CAGCAGCAGCAGCAGCAGCAGCAAC-3') (SEQ ID NO:96) and AsCpf1 RNPs (using crRNA with the spacer sequence of (5'-CGGCTGCGCCGGGGCTATTTGCCA-3') (SEQ ID NO:97) targeting CsLOB1gene could cause mutations.

CRISPR-Cas system is a practical and powerful tool for gene editing, however this system is less efficient in woody plants, and indeed CRISPR-Cas systems could be not suitable for the plants if safety approval is necessary. To cope with these concerns, it is demonstrated herein that the usage of CRISPR/Cpf1-RNPs serves as an efficient and non-transgenic approach to generate foreign DNA-free genome edited citrus. Based on the results provided herein, a protoplast based system transformed with FnCpf1-RNPs, AsCpf1 at the concentration of 60 μg of Cpf1 and 60 μg of crRNA (1:1) for $2\times10^5$ cells/ml density using a PEG method is recommended. Indeed, since the selection of appropriate Cpf1-crRNAs is an essential step toward engineering the CRISPR-Cpf1 system the following criteria for crRNA design should be considered (1) GC content greater than 60% in crRNAs spacers (2) no thymidine in the first position of the crRNA spacer sequence (2) avoiding poly-T sequences in the spacer (3) designing at least on direct repeat in the crRNA compatible with the CPfl protein homologs (in the study presented herein, it was confirmed that the AsCpf1, LbCpf1 direct repeats are active with FnCpf1). FnCpf1-RNP is now demonstrated to be a powerful tool for non-transgenic transformation of Citrus in parallel to classical breeding. Since the the Cpf1-RNP system will be used as an additional tool to edit the plant genome without introducing foreign DNA, the mutant plants edited using CRISPR/Cpf1-RNPs do not have integrated transgenes, their application in practical breeding and commercialization of the citrus should be more public acceptable, and thus it accelerates the precision crop improvement.

Citrus Genome Editing

Huanglongbing (HLB), also known as citrus greening, is the most devastating citrus disease worldwide. HLB is caused by phloem-limited non-cultruable bacteria (Candidatus Liberibacter *asiaticus*), which is transmitted by the insect-vector psyllid. HLB disease management and complete cure is a great challenge because of limitation in the study of disease dynamics of HLB and its transmission. HLB has great economic impact due to severe yield reduction followed by tree decline, and absence of resistance varieties. Improvement of citrus varieties by conventional breeding method is inefficient because citrus has a long juvenile period, sexual incompatibility, heterozygosity and polyembryony.

CRISPR-Cas9 is a potential tool to engineer citrus varieties by targeting HLB susceptible genes in citrus genome.

CRISPR has the advantage of targetting many genes that may greatly shorten the time needed to modify the citrus genomes to achieve the desirable results. Genome editing in citrus has been reported (Jia H. & Wang, N (2014) PLOS one vol9, issue 4, e93806), however, low genome editing efficiency and biallelic homozygous mutation is still an existing challenge (Jia et al. Plant Biotechnol J. 2017 July; 15 (7): 817-823). Previous studies have shown that promoters for Cas9 and sgRNA expression are important for efficient genome editing by CRISPR/Cas9 in plants. As disclosed herein, the citrus U6 promoters have been identified and tested for their efficacy in citrus genome editing as compared with the heterogenous source of *Arabidopsis* U6 promoter. The data shows that endogenous U6 promoter has higher genome editing efficacy in citrus.

General Discussion

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively.

Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14 (6): 6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six).

From the data generated, the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions-50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: ncbi.nlm.gov/cgi-bin/BLAST.

With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. Sec, e.g., Sambrook et al., supra; Nucleic Acid Hybridization: A Practical Approach, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., Molecular Cloning: A Laboratory Manual, Second Edition, (1989) Cold Spring Harbor, N.Y.).

All of the mutations generated by CRISPR-LbCas 12a in citrus in this study were deletions. In the LbCas 12a-mediated mutations of CsPDS and Type I CsLOBP, the indels were relatively long deletions, which are consistent with those in other plants (Begemann et al., 2017; Endo et al., 2016; Ferenczi et al., 2017; Hu et al., 2017; Kim et al., 2017; Tang et al., 2017; Wang et al., 2017; Xu 201 et al., 2016; Yin et al., 2017). The longer deletions could be attributable to 5' overhangs resulting from the stagger cutting of Cas 12a at sites distal to the PAM (Zetsche et al., 2015; Tang et al. 2017). Interestingly, all of the Type II CsLOBP mutations generated by LbCas 12a were 1 bp deletions among the colonies that were sequenced, and they are similar to the short indels (1-2 bp) induced by SpCas9 in citrus (Jia et al., 2016; Jia et al., 2017b; Peng et al., 2017; Zhang et al., 2017).

The mutation frequencies of #D35s1, #D35s4, and #D35s7 were 15%, 55% and 15%, respectively. The average mutant rate in #D35s1, #D35s4, and #D35s7 was 28.3%, which is similar to that of FnCas 12a-transformed tobacco (28.2%), but lower than that of FnCas12a-transformed rice (47.2%) (Endo et al., 2016). The different processes which were employed to develop transgenic tobacco and rice might be the cause for the different mutation frequencies (Endo et al., 2016). Additionally, a low mutation efficacy of 2% was observed for citrus when LbCas 12a transient expression was used. The mutation frequencies induced by the transient expression of AsCas 12a ranged from 0.6 to 10%, whereas the mutation frequencies mediated by LbCas 12a ranged from 15 to 25% in rice (Tang et al. 2017). A nearly 100% biallelic mutation efficiency was observed for LbCas12a-mediated genome editing in rice, whereas the biallelic mutation efficiency from LbCas 12a was only 5% in citrus. The lower mutation efficacy from LbCas 12a in citrus might result from the different crRNA designs that were used (Tang et al. 2017).

CRISPR-LbCas 12a ribonucleoproteins (RNPs) have already been used to edit the genomes to generate transgene-free mutations in soybeans and tobacco (Kim et al., 2017). The delivery of CRISPR-LbCas 12a RNPs bypasses the need to develop a system for removing foreign DNAs from genetically modified plants. The testing disclosed in the present applicationwhether Cas 12a RNPs could be harnessed to generate foreign DNA-free genome-modified citrus. In summary, CRISPR-LbCas 12a was used to edit a citrus genome via Xcc-facilitated agroinfiltration and stable transformation. Because of its unique targeted mutagenesis features, CRISPR-LbCas 12a can enhance the scope and specificity of citrus genome editing, as supported by this study. To enhance the scope of citrus genome editing, single crRNA targeting was used successfully to modify two alleles of EBEPthA4-CsLOBPs. Therefore, CRISPR-LbCas 12a now should be regarded as a powerful complementary tool for citrus genome engineering, in addition to CRISPR-SpCas9 and CRISPR-SaCas9 (Jia and Wang, 2014a; Jia et al., 2016; Jia et al., 2017a; Jia et al., 2017b; Peng et al., 249 2017; Zhang et al., 2017).

4. EXAMPLES

This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Although any methods and materials similar or equivalent to those described herein can be used in the practice or testing of embodiments of the present invention, the preferred methods, devices, and materials are now described. All publications mentioned herein, are incorporated by reference in their entirety; nothing herein is to be construed as an admission that the invention is not entitled to antedate such disclosure by virtue of prior invention.

PCT Pub. No. WO2019/090261 is incorporated herein by reference for teachings of other disease susceptible genes that can be targeted.

Example 1: General Methods

A. Non-transgenic Plant Cell Transfection of RNPs

The methods for non-transgenic plant cell transfection do not depend on a particular method for introducing RNP into the cell. The RNP is provided to the cells and taken up into the cell interior. Introduction of the RNP may be accomplished by any method known, which permits the successful introduction of the RNP into the cells. Methods include but are not limited to such methods as transfection, microinjection, electroporation, nucleofection and lipofection. Preferably, a PEG transfection is used, as further detailed herein below.

B. Transformation Methods and Plant Regeneration

Gene transfer and transformation methods for introducing engineered gRNA-Cas9 constructs into plant cells include, but are not limited to, protoplast transformation through calcium-, polyethylene glycol (PEG)- or electroporation-mediated uptake of naked DNA (see Paszkowski et al. (1984) EMBO J3: 2717-2722, Potrykus et al. (1985) Molec. Gen. Genet. 199:169-177; Fromm et al. (1985) Proc. Nat. Acad. Sci. USA 82:5824-5828; and Shimamoto (1989) Nature 338:274-276) and electroporation of plant tissues (D'Halluin et al. (1992) Plant Cell 4:1495-1505). Additional methods for plant cell transformation include microinjection, silicon carbide mediated DNA uptake (Kaeppler et al. (1990) Plant Cell Reporter 9:415-418), and microprojectile bombardment (see Klein et al. (1988) Proc. Nat. Acad. Sci. USA 85:4305-4309; and Gordon-Kamm et al. (1990) Plant Cell 2:603-618). According to certain embodiments, gene constructs carrying gRNA-Cas9 nuclease can be introduced into plant cells by various methods, which include but are not limited to PEG- or electroporation-mediated protoplast transformation, tissue culture or plant tissue transformation by biolistic bombardment, or the *Agrobacterium*-mediated transient and stable transformation.

Target gene sequences for genome editing and genetic modification can be selected using methods known in the art, and as described elsewhere in this application. In a preferred embodiment, target sequences are identified that include or are proximal to protospacer adjacent motif (PAM). Once identified, the specific sequence can be targeted by synthesizing a pair of target-specific DNA oligonucleotides with appropriate cloning linkers, and phosphorylating, annealing, and ligating the oligonucleotides into a digested plasmid vector, as described herein. The plasmid vector comprising the target-specific oligonucleotides can then be used for transformation of a plant. In specific embodiments, the target gene sequences comprise a disease susceptibility gene.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in Handbook of Plant Cell Culture, pp. 124-176, Macmillian Publishing Company, New York, 1983; and Binding, Regeneration of Plants, Plant Protoplasts, pp. 21-73, CRC Press, Boca Raton, 1985. Regeneration can also be obtained from plant callus, explants, organs, pollens, embryos or parts thereof. Such regeneration techniques are described generally in Klee et al (1987) Ann. Rev. of Plant Phys. 38:467-486.

C. Callus Induction and Suspension Culture Maintenance

Undeveloped ovules of *Citrus sinensis* were separated from the immature fruits and cultured on a DOG medium containing 20 ml/L Murashige and Tucker Medium (MT) macronutrient stock, 10 ml/L MT micronutrient stock, 10 ml/L vitamin stock, 15 ml/L calcium stock, 5 ml/L MT iron stock, 45 g/L sucrose, 0.5 g/L malt extract, 8 gr/L agar, plus 10 mg/L Kinetin. The pH of the DOG medium was adjusted to 5.8 and autoclaved and poured into 100×20 mm Petri dishes, and the undeveloped ovules were maintained in the dark at 28±2° C. and were transferred to a new callus induction medium every 21 days until embryogenic ovules (yellow and friable) were observed. Consequently, the obtained calli were maintained onto the same medium and sub-cultured every 4 weeks for long-term culture. To initiate cell suspension 2 g of calli from embryogenic undifferentiated nucllus-derived cells was transferred to 125 mL Erlenmeyer flask containing 20 mL H+H medium. The suspension culture was maintained on a rotary shaker at 125 rpm under a 16 hour photoperiod (70 μmol/m2/s) at 28±2° C. The suspension culture was subcultured every 14 days by adding/removing 40 mL aliquots of H+H medium.

D. Protoplast Isolation and Transformation.

The maintained suspension culture was used for protoplast isolation. Briefly, after removing cells from the liquid medium, they were incubated overnight in an enzyme solution containing 0.7 M mannitol, 24 mM $CaCl_2$), 6.15 mM MES buffer, 0.92 mM $NaH_2PO_4$, 2% (w/v) Cellulase Onozuka RS (Yakult Honsha), 2% (w/v) Macerozyme R-10 (Yakult Honsha), pH: 5.8. Afterward, the incubated cells were filtered through a sterile 45 μm Falcon Cell strainers to remove the undigested cells and other cellular debris. The filtered protoplasts were transferred to a 15 mL calibrated centrifuge tube and were subjected to centrifugation at 900 rpm for 5-8 minutes. Subsequently, the supernatant was removed, and the pellet was gently re-suspended in 5 mL of CPW 25S solution containing 25% (w/v) sucrose with CPW salts. At the next step, 2 mL of CPW 13M solution containing CPW salts with 13% (w/v) mannitol was added directly on top of the sucrose layer and then the samples were subjected to centrifugation at 900 rpm for 8-10 minutes and the protoplast was isolated from the band at the interface between the sucrose and mannitol layers.

To check the quality of the isolated protoplast, a cell viability test was 5 performed using a fluorescein diacetate (FDA) staining. Briefly, 100-μL aliquot of a FDA stock solution [5 mg of FDA (Sigma™) in 1 mL acetone] was added to 100 μL of protoplasts in a 0.6 M mannitol solution (pH 5.7) and the culture was incubated for 5 minutes in the dark. Next, the protoplasts were washed twice, re-suspended in a 0.6 M mannitol solution and were screened under an Olympus 10 fluorescence microscope U-CMAD3.

To create double standard breaks in the target gene (CsLOB1), the isolated protoplasts were diluted to $2\times10^5$ cells/mL and were transfected with Cpf1-RNP complexes (60 μg of Cpf1 and 60 μg of crRNA, 1:1) in a 20 μL transfection reaction (NEBuffer 2.1). In brief, Cpf1-RNP complexes were mixed with protoplasts along with PEG 40% (w/v), 0.3M glucose, 66 mM $CaCl_2$). 2H2O (pH: 6), and the samples were incubated at room temperature for 30 minutes. To remove the PEG, transfected protoplasts were first washed with elution buffer for PEG removal containing 9:1 of solution A (Glucose: 0.4 M; $CaCl_2$)·$2H_2O$: 66 mM; DMSO: 10%; pH: 6) and solution B (Glycine: 0.3M, pH: 10.5), and next by 2 mL (15 minutes), and 1 mL (10 minutes) of BH3 0.6M medium. Afterward, the protoplasts were collected by centrifuging the samples at 700 rpm and washed with 2 mL of BH3 0.6 M. Lastly the protoplasts were maintained in 1.5 mL of BH3: EME medium (1:1) in the dark at 28±2° C. The FDA test was used to test the viability of the protoplasts after transfection.

E. Recombinant Cpf1 Proteins and crRNAs Preparation

Using an in-fusion method three homologs of Cpf1, including FnCpf1 from *Francisella novicida*, AsCpf1 from Acidaminococcus sp, and LbCpf1 from Lachnospiraceae bacterium were cloned inside pMAL-c5X vector containing a tac promoter with malE translation initiation signals using specific primers (See Table 1, below).

TABLE 1

Primer used to clone Fncp1 homologues inside a pMAL-c5X vector

| | Primer Orientation | PCR Primer Sequence | SEQ ID NO |
|---|---|---|---|
| AsCpf1 | Forward | CCGCGATATCGTCGACATGACACAGTTCGAGGGC | 124 |
| | Reverse | TACCTGCAGGGAATTCCTTTTTCTTTTTTGCCTGGC | 125 |
| SbCpf1 | Forward | CCGCGATATCGTCGACATGAGCAAGCTGGAGAAGT | 126 |
| | Reverse | TACCTGCAGGGAATTCCTTTTTCTTTTTTGCCTGGC | 127 |
| FnCpf1 | Forward | CCGCGATATCGTCGACATGAGCATCTACCAGGAGT | 128 |
| | Reverse | TACCTGCAGGGAATTCCTTTTTCTTTTTTGCCTGGC | 129 |

Proteins (with N-terminal MBP tags) were expressed in *Escherichia coli* Rosetta. Briefly, 1 liter of Terrific Broth (TB) medium containing glucose and ampicillin was inculcated with 10 mL of an overnight culture of *E. coli* Rostea harboring Cpf1-fusion plasmids, and the cells growth (37° C.) was monitored until the OD600-0.6 ($2.4\times10^7$ cells/mL), when a concentration of 0.4 mM isopropyl B-D-1-thiogalactopyranoside (IPTG) was added to the culture, and the cells were incubated for another 4 hours at 37° C. Finally, the cells were harvested by centrifugation at 3500×g for 20 minutes, and were re-suspended and lysed in 25 mL of column buffer containing 20 mM Tris-HCl, 200 mM NaCl, 1 mM EDTA, 10 mM β-mercaptoethanol, 1× complete protease inhibitor cocktail tablets, and 100 μg/mL lysozyme (30 minutes on ice). The crude extracts were centrifuged at 20,000 g for 20 minutes and the supernatant was loaded on an amylose resin column at a flow rate of 4 mL/minute. The column was washed with 12 column volumes of column buffer without lysozyme at a flow rate of 8 mL/minute. The Cpf1 proteins were purified from the amylose resin column using elute buffer containing column buffer+10 mM maltose, and were loaded on an SDS-PAGE gel for analysis. Sulfo-cyanine 5 nhs ester (Cy5) a reactive red emitting fluorescent probe was used to label the Cpf1 proteins. Finally a Bradford™ protein assay was used to quantify the purified Cpf1-proteins.

Varieties of crRNA were designed based on their guanine-cytosine content and off-target effects using the CRISPR design tool (zlab.bio/guide-design-resources) (see Table 3). The PCR fragments coding for arrays, with a short T7-priming sequence on the 5' end, were utilized as templates for in vitro transcription reaction, and the selected crRNAs were synthesized using the HiScribe™ T7 High Yield RNA Synthesis Kit (NEB). T7 transcription was performed for 8 hours (37° C.), and the crRNA was purified using the MEGAclear™ Transcription CleanUp Kit (Ambion).

F. Cpf1-Ribonucleoprotein Complex Preparation and in Vitro Cleavage Assay.

To generate a Cpf1-RNP complex with their corresponding crRNA were mixed with each other in a molar ratio of 1:1 with 20 μL NEB buffer number 2.1 (50 mM NaCl, 10 mM Tris-HCl, 10 mM $MgCl_2$, 100 μg/ml BSA, pH 7.9) at room temperature for 15 minutes. To analyse the activity of CRISPR-Cpf1 RNPs, an in vitro cleavage assay was carried out using the corresponding target sites (CsLOB1). Briefly, the CsLOB1 region was amplified by specific primers as shown in Table 2, below. The purified PCR product (300 ng) was incubated for 1 hour with Cpf1-RNP complexes at 37° C. Reactions were later stopped with 5 μg RNase A (30 min, 37° C.), and consequently were run on an agarose gel (2%) to detect cleavages. To optimize the highest mutation efficiency during protoplast transformation the Cpf1-RNP complexes with higher cleavage activities were used for further investigations.

TABLE 2

Primers Used to Amplify CsLOB1.

| | Primer Orientation | PCR Primer Sequence | SEQ ID NO |
|---|---|---|---|
| CS-1 | Forward | CGCAGATGCGTCGAGAAATG | 130 |
| | Reverse | GGCTCCCAAGCTGATCCAAT | 131 |
| CS-2 | Forward | GCAGTGAGCAGCATGGTCTA | 132 |
| | Reverse | ACCGCGCAGCAAATAACTTT | 133 |
| CS-3 | Forward | TCTCCGCCGCCTATAGTTCT | 134 |
| | Reverse | ATCATGTCCACAGAGGCTCC | 135 |
| CS-4 | Forward | TCTCTCCGCCGCCTATAGTT | 136 |
| | Reverse | ATGTCCACAGAGGCTCCCAA | 137 |
| CS-5 | Forward | GAAGAACACTCAATTCTCATCTCC | 138 |
| | Reverse | GTCCACAGAGGCTCCCAAG | 139 |

G. Detection of Mutations.

To identify the mutations, the genomic DNA was isolated from pooled protoplasts using the CTAB (cetyl trimethylammonium bromide) method. Later, the target DNA was amplified and treated with a T7 endonuclease I (T7EI) assay. In brief, the PCR products were denatured at 95° C., and ramped down to 85° C. at −2° C./second and 25° C. at −0.1° C./second. Subsequently, T7EI was added and the samples were incubated at 37° C. for 30 minutes. The reaction was stopped by adding 0.25M EDTA, and samples were run on a 2% agarose gel to estimate the mutation frequency by measuring the fluorescence intensity of the PCR amplicons and the cleaved bands using gel quantification software. Finally the samples which demonstrated positive T7EI results were cloned inside the pGEM-T Easy™ Vectors, and clones were randomly sent for Sanger sequencing.

H. PCR Amplification of Mutagenized CsPDS and CSLOBP.

For PCR amplification of mutagenized CsPDS and CsLOBP, genomic DNA was extracted from the Duncan leaves that were treated with Xcc facilitated agroinfiltration or each transgenic Duncan line. To test the GFP-p1380N-35S-LbCas12a-crRNA-cspds-mediated indels in the CsPDS gene, PCR was performed using the primers CsPDS-5-P7 (5'-TGGCAATGTGATTGACGGAGATGC-3') (SEQ ID NO:98) and CsPDS-3-P8 (5'-ATGAGTCCTCCTTGTTACTTCAGT-3') (SEQ ID NO:99), which flanked the targeted site of CsPDS. The template was genomic DNA, which was extracted from Duncan leaves treated with GFP-p1380N-35S-LbCas12a-crRNA-cspds. Using blunt-end cloning, the CsPDS PCR products were ligated into a PCR BluntII-TOPO vector (Life Technologies™). A total of one hundred random colonies were chosen for DNA sequencing. A Chromas Lite program was employed to analyze the sequencing results.

To analyze the LbCas 12a-crRNA-lobp-mediated CsLOBP mutations, PCR was performed using a pair of primers, LOBP3 (5'-AGGTAAGCTTATTCATATTAACGTTATCAATGATT-3') (SEQ ID NO:100) and LOBP2 (5'-ACCTGGATCCTTTTGAGAGAAGAAAACTGTTGGGT-3') (SEQ ID NO:101) (Jia et al., 2016). Following purification, the PCR products were subjected to either ligation or direct PCR product sequencing using the primer CsLOB4 (5'-CGTCATTCAATTAAAATTAATGAC-3') (SEQ ID NO:102). After transformation, 20 random colonies for each transgenic Duncan line were chosen for detailed sequencing. The sequencing results were further analyzed using the Chromas Lite program.

I. GFP Detection.

A Zeiss Stemi SV11 dissecting microscope (Thornwood, NY, USA) equipped with an Omax camera was used to study the GFP-p1380N-35S-LbCas 12a-crRNA-lobp-transformed and GFP-p1380N-Yao-LbCas12a-crRNA-lobp-transformed Duncan plants under illumination by a Stereo Microscope Fluorescence Adapter (NIGHTSEA). Subsequently, the transgenic plant leaves were photographed with Omax Toup View software.

J. GUS Assay.

Four days after the Xcc-facilitated agroinfiltration, the histochemical staining of GUS and a quantitative GUS assay were performed on the treated citrus leaves as described previously (Jia and Wang, 2014b).

K. Canker Symptom Assay in Citrus.

All the citrus plants were grown in a greenhouse. Prior to the canker pathogen inoculation, the Duncan grapefruit (*Citrus paradisi*), pummelo (Citrus maxima), Willowleaf mandarin (*Citrus reticulata*) and transgenic Duncan grapefruit plants were pruned to promote shooting. With a needleless syringe, the same aged leaves were inoculated with Xcc or XccΔpthA4: dCsLOB1.4, which were resuspended in sterile tap water ($5\times10^8$ CFU/mL). The ensuing canker development was observed and photographed at different time points.

Example 2: Validation of Cpf1-RNPs Activities

Figures 6B, 6C, 6D:
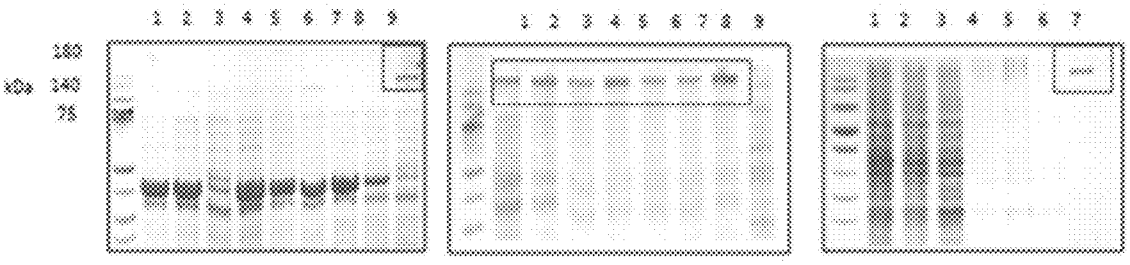
FIG. 6B, FIG. 6C, and FIG. 6D are western blots showing the identification of colon with the ability to express Cpf1 protein (FIG. 6B and FIG. 6C), and the purification of the Cpf1protein using amylose resin column (1-3) pallet run, (4-6) column wash (7) elution and purification of Cpf1 (FIG. 6D).

Whether the CRISPR-Cpf1 RNPs are potent to cleave the target gene (CsLOB1) and induce the mutation were examined. CsLOB1 functions as the disease susceptibility gene in citrus bacterial canker (CBC) and the sequences of spacer for the selected crRNAs were designed to match completely with their recognition sites (Table 1). To obtain the Cpf1-RNPs, first we expressed, and purified three homologs of Cpf1, including AsCpf1, LbCpf1, and FnCpf1 in *E. coli* (see FIG. 6, which presents information on expression and purification of Cpf1 homologs. For the results in this figure, three types of Cpf1 (AsCpf1, LbCpf1, and FnCpf1) were cloned inside the pMAL-c5X vector containing a tac promoter with malE translation initiation signals (see FIG. 6A). FIG. 6B and FIG. 6C present data on the identification of colon with the ability to express Cpf1 protein purification of the Cpf1protein using amylose resin column (1-3) pallet run, (4-6) column wash (7) elution and purification of Cpf1.

Figure 8:
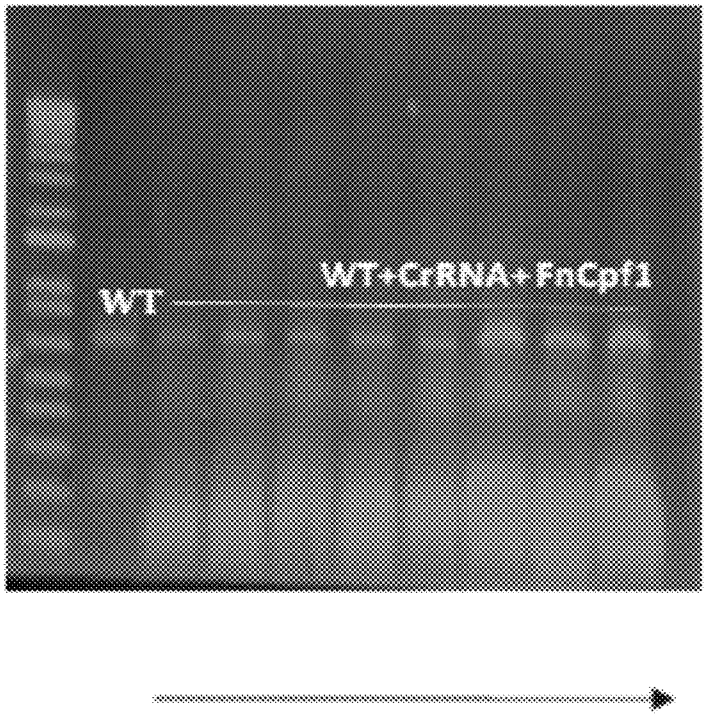
FIG. 8 is a blot showing sample with increasing concentration of RNPs from left to right.
Figure 9A:
FIG. 9A shows sequences of the mutants identified in PCR products, three alternative alleles to the wild type were identified for Fncpf1 (SEQ ID NO: 12 (WT); SEQ ID NO: 13 (Alt-allele 1); SEQ ID NO:14 (Alt-allele 2); SEQ ID NO:15 (Alt-allele 3).
Figure 9B:
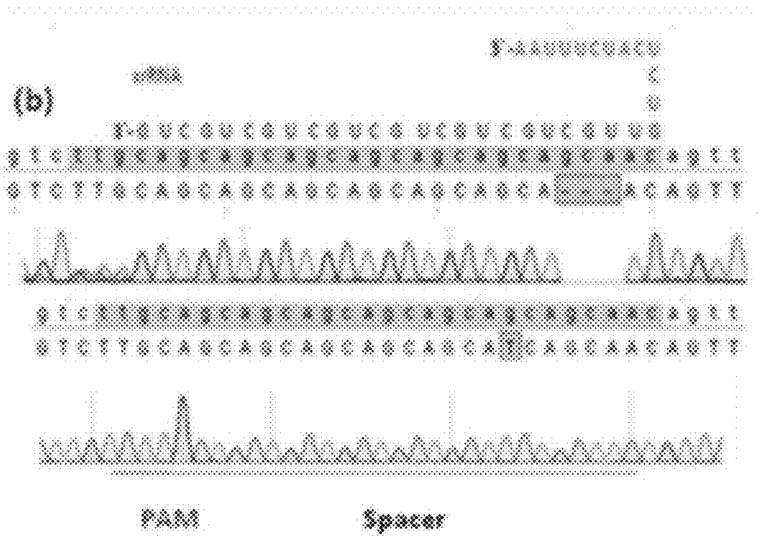
FIG. 9B presents the crRNA (SEQ ID NO: 16); FnCpf1 (WT, SEQ ID NO: 17) identified mutants (SEQ ID NO:18; and SEQ ID NO:19).
Figure 9C:
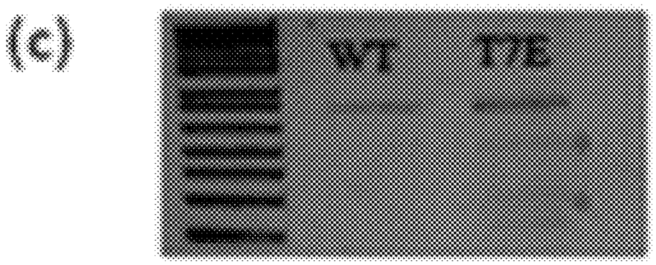
FIG. 9C is a blot which identified the mismatches by T7EI assay for FnCpf1 RNPs.
Figure 9D:
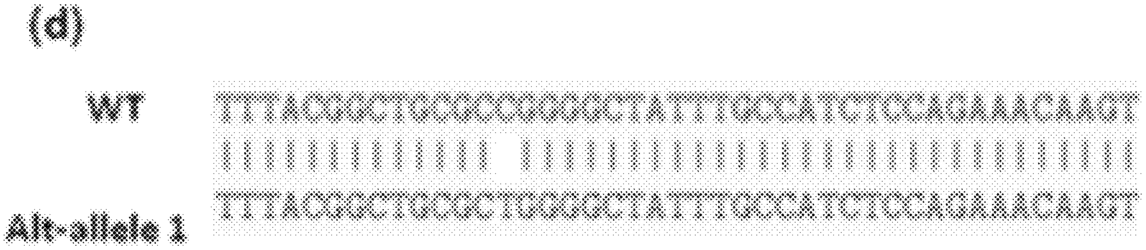
FIG. 9D shows the mutants identified in PCR products, one alternative allele to the wild type were identified (SEQ ID NO:24 and SEQ ID NO:25 mutant are shown).
Figure 9E:
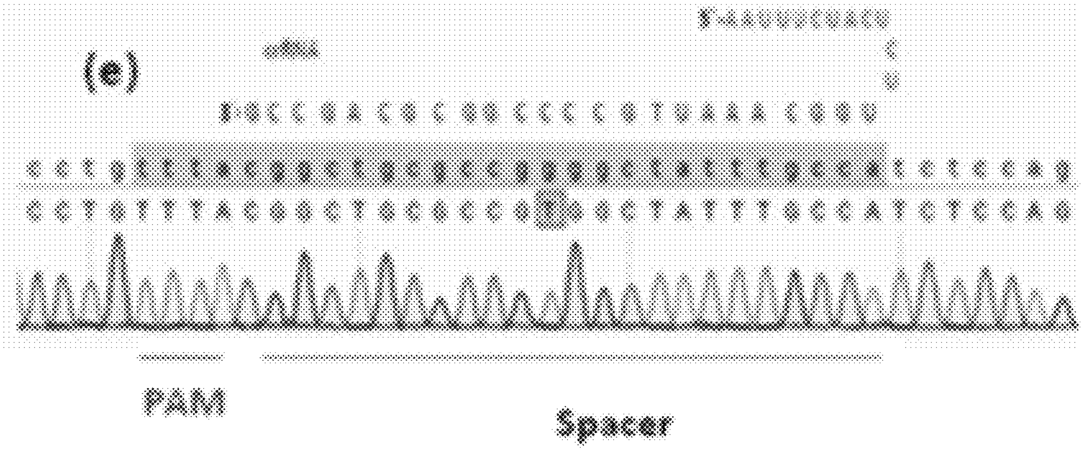
FIG. 9E presents a crRNA sequence (SEQ ID NO: 20 with extension SEQ ID NO: 21) and the wild type target SEQ ID NO: 22 and identified mutant (SEQ ID NO: 23).
Figure 9F:
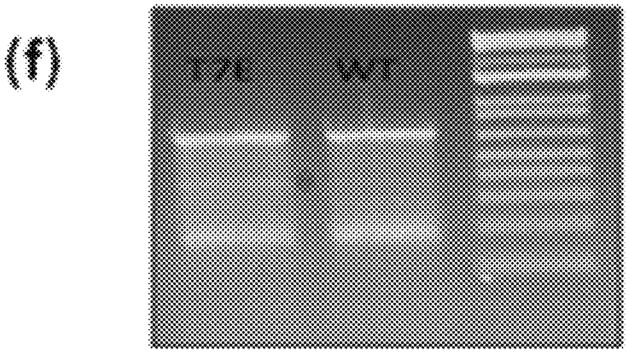
FIG. 9F is a blot which identified the mismatches by T7EI assay for Ascpf1 RNPs.

Next, the isolated Cpf1 protein was complexed with their corresponding crRNA to form the Cpf1-RNPs complexes. As the direct repeats (DRs) sequence is one of the key elements for Cpf1-RNP genome editing, it was possible that the engineering of DR should affect the related activity of Cpf1-RNPs genome-editing. The template of the mature crRNA starts with 19nt of the DRs followed by a spacer with 23-25nt length To assess the efficiency of direct repeats on the activity of Cpf1-RNPs, three sets of crRNAs were synthesized for each selected Cpf1 homolog as follows: (1) containing one DR (2) containing two DRs, and (3) crRNAs without DR. FIG. 8E shows the in vitro cleavage assay describing the activity of Fncpf1 with As/Lb Cpf1 direct repeat.

The findings confirmed that the DR is an essential factor for the crRNA activity, and although some of the selected crRNAs without DR were able to cleave the CsLOB1, their cleavage efficiency were observed significantly lower than the crRNAs with the DR and the same spacer sequences. We had observed that for an efficient cleavage at least one DR should be existed in crRNA sequence, however it was not possible to confirm that the existence of more DR in crRNA sequence could potentially lead to an increase in the cleavage and editing activity of crRNA (in vivo and in vitro). In this case, as the crRNAs with two DRs demonstrated similar cleavage activity of crRNA with one DR. Studying different spacers on cleavage activity of crRNA showed not all the selected spacers were potent to cleave the CsLOB1, and each of selected crRNA exhibit different cleavage efficiency. The active crRNAs were able to cleave the target with one or two DRs. Furthermore, increasing the DRs to two in the crRNAs sequence did not enhance the effectiveness of the Cpf1-RNPs with no or less efficient spacers. Increasing the RNP concentration had also no effectiveness on cleavage activity of crRNA on non-efficient crRNA. See FIG. 8, which shows data demonstrating that by increasing the concentration of RNPs, the inefficient crRNAs were not able to cleave the target (CsLOB1).

Figure 7:
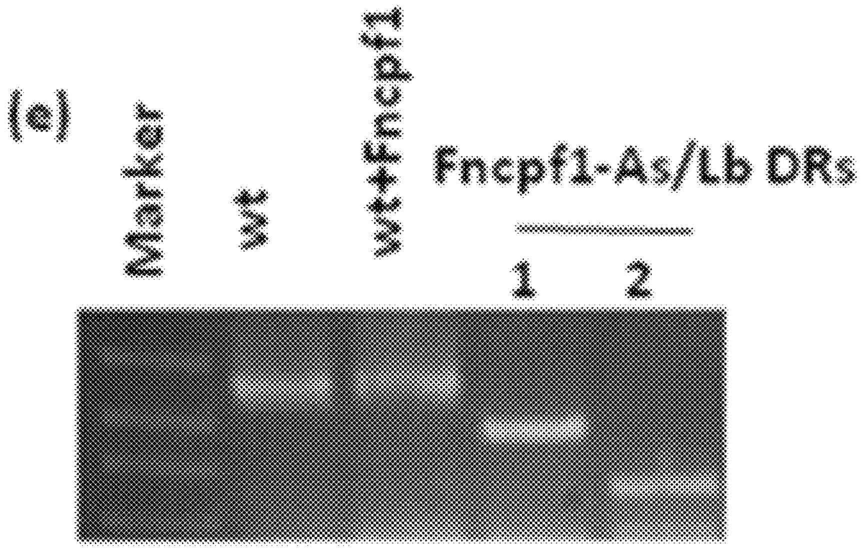
FIG. 7 shows results of the in vitro cleavage assay describing the activity of Fncpf1 with As/Lb Cpf1 direct repeat.

Example 3: FnCpf1 Protein Preserves its Activities with as/Lb-Cpf1 Direct Repeat Cpf1, a type V CRISPR-Cas system, is an RNA-guided endonuclease with a single ~44-nucleotide (nt) crRNA with a 5'-located DRs sequence and a spacer sequence that complements the target. Nevertheless, it is not clear if Cpf1 proteins can recognize and be active with the other specific direct repeats from other homologs. To study the behaviors of Cpf1-RNPs on the dissimilarity of DRs, different Cpf1-RNPs were produced using AsCpf1, LbCpf1, and FnCpf1 proteins with non-corresponding DRs. The results revealed that the AsCpf1-RNPs formed from DRs correspond to FnCpf1 and LbCpf1 did not have any cleavage activities. The same result was observed for LbCpf1-RNP, and FnCpf1-RNP, even though their spacers were sufficiently potent to cleave their target in vitro. However, the RNPs from the FnCpf1 were active with the DRs that correspond for AsCpf1, and LbCpf1 proteins. This result shows that the Cpf1 protein from *F. novicida* can make an active RNP complex with crRNA corresponding to the Cpf1-proteins isolated from Acidaminococcus sp, and *L. bacterium*. (see FIG. 7). Thus, the results confirm the findings by Tu et al. (2017) that suggested the cleavage activity of FnCpf1 (5'-TTN-3') could be preserved if its DR is replaced with other DR sequences from AsCpf1, LbCpf1, Lb2Cpf1 (Lachnospiraceae bacterium MA2020 Cpf1), PcCpf1 (*Porphyromonas* creviоricanis Cpf1) and PmCpf1 (*Porphyromonas macacae* Cpf1).

Structural studies of FnCpf1 protein demonstrate its molecular structure with a recognition lobe (REC) and a nuclease lobe (NUC) linked to a wedge domain (L. Lin et al., 2018; Tu et al., 2017). The N-terminal REC lobe includes two α-helical domains, REC1 and REC2, that are recognized for their role in crRNA-target DNA heteroduplexes. The C-terminal NUC lobe (containing C-terminal RuvC and Nuc domains) is active in PAM-interacting domains, bridge helices, and in the cleavage of the target (Swarts et al., 2017). The narrow minor groove shaped by the wedge domain, REC1, and PAM-interacting domain recognized the suitable PAM, and lastly the complex of FnCpf1-crRNA and DNA shapes a sticky end DSB in the position of 5' overhangs far from to the PAM site, with a single catalytic site positioned close to the RuvC and Nuc domains (L. Lin et al., 2018; Swarts et al., 2017). Regardless of CRISPR-Cas system verities, CRISPR constantly relies on a common set of roles to detect the target (1) complementary between the crRNA (guide-RNA in case of Cas9) and the target sequence (2) Recognition of the PAM which is considered to destabilize the adjacent sequence, allowing interrogation of the sequence by the crRNA, and consequential in RNA-DNA coupling when a similar sequence is exist.

Example 4: Optimized Protoplast Isolation and Analysis of Transfection Efficiency The isolation of high-quality protoplasts is the main step for a successful protoplast transfection, and much evidence indicates the materials selected for the protoplast isolation were of significant value to an efficient isolate protoplast. A range of parameters were considered for methods to obtain the maximum quantity of protoplasts from *C. sinensis*. The suspension cultures of *C. sinensis* were used for protoplast isolation, and the cells were separated from the liquid medium at the mid-exponential phase (10th day after subculture; packed cell volume: 58.7 ±6.2).

To determine the optimal digestive combination of the enzymes, seven different concentrations of Cellulase Onozuka RS and Macerozyme R-10 from 0.5 to 3.5% were applied to treat the cells for a duration of 12 hours (0.4 M Mannitol). The protoplast yield and viability of the cells were studied. A concentration of 2% Cellulase Onozuka RS and 2% Macerozyme R-10 could result in $5.9\pm0.2\times10^6$ protoplasts per gram fresh weight, (cell viability 90.5±1.92%). Treating the cells with higher concentrations of enzymes mixture (2.5%≥) had negative impacts the protoplast yield and cells' viability (see Table 3). Note that the protoplast yield and viability were influenced by the concentration of the enzymes. The highest protoplast yield and viability were received with 2% Cellulase Onozuka RS and Macerozyme R-10. All data were expressed as mean±standard error (n=3) of three separate tests.

TABLE 3

Efficiency of Enzyme Concentration on the Yield and Viability of the Protoplast.

| Cellulase Onozuka RS (%) | Macerozyme R-10 (%) | Protoplast yield (mean + SD × $10^6$/gFW) | Protoplast viability (%) |
|---|---|---|---|
| 0.5 | 0.5 | 0.75 + 0.1 | 88.7 + 3.4 |
| 1 | 1 | 3.47 + 0.3 | 92.1 + 1.63 |
| 1.5 | 1.5 | 5.5 + 0.25 | 91.2 + 2.21 |
| 9 | 9 | 5.9 + 0.2 | 90.5 + 1.92 |
| 2.5 | 2.5 | 5.12 + 0.3 | 88 + 2.44 |
| 3 | 3 | 4.37 + 0.4 | 85.2 + 1.4 |
| 3.5 | 3.5 | 3.9 + 0.3 | 81.7 + 3.3 |

Mannitol is a sugar alcohol, which efficiently can stabilize the osmotic pressure. To obtain high quality protoplasts the concentration of the mannitol during the enzyme digestion process is a critical factor. Thus to find the best mannitol concentration for the isolation of protoplast from *C. sinensis* we examined different concentrations of mannitol (0.4 to 0.8 M) by adding it to our optimal concentration of enzyme mixture (2% Cellulase Onozuka RS and 2% Macerozyme R-10). Mannitol at 0.7 M gave rise to the maximum protoplast viability at the isolation (90.2±3.8), wash (88.5±3.4), and PEG-transfection (75.5±4.2) steps (protoplast was diluted to $2\times10^5$ cells/mL). Using concentrations below 0.6 and greater than 0.8 negatively impacted the protoplast viability even at the PEG-transfection step (see Table 4). Note that the protoplast viability was influenced by the concentration of the mannitol. The highest protoplast yield and viability were received with 0.7 M mannitol during the protoplast isolation process. All data were expressed as mean±standard error (n=3) of three separate tests.

TABLE 4

Influence of Mannitol Concentration on the Viability of Protoplast through the Isolation Process.

| Mannitol (M) | Protoplast Viability (%) Isolation | Wash | PEG-Transfection |
|---|---|---|---|
| 0.4 | 90 ± 3.5 | 82 ± 3.5 | 67.7 ± 3.1 |
| 0.6 | 92 ± 3 | 88.7 ± 2.8 | 71.2 ± 6.4 |
| 0.7 | 90.2 ± 3.8 | 88.5 ± 3.4 | 75.5 ± 4.2 |
| 0.8 | 87.2 ± 4.5 | 73.2 ± 4.2 | 61.5 ± 3.4 |

Example 5: Editing the CsLOB1 Gene in *C. sinensis* Protoplasts

To induce DSBs and edit the CsLOB1 in vivo, first we isolated the protoplast from embryogenic calli. In *C. sinensis*, the mid-exponential phase (10th day) of suspension culture from embryogenic calli could provide protoplast up to $5.9\pm0.2\times10^6$ protoplasts per gram fresh weight (cell viability: 90.5±1.92%) using an overnight incubated cultures with a solution containing 0.7 M mannitol, 24 mM $CaCl_2$), 6.15 mM MES buffer, 0.92 mM $NaH_2PO_4$, 2% (w/v) Cellulase Onozuka RS and 2% (w/v) Macerozyme R-10 (rpm: 80, 25° C.). The isolated protoplasts were diluted to $2\times10^5$ cells/mL. Next, Lbcpf1, AsCpf1 and Fncpf1 proteins (60 μg) were delivered, mixed with their corresponding crRNA (60 μg) to the *C. sinensis* protoplast applying a PEG-mediated RNP transfection method. Within three days after transfection the genomic DNA was isolated and the target region amplified with specific primers (see Table 2). As a preliminary step to find the mutants, a T7EI assay was performed to find any mismatches on CsLOB1, and the PCR products from positive T7EI treatments were sent for Sanger sequencing. Subsequently the obtained sequences were explored for indel and SNPs by sequence alignment of wild-type and mutant using poly peak parser software. The overall efficiency of alternative sequences was calculated using TIDE software.

The analysis of our PCR products after transfection as shown in FIG. 9 resulted in various mutation patterns with an efficiency of 8.6-10% for Fncpf1 RNP and 5% for AsCpf1 RNP. Using Cpf1-RNPs, Indels and SNPs were observed at target sites on CsLOB1 with an editing efficiency from 10 to 5%, for FnCpf1 (using crRNA with the spacer sequence of

```
                          (SEQ ID NO: 103)
5'-CAGCAGCAGCAGCAGCAGCAGCAAC-3'
```

and AsCpf1 RNPs (using crRNA with the spacer sequence of

Figure 10A:
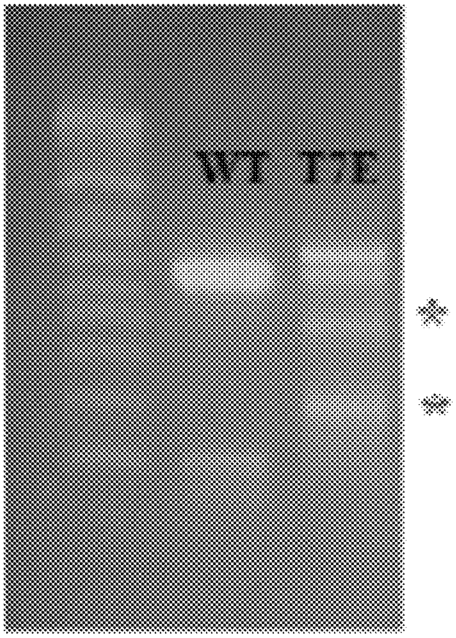
FIG. 10A is a blot demonstrating the identified mismatches by T7EI assay, using LbCpf1 RNPs.
Figure 10B:
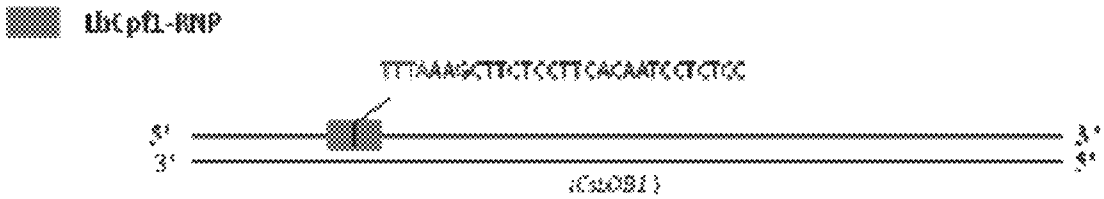
FIG. 10B is a schematic of the CsLOB1 gene, showing the LbCpf1-RNP as the shaded rectangle. SEQ ID NO:26 is shown.

```
5'-CGGCTGCGCCGGGGCTATTTGCCA-3' (104)
```

respectively, even though that the T7 assay was showing mismatches using LbCpf1 RNPs we couldn't identify any reliable mutant cell lines in our study (FIG. 10 which demonstrates the identified mismatches by T7EI assay using LbCpf1 RNPs).

Among the tested homologs of Cpf1-RNPs (As, Lb, and Fn), Fn-Cpf1 showed the highest editing activity with an editing efficiency of 8.6-10%. The results from sending colons for the sanger showed that in our cell population we have mutant cells lines from the Fn-Cpf1 due to deletion (3 bp) or single nucleotide polymorphisms nucleotides (SNPs) (FIG. 9). However, the mutation from AsCpf1-RNPs was due to SNPs. Also, the Cpf1-spacer with GC content in a range of 48-70% has the optimum cleavage in vitro, while in vivo only mutations by the crRNA with a GC content higher than 60% in their spacers could be confirmed. In general, the Cpf1-crRNA with GC content in the range of 30-70% possesses greater activity and some key rules for optimizing crRNA design includes avoiding poly-T sequences and a guanine immediately and hesitating thymidine after the PAM. However, as the PAM areas are highly conserved on the targets finding a superior crRNA which meet all of these factors is challenging.

Example 6: Improvement of CRISPR/Cas9 Genome Editing Efficacy in Citrus

Citrus is one of the top fruit crops in the world. Citrus breeding is critical to improve fruit quality and to overcome the disease challenges such as Huanglongbing. However, conventional citrus breeding is difficult, inefficient and time-consuming because of long juvenile period, heterozygosity, sexual incompatibility and polyembryony in citrus. CRISPR/Cas9 mediated genome editing is a promising tool with great potentials. CRISPR/Cas9 mediated genome editing has been successfully used to modify the citrus genome. However, the efficacy of CRISPR/Cas9 mediated genome editing of citrus needs to be improved. In a previous study, *Arabidopsis* U6 and 35S promoters have been used to drive the expression of sgRNA. In this example, the U6 promoters in citrus have been identified and tested for their efficacies in CRISPR/Cas9 mediated genome editing in citrus compared with the heterogenous U6 promoter (AtU6). The data demonstrates that the endogenous promoter has higher genome editing efficiency in citrus.

A. Methods

Figure 11A:
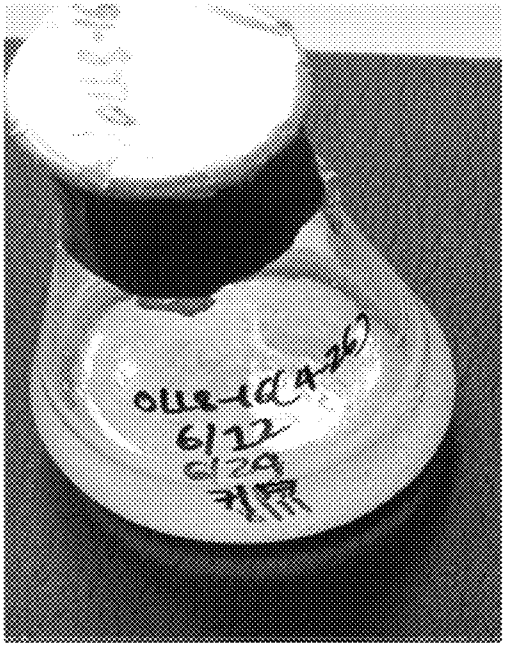
FIG. 11A is a photograph showing the suspension culture established from immature ovules.
Figure 11B:
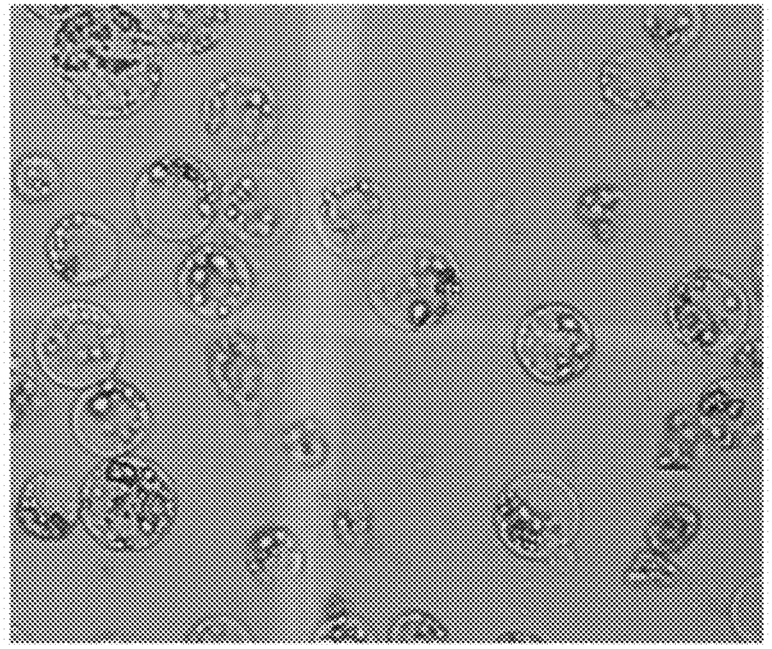
FIG. 11B is a photograph of suspended cells in culture after enzymatic digestion for about 16 hours.
Figure 11C:
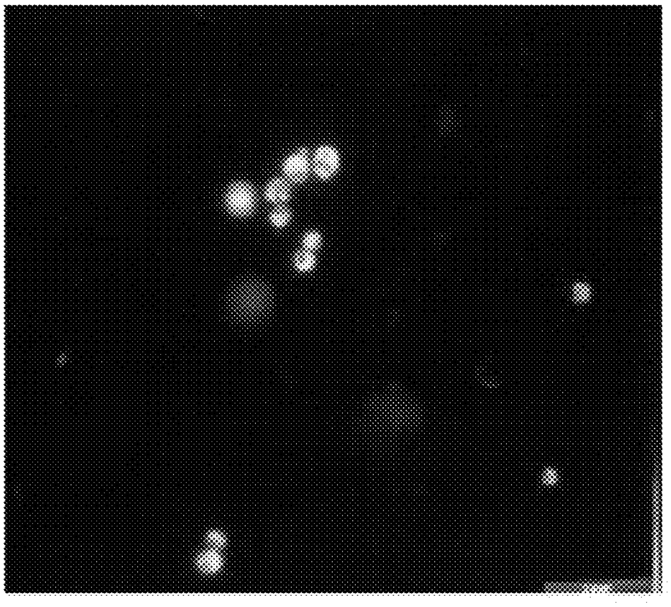
FIG. 11C is a photograph showing cells in which the CRISPR vector was transformed by the PEG method.
Figure 11D:
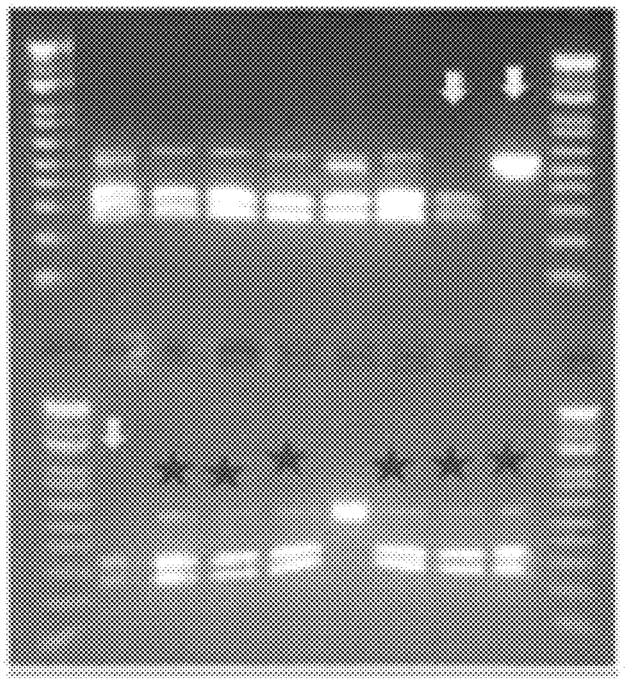
FIG. 11D is a gel of genomic DNA isolated from protoplast samples after a 48 hours and an overnight PCR/RE assay. Restriction enzyme digestion resistant bands were used for the next step of TA cloning.
Figure 11E:
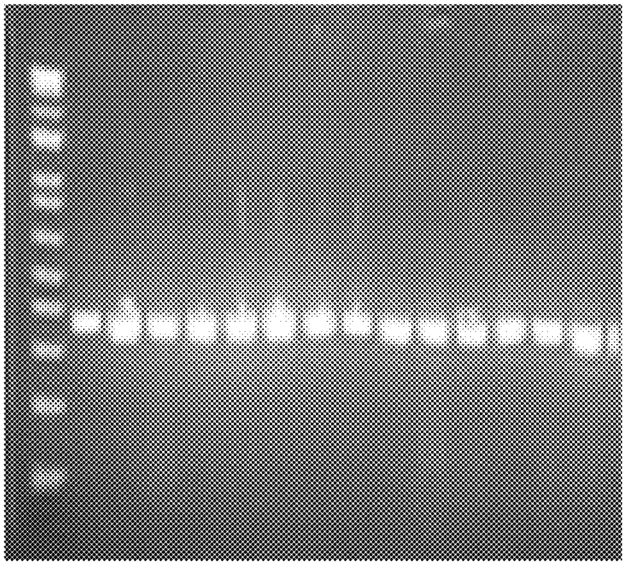
FIG. 11E is a gel of cloning CRISPR samples showing resistant bands and performance of a colony PCR, and subsequently sent for sequencing.
Figure 12A:
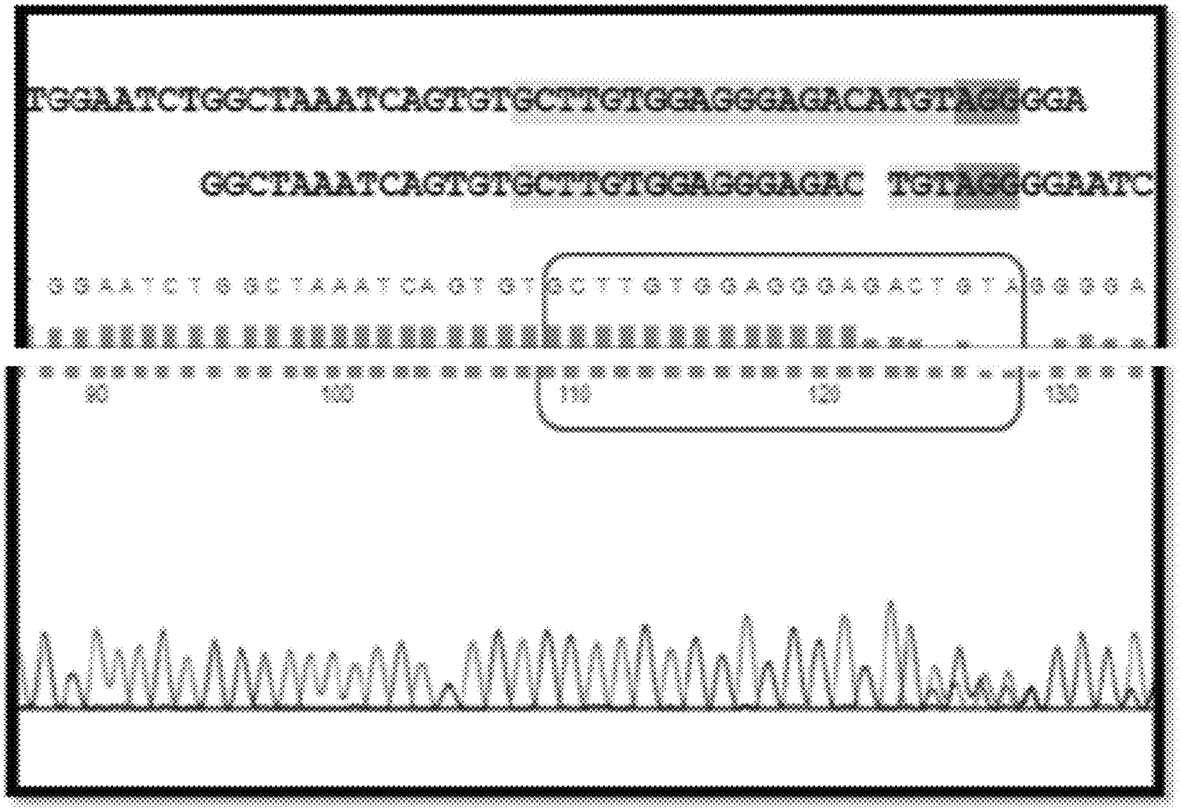
FIG. 12A is the sequencing result analysis of CRISPR target site to detect targeted mutation (SEQ ID NO:27, 28 and 29 are shown).
Figure 12B:
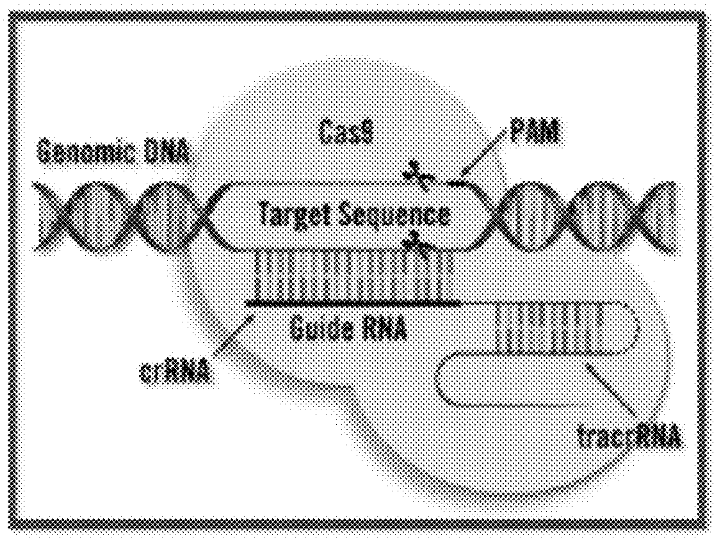
FIG. 12B is a diagram showing the Cas9 construct.
Figure 12C:
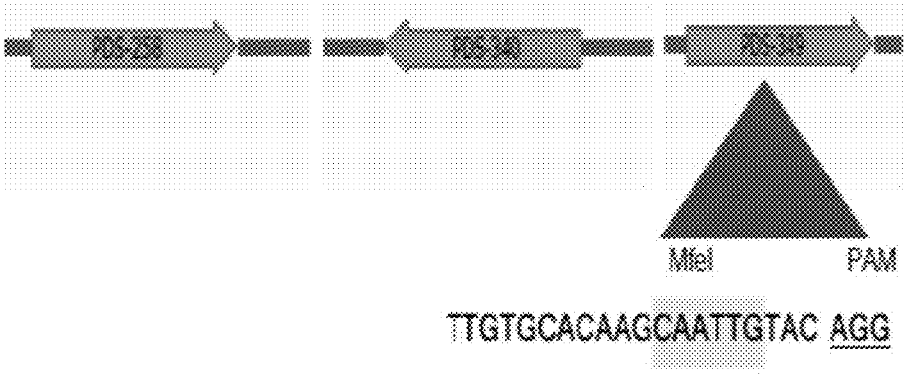
FIG. 12C is diagram showing placement of Mffel and PAM (SEQ ID NO: 30).
Figure 12D:
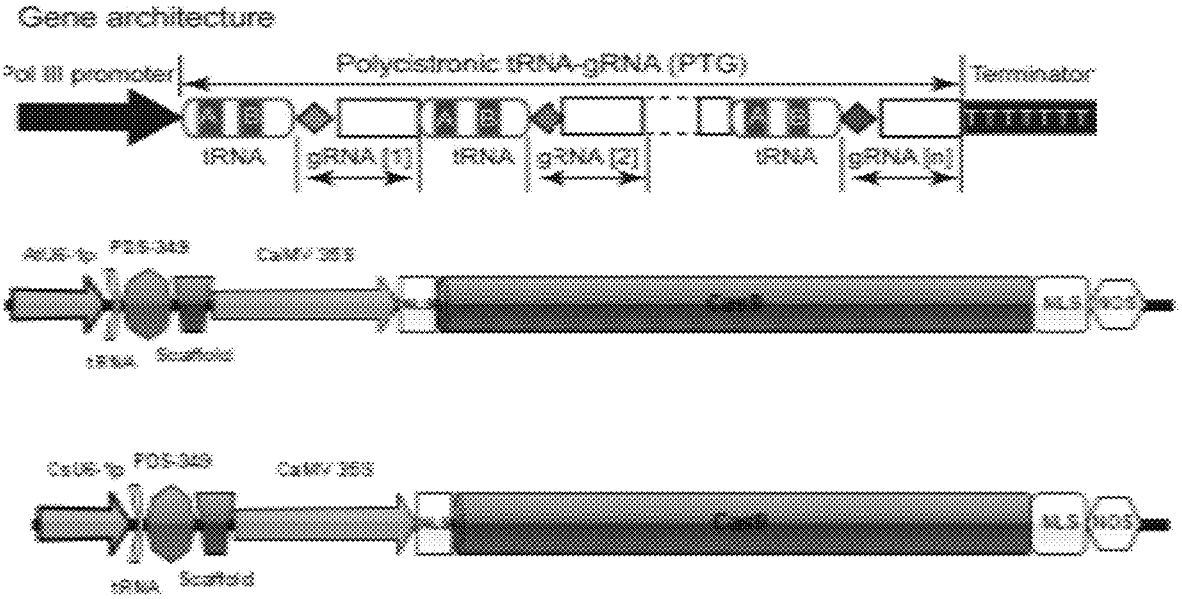
FIG. 12D shows the gene architecture of Polycistronic tRNA-gRNA contstruct.

Embryogenic suspension culture was used for the isolation of protoplast for CRISPR-Cas9 genome editing experiment in citrus. Enzymatic digestion of callus is performed with the Cellulase and Macerozyme enzymes overnight (about 16-20 hours). See FIG. 11A and FIG. 11B. Citrus protoplast isolation and transformation protocol is followed for further steps with slight modification. After 48 hours of dark incubation, transformed protoplast samples were taken for reporter gene expression (eYFP) to determine the transformation efficiency under fluorescence microscope. See FIG. 11C. Then protoplast samples were collected for genomic DNA isolation (gDNA) and further analysis. First, PCR was performed by using gDNA of CRISPR samples as PCR template to amplify the target region. Second, amplified PCR products were digested with restriction enzyme corresponding to the gRNA. See FIG. 11D. The undigested bands seen on the gel run were taken for cloning and sequencing analysis of mutation at target site. See FIG. 11E. Scc also FIG. 12.

The composition of media used for citrus tissue culture in this study is listed below.

1. Composition of MT (Murashige and Tucker) medium for citrus tissue culture
   - 1.1. MT Macro (50X): KNO3: 95 g/L; NH4NO3: 82.5 g/L; MgSO4: 18.5 g/L; KH2PO4: 7.5 g/L; K2HPO4: 1 g/L.
   - 1.2. MT Micro (100×): $H_3BO3$: 0.62 g; MnSO4*$H_2O$: 1.68 g/L; ZnSO4*7$H_2O$: 0.86 g/L; KI: 0.083 g/L; Na2MoO4: 0.025 g/L; CusO4*5H2O: 1 ml of stock (0.25 g/100 ml stock); CoC12: 1 ml of stock (0.25 g/100 ml stock).
   - 1.3. MT Iron (100×): Na2EDTA: 7.45 g/L; FeSO4*7H2O: 5.57 g/L FcSO4*7$H_2O$: 5.57 g/L
   - 1.4. MT Vitamin (100×): Myo-inositol: 10 g/L; thiamine-HCl: 1 g/L; Pyridoxin-HCl: 1 gr/L; nicotinic acid: 0.5 g/L; glycine 0.2 g/L
   - 1.5. MT Calcium (66×): CaCl2*2$H_2O$: 29.33 g/L
2. Composition of DOG medium for embryogenic callus
   MT macro stock: 20 ml/L;
   MT micro stock: 10 ml/L;
   MT vitamin stock: 10 ml/L,
   Calcium stock: 15 ml/L;
   Iron stock: 5 ml/L;
   Sucrose: 50 g/L;
   Malt extract: 0.5 g/L;
   Kinetin: 5 mg/L; Agar: 8 g/L; pH=5.8 adjust with KOH.
3. H+H medium for cell suspension maintenance
   Macro nutrient stock: 10 ml/L;
   Bh3 macronutrient stock: 5 ml/L;
   micronutrient stock: 10 ml/L;
   Vitamin stock: 10 ml/L;

Calcium stock: 15 ml/L;
Iron stock: 5 ml/L;
sucrose: 35 gr/L;
Malt: 0.5 gr/L;
glutamine: 1.55 gr/L; pH=5.8 adjust with KOH.

4. CPW salts stock
  4.1. Solution 1:
    $MgSO_4.7H_2O$: 25 g/L;
    $KNO_3$: 10 g/L;
    $KH_2PO_4$: 2.72 g/L;
    KI: 0.016 g/L;
    $CuSO_4.5\ H_2O$: 0.025 ng/L.
  4.2. Solution 2:
    $CaCl_2.2\ H_2O$: 15 g/L;
5. Composition BH3 Stock for protoplast culture
  5.1. BH3 Multivitamin A
    Ascorbic acid: 0.1 g/100 ml;
    Calcium pantothenate: 0.05 g/100 ml;
    Choline chloride: 0.05 g/100 ml;
    folic acid (dissolved in 1M KOH): 0.02 g/100 ml;
    Riboflavin: 0.01 g/100 ml;
    p-aminobenzoic acid: 0.001 g/100 ml;
    biotin: 0.001 g/100 ml.
  5.2. BH3 Multivitamin B
    Retinol: 0.001 g/100 ml;
    Cholecalciferol: 0.001 g/100 ml;
    Vitamin B12: 0.002 g/100 ml.
6. Retinol and Cholecalciferol were dissolved in Ethanol.
  6.1. BH3 Macronutrients (100×)
    KCl: 150 g/l;
    $MgSO_4{*}7H_2O$: 37 g/l;
    $KH_2PO_4$: 15 g/l;
    $K_2HPO_4$: 2 gr
  5.2. BH3 KI Stock
    KI: 0.083 g/100 ml
  5.3. BH3 organic acid (50×)
    Fumaric acid: 0.2 g/100 ml;
    citric acid: 0.2 g/100 ml;
    malic acid: 0.2 g/100 ml;
    pyruvic acid: 0.1 g/100 ml
  5.4. SUG+SUG Alcohols (100×)
    Fructose: 2.5 g/100 ml;
    Ribose: 2.5 g/100 ml;
    Xylose: 2.5 g/100 ml;
    Mannose: 2.5 g/100 ml;
    Rhamnose: 2.5 g/100 ml;
    Cellobiose: 2.5 g/100 ml;
    galactose: 2.5 g/100 ml;
    Mannitol: 2.5 g/100 ml.
6. Composition of 0.6M BH3 for protoplast culture
  BH3 macro stock: 10 ml/L;
  MT micro stock: 10 ml/L;
  MT vitamin stock: 10 ml/L;
  MT calcium stock: 15 ml/L;
  MT iron stock: 5 ml/L;
  BH3 multivitamin stock A: 2 ml/L;
  BH3 multivitamin stock B: 1 ml/L;
  BH3 KI stock: 1 ml/L;
  Sugar alcohol stock: 1 ml/L;
  BH3 organic acid stock: 20 ml/L;
  Coconut water: 20 ml/L;
  malt extract: 1 g/L;
  sucrose: 51.3 g/L;
  Mannitol: 82 g/L;
  glutamine: 3.1 g/L;
  casein enzyme hydrolysate: 0.25 g/L. pH=5.8 with KOH
7. EME (0.146M) with sucrose for protoplast isolation
  MT macro stock: 20 ml/L;
  MT micro stock: 10 ml/L;
  MT vitamin stock: 10 ml/L;
  MT calcium: 15 ml/L;
  MT iron stock: 5 ml/L;
  sucrose: 50 g/L;
  Malt extract: 0.5 g/L. For 0.6 EME add 15.5 g/100 ml sucrose.
8. EME (0.146M) with Maltose for protoplast isolation
  MT macro stock: 20 ml/L;
  MT micro stock: 10 ml/L;
  MT vitamin stock: 10 ml/L;
  MT calcium: 15 ml/L;
  MT iron stock: 5 ml/L;
  Maltose: 50 g/L;
  malt extract: 0.5 g/L. pH=5.8 with KOH.

The sequences of Cpf1 homologs cloned inside pMAL-C5X vector are provided in FIG. 13 S8A-D-17A-D (pMAL-C5X/AsCpf1, SEQ ID NO:31), FIG. 14 (pMAL-C5X.LbCpf1; SEQ ID NO: 32), and FIG. 15 (pMAL-C5X/FnCpf1; SEQ ID NO:33). The Citrus canker susceptibility gene CsLOB1 sequence is provided in FIG. 16 (SEQ ID NO:34).

B. Results

Figure 17A:
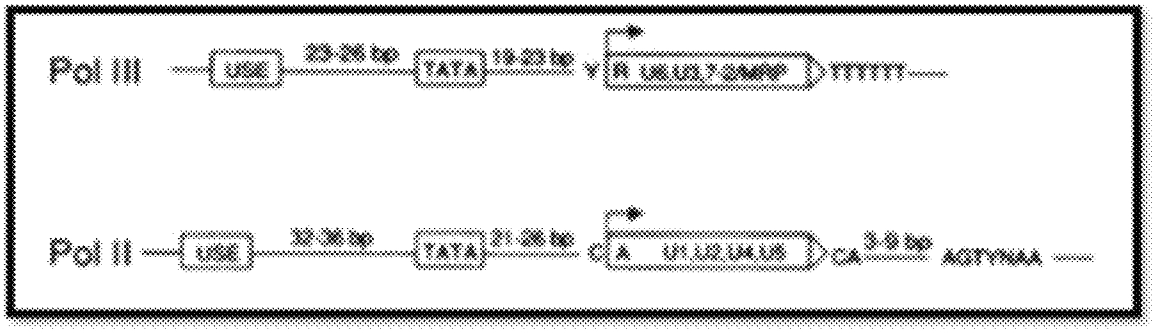
FIG. 17A shows U6 promoter analysis.
Figure 17B:
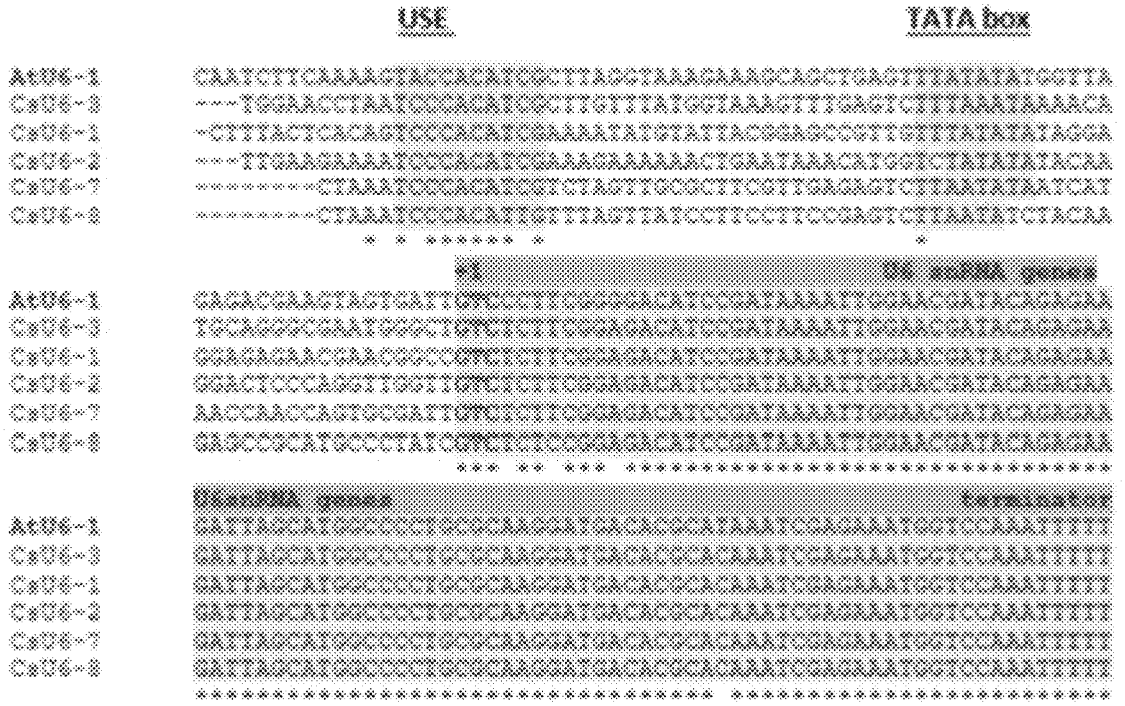
FIG. 17B provides sequence analysis of AtU6-1, CsUS-3, CsU6-1, CsU6-2, CsU6-7, and CsU6-8 (SEQ ID NOs: 3, 4, 5, 6, 7, and 8 respectively).
Figure 18A:
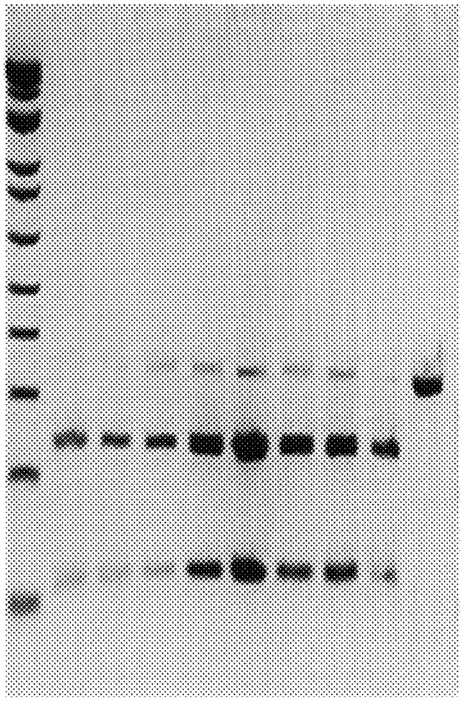
FIG. 18A and FIG. 18B are photographs of western blots for the PCR/RE assay of CsPDS (PDS-349).
Figure 18B:
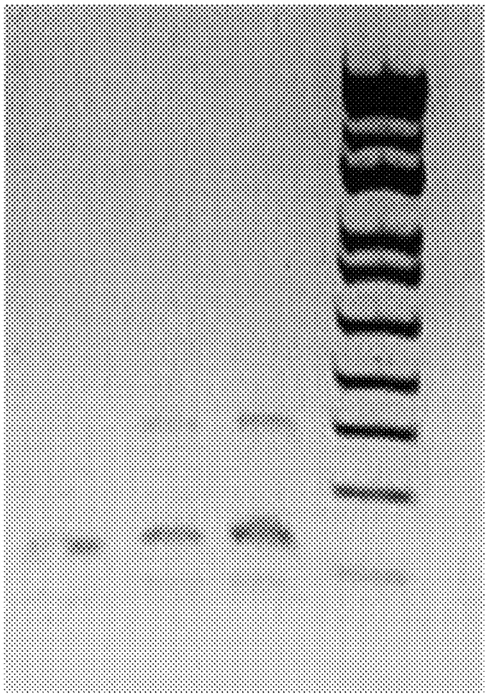
Figure 19:
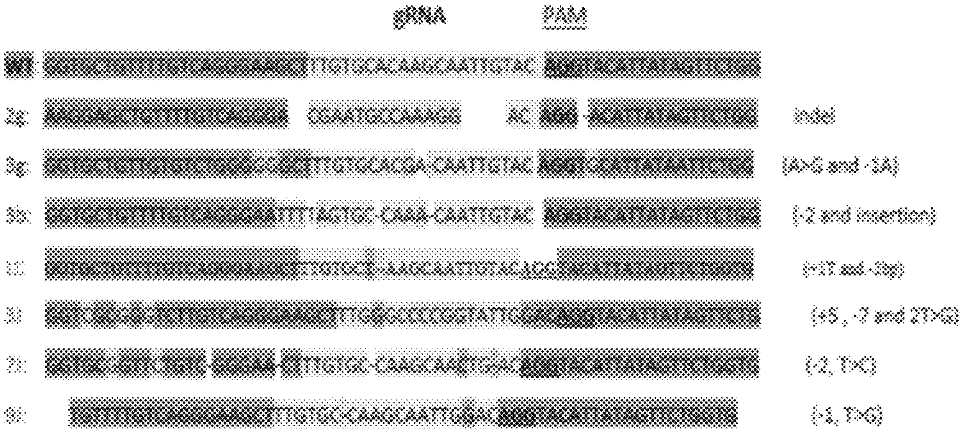
FIG. 19 shows the results of sequencing results analysis (PDS-349) (wild-type wt), (A>G and 1A), (−2 and insertion), (+1T and +2 bp), (+5,−7, and 2T>G), (−2,T>C), (−1, T>G) (SEQ ID NOs: 35, 36, 37, 38, 39, 40, 41 and42, and, respectively) are shown.

Citrus U6 promoter is predicted based on *Arabidopsis* U6 promoter. See FIG. 12 and FIG. 17. The herein identified citrus U6 promoter referred to as CsU6-1 is used for further CRISPR genome editing experiment to drive a sgRNA PCR/RE assay show that CsU6-1 has higher genome editing efficiency as compared with *Arabidopsis* U6 promoter (AtU6-1). Furthermore, vector design with tRNA-gRNA strategy is useful to improve the CRISPR activity in citrus protoplast assay. See FIG. 12 and FIG. 19.

C. Outcomes of citrus protoplast transient assay

AtU6-1/tRNA: ~ 10-15%

CsU6-1/tRNA: ~ 17-30%

D. Discussion

Results of the protoplast transient assay in citrus have shown improved genome editing efficiency with the endogenous citrus U6 promotor. These results show a new way to improve genome editing efficacy in citrus protoplast. This is a crucial step of the CRISPR plant regeneration process from the single cells to avoid chimera. This method is being employed to regenerate plants by targeting HLB susceptible genes in citrus and preliminary tests in protoplasts have also higher genome editing efficient with the endogenous U6 promoter (CsU6-1). See FIG.-9 (showing that increasing the concentration of RNPs were not able to cleave the target CsLOB1 by the inefficient crRNAs) and FIG. 10 (demonstrating the identified mismatches by T7EI assay using RNP-LbCpf1) for additional information.

Example 7: Tests of Parameters for Citrus Protoplast Transformation

Figure 20A:
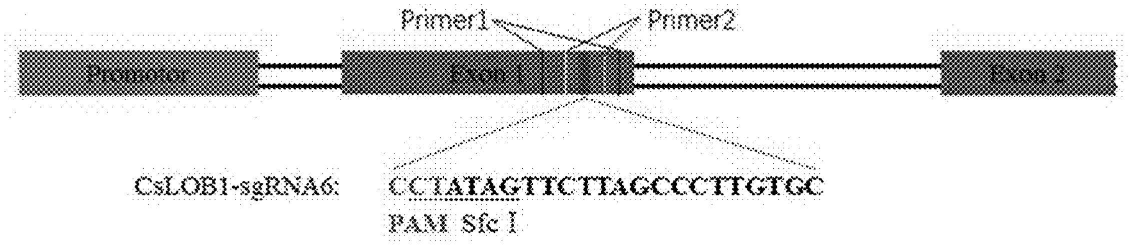
FIG. 20A is a schematic showing the gene structure of CsLOB1. CsLOB1-sgRNA6 with PAM site is shown as SEQ ID NO: 43).
Figure 20B:
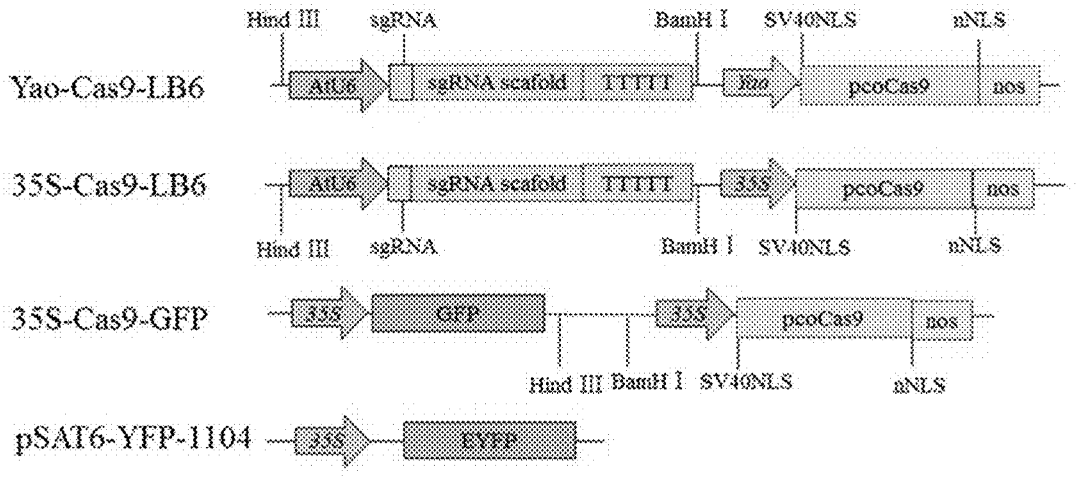
FIG. 20B provides a schematic structure of the vectors used for transformation.

To optimize transformation, different parameters of citrus protoplast transformation and the corresponding transformation efficacy were tested. For this purpose, the plasmid 35S-Cas9-GFP (8 kb) (see FIG. 20A), which contains GFP for verification of transformation based on fluorescence. In the sequence, there were one promotor and two exon regions; sgRNA was in the first exon regions, and Primer1 and Primer2 were used for the mutant detection.

pSAT6-EYFP-1104 (4.612 kb), which contains EYFP and has a smaller size (FIG. 20B), was included for comparison and optimization purposes. Yao-Cas9-LB6 and 35S-Cas9-

LB6 were used for CRISPR/Cas9-mediated modification, which were driven by Yao promotor and 35S promotor respectively, and 35S-Cas9-GFP was used for the optimization of transforming efficiency.

First, the effect of protoplast cell density on transformation efficiency was tested. Three protoplast densities ($1\times10^5$, $5\times10^5$, $1\times10^6$ cell/mL) were tested with the EYFP-1104 construct. Transformation efficacies calculated at 24 hours after transfection were 10.17±0.02, 6.68±0.02, and 10.11±0.02% for $1\times10^5$, $5\times10^5$, $1\times10^6$ cell/mL, respectively. Increasing protoplast did not increase transformation efficiency, but does provide better chance for mutant identification in the next step. Thus, $1\times10^6$ cell/mL was used for future transformations in this study.

The effect of incubation time (15, 20, and 30 minutes) after adding PEG and plasmid on transformation efficiency was tested with the EYFP-1104 construct at the room temperature. The transformation efficacies were 10.54±0.01, 12.45±0.03, and 9.48±0.02% for 15, 20, and 30 minutes, respectively. Thus, 20 minutes was used for convenience in transformations in this study. In addition, the effect of heat shock at 47° C. for 10 minutes on transformation efficiency was tested. The resulting transformation efficacy was 10.8±0.02%, not markedly higher than room temperature. Thus heat shock was not employed in further testing.

The transformation efficiency (transformants per microgram plasmid DNA) decreases with increases of size of the DNA. Here the transformation efficiency of 35S-Cas9-GFP (8 kb) and pSAT6-EYFP-1104 (4.612 kb) were compared. The transformation efficacies for 35S-Cas9-GFP and EYFP-1104 were 10.50±0.02% and 12.73±0.02%, respectively, with incubation times of 20 minutes at room temperature, and were 5.46±0.01% and 8.51±0.03%, respectively, at 47° C. for 10 minutes. The transformation efficacies were higher for EYFP-1104, the plasmid with lower DNA size, than 35S-Cas9-GFP significantly in both occasions, suggesting the need to minimize the plasmid DNA in order to improve transformation efficacy.

Example 8: Genome Modification Efficiency from PEG-Mediated Plasmid Transfection of Protoplast Based on the sequence of the CsLOB1 gene, sgRNA was designed using CRISPR-P online, found at crispr.hzau.edu.cn.CRISPR. The sgRNA oligos and their complementary oligos containing a Bbsl site were synthesized by IDT Integrated DNA Technologies, Inc. (San Jose, CA, USA). The synthesized paired sgRNA oligos were annealed and inserted into vector pUC119-gRNA after digestion of both with Bbsl. The sgRNA in the resultant vector is driven by AtU6-1 promoter from *Arabidopsis thaliana* (Peng et al. 2017). The HBT-35ST7: pcoCas9 vector, which contains the BamHI/HindIII sites, was used to construct CRISPR/Cas9 expression vectors for citrus protoplast transformation).

After digestion by restriction enzyme BamHI and HindIII, the fragment containing the sgRNA from pUC119-gRNA was inserted into the BamHI/HindIII-digested HBT-35ST7: pcoCas9 vector to generate the 35S: Cas9-CsLOB1sgRNA plant expression vector. A GFP gene driven by 35S promoter was inserted into the HBT-35ST7: pcoCas9 vector to serve as a reporter vector to optimize the protoplast transformation efficiency.

Using the parameters developed in the Example above, genome editing efficiency via protoplast transformation was evaluated. For this purpose, the CsLOB1 gene, which is the susceptibility gene to citrus canker caused by *Xanthomonas citri* (Hu et al., 2014; Hu et al., 2016), was targeted. The CsLOB1 gene is induced by a type III effector PthA4 of *X. citri*, which binds to the effector binding elements in the promoter region of CsLOB1, a transcriptional factor, to induce its gene expression. Consequently, CsLOB1 upregulates downstream genes leading to hypertrophy and hyperplasia symptoms. Mutation of the effector binding elements or the coding region of CsLOB1 thus renders citrus resistant to citrus canker. However, the CsLOB1 modified plants contain Cas9 and sgRNA in their chromosome and their consequent usage requires a lengthy and expensive deregulation process. The genome editing approach via transient expression of Cas9/sgRNA in protoplast has potential to generate non-transgenic genome modified plants.

To analyze the efficacy of the designed sgRNA, in vitro analysis of sgRNA was conducted. The sgRNA was synthesized using EnGen NEB sgRNA Synthesis Kit (New England Biolabs, Ipswich, MA, USA) according to the manufacturer's protocol. The target DNA fragment was amplified using the Primer1-F/R primers and purified for in vitro digestion of DNA with Cas9 Nuclease, *S. pyogenes* (NEB). The reaction consisted of Cas9 Nuclease 1 μL, 10× Cas9 nuclease reaction buffer 3 μL, 30 nM sgRNA and nuclease-free water 20 μL, which was kept at 25° C. for 10 minutes. Then the in vitro digestion was conducted for 1 hour at 37° C. after adding 30 nM substrate DNA. Proteinase K and RNase A were added at the end to stop the in vitro digestion. The digested products were electrophoresed on a 2% agarose gel. Cleavage activity was measured by the amount of digested products over the total amount of input target DNA using the Image J software.

Figure 23:
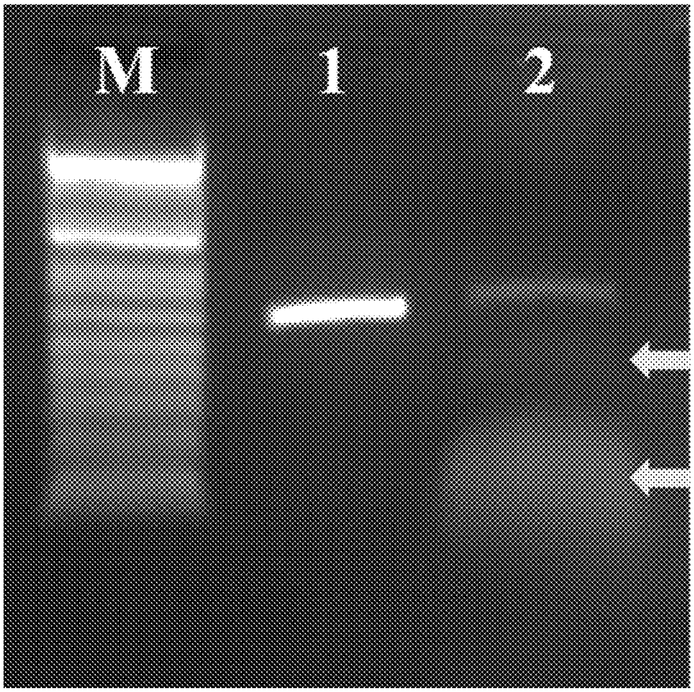
FIG. 23 Confirmation of sgRNA efficacy via in vitro digestion of DNA fragment containing target sequence by using Cas9. M: Marker, 1: control, 2 Target DNA, arrows indicate the fragments cut from target DNA.

An sgRNA, herein designated as sgRNA6, was selected. sgRNA6 has a restriction enzyme site upstream of the PAM (Protospacer Adjacent Motif) to assist with mutation analysis by PCR-RE. See FIG. 20C (FIG. 1 of nontrasngen paper) and FIG. 20D. In this figure, the arrows represent the undigested PCR product. The sgRNA was shown to be functional in directing the recognition and in vitro digestion of target DNA (see FIG. 23).

The protoplast was isolated from the Hamlin sweet orange (*Citrus sinensis* [L.] Osbeck) 15-4 callus line induced in 2015 as described previously (Omar et al. 2007). The embryonic callus was suspended in DOG liquid medium (MT medium supplemented with 0.5 g/L malt extract, 50 g/L sucrose, 5 mg/L Kinetin, pH 5.8) (Murashige and Tucker, 1969; Omar et al., 2016) and sub-cultured every two weeks. After sub-culturing for 10 days, 2 mL suspension callus was collected for digestion using the enzyme solution (1.5% Cellulose RS, 0.75% Macerozyme, 0.7 M mannitol, 10 mM MES [pH 5.8], 0.1% BSA, 1 mM $CaCl_2$)) with horizontal shaking (40 rpm) at 27° C. overnight in the dark. After digestion, the shaking speed was increased to 80 rpm for 30 seconds to release protoplast. The solution was diluted by adding 10 mL W5 solution (154 mM NaCl, 125 mM $CaCl_2$), 5 mM KCl, 2 mM MES [pH 5.8]) and continued to release the protoplast for 10 minutes.

Then the protoplast mixture was passed through a 100 μm nylon mesh screen to remove the undigested callus cells and debris. The filtered solution was centrifuged in a 15 mL centrifuge tube for 9 minutes at 100×g. The supernatant was removed and the protoplast was re-suspended using the W5 solution to wash away the enzyme solution, and the protoplast suspension was subjected to centrifuge again. The protoplast was suspended in 5 mL CPW solution ($KH_2PO4$ 27.2 $mg\cdot L^{-1}$, KNO3 101 $mg\cdot L^{-1}$, $CaCl_2$) 150 $mg\cdot L^{-1}$, $MgSO_4$ 250 $mg\cdot L^{-1}$, $Fe_2$ $(SO_4)\cdot 6H_2O$ 2.5 $mg\cdot L^{-1}$, KI 0.16 $mg\cdot L^{-1}$, $CuSO_4$ 0.025 $mg\cdot L^{-1}$) with 25% sucrose. Two mL CPW solution with 13% mannitol was added gently though the tube wall on the top of the sucrose layer directly to make sure these two layers could not be mixed. After centrifuge for 5 minutes at 100×g, a ring with purified protoplast should appear at the interface between the two layers. The ring was transferred into a new tube and suspended by adding 10 mL W5 solution. After centrifugation, the suspension was removed. The purified protoplast was resuspended using W5 solution and kept in the dark to incubate for 1 hour at room temperature. At the same time, the protoplast amount was calculated using a hemacytometer. Finally, the protoplast was diluted to a density of $10^5$-106/mL in MMG solution (0.7M Mannitol, 15 mM $MgCl_2$, 4 mM MES [pH 5.8]).

The protoplast transformation was conducted with the polyethylene glycol (PEG)-mediated method as described previously (Fang et al. 2014) with modifications. Briefly, fresh PEG solution and the plasmid was prepared right before transformation. The PEG solution was made with 0.4 M mannitol, 40% w/v PEG4000 and 0.1 mg/mL $CaCl_2$). 0.5 mL of the protoplast suspended in the MMG solution was kept in a 15 mL round bottom Falcon tube and mixed with 20 μg plasmid. After adding 0.5 mL PEG solution, the mixed solution was shaken gently and thoroughly and incubated for 15-30 minutes at room temperature or for 10 minutes at 47° C. using a heating block. Then 2 mL W5 solution was added to dilute the reaction mixture to stop the transformation by shaking gently and thoroughly. Five minutes later, another 2 mL W5 solution was added to further dilute the transformation solution and shaken gently. The mixture was centrifuged at 150×g to collect the protoplast, which was then re-suspended in 1.5 mL WI solution and kept in darkness at room temperature for the direct analysis. For the regeneration, after centrifuge, the protoplast was kept in 2 mL BH3 (Omar et al. 2016) medium. The following steps for protoplast culturing and plant regeneration were conducted as described by Omar et al. (2016), which is hereby incorporated by reference for these methods. See FIG. 22.

Protoplast isolated from Hamlin callus was transformed with plasmids Yao-Cas9-LB6 and 35S-Cas9-LB6, in which the pcoCas9 gene is driven by YAO promoter and 35S promoter respectively and the sgRNA6 is driven by the U6 promoter. At 48 hours after transformation, the mutation rate was determined based on PCR-RE (FIG. 20C and FIG. 20D).

The transfected protoplast was collected for observation of fluorescence at 24 hours after transformation and mutation identification after 2 days. PCR-RE assay was conducted to detect the mutation as described previously (Shan et al., 2014). Briefly, genomic DNA was extracted using Wizard Genomic DNA Purification Kit (Promega™) according to the manufacturer's protocol. The target DNA region was amplified using two pairs of primers (Primer 1F/R and Primer 2F/R) (see FIG. 22A), with the first PCR product amplified by Primer 1F/R longer than the second one amplified by Primer 2F/R. The PCR consisted of an initial denaturation at 94° C. for 5 minutes, and 35 cycles of 94° C. for 30 seconds, annealing at 58° C. for 30 seconds, and extension at 72° C. for 30 seconds, followed by 72° C. for 5 minutes. The PCR production was digested with restriction enzyme Sfcl at 37° C. for 2 hours. After electrophoresis in a 2% agarose gel, the undigested PCR DNA fragment was purified using the Wizatd SV Gel and PCR Clean-up System (Promega™), which served as the template for the second PCR amplification by Primer 2F/R. The secondary PCR product was digested again by ScfI, followed by gel purification as described above. The undigested DNA fragment from the second PCR amplification was cloned into the pGEM-T Easy vector (Promega™) for TA cloning. Colonies were selected for sequencing directly. All sequences were compared to the wild type target sequence using the Vector NTI™ software.

The Image J™ software was used for calculating the mutation efficiency. The gel images were scanned to calculate the digestion efficiency by Image J™. The first digestion efficiency was designated as X (the amount of undigested DNA over the total amount of input DNA), the second digestion efficiency was designated as Y, and mutation efficiency based on sequencing result was designated as K (the amount of sequenced mutant clones over the total amount of sequenced clones). Consequently, the final mutation efficiency (E) was calculated using the following equation:

$$E=X\times Y\times K\times 100\%.$$

Figure 20F:
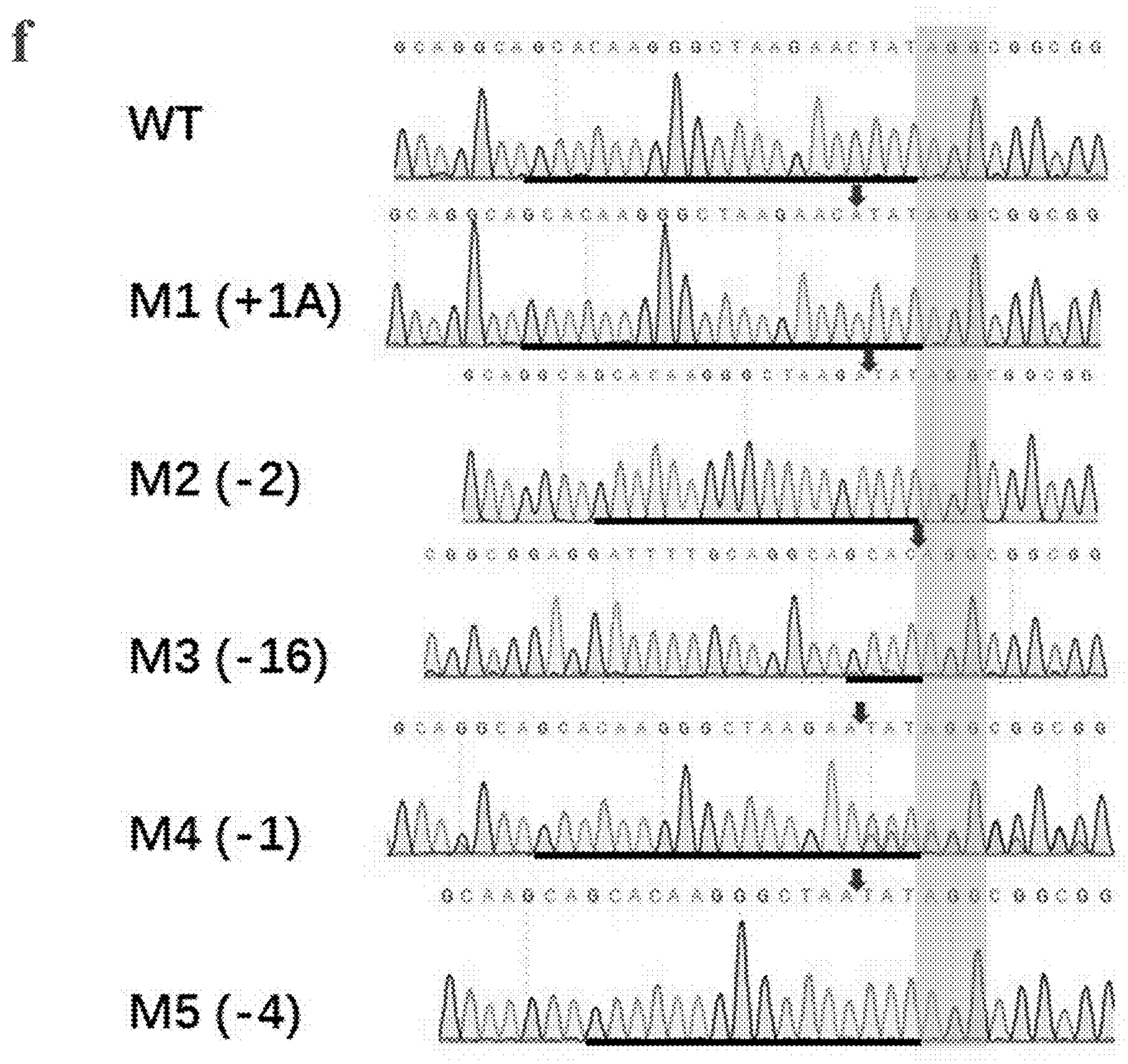
Figure 21:
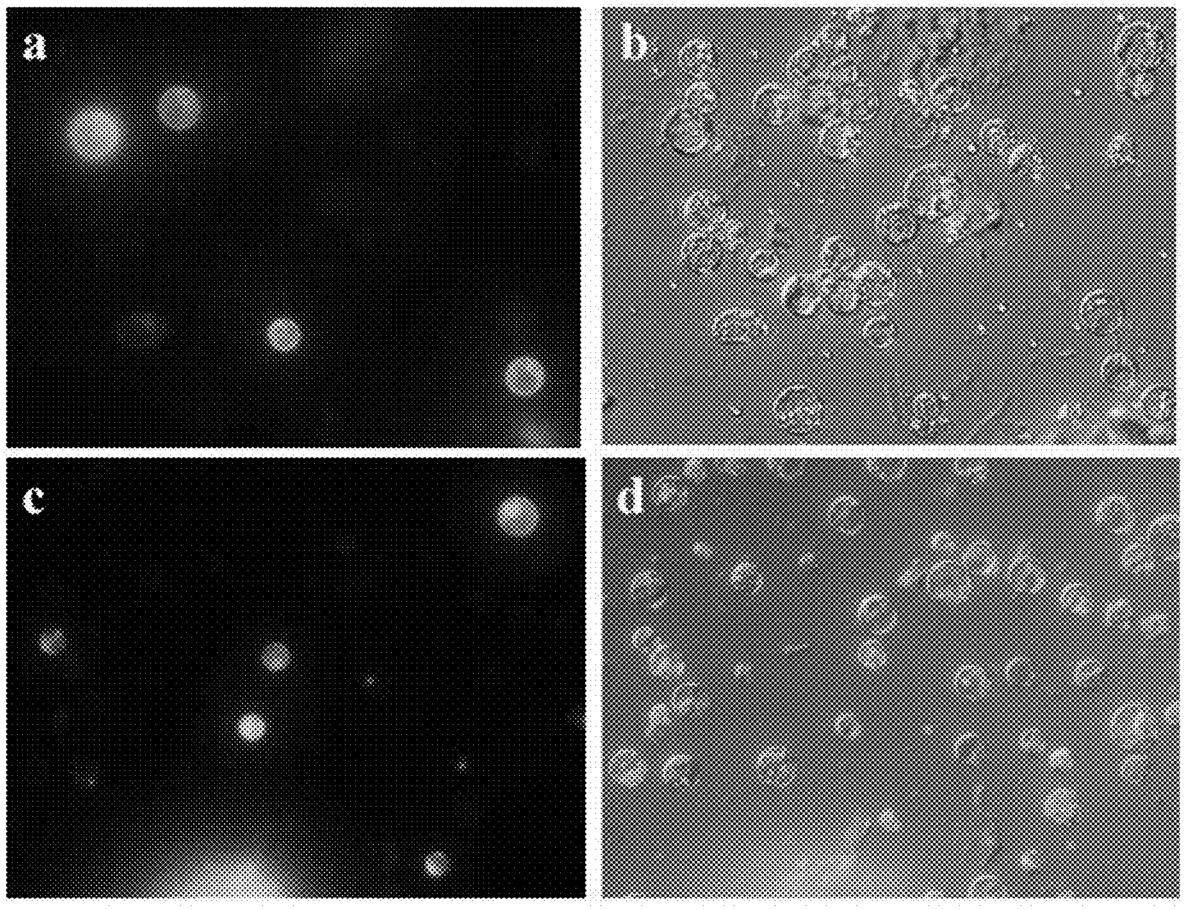
FIG. 21A and FIG. 21B show the protoplast transfected plasmid 35S-Cas9-GFP under dark field and light field, respectively.
FIG. 21C and FIG. 21D show the protoplast transfected plasmid 35S-Cas9-GFP under dark field and light field, respectively.

The non-digested band, which suggests mutations caused by genome editing, was cloned for sequencing. Of the 100 clones sequenced, 57 contained mutations induced by Yao-Cas9-LB6 plasmid. See FIG. 20E and FIG. 20F; FIG. 22. In these figures, red letters were PAM, the letters with underline indicate sgRNA sequence, the blue letters indicate inserted bases, and the '-' indicate deleted bases. The yellow highlighted bases under yellow shadow indicate PAM in FIG. 20F.

The final mutation efficiency was 5.76%, which is a very high efficiency in the CRISPR/Cas9 mediated gene editing technology using protoplast transformation. The mutation efficiencies in rice and maize have been reported to be 7.3% and 1.1%, respectively (Lin et al., 2018). Most of the mutations were deletions, even though insertions and changes were also identified (see FIG. 23). For the 35S-Cas9-LB6 plasmid, no mutations were identified despite repeated attempts.

The DNA samples of transformed protoplast cells and Cas9/sgRNA transgenic plants were used for hiTAIL-PCR analysis. As expected, several bands were observed in the positive control which indicate that there are foreign DNA insertion in the citrus. No amplification was observed for protoplast cells transformed with Cas9/sgRNA, indicating the transformed protoplast cells do not contain foreign DNA.

To analyze putative off-targets, the Cas9/sgRNA analysis software (see online at cbi.hzau.edu.c. Vcgi-bin/CRISPR) was used to identify potential off-target sequences.

Primers (Table 6) were designed to amplify the potential off-target fragments. The PCR products were cloned into the pGEM-T Easy™ vector for sequencing. The sequencing results were analyzed by the Vector NTI™ software.

To check the unpredicted mutations in non-target gene regions (off-target), we predicted the potential off-target sites of CsLOB1, which were listed in Table 7). There were four 4 sites for the sgRNA6, but among them, 2 sites had the SNP sites, which also were shown in Table 7). Each off-target site was cloned, and 40 colonies were sent for sequencing. In the potential off-target site 1, two off-target mutations were identified; the off-target efficiency is 0.05%. No off-target mutations were identified in other three potential off-target sites.

TABLE 6

| Primers Sequences SEQ ID NOs: 152-163 | | |
|---|---|---|
| Name | Sequencing (5'-3') | Usage |
| Primer1-F | CAGCTCCTCCTCATCCCTTAC | Amplify the target region |
| Primer1-R | AGTGGAACAATCAACCACTCCAA | |
| Primer2-F | AGCTCCTCCTCATCCCTTAC | Amplify the target region |
| Primer2-R | ACCACTCCAAAGTCTAATCACACA | |
| Yao-F | | Amplify the YAO promotor |
| Yao-R | | |
| LOB1-off1-F | AGCGTTTGCTTCGTAGACCA | Amplify the off-target 1 |
| LOB1-off1-R | TATGGGGCTAGCCAATCACG | |
| LOB1-off2-F | TCAGAATCACGTCTGCACCA | Amplify the off-target 1 |
| LOB1-off2-R | GTGTAAAACCCACAACCCGC | |
| LOB1-off3-F | AAACGTGCATAACCACCCCT | Amplify the off-target 1 |
| LOB1-off3-R | ATCTGGTTGATCGCATGGCT | |
| LOB1-off4-F | ATGGATGCGTTCAGGGGAAG | Amplify the off-target 1 |
| LOB1-off4-R | ATAGGCCCAAGAATGTGCAA | |

TABLE 7

| Putative CRISPR/Cas9 off-target sites of CsLOB1-sgRNA-6 SEQ ID NOs 140-147 | | | |
|---|---|---|---|
| Name | Off-target location | Sequencing of off-target (5'-3') | Off-target No. |
| Off-1 | Cs7g27620 | GCGCATGGACTAAGAACAATAGG | GCGCATGGACTAAGAACAATAAG(SNP)<br>GCGCATGGACCAAGAACAATAAG(1)<br>GCGCGTGGACTAAGAACAATAGG(1) |
| Off-2 | Cs7g02090 | GCACAAGATCTAAGAACATTAAG | |
| Off-3 | orange1.1t01786 | TCACAAGGACCAAGAAGTATTGG | |
| Off-4 | Cs2g10860 | GCAGAAAGGGTAAGAGCTATAAG | ACAGAAAGGGTAAGAGCTATAAG(SNP) |

Example 9: Modification of CsPDS in Duncan Grapefruit

For xcc-facilitated agroinfiltration in Duncan grapefruit, the Duncan grapefruit (*Citrus paradisi*) was grown in a greenhouse at approximately 27° C. and then pruned for uniform shooting before Xcc-facilitated agroinfiltration. The Duncan leaves were first inoculated with a culture of actively growing Xcc, which was resuspended in sterile tap water at a concentration of $5\times10^8$ CFU/mL. Twenty-four hours later, the leaf areas, which were pretreated with XccΔgumC, were subjected to agroinfiltration with recombinant *Agrobacterium* cells harboring GFP-p1380N-35S-LbCas12a-crRNA-cspds. Four days after the agroinfiltration, the genomic DNA was extracted from the treated leaves. Similarly, the XccΔpthA4: dCsLOB1.4-treated leaf areas were agroinfiltrated with recombinant *Agrobacterium* containing p1380-TI CsLOBP-GUSin, p1380-TII CsLOBP-GUSin, p1380-MTII CsLOBP-GUSin or p1380-AtHSP70BP-GUSin. Four days later, the leaves were collected for a GUS assay.

CaMV 35S-SpCas9/CaMV 35S-sgRNA and CaMV 35S-SaCas9/CaMV 35S-sgRNA were used to test the CRISPR-Cas9 function through Xcc-facilitated agroinfiltration (Jia et al., 2014a; Jia et al., 2017a). Therefore, CaMV 35S alone was used to drive both LbCas12a and crRNA in vector GFP-p1380N-35S-LbCas12a-crRNA-cspds, which was harnessed for Xcc-facilitated agroinfiltration. Sec FIG. 24A.

For plasmid construction, the CaMV 35S promoter was amplified using the primers CaMV35-5-SbfI and CaMV35-3-KpnI-BamHI and then cloned into SbfI-BamHI-digested GFP-p1380N-Cas9 to produce GFP-p1380N-KpnI-Cas9. GFP-p1380N-Cas9 was constructed in a previous study (Jia et al., 2017a). LbCas 12a harboring a nuclear localization signal (NLS) and an HA tag at its C-terminus was obtained from Addgene plasmid pY016 after a KpnI and EcoRI cut (Zetsche et al., 2015). The KpnI-LbCas12a-EcoRI fragment was inserted into KpnI-EcoRI-cut GFP-p1380N-KpnI-Cas9 to generate GFP-p1380N-35S-LbCas12a. By using *Arabidopsis* genomic DNA as a template, the Yao promoter was amplified with a pair of primers, Yao-5-Sbfl and Yao-3-KpnI. The SbfI-KpnI-digested Yao promoter was cloned into SbfI-KpnI-cut GFP-p1380N-35S-LbCas12a to obtain GFP-p1380N-Yao-LbCas12a. The Nos terminator (NosT) was amplified using NosT-5-EcoRI and NosT-3-XhoI-AscI-Xbal-PmeI. After EcoRI digestion, NosT was inserted into EcoRI-Sfol-digested pUC18 to generate pUC-NosT-MCS.

From p1380N-sgRNA (Jia et al., 2017a), the CaMV 35S promoter was amplified using the primers CaMV35-5-XhoI and CaMV35-crRNA-3, and the crRNA-cspds-NosT fragment was amplified using the primers crRNA-cspds-P and NosT-3-AscI. Through three-way ligation, XhoI-cut CaMV35S and AscI-digested crRNA-cspds-NosT were inserted into XhoI-AscI-treated pUC-NosT-MCS to build pUC-NosT-crRNA-cspds. Subsequently, the EcoRI-NosT-crRNA-cspds-NosT-PmeI fragment was cloned into EcoRI-PmeI-cut GFP-p1380N-35S-LbCas 12a to construct GFP-p1380N-35S-LbCas12a-crRNA-cspds (FIG. 24A), which was designed to edit the sequence located 15641 bp downstream of the ATG in CsPDS. See FIG. 25, which shows a schematic). The CsPDS-targeting crRNA is located in the ninth exon of CsPDS, 15641 bp downstream of CsPDS ATG. The intron parts were indicated by gray.

Similarly, the CaMV 35S promoter was PCR-amplified using the primers CaMV35-5-XhoI and CaMV35-crRNA-3, and the crRNA1-lobp-NosT was PCR-amplified using the primers crRNA-lobp-P and NosT-3-AscI. XhoI-cut CaMV35S and AscI-digested crRNA-lobp-NosT were inserted into XhoI-AscI-cut pUC-NosT-MCS to build pUC-NosT-35S-crRNA-lobp through three-way ligation. With GFP-p1380N-SaCas9/35S-sgRNA1: AtU6-sgRNA2 as a template (Jia et al., 2017a), the AtU6-1 was amplified using AtU6-1-5-AscI and AtU6-1-crRNA-3. Using crRNA-lobp-P and NosT-3-SpeI, the crRNA2-lobp-NosT fragment was amplified. Through three-way ligation, AscI-cut AtU6-1 and SpeI-digested crRNA2-lobp-NosT were inserted into AscI-XbaI-treated pUC-NosT-35S-crRNA-lobp to form pUC-NosT-crRNA-lobp. Finally, the EcoRI-NosT-35S-crRNA-lobp-NosT-AtU6-1-crRNA-lobp-NosT-PmeI fragment was cloned into EcoRI-PmeI-cut GFP-p1380N-35S-LbCas 12a to construct GFP-p1380N-35S-LbCas12a-crRNA-lobp (see FIG. 24B); a 23 bp crRNA, driven by CaMV 35S and AtU6-1, was employed to target EBEPthA4-CsLOBP), or into EcoRI-PmeI-cut GFP-p1380N-Yao-LbCas12a to form GFP-p1380N-Yao-LbCas12a-crRNA-lobp (see FIG. 24C). A 23 bp sgRNA of the GFP-p1380N-Yao-LbCas12a-crRNA-lobp primer was designed to edit the EBEPthA4-CsLOBP. CsVMV, the cassava vein mosaic virus promoter; GFP, green fluorescent protein; CaMV 35S and 35T, the cauliflower mosaic virus 35S promoter and its terminator; AtU6-1, *Arabidopsis* U6-1 promoter.

Using forward primer LOBP1 and reverse primer LOBP2 (Jia et al., 2016), the mutant Type II CsLOBP, which contains a thymine deletion, was amplified from transgenic line #D35s4. After sequencing, the HindIII-BamHI-digested PCR fragment was inserted into HindIII-BamHI-treated p1380-35S-GUSin to form binary vectors p1380-MTII CsLOBP-GUSin (scc FIG. 31B). Binary vectors p1380-AtHSP70BP-GUSin, p1380-TI CsLOBP-GUSin and p1380-TII CsLOBP-GUSin were developed previously (Jia et al., 2016). Through the electroporation method, the binary vectors were introduced into *A. tumefaciens* strain EHA105. Recombinant *Agrobacterium* cells were cultivated for Xcc-facilitated agroinfiltration or epicotyl citrus transformation. For primer sequences, see Table 8, below.

TABLE 8

Primer Sequences.

| Primer Name | Primer Sequence | SEQ ID NO |
|---|---|---|
| CaMV35-5-SbfI | 5'-AGGTCCTGCAGGTCCCCAGATTAGCCTTTTCAATTT-3' | 105 |
| CaMV35-3-KpnI-BamHI | 5'-AGGTGGATCCGGTACCTATCGTTCGTAAATGGTGAAAATT-3' | 106 |
| Yao-5-SbfI | 5'-AGGTCCTGCAGGATGGGAAATTCATTGAAAACCCT-3' | 107 |
| Yao-3-KpnI 0 | 5'-AGGTGGTACCGGATCCTTTCTTCTTCTCGTTGTTGTACTTCAT-3' | 108 |
| NosT-5-EcoRI | 5'-AGGATCCACCGGTGCACGAATTCCGAATTTCCCCGATCGTTCAA-3' | 109 |
| NosT-3-XhoI-AscI-XbaI-PmeI | 5'-AGTTTAAACTCTAGACAAGGCGCGCCATTTAAATCTCGAGCCGATC TAGTAACATAGATGACAC-3' | 110 |
| CaMV35-5-XhoI | 5'-ACTCGAGACTAGTACCATGGTGGACTCCTCTTAA-3' | 111 |
| CaMV35-crRNA-3 | 5'-phosphorylated CTACACTTAGTAGAAATTCCTCTCCAAATGAAATGAA CTTCCT-3' | 112 |
| crRNA-cspds-P | 5'-phosphorylated-ATAGGTAACTGAAGCTTGAGGATATGAATTTCCCCGA TCGTTCAAACATTTG-3' | 113 |
| NosT-3-AscI | 5'-ACCTGGGCCCGGCGCGCCGATCTAGTAACATAGATGA-3' | 114 |
| crRNA-lobp-P | 5'-phosphorylated-ATCTTTCTCTATATAAACCCCTTTTGAATTTCCCCGATCGTTCAAA CATTTG-3' | 115 |

TABLE 8-continued

| Primer Sequences. | | |
|---|---|---|
| Primer Name | Primer Sequence | SEQ ID NO |
| AtU6-1-5-AscI | 5'-AGGTGGCGCGCCTCTTACAGCTTAGAAATCTCAAA-3' | 116 |
| AtU6-1-crRNA-3 | 5'-phosphorylated-CTACACTTAGTAGAAATTCAATCACTACTTCGTCTCT AACCATATA-3' | 117 |
| NosT-3-SpeI | 5'-AGGTACTAGTCCGATCTAGTAACATAGATGACA-3' | 118 |

Figure 25:
FIG. 25 is a schematic map of CsPDS.
Figure 26:
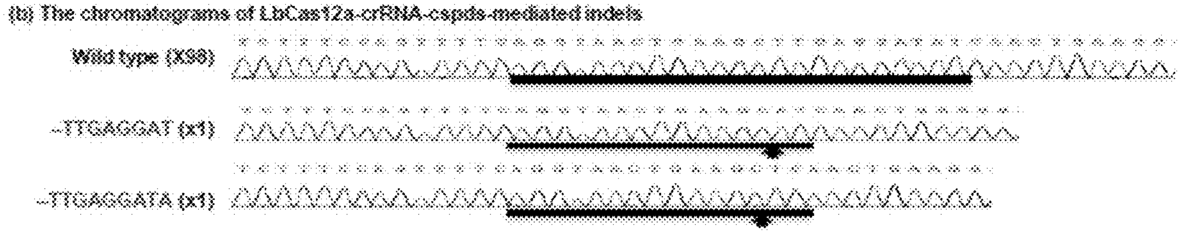
FIG. 26A shows the targeted mutations induced by GFP-p1380N-35S-LbCas12a-crRNA-cspds in the 487 CsPDS gene in Duncan grapefruit (SEQ ID NOs: 74, 75, and76. The crRNA-targeted CsPDS sequence is highlighted in red, 488 and the indels are shown in purple.
FIG. 26B shows the CRISPR-LbCas 12a-mediated indel chromatograms in the 489 CsPDS gene. Mutations are indicated by arrows.

CRISPR-LbCas12a was used to edit the ninth exon of CsPDS in Duncan plants via transient expression (See FIG. 25) using Xcc-facilitated agroinfiltration (for methods see Jia and Wang, 2014b, which is hereby incorporated by reference for method disclosures). The binary vector GFP-p1380N-35S-LbCas12a-crRNA-cspds was constructed and agroinfiltrated into Duncan leaves (FIG. 24A), which were pretreated with Xcc (Jia and Wang, 2014b). See FIG. 24A. A 23 bp crRNA was used to target the CsPDS coding region, 473 which is located in the ninth extron. Genomic DNA that was extracted from treated Duncan leaves four days later was subjected to PCR amplification, vector ligation, and colony sequencing. The sequencing results confirmed that two colonies harbored LbCas12a-directed CsPDS indels among the 100 random colonies sequenced here. See results in FIG. 26). These results show that CRISPR/LbCfp1 is functional for citrus genome editing.

Example 10: Targeted Mutagenesis of EBEPthA4-CsLOBP in Duncan Grapefruit

Figure 24:
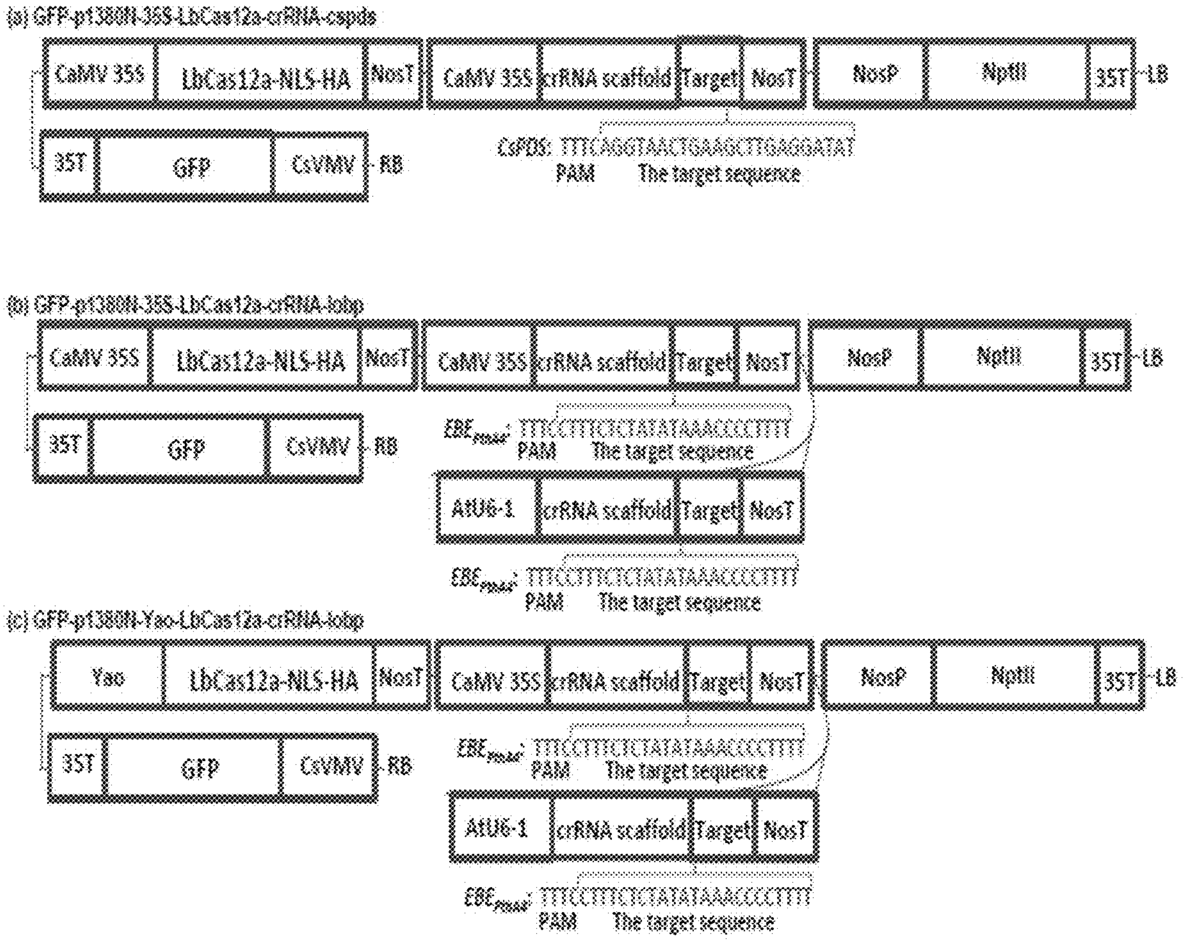
FIG. 24A is a schematic diagram of GFP-p1380N-472 35S-LbCas12a-crRNA-cspds. SEQ ID NO:72 is shown.
FIG. 24B is a schematic diagram of GFP-p1380N-35S-LbCas12a-474 crRNA-lobp. SEQ ID NO: 73 is shown.
FIG. 24C is a schematic diagram of GFP-p1380N-Yao-LbCas 12a-crRNA-lobp. SEQ ID NO:73 is shown. In these figures: Yao indicates Yao promoter; LbCas 12a-NLS-HA, the LbCas 12a endonuclease containing nuclear location signal and HA tag at its C-terminal. Targets were highlighted in blue; PAM, protospacer-adjacent motif, were highlighted in red. crRNA scaffold is the CRISPR RNA scaffold; NosP and NosT are the nopaline synthase gene promoter and its terminator; NptII is neomycin phosphotransferase II; and LB and RB are the left and right borders of the T-DNA region.
Figure 29:
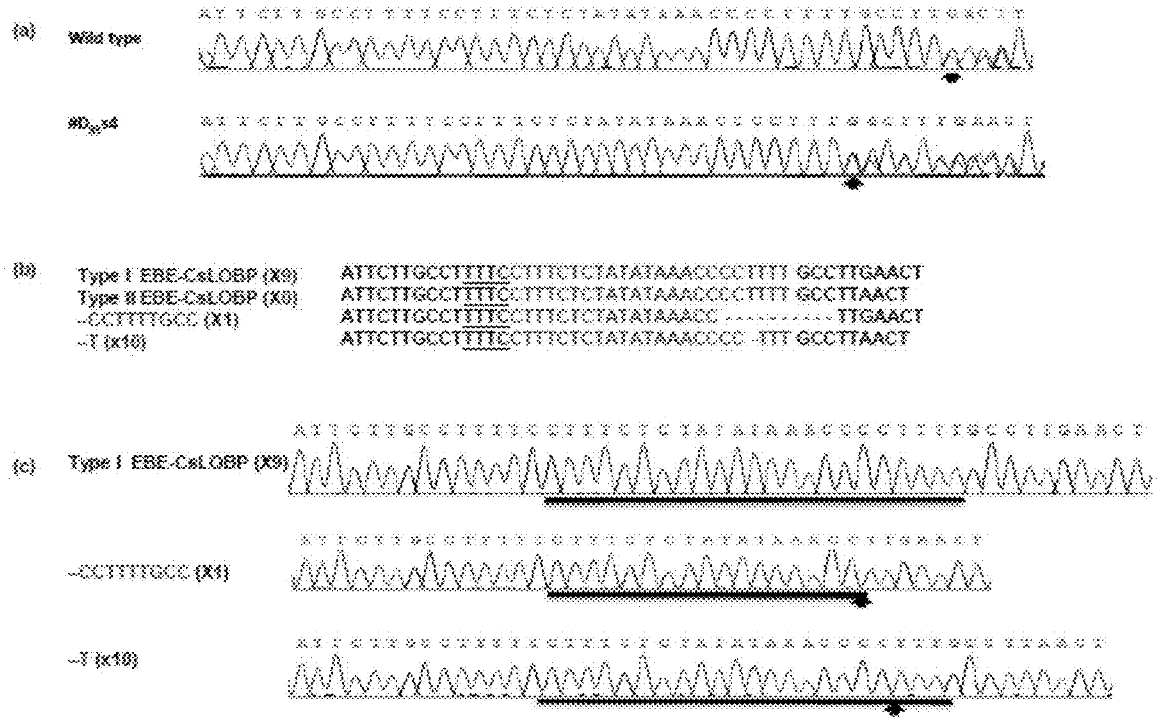
FIG. 29A presents chromatograms of direct PCR product sequencing showing SEQ ID NOs: 79 and 80).
FIG. 29B shows targeted CsLOBP mutations directed by GFP-p1380N-35S-LbCas12a-crRNA-lobp in transgenic Duncan #D35s4; SEQ ID NOs: 81, 82, 983, and 84).

Two binary vectors, GFP-p1380N-35S-LbCas12a-crRNA-lobp and GFP-p1380N-Yao-LbCas12a-crRNA-lobp, were constructed to edit EBEPthA4-CsLOBP. When driven by either the CaMV35 promoter or the Yao promoter, SpCas9 was successfully used to edit the citrus genome in a previous study (Jia et al., 2016; Peng et al., 2017; Zhang et al., 2017). Here, the CaMV 35S promoter and the Yao promoter were employed to drive LbCas 12a expression (see FIG. 24B). However, in transgenic citrus, both CaMV 35S and AtU6-1 were successfully used to drive sgRNAs for CRISPR-SpCas9 (Jia et al., 2016; Peng et al., 2017) and for CRISPR-SaCas9 (Jia et al., 2017a). To guarantee that the crRNA could be efficiently expressed in LbCas12a-crRNA-lobp-transformed citrus, both CaMV 35S and AtU6-1 were employed to drive crRNA (FIG. 24B and FIG. 24C). There are two types of CsLOBPs in Duncan grapefruits, Type I CsLOBP and Type II CsLOBP (see FIG.-32) (Jia et al., 2016; Peng et al., 2017). A single crRNA was selected to target the conserved EBEPthA4-CsLOBP region (see FIG. 24B, FIG. 24C, and FIG. 27). By contrast, a single sgRNA could not be used to modify both types of CsLOBPs, since the sgRNA targeting region in the EBEPthA4-CsLOBP contains single nucleotide polymorphisms between the two types of CsLOBPs in Duncan plants (Jia et al., 2006). Unexpectedly, no indels were detected in the Yao-LbCas 12a-transformed Duncan plants where Duncan grapefruit was transformed by Yao-LbCas12a, and AtU6-1 and CaMV 35S were employed to drive crRNA (see FIG. 29C).

A citrus transformation was performed as reported before (Jia et al., 2017b). In summary, Duncan epicotyl explants were coincubated with recombinant *Agrobacterium* cells harboring a binary vector, with either GFP-p1380N-35S-LbCas12a-crRNA-lobp or GFP-p1380N-Yao-LbCas 12a-crRNA-lobp. Five weeks later, all the explants were inspected for GFP fluorescence. Later, GFP-positive sprouted shoots were micrografted onto 'Carrizo' citrange rootstock plants [*Citrus sinensis* (L.) Osbeck x *Poncirus trifoliata* (L.) Raf.] for continuous cultivation and further analysis. The transgenic plants were subjected to PCR analysis with a pair of primers, Npt-Seq-5 (5'-TGTGCTCGACGTTGTCACTGAAGC-3') (SEQ ID NO: 119) and 35T-3 (5'-TTCGGGGGATCTGGATTTTAGTAC-3') (SEQ ID NO: 120).

Figure 28:
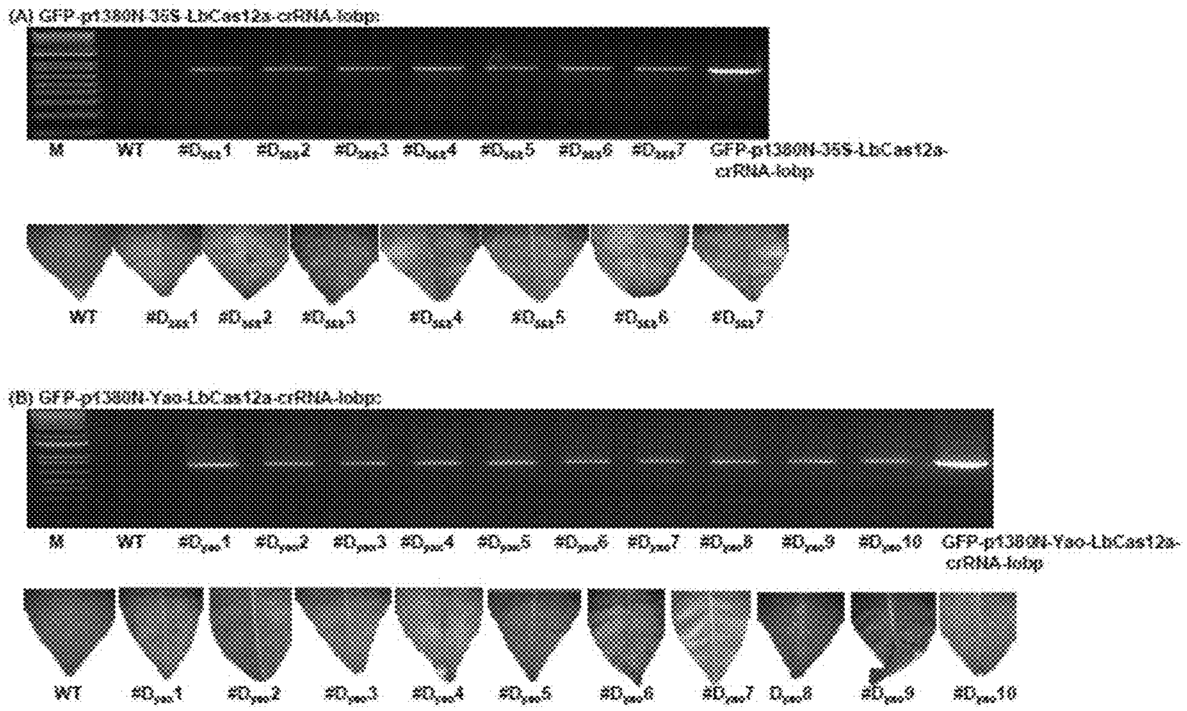
FIG. 28A shows seven GFP-p1380N-35S-LbCas12a-crRNA-lobp-transformed Duncan grapefruit plants (from #D35s1 to #D35s7), evaluated by PCR analysis using the primers Npt-Seq-5 and 35T-3.
FIG. 28B shows 10 GFP-p1380N-Yao-LbCas12a-crRNA-lobp-transformed Duncan plants (from #DYaol to #DYao10) were tested by PCR analysis and GFP observation.

The Duncan epicotyls were transformed by *Agrobacterium* cells containing the binary vector. A total of seven GFP-p1380N-35S-LbCas12a-crRNA-lobp-transformed Duncan plants (#D35s1 to #D35s7) were generated, and ten GFP-p1380N-Yao-LbCas12a-crRNA-lobp transformants (#Dyaol to #Dyao10) were generated. GFP fluorescence was detected in all of the transgenic plants (FIG. 28A and FIG. 28B). Using Npt-Seq-5 and 35T-3 as a pair of primers, the transgenic Duncan plants were further verified by PCR amplification. FIG. 28A: Seven GFP-p1380N-35S-LbCas12a-crRNA-lobp-transformed Duncan grapefruit plants (from #D35s1 to #D35s7) were evaluated by PCR analysis using the primers Npt-Seq-5 and 35T-3. The plasmid GFP-p1380N-35S-LbCas12a-crRNA-lobp was used as a positive control. The seven plants were GFP-positive. The wild-type grapefruit plant did not show GFP. FIG. 28B: Ten GFP-p1380N-Yao-LbCas 12a-crRNA-lobp-transformed Duncan plants (from #DYaol to #DYao10) were tested by PCR analysis and GFP observation. M, 1 kb DNA ladder; WT, wild type.

As expected, a band measuring 750 128 bp was observed in transgenic plants and the positive plasmid control, whereas there was no band in the wild-type Duncan grapefruit sample (see FIG. 28A and FIG. 28B). The results indicated that LbCas 12a-crRNA-lobp-transformed Duncan plants were successfully established.

Example 11: Analysis of LbCas12a-crRNA-Lobp-Mediated Indels in Duncan Transformants The PCR products were sequenced directly to evaluate the LbCas 12a-crRNA-lobp-mediated indels in seventeen transgenic Duncan plants. See Table 9, below. The results indicated that one transgenic Duncan line, #D35s4, contains changes in its chromatogram in comparison to that of the wild type (see results in FIG. 29A), whereas the other lines exhibited no changes (see Table 9). It should be noted that Type I CsLOBP has one more G nucleotide next to EBEPthA4 than the Type II CsLOBP (see FIG. 27), and thus, double peaks were present from the unique guanine in wild-type Duncan plants (see FIG. 29A) (Jia et al., 2016). In FIG. 29A: The chromatograms of direct PCR product sequencing. Using the primers LOBP2 and LOBP3, the CsLOBPs were amplified from wild-type Duncan and #D35s4, and the CsLOB4 primer was employed for direct sequencing. The beginnings of double peaks are highlighted by arrows.

TABLE 9

LbCas12a-crRNA-lobp-mediated Indel Analysis and Canker Resistance of Transgenic Duncan.

| Lines Analysis | $\#D3_{5s}1$ | $\#D_{35s}2$ | $\#D_{35s}3$ | $\#D_{35s}4$ | $\#D_{35s}5$ | $\#D_{35s}6$ | $\#D_{35s}7$ |
|---|---|---|---|---|---|---|---|
| Direct sequencing of PCR products | WT | WT | WT | Mutant | WT | WT | WT |
| Sequencing of 20 random colonies | 5 Mutants | No Mutant | No Mutant | 11 Mutants | No Mutant | No Mutant | 3 mutants |
| Mutation rates | 15% | 0% | 0% | 55% | 0% | 0% | 15% |
| Xcc (PthA/I)-eliciting canker | Yes | Yes | Yes | Yes | Yes | Yes | Yes |
| dCsLOB.4-eliciting canker | Yes | Yes | Yes | Ni | Yes | Yes | Yes |

| Lines Analysis | $\#D_{y50}1$ | $\#D_{y50}2$ | $\#D_{y50}3$ | $\#D_{y50}4$ | $\#D_{y50}5$ | $\#D_{y50}6$ | $\#D_{y50}6$ | $\#D_{y50}6$ | $\#D_{y50}6$ | $\#D_{y50}6$ |
|---|---|---|---|---|---|---|---|---|---|---|
| Direct sequencing of PCR products | WT | WT | WT | WT | WT | WT | WT | WT | WT | WT |
| Sequencing of 20 random colonies | No mutant | No mutant | No mutant | No mutant | No mutant | No mutant | No mutant | No mutant | No mutant | No mutant |
| Mutation rates | 0 | 0 | 0 | 0 | 0 | 0 | 0 | 0 | 0 | 0 |
| Xcc (PthA/I)-eliciting canker | Yes | Yes | Yes | Yes | Yes | Yes | Yes | Yes | Yes | Yes |
| dCsLOB.4-eliciting canker | Yes | Yes | Yes | Yes | Yes | Yes | Yes | Yes | Yes | Yes |

Next, colony sequencing was performed to analyze CRISPR-LbCas12a-mediated mutations in transgenic Duncan grapefruit plants. Among the 20 colonies sequenced for each transgenic line, no mutations were observed in all the Yao-LbCas 12a-transformed Duncan plants and four 35S-LbCas 12a transformed lines (#D35s2, #D35s3, #D35s5 and D35s6) (see Table 9), whereas #D35s1, #D35s4 and #D35s7 contained indels (see FIG. 29B, FIG. 29C and FIG. 35). FIG. 29B: Targeted CsLOBP mutations directed by GFP-p1380N-35S-LbCas12a-crRNA-lobp in transgenic Duncan #D35s4. The crRNA-targeted sequence is shown in red, and the indels are highlighted in purple; FIG. 29C: CRISPR-LbCas12a-mediated indel chromatograms in CsLOBP. Arrows are used to indicate the mutation sites.

The mutation rates of #D35s1, #D35s4 and #D35s7 were 15%, 55% and 15%, respectively (see Table 9); The Type II EBE-CsLOBPs were 100% mutated according to the results in FIG. 29. All the mutation genotypes were deletions (see FIG. 29B and FIG. 29C). Specifically, the deletion of one thymine took place only in Type II EBE-CsLOBP among the sequenced colonies, whereas a longer deletion occurred only on Type I EBE-CsLOBP (see FIG. 29B, FIG. 29C, and FIG. 30). Most importantly, as expected, both Type I EBE-CsLOBP and Type II EBE-CsLOBP were readily modified by the single crRNA targeting sequence (see FIG. 29B, FIG. 29C, and FIG. 30).

Example 12: #D35s4 Transgenic Plant Alleviating XccΔpthA4: DCsLOB1.4 Infection

Seventeen transgenic Duncan plants were treated with Xcc at a concentration of $5\times10^8$ CFU/mL. Canker symptoms were observed in all transgenic lines, similar to the wild-type control plants, at five days post-inoculation (DPI). See Table 9). The results are consistent with those of a previous study, in which canker could readily develop on Cas9/sgRNA: CsLOBP1-transformed Duncan plants harboring one intact CsLOBP allele (Jia et al., 2016).

dCsLOB1.1 and dCsLOB1.2 were developed to activate two types of CsLOBPs (Hu et al., 2014). The dCsLOB1.1 binding site is 5'TAAAGCAGCTCCTCCTC3' (SEQ ID NO:121) and the dCsLOB1.2 recognition sequence is 5'TATAAACCCCTTTTGCCTT3' (SEQ ID NO: 122) (see FIG. 27). Later, dCsLOB1.3 was built to recognize the Type I EBE-CsLOBP allele only, the binding sequence of which is 5'CCTTTTGCCTTGAACTTT3' (SEQ ID NO:123) (scc FIG. 27) (Jia ct al., 2016). Two Cas9/sgRNA: CsLOBP1-transformed lines with the highest mutation rate for the Type I EBE-CsLOBP allele could resist XccΔpthA4: dCsLOB1.3 (Jia et al., 2016). Here, a novel dTALE, dCsLOB1.4 was constructed. See FIG. 31A). The repeat variable di-residues (RVDs) specifically bind to the 21-nucleotide sequence 5'TAAACCCCTTTTGCCTTAACTT3' (SEQ ID NO:151) in the Type II CsLOBP (see FIG. 27 and FIG. 31A), whereas one extra "G" nucleotide is present in the Type I CsLOBP and one "T" nucleotide is absent from the mutated Type II CsLOBP compared to the wild-type II CsLOBP.

Figure 31:
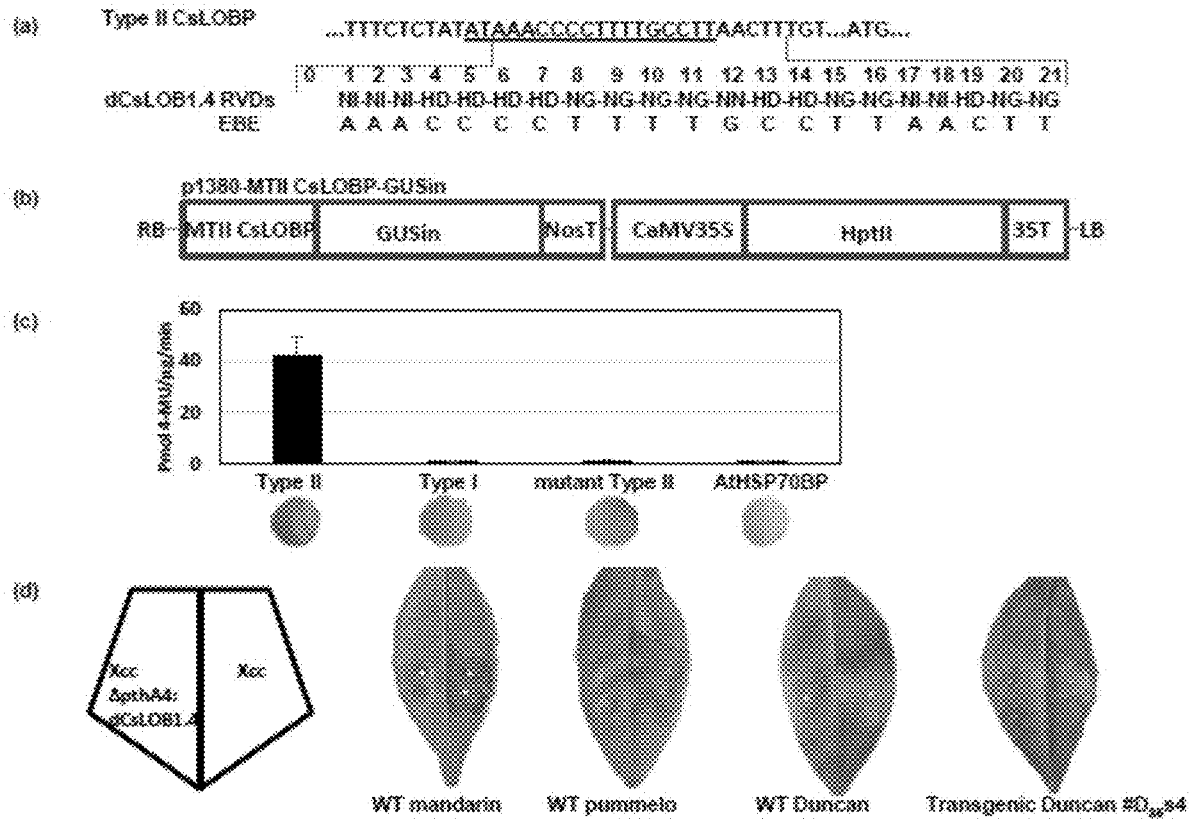
FIG. 31 relates to transgenic Duncan #D35s4 resistant against Xcc306ΔpthA4: dCsLOB1.4.

The designed TALE dCsLOB1.4 was developed here to specifically activate Type II EBE-CsLOBP (see FIG. 31A), but not the Type I CsLOBP and mutant Type II CsLOBP. To confirm dCsLOB1.4-specific recognition, the binary vectors p1380-AtHSP70BP-GUSin, p1380-TI CsLOBP-GUSin, p1380-TII CsLOBP-GUSin, and p1380-MTII CsLOBP-GUSin (FIG. 31B) were used to perform an XccΔpthA4: dCsLOB1.4-facilitated agroinfiltration. p1380-AtHSP70BP-GUSin was used as a negative control (Jia and Wang, 2014b). Via 523 Xcc306ΔpthA4: dCsLOB1.4-facilitated agroinfiltration, a quantitative GUS assay and GUS histochemical staining were used to study the effects of Xcc-derived dCsLOB1.4 on CsLOBPs. Notably, only under the control of Type II CsLOBP could GUS expression be activated. The experiments were repeated twice. As expected, only Type II CsLOBP-driven GUS expression could be specifically activated, whereas neither MTII CsLOBP-GUSin nor TI CsLOBP-GUSin was activated (FIG. 31C). The results indicated that dCsLOB1.4 specifically recognizes the Type II CsLOBP.

Figures 30A, 30B:
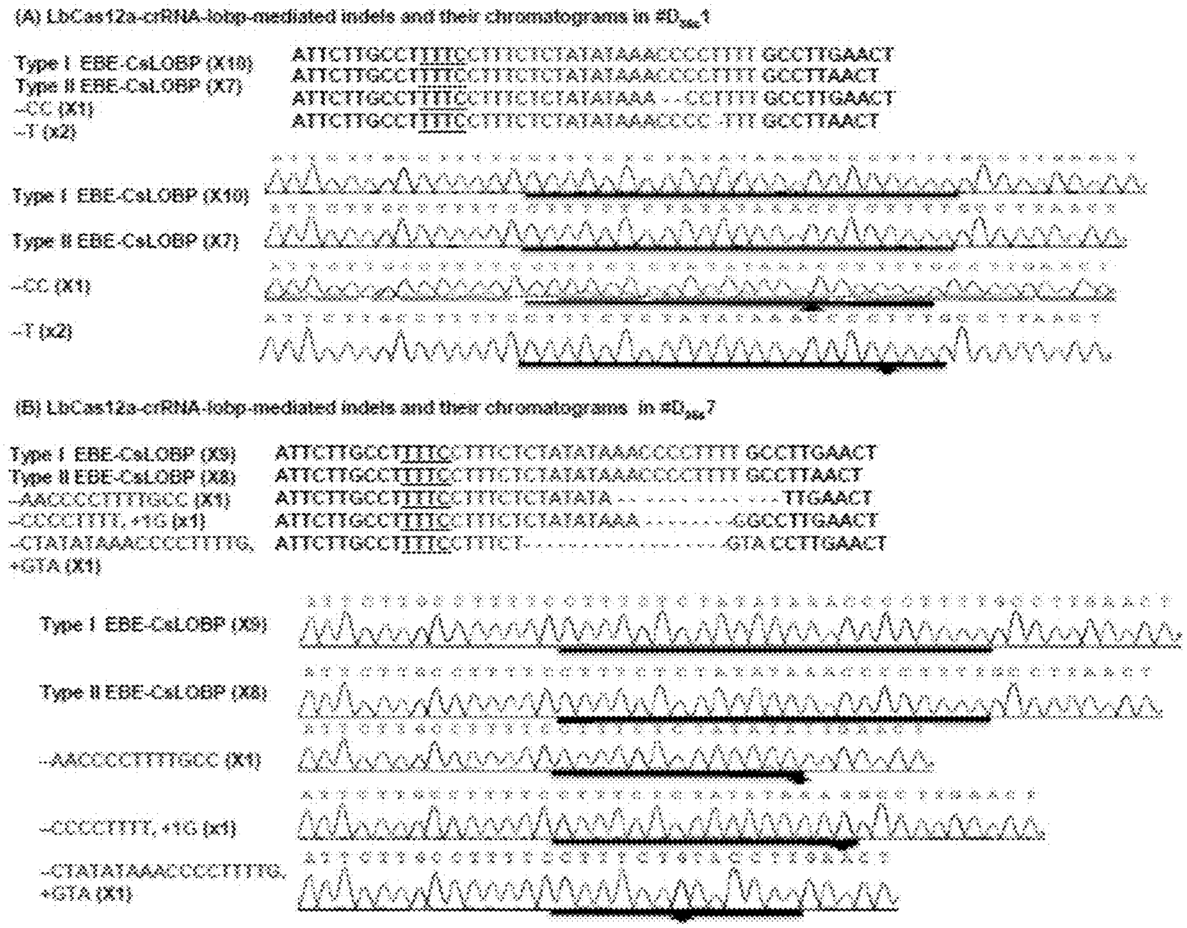
FIG. 30A and FIG. 30B show CRISPR-LbCas 12a-mediated CsLOBP indels in transgenic Duncan #D35S1 (FIG. 30A; SEQ ID NOs: 85, 86. 87, and 88) and #D35$7 (FIG. 30B; SEQ ID NOs: 89, 90, 91, 92, and 93).

The mandarin has two Type I EBE-CsLOBP alleles, and the pummelo contains two Type II EBE-CsLOBP (Wu et al., 179 2014). Five days post-Xcc inoculation, citrus canker symptoms were observed on mandarin (containing Type I CsLOBP), pummelo (containing Type II CsLOBP), Duncan grapefruit (containing Type I CsLOBP and Type II CsLOBP) and transgenic Duncan #D35s4 (containing Type I CsLOBP and mutant Type II CsLOBP) grapefruit, since the PthA4 derived from Xcc could activate Type I CsLOBP and Type II CsLOBP. In the presence of XccΔpthA4: dCsLOB1.4, canker symptoms develop on pummelo but not on mandarin (FIG. 30D). Five days after Xcc306ΔpthA4: dCsLOB1.4 treatment, citrus canker symptoms were not observed on mandarin and transgenic Duncan #D35s4, since dCsLOB1.4 could not activate Type I CsLOBP and mutant Type II CsLOBP. The results further confirmed that, as expected, dCsLOB1.4 specifically activates Type II EBE-CsLOBP, resulting in canker on pummelo. After XccΔpthA4: dCsLOB1.4 infection, #D35s4 showed alleviated XccΔpthA4: dCsLOB1.4 infection owing to its 100% mutation on Type II EBE-CsLOBP (see FIG. 31B, FIG. 31C, FIG. 31D, and Table 9), whereas canker symptoms were observed in other transgenic Duncan lines (Table 9).

Example 14: Superior Editing Efficiency of CsU6-2 Promoter

FIG. 32A provides an alignment of selected CsU6 promoters with the *Arabidopsis* U6-26 promoter; FIG. 32B presents a mutation analysis as measured by the loss of the BsrGI restriction enzyme site due to targeted mutagenesis at the selected BsrGI site. The BsrGI-resistant band shows edited alleles. The comparison data for the editing efficiency between CsU6-2 and AtU6-26 in FIG. 32C shows that the CsU6-2 promoter provides about twice the editing efficiency of the AtU6-1 promoter (17%-30% versus 10%-15%).

REFERENCES

All references listed below and throughout the specification are hereby incorporated by reference in their entirety.

1. Adli, M. (2018) The CRISPR tool kit for genome editing and beyond. *Nat. Commun.,* 9.
2. Anand, A. and Jones, T. J. (2018) Advancing *Agrobacterium*-Based Crop Transformation and Genome Modification Technology for Agricultural Biotechnology. In: *Agrobacterium* Biology: From Basic Science to Biotechnology (Gelvin, S. B., ed), pp. 489-507. Cham: Springer International Publishing.
3. Andersson, M., Turesson, H., Olsson, N., Fält, A., and Ohlsson, P. (2018) *Genome editing in potato via CRISPR-Cas9 ribonucleoprotein.* 378-384.
4. Bae, S., Park, J., Kim, J. S. (2014) Cas-OFFinder: a fast and versatile algorithm that searches for 372 potential off-target sites of Cas9 RNA-guided endonucleases. *Bioinformatics* 30, 1473-1475.
5. Begemann, M. B., Gray, B. N., January, E., Gordon, G. C., He, Y., Liu, H., Wu, X., Brutnell, T. P., 374 Mockler, T. C. and Oufattole, M. (2017). Precise insertion and guided editing of higher plant 375 genomes using Cpf1 CRISPR nucleases. *Sci Rep* 7, 11606.
6. Bergès, T., and Barreau, C. 1989. Heat shock at an elevated temperature improves transformation efficiency of protoplasts from *Podospora anserina*. J Gen Microbiol 135:601-604.
7. Chen, L., Li, W., Katin-grazzini, L., Ding, J., Gu, X., Li, Yanjun, et al. (2018) A method for the production and expedient screening of CRISPR/Cas9-mediated non-transgenic mutant plants.
8. Clark, K., Franco, J. Y., Schwizer, S., Pang, Z., Hawara, E., Liebrand, T. W. H., et al. (2018) An effector from the Huanglongbing-associated pathogen targets citrus proteases. *Nature Communications,* 9.
9. Duan, S., Jia, H., Pang, Z., Teper, D., White, F., Jones, J., et al. (2018) Functional characterization of the citrus canker susceptibility gene CsLOB1. *Mol. Plant Pathol.,* 19, 1908-1916.
10. El-Otmani, M., Ait-Oubahou, A., and Zacarías, L. (2011) Citrus spp.: orange, mandarin, tangerine, clementine, grapefruit, pomelo, lemon and lime. *Postharvest Biol. Technol. Trop. Subtrop. Fruits,* 437-516e.
11. Endo, A., Masafumi, M., Kaya, H. and Toki, S. (2016). Efficient targeted mutagenesis of rice and tobacco genomes using Cpf1 from *Francisella novicida. Sci Rep* 6, 38169.
12. Fan, D., Liu, T., Li, C., Jiao, B., Li, S., Hou, Y., and Luo, K. (2015) Efficient CRISPR/Cas9-mediated Targeted Mutagenesis in *Populus* in the First Generation. *Sci. Rep.,* 5, 1-7.
13. Fang, Y., Xie, K., and Xiong, L. (2014) Conserved miR164-targeted NAC genes negatively regulate drought resistance in rice. *Journal of Experimental Botany,* 65, 2119-2135.
14. Ference, C. M., Gochez, A. M., Behlau, F., Wang, N., Graham, J. H., and Jones, J. B. (2018) Recent advances in the understanding of *Xanthomonas citri* ssp. *citri* pathogenesis and citrus canker disease management. Mol *Plant Pathol* 19, 1302-1318.
15. Ferenczi, A., Pyott, D. E., Xipnitou, A. and Molnar, A. (2017) Efficient tar-geted DNA editing and replacement in *Chlamydomonas reinhardtii* using Cpf1 ribonucleoproteins and single-stranded DNA. *Proc Natl Acad Sci USA* 114, 13567-13572.
16. Fu, Y., Foden, J. A., Khayter, C., Maeder, M. L., Reyon, D., Joung, J. K. and Sander, J. D. (2013). 385 High-frequency off-target mutagenesis induced by CRISPR-Cas nucleases in human cells. *Nat* 386 *Biotechnol* 31, 822-826.
17. Hu, X., Wang, C., Liu, Q., Fu, Y. and Wang, K. (2017). Targeted mutagenesis in rice using 388 CRISPR-Cpf1 system. *J Genet Genomics* 44, 71-73.
18. Hu, Y., Zhang, J., Jia, H., Sosso, D., Li, T., Frommer, W. B., Yang, B., White, F. F., Wang, N. and Jones, J. B. (2014) Lateral organ boundaries 1 is a disease susceptibility gene for citrus bacterial canker disease. *Proc Natl Acad Sci USA* 111, E521-529.
19. Hu, Y., Duan, S., Zhang, Y., Shantharaj, D., Jones, J. B., and Wang, N. 2016. Temporal Transcription Profiling of Sweet Orange in Response to PthA4-Mediated *Xanthomonas citri* subsp. *citri* Infection. Phytopathology 106:442-451.
20. Islam, W. (2018) CRISPR-Cas9; an efficient tool for precise plant genome editing. *Mol Cell Probes* 39, 47-52.
21. Jia, H. and Wang, N. (2014a) Targeted Genome Editing of Sweet Orange Using Cas9/sgRNA. *PLOS One* 9, e93806.

22. Jia, H. and Wang, N. (2014b) Xcc-facilitated agroinfiltration of citrus leaves: a tool for rapid functional analysis of transgenes in citrus leaves. *Plant Cell Rep* 33, 1993-2001.
23. Jia, Hongge, Orbovic, Vladimir, Jones, B., J., and Wang, N. 2015. Modification of the PthA4 effector binding elements in Type I CsLOB1 promoter using Cas9/sgRNA to produce transgenic Duncan grapefruit alleviating XccΔpthA4: dCsLOB1.3 infection. Plant Biotechnol J.
24. Jia, H., Orbovic, V., Jones, J. B., and Wang, N. 2016a. Modification of the PthA4 effector binding elements in Type I CsLOB1 promoter using Cas9/sgRNA to produce transgenic Duncan grapefruit alleviating XccΔpthA4: dCsLOB1.3 infection. Plant Biotechnol J 14:1291-1301.
25. Jia, H., Zhang, Y., Orbović, V., Xu, J., White, F. F., Jones, J. B., and Wang, N. 2016b. Genome editing of the disease susceptibility gene CsLOB1 in citrus confers resistance to citrus canker. Plant Biotechnol J.
26. Jia, H., Orbovic, V., Jones, J. B. and Wang, N. (2016) Modification of the PthA4 effector binding elements in Type I CsLOB1 promoter using Cas9/sgRNA to produce transgenic Duncan grapefruit alleviating XccΔpthA4: dCsLOB1.3 infection. *Plant Biotechnol J* 14, 1291-1301.
27. Jia, H., Xu, J., Orbović, V., Zhang, Y. and Wang, N. (2017a) Editing citrus gneome via SaCas9/sgRNA system. *Front Plant Sci* (doi.org/10.3389/fpls.2017.02135).
28. Jia, H., Zhang, Y., Orbović, V., Xu, J., White, F. F., Jones, J. B. and Wang, N. (2017b) Genome editing of the disease susceptibility gene CsLOB1 in citrus confers resistance to citrus canker. *Plant Biotechnol J* 15, 817-823.
29. Kim, D., Kim, J., Hur, J. K., Been, K. W., Yoon, S. H., and Kim, J. S. (2016) Genome-wide analysis reveals specificities of Cpf1 endonucleases in human cells. *Nat.* 5 *Biotechnol.,* 34, 863-868.
30. Kim, H., Kim, S. T., Ryu, J., Kang, B. C., Kim, J. S. and Kim, S. G. (2017). CRISPR/Cpf1-mediated DNA-free plant genome editing. *Nat Commun* 8, 14406.
31. Kleinstiver, B. P., Tsai, S. Q., Prew, M. S., Nguyen, N. T., Welch, M. M., Lopez, J. M., McCaw, Z. R., Aryee, M. J. and Joung, J. K. (2016). Genome-wide specificities of CRISPR-Cas Cpf1 nucleases in human cells. *Nat Biotechnol* 34, 869-874.
32. Kleter, G. A., Kuiper, H. A., and Kok, E. J. (2019) *Gene-Edited Crops: Towards a Harmonized Safety Assessment.* 37, 443-447.
33. Lanza, F. E., Marti, W., Silva, G. J., and Behlau, F. (2018) Characteristics of Citrus Canker 10 Lesions Associated with Premature Drop of Sweet Orange Fruit. *Phytopathology,* 109, 44-51.
34. LeBlanc, C., Zhang, F., Mendez, J., Lozano, Y., Chatpar, K., Irish, V. F., and Jacob, Y. 2018. Increased efficiency of targeted mutagenesis by CRISPR/Cas9 in plants using heat stress. Plant J 93:377-386.
35. Liang, Z., Chen, K., Li, T., Zhang, Y., Wang, Y., Zhao, Q., et al. (2017) Efficient DNA-free genome editing of bread wheat using CRISPR/Cas9 ribonucleoprotein complexes. *Nat. Publ. Gr.,* 8, 1-5.
36. Lin, C., Hsu, C., Yang, L., Lee, L., Fu, J., Cheng, Q., et al. (2018) *Application of protoplast technology to CRISPR/Cas9 mutagenesis: from single-cell mutation detection to mutant plant regeneration.* 1295-1310.
37. Martín-Pizarro, C. and Posé, D. (2018) Genome Editing as a Tool for Fruit Ripening Manipulation. Front *Plant Sci* 9, 1415.
38. Lin, L., He, X., Zhao, T., Gu, L., Liu, Y., Liu, X., et al. (2018) Engineering the Direct Repeat Sequence of crRNA for Optimization of FnCpf1-Mediated Genome Editing in Human Cells. *Mol. Ther.,* 26, 2650-2657.
39. Liu, H., Liu, C., Zhao, Y. hang, Han, X. jie, Zhou, Z. wei, Wang, C., et al. (2018) Comparing successful gene knock-in efficiencies of CRISPR/Cas9 with ZFNs and TALENs gene editing systems in bovine and dairy goat fetal fibroblasts. *J. Integr. Agric.,* 17, 406-414.
40. Moreno-Mateos, M. A., Fernandez, J. P., Rouet, R., Vejnar, C. E., Lane, M. A., Mis,E., Khokha, M. K., Doudna, J. A. and Giraldez A. J. (2017) CRISPR-Cpf1 mediates efficient homology-directed repair and temperature-controlled genome editing. *Nat Commun* 8, 2024.
41. Ohse, M., Takahashi, K., Kadowaki, Y., and Kusaoke, H. 1995. Effects of plasmid DNA sizes and several other factors on transformation of *Bacillus subtilis* ISW1214 with plasmid DNA by electroporation. *Biosci Biotechnol Biochem* 59:1433-1437.
42. Omar, A. A., Dutt, M., Gmitter, F. G., and Grosser, J. W. (2016) Somatic Embryogenesis: Still a Relevant Technique in Citrus Improvement. In: In Vitro Embryogenesis in Higher Plants (Germana, M. A. and Lambardi, M., eds), pp. 289-327. New York, NY: Springer New York.
43. Park, J., Choi, S., Park, S., Yoon, J., Park, A. Y., and Choe, S. (2019) DNA-Free Genome Editing via Ribonucleoprotein (RNP) Delivery of CRISPR/Cas in Lettuce. In: Plant Genome Editing with CRISPR Systems: *Methods and Protocols* (Qi, Y., ed), pp. 337-354. New York, NY: Springer New York.
44. Peng, A., Chen, S., Lei, T., Xu, L., He, Y., Wu, L., Yao, L. and Zou, X. (2017) Engineering canker-resistant plants through CRISPR/Cas9-targeted editing of the susceptibility gene CsLOB1 promoter in citrus. *Plant Biotechnol J* 15, 1509-1519.
45. Port, F. and Bullock, S. L. (2016) Augmenting CRISPR applications in *Drosophila* with tRNA-flanked sgRNAs. *Nat Methods* 13, 852-854.
46. Safari, F., Zare, K., Negahdaripour, M., Barekati-Mowahed, M., and Ghasemi, Y. (2019) CRISPR Cpf1 proteins: structure, function and implications for genome editing. *Cell Biosci.,* 9, 36.
47. Shankar, S., Sreekumar, A., Prasad, D., Das, A. V., and Pillai, M. R. (2018) Genome editing of oncogenes with ZFNs and TALENs: caveats in nuclease design. *Cancer Cell Int.,* 18, 1-11.
48. Shan, Q., Wang, Y., Li, J., and Gao, C. (2014) Genome editing in rice and wheat using the CRISPR/Cas system. *Nature Protocols,* 9, 2395-2410.
49. Stella, S., Alcón, P., and Montoya, G. (2017) Structure of the Cpf1 endonuclease R-loop complex after target DNA cleavage. *Nature,* 5 546, 559-563.
50. Swarts, D. C., van der Oost, J., and Jinek, M. (2017) Structural Basis for Guide RNA Processing and Seed-Dependent DNA Targeting by CRISPR-Cas12a. *Mol. Cell,* 66, 221-233.e4.
51. Tang, X., Lowder, L. G., Zhang, T., Malzahn, A. A., Zheng, X., Voytas, D. F., et al. (2017) A CRISPR-Cpf1 system for efficient genome editing and transcriptional repression in plants. 10 Nat. *Plants,* 3, 1-5.
52. Tang, X., Ren, Q., Yang, L., Bao Y., Zhong Z., He, Y., Liu, S., Qi, C., Liu, B., Wang, Y., et al. (2018). *Single transcript unit CRISPR* 2.0 systems for robust Cas9 and Cas 12a mediated plant genome editing. *Plant Biotechnol J* doi: 10.1111/pbi.13028. https://doi.org/10.1111/pbi.13068
53. Tu, M., Lin, L., Cheng, Y., He, X., Sun, H., Xie, H., et al. (2017) A new lease of life': FnCpf1 possesses DNA cleavage activity for genome editing in human cells. *Nucleic Acids Res.*, 45, 11295-11304.

54. Velasco, R. and Licciardello, C. (2014) A genealogy of the citrus family. *Nat Biotechnol* 32, 433 640-642.
55. Wang, M., Mao, Y., Lu, Y., Tao, X. and Zhu, J. K. (2017). Multiplex gene editing in rice using the CRISPR-Cpf1 system. *Mol Plant* 10, 1011-1013.
56. Wang, M., Mao, Y., Lu, Y., Wang, Z., Tao, X. and Zhu, J.-K. (2018) Multiplex gene editing in rice with simplified CRISPR-Cpf1 and CRISPR-Cas9 systems. *J Int Plant Biol* 60, 626-631.
57. Wang, N.; Trivedi, P. (2013) Citrus Huanglongbing—an old problem with an unprecedented challenge. *Phytopathology.* 103, 652-665.
58. Wang N. Pierson EA, Setubal JC, Xu J, Levy J G., Zhang Y, Li J. Rangel LT, and J., M. (2017) The Candidatus Liberibacter-Host Interface: Insights into Pathogenesis Mechanisms and Disease Control. *Annual Review of Phytopathology.* 55, 451-482.
59. Wang, N., Stelinski, L. L., Pelz-Stelinski, K. S., Graham, J. H., and Zhang, Y. (2017) Tale of the Huanglongbing Disease Pyramid in the Context of the Citrus Microbiome. *Phytopathology* 107, 445 380-387.
60. Wu, W. Y., Lebbink, J. H. G., Kanaar, R., Geijsen, N., and Van Der Oost, J. (2018) Genome editing by natural and engineered CRISPR-associated nucleases. *Nat. Chem. Biol.,* 14, 642-651.
61. Wu GA, Prochnik S, Jenkins J, Salse J, Hellsten U, et al. (2014) Sequencing of diverse mandarin, pummelo and orange genomes reveals complex history of admixture during citrus domestication. *Nat Biotechnol* 32, 656-663.
62. Xu, Q., Chen, L. L., Ruan, X., Chen, D., Zhu, A., Chen, C., Bertrand, D., Jiao, W. B., Hao, B. H., Lyon, M. P., et al. (2013) The draft genome of sweet orange (*Citrus sinensis*). *Nat Genet* 45, 59-451 66. 452.
63. Xu, R., Qin, R., Li, H., Li, D., Li, L., Wei, P., and Yang, J. (2016). Generation of targeted mutant rice using a CRISPR-Cpf1 system. *Plant Biotechnol J* 15, 713-717.
64. Xu, R., Qin, R., Li H., Li J., Yang J. and Wei, P. (2018) Enhanced genome editing in rice using single transcript unit CRISPR-LbCpf1 systems. *Plant Biotechnol J.* https://doi.org/10.1111/pbi.13028
65. Yan, L., Wei, S., Wu, Y., Hu, R., Li, H., Yang, W., and Xie, Q. (2015) High-Efficiency Genome Editing in *Arabidopsis* Using YAO Promoter-Driven CRISPR/Cas9 System. Molecular Plant, 8, 1820-1823.
66. Yin, X., Biswal, A. K., Dionora, J., Perdigon, K. M., Balahadia, C. P., Mazumdar, S., Chater, C., Lin, H. C., Coe, R. A., Kretzschmar, T., Gray, J. E., Quick, W. P. and Bandyopadhyay, A. (2017) CRISPR-Cas9 and CRISPR-Cpf1 mediated targeting of a stomatal developmental gene EPFL9 in rice. Plant Cell Rep 36, 745-757.
67. Zeng, Y., Cui, Y., Zhang, Yong, Zhang, Yanruo, Liang, M., Chen, H., et al. (2018) The initiation, propagation and dynamics of CRISPR-SpyCas9 R-loop complex. *Nucleic Acids Res.,* 46, 350-361.
68. Zetsche, B., Gootenberg, J. S., Abudayyeh, O. O., Slaymaker, I. M., Makarova, K. S., Essletzbichler, P., et al. (2015) Cpf1 Is a Single RNA-Guided Endonuclease of a Class 2 CRISPR-Cas System. *Cell.*

What is claimed is:

1. A method of altering expression of at least one gene product comprising introducing into a citrus plant cell an engineered, non-naturally occurring gene editing system comprising one or more vectors, said citrus plant cell containing and expressing a DNA molecule having a target sequence present within a gene encoding the at least one gene product, said gene editing system comprising: (a) a first regulatory element operable in a plant cell operably linked to at least one nucleotide sequence encoding a CRISPR-Cas system guide RNA (gRNA) that hybridizes with the target sequence, and (b) a second regulatory element operable in a plant cell operably linked to a nucleotide sequence encoding a Type-II CRISPR-associated nuclease, wherein components (a) and (b) are located on same or different vectors of the system, whereby the guide RNA targets the target sequence and the CRISPR-associated nuclease cleaves the DNA molecule, whereby expression of the at least one gene product is altered; and, wherein the CRISPR-associated nuclease and the guide RNA do not naturally occur together; wherein said first regulatory element comprises SEQ ID NO: 6 or a nucleotide sequence having at least 98% nucleotide sequence identity to the nucleotide sequence as set forth in SEQ ID NO: 6; and wherein said class II CRISPR-associated nuclease comprises Cas9 or cpf1.

2. The method of claim 1, wherein said at least one nucleotide sequence encoding said CRISPR-Cas system guide RNA (gRNA) and said at least one nucleotide sequence encoding said Type-II CRISPR-associated nuclease are operably linked to a terminator sequence functional in a plant cell.

3. The method of claim 1, wherein the Cas9 is codon-optimized Cas9 gene having the nucleotide sequence as set forth in of SEQ ID NO:1, or a nucleotide sequence having at least 95%, 97% or 98% nucleotide sequence identity with the nucleotide sequence as set forth in SEQ ID NO: 1.

* * * * *

SEQUENCE LISTING

<160> NUMBER OF SEQ ID NOS: 163

<210> SEQ ID NO 1
<211> LENGTH: 4107
<212> TYPE: DNA
<213> ORGANISM: Artificial Sequence
<220> FEATURE:
<223> OTHER INFORMATION: optimzed Cas sequence

<400> SEQUENCE: 1
atggacaaga agtacagcat cggtcttgat attggtacta actctgtggg ttgggctgtt 60
attactgatg agtataaggt gcctagcaag aagtttaagg tgcttggtaa taccgacaga 120
cattctatta agaagaatct tattggtgct cttcttttttg attctggcga gactgctgag 180
gctactagac ttaagagaac tgctagaaga aggtacacta gaagaaagaa caggatctgc 240
taccttcaag agattttctc taatgagatg gccaaggttg acgattcttt ttttcacaga 300
ctcgaggagt ctttccttgt tgaggaggat aagaagcatg agagacatcc tattttcggt 360
aacatcgttg acgaggttgc ttatcatgag aagtatccta ctatctacca ccttagaaag 420
aagcttgtgg attctactga caaggctgat cttagactta tctaccttgc tcttgctcat 480
atgatcaagt tcagaggtca tttcctcatc gagggtgatc ttaatcctga taatagcgat 540
gtggacaagc tttttatcca gcttgttcaa acctacaacc agctttttga ggagaatcct 600
atcaacgctt ctggtgttga tgctaaggct attctttctg ctagactttc taagagcagg 660
agacttgaga atcttatcgc tcaacttcct ggtgagaaga agaatggtct tttggtaac 720 ctcatcgctc tttctcttgg tcttactcct aatttcaaga gcaacttcga ccttgctgag 780
gatgctaagc ttcaactttc taaggatacc tacgacgatg atcttgataa ccttcttgct 840

-continued

```
caaatcggtg atcaatacgc tgatcttttc cttgctgcta agaatcttag cgatgctatt    900

cttctcagcg atattcttag ggttaacact gagatcacca aggctcctct ttctgcttct    960

atgattaaga gatacgacga gcatcaccaa gatcttactc ttcttaaggc tcttgtgaga   1020

caacaacttc ctgagaagta taaggagatc ttcttcgatc agagcaagaa tggttacgct   1080

ggttatattg acggtggtgc ttctcaagag gagttttata agttcatcaa gcccatcctc   1140

gagaagatgg atggtactga ggagcttctt gttaagctta atagggagga tctccttaga   1200

aagcaaagaa ctttcgacaa cggttctatc cctcatcaaa ttcatctcgg tgagcttcat   1260

gctattctta gaagacaaga ggacttctac cctttttctta aggataacag ggagaagatc   1320

gagaagattc ttactttcag gattccttac tacgtgggtc ctcttgctag aggtaattct   1380

agatttgctt ggatgaccag aaagtctgag gagactatta ctccttggaa tttcgaggag   1440

gttgttgata agggtgcttc tgctcaatct tttatcgaga gaatgaccaa cttcgacaag   1500

aatcttccta acgagaaggt tcttcctaag cattctcttc tttacgagta cttcaccgtt   1560

tacaacgagc ttactaaggt taagtacgtg actgagggta tgagaaagcc tgcttttctt   1620

tctggtgagc aaaagaaggc tatcgttgat cttcttttca agaccaacag gaaggttact   1680

gttaagcaac ttaaggagga ctacttcaag aagatcgagt gctttgatag cgttgagatt   1740

tctggtgttg aggatagatt caacgcttct cttggtactt accatgatct tcttaagatc   1800

atcaaggaca aggacttcct tgataacgag gagaatgagg atatccttga ggatattgtg   1860

ctcactctta ctcttttcga ggatagagag atgatcgagg agagacttaa gacttatgct   1920

catcttttcg acgacaaggt tatgaagcaa cttaagagaa ggaggtacac tggttggggt   1980

agactttcta gaaagcttat taacggcatc agggataagc aatctggtaa gactatcctt   2040

gacttcctta agtctgacgg ttttgctaat aggaacttca tgcaactcat ccatgacgat   2100

tctcttactt tcaaggagga tatccagaag gctcaagttt ctggtcaagg tgattctctt   2160

catgagcata ttgctaacct cgctggttct cctgctatta agaagggtat tcttcagact   2220

gtgaaggttg ttgatgagct tgttaaggtt atgggtagac ataagcctga gaatatcgtt   2280

atcgagatgg ctagagagaa ccaaactact caaaagggtc aaaagaacag cagagagaga   2340

atgaagagaa tcgaggaggg tattaaggag cttggttctc aaattctcaa ggagcatcct   2400

gttgagaata ctcaacttca aaacgagaag ctctaccttt actaccttca aaacggtaga   2460

gacatgtacg ttgatcaaga gcttgatatc aacaggcttt ctgattacga cgttgatcat   2520

atcgtgcctc aatcttttct caaggatgat tctatcgaca acaaggttct cactagatct   2580

gataagaaca ggggtaagtc tgataacgtt ccttctgagg aggttgttaa gaagatgaag   2640

aactactgga ggcaacttct taacgctaag cttattaccc agagaaagtt cgataacctc   2700

actaaggctg agagaggtgg tctttctgag cttgataagg ctggttttat caagagacag   2760

cttgttgaga ctaggcaaat tactaagcac gttgctcaaa tcctcgattc tagaatgaac   2820

actaagtacg acgagaacga taagcttatc agagaggtta aggtgatcac tcttaagtct   2880

aagctcgttt ctgacttcag aaaggatttc caattctaca aggtgaggga gattaacaac   2940

taccatcatg ctcatgacgc ttatcttaac gctgttgttg gtactgctct tattaagaag   3000

taccctaagc tcgagtctga gtttgtttat ggtgattaca aggtgtacga cgttagaaag   3060

atgatcgcta agtctgagca agagattggt aaggctactg ctaagtattt cttctacagc   3120

aacatcatga acttcttcaa gaccgagatc actcttgcta atggtgagat tagaaagagg   3180

cctcttatcg agactaacgg tgagactggt gagattgttt gggataaggg tagagatttc   3240
```

gctactgtta gaaaggttct ctctatgcct caagttaaca tcgttaagaa gaccgaggtt 3300
caaactggtg gtttttctaa ggagtctatc cttcctaaga ggaatagcga taagcttatc 3360
gctagaaaga aggattggga ccctaagaag tatggtggtt ttgattctcc taccgttgct 3420
tattctgtgc ttgttgttgc taaggttgag aagggtaagt ctaagaagct taagtctgtg 3480
aaggagcttc ttggtattac tatcatggag agaagctctt tcgagaagaa tcctattgac 3540
ttcctcgagg ctaagggtta taaggaggtt aagaaggatc tcatcatcaa gcttcctaag 3600
tactctcttt tcgagcttga gaatggtaga aagagaatgc ttgcttctgc tggtgagctt 3660
caaaagggta atgagcttgc tcttccttct aagtatgtga atttcctcta cctcgcttct 3720
cattatgaga agcttaaggg ttctcctgag gataatgagc aaaagcaact tttcgtggag 3780
caacataagc attaccttga tgagatcatc gagcaaatct ctgagttttc taagagggtt 3840
atcctcgctg atgctaatct tgataaggtt cttagcgctt acaacaagca tagagataag 3900
cctatcaggg agcaagctga gaatattatt caccttttca ccctcaccaa ccttggtgct 3960
cctgctgctt ttaagtattt tgataccacc atcgacagga agagatatac ttctactaag 4020
gaggtgctcg atgctactct tattcatcaa tctatcaccg gtctctacga gactagaatt 4080
gatctttctc agctcggtgg tgattaa 4107

<210> SEQ ID NO 2
<211> LENGTH: 3794
<212> TYPE: DNA
<213> ORGANISM: Artificial Sequence
<220> FEATURE:
<223> OTHER INFORMATION: optimized Cas12a sequence

<400> SEQUENCE: 2
atggccccca agaagaagag aaaggttggc attcacggcg ttcccgcagc aagcaagtta 60
gagaagttta cgaattgtta ctcactgtca aagacgctgc gttttaaggc tatccctgtc 120
gggaagacgc aagagaatat cgacaataag cgactgttag tcgaggacga gaagcgcgcc 180
gaggactaca agggcgtcaa gaagctgtta gaccgctatt acctgagctt tatcaatgac 240
gtcttacact caatcaagct gaagaatctg aataactaca tctcactgtt tcgtaagaag 300
acgagaacgg agaaggagaa taaggagctg gagaatctgg agatcaatct gcgtaaggag 360
atcgcgaagg cttttaaggg aaatgagggg tacaagtcac tgtttaagaa ggacatcatc 420
gagacgatcc tgcctgagtt tttagacgac aaggacgaga tcgccctggt caatagcttt 480
aatggcttta cgacggcgtt tacgggcttt ttcgacaatc gggagaatat gttttcagag 540
gaagcgaagt caacgtcaat cgcttttcgt tgcatcaatg agaatctgac gcggtatatc 600
tcaaatatgg acatctttga gaaggtcgac gctatctttg acaagcacga ggtccaagag 660
atcaaggaga agatcctgaa ttcagactac gacgtcgagg actttttcga gggagagttt 720
ttcaattttg tcttaacgca agaggggatc gacgtctata atgccatcat cggcggtttt 780
gtcacggagt caggagagaa gatcaagggg ctgaatgagt atatcaatct gtacaatcaa 840
aagacgaagc aaaagctgcc taagtttaag cctctgtaca agcaagtctt atcagacagg 900
gagtcattat cattttatgg cgagggttac acgtcagacg aggaagtcct ggaggtcttt 960
agaaatacgc tgaataagaa ttcagagatc ttttcatcaa tcaagaagct ggagaagctg 1020
tttaagaatt ttgacgagta ttcatcagct ggaatctttg tcaagaatgg gcctgccatc 1080
tcaacgatct caaaggacat ctttggcgag tggaatgtca tccgtgacaa gtggaatgct 1140

-continued gagtacgacg acatccacct gaagaagaag gccgtcgtca cggagaagta tgaggacgac 1200
cgtcgtaaga gctttaagaa gatcgggtca ttttcactgg agcaattaca agagtacgcc 1260
gacgcggacc tgtcagtcgt cgagaagtta aaggagatca tcatccaaaa ggtcgacgag 1320
atctataagg tctacggctc atcagagaag ttatttgacg ccgactttgt cctggagaag 1380
tcattaaaga agaatgacgc ggtcgtcgct atcatgaagg acctgttaga ctcagtcaag 1440
tcatttgaga attatatcaa ggcgtttttc ggagagggga aggagacgaa tagggacgag 1500
tcattttacg gtgactttgt cctggcctat gacatcctgt taaaggtcga ccacatctat 1560
gacgcgatca gaaattacgt cacgcaaaag ccttactcaa aggacaagtt taagctgtac 1620
tttcaaaatc ctcagtttat gggcggctgg gacaaggaca aggagacgga ctaccgtgcg 1680
acgatcctgc ggtatggatc aaagtattac ttagccatca tggacaagaa gtatgcgaag 1740
tgcctgcaaa agatcgacaa ggacgacgtc aatggcaatt acgagaagat caattacaag 1800
ctgctgcctg gtcctaataa gatgttacct aaggtctttt tctcaaagaa gtggatggct 1860
tattacaatc cttcagagga catccaaaag atctataaga atggcacgtt taagaagggt 1920
gacatgttta atctgaatga ctgtcacaag ttaatcgact tttcaagga ctcaatctca 1980 cgataccta agtggtcaaa tgcttacgac tttaattttt cagagacgga gaagtacaag 2040
gacatcgccg gcttttatcg cgaggtcgag gagcaaggtt ataaggtcag ctttgagtca 2100
gcgtcaaaga aggaagtcga caagctggtc gaggaaggca agctgtacat gtttcaaatc 2160
tacaataagg acttttcaga caagtcacac gggacgccta atctgcacac gatgtacttt 2220
aagctgctgt ttgacgagaa taaccacggg caaatcaggc tgtcaggcgg tgctgagctg 2280
tttatgagga gagcctcact gaagaaggaa gagttagtcg tccaccctgc taattcacct 2340
atcgccaata agaatcccga caatcctaag aagacgacga cgctgtcata tgacgtctac 2400
aaggacaagc gtttttcaga ggaccaatat gagttacaca tccctatcgc gatcaataag 2460
tgtcctaaga atatctttaa gatcaatacg gaggtccggg tcctgttaaa gcacgacgac 2520
aatccttacg tcatcggcat cgaccgtggt gagcggaatc tgttatatat cgtcgtcgtc 2580
gacggcaagg gtaatatcgt cgagcaatac tcactgaatg agatcatcaa taactttaat 2640
ggtatcagaa tcaagacgga ctatcactca ctgttagaca agaaggagaa ggagcgattt 2700
gaggcgcgcc aaaattggac gtcaatcgag aatatcaagg agctgaaggc tggttacatc 2760
tcacaagtcg tccacaagat ctgcgagtta gtcgagaagt atgacgccgt catcgcgctg 2820
gaggacttaa attcaggctt taagaattca cgagtcaagg tcgagaagca agtctaccaa 2880
aagtttgaga agatgctgat cgacaagctg aattacatgg tcgacaagaa gtcaaatcct 2940
tgtgctacgg gaggggccct gaagggctac caaatcacga ataagtttga gagctttaag 3000
tcaatgtcaa cgcaaaatgg ttttatcttt tatatccctg cgtggttaac gtcaaagatc 3060
gacccttcaa cgggatttgt caatctgtta aagacgaagt acacgtcaat cgctgactca 3120
aagaagttta tctcatcatt tgaccgaatc atgtatgtcc ctgaggaaga cctgtttgag 3180
tttgcgttag actacaagaa tttttcacgc acggacgctg actatatcaa gaagtggaag 3240
ctgtattcat acggcaatcg aatccgcatc tttaggaatc ctaagaagaa taacgtcttt 3300
gactgggagg aagtctgcct gacgtcagcc tacaaggagc tgtttaataa gtacggcatc 3360
aattaccaac aaggtgacat cagagcgctg ttatgtgagc aatcagacaa ggcgttttat 3420
tcaagcttta tggctctgat gtcactgatg ttacaaatga ggaattcaat cacgggcaga 3480
acggacgtcg actttttaat ctcacctgtc aagaattcag acggtatctt ttatgactca 3540
cgtaattacg aggcgcaaga gaatgctatc ctgcctaaga atgctgacgc caatggcgcc 3600
tacaatatcg cgcggaaggt cttatgggcc atcgggcagt ttaagaaggc ggaggacgag 3660
aagctggaca aggtcaagat cgcgatctca aataaggagt ggttagagta tgctcaaacg 3720
tcagtgaagc acaagcgacc cgcagcaacc aagaaggcag ggcaggcgaa gaagaagaag 3780
taagacgact agtg 3794

<210> SEQ ID NO 3
<211> LENGTH: 180
<212> TYPE: DNA
<213> ORGANISM: Arabidopsis thaliana

<400> SEQUENCE: 3
caatcttcaa aagtaccaca tcgcttaggt aaagaaagca gctgagttta tatatggtta 60
gagacgaagt agtgattgtc ccttcgggga catccgataa aattggaacg atacagagaa 120
gattagcatg gcccctgcgc aaggatgaca cgcataaatc gagaaatggt ccaaattttt 180

<210> SEQ ID NO 4
<211> LENGTH: 177
<212> TYPE: DNA
<213> ORGANISM: Citrus sinensis

<400> SEQUENCE: 4
tggaacctaa tcccacatcg cttgtttatg gtaaagtttg agtctttaaa taaaacatgc 60
agggcgaatg ggctgtctct tcggagacat ccgataaaat tggaacgata cagagaagat 120
tagcatggcc cctgcgcaag gatgacacgc acaaatcgag aaatggtcca aatttt 177

<210> SEQ ID NO 5
<211> LENGTH: 179
<212> TYPE: DNA
<213> ORGANISM: Citrus sinensis

<400> SEQUENCE: 5
ctttactcac agtcccacat cgaaaatatg tattacggag ccgttgttta tatataggag 60
gagagaacga acggccgtct cttcggagac atccgataaa attggaacga tacagagaag 120
attagcatgg cccctgcgca aggatgacac gcacaaatcg agaaatggtc caaatttt 179

<210> SEQ ID NO 6
<211> LENGTH: 177
<212> TYPE: DNA
<213> ORGANISM: Citrus sinensis

<400> SEQUENCE: 6
ttgaagaaaa tcccacatcg aaagaaaaaa ctgaataaac atggtctata tatacaagga 60
ctcccaggtt ggttgtctct tcggagacat ccgataaaat tggaacgata cagagaagat 120
tagcatggcc cctgcgcaag gatgacacgc acaaatcgag aaatggtcca aatttt 177

<210> SEQ ID NO 7
<211> LENGTH: 172
<212> TYPE: DNA
<213> ORGANISM: Citrus sinensis

<400> SEQUENCE: 7
ctaaatccca catcgtctag ttgcgcttcg ttgagagtct taatataatc ataaccaacc 60
agtgcgattg tctcttcgga gacatccgat aaaattggaa cgatacagag aagattagca 120
tggcccctgc gcaaggatga cacgcacaaa tcgagaaatg gtccaaattt tt 172

<210> SEQ ID NO 8
<211> LENGTH: 172
<212> TYPE: DNA
<213> ORGANISM: Citrus sinensis

<400> SEQUENCE: 8
ctaaatccca cattgtttag ttatccttcc ttccgagtct taatatctac aagagccgca 60
tgccctatcg tctctccgga gacatccgat aaaattggaa cgatacagag aagattagca 120
tggcccctgc gcaaggatga cacgcacaaa tcgagaaatg gtccaaattt tt 172

<210> SEQ ID NO 9
<211> LENGTH: 694
<212> TYPE: DNA
<213> ORGANISM: Citrus sinensis

<400> SEQUENCE: 9
tatgataata aaactcccag aggggtcaca tttatttgag gagaatttaa aaaaaaaaaa 60
atcaccagaa agaggtgccg atgaatgcaa taagggatgc aaattattta tttaccttta 120
caggcattta gtatttaatt ttattttcag ttattgttca ctgataatcg aattttaatg 180
gagtcggtca tggaaggcat gcacataaaa tatgaggatg caggtaaggt ttgcgcggtc 240
tgaaatttca atgacggcgt acctctctct atcacaagaa atatgtaata atatgtttgt 300
aatttagaat ttttttctgt aattgacagt attttgtaga taaggaatgc cactctatag 360
gtactgctaa aagatgggcc aatataggtg cggcccatga gcccattgta tttaaagaat 420
ctttactcac agtcccacat cgaaaatatg tattacggag ccgttgttta tatataggag 480
gagagaacga acggccgtct cttcggagac atccgataaa attggaacga tacagagaag 540
attagcatgg cccctgcgca aggatgacac gcacaaatcg agaaatggtc caaatttttt 600 tcttcccccct cattcgggct tgtttaatca gtcggcagtt tgacgatgtt agcttctgca 660
gtttgattcc atcgttaacc atataaattt tttt 694

<210> SEQ ID NO 10
<211> LENGTH: 662
<212> TYPE: DNA
<213> ORGANISM: Citrus sinensis

<400> SEQUENCE: 10
tcaggagccg gttgaatttg attgttgttt gatgtttagg tatgcttaca attttttact 60
aaataaggta ataattgttc cttttatttt attcatttag cttggtactt gtcgtaatct 120
atctccgtca atgtcagctt cttctgtgtc ggaagaagct gaaaaatgtt gttgaaggcc 180
ctttcattta ttattatcat tattatgttt aattttgttc ggcaaatgtg tactaatttg 240
gttcgaatcg ttcgatctca taatacaaac atgtaatgag ttatttatga cgtcatggat 300
gcggttagtt tgcgtggtct gaaatttcaa ccaaattatt caatcatggt ggtggccggc 360
tggtgcctat cccttgattg aaatatgcaa ttaaaattct cgtaataatg ttgatttgtt 420
ctatatactt gaattgatgg tattaattat tgttataaaa gcactaactt gtttgagaaa 480
ggggataact aaaaggtaat aataataata ataaaataaa gaaaaggccc aacacatggg 540
cgccctatct gttgggccaa atgccataag aggatccagc tagcccgttg aagaaaatcc 600
cacatcgaaa gaaaaaactg aataaacatg gtctatatat acaaggactc ccaggttggt 660
tg 662

<210> SEQ ID NO 11
<211> LENGTH: 522
<212> TYPE: DNA
<213> ORGANISM: Citrus sinensis

<400> SEQUENCE: 11
tgttgtgcgg gatcttttaa gtaggaactg acaagtttcc ctcacccaca tctttcgtga 60
agcgaattca gctacagatt tcatggctaa tatggctcat tcaatctctc atgggttaca 120
tttatttact agcctacatg tgtgtattta ttcaagttta ttgcaagaca tgtttggggt 180
tgctaaactc cgtattgttc cggtttagct cgctttattg agcccatctt aataaaaaaa 240
aaaaaaagac ttccttctat gattttaggg aaaattacta taatattatc cataagagta 300
aattttggac ctacgcgtgc agatatgtac atatattttt taataaaaac aattactgca 360
tggactggac ttcgtagcat ctttttttggg ctcaggaagg gcctaaagtt atgatagcca 420
gacagacgtc atgtggttcg gttcaaattg aactaaatcc cacatcgtct agttgcgctt 480
cgttgagagt cttaatataa tcataaccaa ccagtgcgat tg 522

<210> SEQ ID NO 12
<211> LENGTH: 44
<212> TYPE: DNA
<213> ORGANISM: Francisella novicida

<400> SEQUENCE: 12
ttgcagcagc agcagcagca gcagcaacag ttcatggata ctag 44

<210> SEQ ID NO 13
<211> LENGTH: 44
<212> TYPE: DNA
<213> ORGANISM: Artificial Sequence
<220> FEATURE:
<223> OTHER INFORMATION: Alt-allele 1 FnCPf1

<400> SEQUENCE: 13
ttgcagcagc agcagcagca gcagcaaggg ttcatggata ctag 44

<210> SEQ ID NO 14
<211> LENGTH: 44
<212> TYPE: DNA
<213> ORGANISM: Artificial Sequence
<220> FEATURE:
<223> OTHER INFORMATION: Alt-allele 2 FnCpf1

<400> SEQUENCE: 14
ttgcagcacc agcagcacca gcagcaacag ttcatggata ctag 44

<210> SEQ ID NO 15
<211> LENGTH: 44
<212> TYPE: DNA
<213> ORGANISM: Artificial Sequence
<220> FEATURE:
<223> OTHER INFORMATION: Alt-allele3 FnCpf1

<400> SEQUENCE: 15
ttgcatcagc ggcagcagca gcagcaacag ttcatggata ctag 44

<210> SEQ ID NO 16
<211> LENGTH: 37
<212> TYPE: RNA
<213> ORGANISM: Artificial Sequence
<220> FEATURE:
<223> OTHER INFORMATION: crRNA

<400> SEQUENCE: 16
gucgucgucg ucgucgucgu cguugucuca ucuugaa 37

<210> SEQ ID NO 17
<211> LENGTH: 35
<212> TYPE: DNA
<213> ORGANISM: Francisella novicida

<400> SEQUENCE: 17
gtcttgcagc agcagcagca gcagcagcaa cagtt 35

<210> SEQ ID NO 18
<211> LENGTH: 32
<212> TYPE: DNA
<213> ORGANISM: Artificial Sequence
<220> FEATURE:
<223> OTHER INFORMATION: FnCpf1 mutatnt

<400> SEQUENCE: 18
gtcttgcagc agcagcagca gcagcaacag tt 32

<210> SEQ ID NO 19
<211> LENGTH: 35
<212> TYPE: DNA
<213> ORGANISM: Artificial Sequence
<220> FEATURE:
<223> OTHER INFORMATION: FnCpf1 mutant

<400> SEQUENCE: 19
gtcttgcagc agcagcagca gcatcagcaa cagtt 35

<210> SEQ ID NO 20
<211> LENGTH: 24
<212> TYPE: RNA
<213> ORGANISM: Artificial Sequence
<220> FEATURE:
<223> OTHER INFORMATION: crRNA

<400> SEQUENCE: 20
gccgacgcgg ccccgauaaa cggu 24

<210> SEQ ID NO 21
<211> LENGTH: 12
<212> TYPE: RNA
<213> ORGANISM: Artificial Sequence
<220> FEATURE:
<223> OTHER INFORMATION: extension of crRNA

<400> SEQUENCE: 21
ucucaucuuu aa 12

<210> SEQ ID NO 22
<211> LENGTH: 39
<212> TYPE: DNA

<213> ORGANISM: Artificial Sequence
<220> FEATURE:
<223> OTHER INFORMATION: wild type target

<400> SEQUENCE: 22
cctgtttacg gctgcgccgg ggctatttgc catctccag 39

<210> SEQ ID NO 23
<211> LENGTH: 39
<212> TYPE: DNA
<213> ORGANISM: Artificial Sequence
<220> FEATURE:
<223> OTHER INFORMATION: mutant allele

<400> SEQUENCE: 23
cctgtttacg gctgcgccgt ggctatttgc catctccag 39

<210> SEQ ID NO 24
<211> LENGTH: 43
<212> TYPE: DNA
<213> ORGANISM: Artificial Sequence
<220> FEATURE:
<223> OTHER INFORMATION: wild-type target

<400> SEQUENCE: 24
tttacggctg cgccggggct atttgccatc tccagaaaca agt 43

<210> SEQ ID NO 25
<211> LENGTH: 43
<212> TYPE: DNA
<213> ORGANISM: Artificial Sequence
<220> FEATURE:
<223> OTHER INFORMATION: mutant target

<400> SEQUENCE: 25
tttacggctg cgctggggct atttgccatc tccagaaaca agt 43

<210> SEQ ID NO 26
<211> LENGTH: 29
<212> TYPE: DNA
<213> ORGANISM: Artificial Sequence
<220> FEATURE:
<223> OTHER INFORMATION: CslOB1 target

<400> SEQUENCE: 26
tttaaagctt ctccttcaca atcctctcc 29

<210> SEQ ID NO 27
<211> LENGTH: 48
<212> TYPE: DNA
<213> ORGANISM: Artificial Sequence
<220> FEATURE:
<223> OTHER INFORMATION: target site

<400> SEQUENCE: 27
tggaatctgg ctaaatcagt gtgcttgtgg agggagacat gtagggga 48

<210> SEQ ID NO 28
<211> LENGTH: 42
<212> TYPE: DNA
<213> ORGANISM: Artificial Sequence
<220> FEATURE:
<223> OTHER INFORMATION: target site

<400> SEQUENCE: 28
ggctaaatca gtgtgcttgt ggagggagac tgtaggggaa tc 42

<210> SEQ ID NO 29
<211> LENGTH: 47
<212> TYPE: DNA
<213> ORGANISM: Artificial Sequence
<220> FEATURE:
<223> OTHER INFORMATION: mutant target site

<400> SEQUENCE: 29
tggaatctgg ctaaatcagt gtgcttgtgg agggagactg tagggga 47

<210> SEQ ID NO 30
<211> LENGTH: 23
<212> TYPE: DNA
<213> ORGANISM: Artificial Sequence
<220> FEATURE:
<223> OTHER INFORMATION: target site

<400> SEQUENCE: 30
ttgtgcacaa gcaattgtac agg 23

<210> SEQ ID NO 31
<211> LENGTH: 9640
<212> TYPE: DNA
<213> ORGANISM: Artificial Sequence
<220> FEATURE:
<223> OTHER INFORMATION: pMAL-C5X/AsCpf1 vector

<400> SEQUENCE: 31
gaattccctg caggtaatta aataagcttc aaataaaacg aaaggctcag tcgaaagact 60
gggcctttcg ttttatctgt tgtttgtcgg tgaacgctct cctgagtagg acaaatccgc 120
cgggagcgga tttgaacgtt gcgaagcaac ggcccggagg gtggcgggca ggacgcccgc 180
cataaactgc caggcatcaa attaagcaga aggccatcct gacggatggc ctttttgcgt 240
ttctacaaac tctttcggtc cgttgtttat ttttctaaat acattcaaat atgtatccgc 300
tcatgagaca ataaccctga taaatgcttc aataatattg aaaaaggaag agtatgagta 360
ttcaacattt ccgtgtcgcc cttattccct tttttgcggc attttgcctt cctgtttttg 420
ctcacccaga aacgctggtg aaagtaaaag atgctgaaga tcagttgggt gcacgagtgg 480
gttacatcga actggatctc aacagcggta agatccttga gagttttcgc cccgaagaac 540
gttttccaat gatgagcact tttaaagttc tgctatgtgg cgcggtatta tcccgtgttg 600
acgccgggca agagcaactc ggtcgccgca tacactattc tcagaatgac ttggttgagt 660
actcaccagt cacagaaaag catcttacgg atggcatgac agtaagagaa ttatgcagtg 720
ctgccataac catgagtgat aacactgcgg ccaacttact tctgacaacg atcggaggac 780
cgaaggagct aaccgctttt ttgcacaaca tgggggatca tgtaactcgc cttgatcgtt 840
gggaaccgga gctgaatgaa gccataccaa acgacgagcg tgacaccacg atgcctgtag 900
caatggcaac aacgttgcgc aaactattaa ctggcgaact acttactcta gcttcccggc 960
aacaattaat agactggatg gaggcggata aagttgcagg accacttctg cgctcggccc 1020
ttccggctgg ctggtttatt gctgataaat ctggagccgg tgagcgtggg tctcgcggta 1080
tcattgcagc actggggcca gatggtaagc cctcccgtat cgtagttatc tacacgacgg 1140
ggagtcaggc aactatggat gaacgaaata gacagatcgc tgagataggt gcctcactga 1200
ttaagcattg gtaactgtca gaccaagttt actcatatat actttagatt gatttcctta 1260
ggactgagcg tcaaccccgt agaaaagatc aaaggatctt cttgagatcc tttttttctg 1320
cgcgtaatct gctgcttgca aacaaaaaaa ccaccgctac cagcggtggt ttgtttgccg 1380
gatcaagagc taccaactct ttttccgaag gtaactggct tcagcagagc gcagatacca 1440
aatactgtcc ttctagtgta gccgtagtta ggccaccact tcaagaactc tgtagcaccg 1500
cctacatacc tcgctctgct aatcctgtta ccagtggctg ctgccagtgg cgataagtcg 1560
tgtcttaccg ggttggactc aagacgatag ttaccggata aggcgcagcg gtcgggctga 1620
acggggggtt cgtgcacaca gcccagcttg gagcgaacga cctacaccga actgagatac 1680
ctacagcgtg agctatgaga aagcgccacg cttcccgaag ggagaaaggc ggacaggtat 1740
ccggtaagcg gcagggtcgg aacaggagag cgcacgaggg agcttccagg gggaaacgcc 1800
tggtatcttt atagtcctgt cgggtttcgc cacctctgac ttgagcgtcg atttttgtga 1860
tgctcgtcag gggggcggag cctatggaaa aacgccagca acgcggcctt tttacggttc 1920
ctggcctttt gctggccttt tgctcacatg ttctttcctg cgttatcccc tgattctgtg 1980
gataaccgta ttaccgcctt tgagtgagct gataccgctc gccgcagccg aacgaccgag 2040
cgcagcgagt cagtgagcga ggaagcggaa gagcgcctga tgcggtattt tctccttacg 2100
catctgtgcg gtatttcaca ccgcatataa ggtgcactgt gactgggtca tggctgcgcc 2160
ccgacacccg ccaacacccg ctgacgcgcc ctgacgggct tgtctgctcc cggcatccgc 2220
ttacagacaa gctgtgaccg tctccgggag ctgcatgtgt cagaggtttt caccgtcatc 2280
accgaaacgc gcgaggcagc tgcggtaaag ctcatcagcg tggtcgtgca gcgattcaca 2340
gatgtctgcc tgttcatccg cgtccagctc gttgagtttc tccagaagcg ttaatgtctg 2400
gcttctgata aagcgggcca tgttaagggc ggtttttttcc tgtttggtca ctgatgcctc 2460
cgtgtaaggg ggatttctgt tcatgggggt aatgataccg atgaaacgag agaggatgct 2520
cacgatacgg gttactgatg atgaacatgc ccggttactg gaacgttgtg agggtaaaca 2580
actggcggta tggatgcggc gggaccagag aaaaatcact cagggtcaat gccagcgctt 2640
cgttaataca gatgtaggtg ttccacaggg tagccagcag catcctgcga tgcagatccg 2700
gaacataatg gtgcagggcg ctgacttccg cgtttccaga ctttacgaaa cacggaaacc 2760
gaagaccatt catgttgttg ctcaggtcgc agacgttttg cagcagcagt cgcttcacgt 2820
tcgctcgcgt atcggtgatt cattctgcta accagtaagg caaccccgcc agcctagccg 2880
ggtcctcaac gacaggagca cgatcatgcg cacccgtggc caggacccaa cgctgcccga 2940
aattccgaca ccatcgaatg gtgcaaaacc tttcgcggta tggcatgata gcgcccggaa 3000
gagagtcaat tcagggtggt gaatgtgaaa ccagtaacgt tatacgatgt cgcagagtat 3060
gccggtgtct cttatcagac cgtttcccgc gtggtgaacc aggccagcca cgtttctgcg 3120
aaaacgcggg aaaaagtgga agcggcgatg gcggagctga attacattcc caaccgcgtg 3180
gcacaacaac tggcgggcaa acagtcgttg ctgattggcg ttgccacctc cagtctggcc 3240
ctgcacgcgc cgtcgcaaat tgtcgcggcg attaaatctc gcgccgatca actgggtgcc 3300
agcgtggtgg tgtcgatggt agaacgaagc ggcgtcgaag cctgtaaagc ggcggtgcac 3360
aatcttctcg cgcaacgcgt cagtgggctg atcattaact atccgctgga tgaccaggat 3420
gccattgctg tggaagctgc ctgcactaat gttccggcgt tatttcttga tgtctctgac 3480
cagacaccca tcaacagtat tattttctcc catgaagacg gtacgcgact gggcgtggag 3540
catctggtcg cattgggtca ccagcaaatc gcgctgttag cgggcccatt aagttctgtc 3600
tcggcgcgtc tgcgtctggc tggctggcat aaatatctca ctcgcaatca aattcagccg 3660
atagcggaac gggaaggcga ctggagtgcc atgtccggtt ttcaacaaac catgcaaatg 3720
ctgaatgagg gcatcgttcc cactgcgatg ctggttgcca acgatcagat ggcgctgggc 3780
gcaatgcgcg ccattaccga gtccgggctg cgcgttggtg cggatatttc ggtagtggga 3840
tacgacgata ccgaagacag ctcatgttat atcccgccgt taaccaccat caaacaggat 3900
tttcgcctgc tggggcaaac cagcgtggac cgcttgctgc aactctctca gggccaggcg 3960
gtgaagggca atcagctgtt gcccgtctca ctggtgaaaa gaaaaaccac cctggcgccc 4020
aatacgcaaa ccgcctctcc ccgcgcgttg gccgattcat taatgcagct ggcacgacag 4080
gtttcccgac tggaaagcgg gcagtgagcg caacgcaatt aatgtaagtt agctcactca 4140
ttaggcacaa ttctcatgtt tgacagctta tcatcgactg cacggtgcac caatgcttct 4200
ggcgtcaggc agccatcgga agctgtggta tggctgtgca ggtcgtaaat cactgcataa 4260
ttcgtgtcgc tcaaggcgca ctcccgttct ggataatgtt ttttgcgccg acatcataac 4320
ggttctggca aatattctga aatgagctgt tgacaattaa tcatcggctc gtataatgtg 4380
tggaattgtg agcggataac aatttcacac aggaaacagc cagtccgttt aggtgttttc 4440
acgagcaatt gaccaacaag gaccatagat tatgaaaatc gaagaaggta aactggtaat 4500
ctggattaac ggcgataaag gctataacgg tctcgctgaa gtcggtaaga aattcgagaa 4560
agataccgga attaaagtca ccgttgagca tccggataaa ctggaagaga aattcccaca 4620
ggttgcggca actggcgatg gccctgacat tatcttctgg gcacacgacc gctttggtgg 4680
ctacgctcaa tctggcctgt tggctgaaat caccccggac aaagcgttcc aggacaagct 4740
gtatccgttt acctgggatg ccgtacgtta caacggcaag ctgattgctt acccgatcgc 4800
tgttgaagcg ttatcgctga tttataacaa agatctgctg ccgaacccgc caaaaacctg 4860
ggaagagatc ccggcgctgg ataaagaact gaaagcgaaa ggtaagagcg cgctgatgtt 4920
caacctgcaa gaaccgtact tcacctggcc gctgattgct gctgacgggg gttatgcgtt 4980
caagtatgaa aacggcaagt acgacattaa agacgtgggc gtggataacg ctggcgcgaa 5040
agcgggtctg accttcctgg ttgacctgat taaaaacaaa cacatgaatg cagacaccga 5100
ttactccatc gcagaagctg cctttaataa aggcgaaaca gcgatgacca tcaacggccc 5160
gtgggcatgg tccaacatcg acaccagcaa agtgaattat ggtgtaacgg tactgccgac 5220
cttcaagggt caaccatcca aaccgttcgt tggcgtgctg agcgcaggta ttaacgccgc 5280
cagtccgaac aaagagctgg caaaagagtt cctcgaaaac tatctgctga ctgatgaagg 5340
tctggaagcg gttaataaag acaaaccgct gggtgccgta gcgctgaagt cttacgagga 5400
agagttggtg aaagatccgc gtattgccgc cactatggaa aacgcccaga aaggtgaaat 5460
catgccgaac atcccgcaga tgtccgcttt ctggtatgcc gtgcgtactg cggtgatcaa 5520
cgccgccagc ggtcgtcaga ctgtcgatga agccctgaaa gacgcgcaga ctaattcgag 5580
ctcgaacaac aacaacaata acaataacaa caacctcggg atcgagggaa ggatttcaca 5640
tatgtccatg ggcggccgcg atatcgtcga catgacacag ttcgagggct ttaccaacct 5700
gtatcaggtg agcaagacac tgcggtttga gctgatccca cagggcaaga ccctgaagca 5760
catccaggag cagggcttca tcgaggagga caaggcccgc aatgatcact acaaggagct 5820
gaagcccatc atcgatcgga tctacaagac ctatgccgac cagtgcctgc agctggtgca 5880
gctggattgg gagaacctga gcgccgccat cgactcctat agaaaggaga aaaccgagga 5940
gacaaggaac gccctgatcg aggagcaggc cacatatcgc aatgccatcc acgactactt 6000
catcggccgg acagacaacc tgaccgatgc catcaataag agacacgccg agatctacaa 6060
gggcctgttc aaggccgagc tgtttaatgg caaggtgctg aagcagctgg gcaccgtgac 6120
cacaaccgag cacgagaacg ccctgctgcg gagcttcgac aagtttacaa cctacttctc 6180
cggcttttat gagaacagga agaacgtgtt cagcgccgag gatatcagca cagccatccc 6240
acaccgcatc gtgcaggaca acttccccaa gtttaaggag aattgtcaca tcttcacacg 6300
cctgatcacc gccgtgccca gcctgcggga gcactttgag aacgtgaaga aggccatcgg 6360
catcttcgtg agcacctcca tcgaggaggt gttttccttc ccttttata accagctgct 6420
gacacagacc cagatcgacc tgtataacca gctgctggga ggaatctctc gggaggcagg 6480
caccgagaag atcaagggcc tgaacgaggt gctgaatctg gccatccaga agaatgatga 6540
gacagcccac atcatcgcct ccctgccaca cagattcatc cccctgttta agcagatcct 6600
gtccgatagg aacaccctgt ctttcatcct ggaggagttt aagagcgacg aggaagtgat 6660
ccagtccttc tgcaagtaca agacactgct gagaaacgag aacgtgctgg agacagccga 6720
ggccctgttt aacgagctga acagcatcga cctgacacac atcttcatca gccacaagaa 6780
gctggagaca atcagcagcg ccctgtgcga ccactgggat acactgagga atgccctgta 6840
tgagcggaga atctccgagc tgacaggcaa gatcaccaag tctgccaagg agaaggtgca 6900
gcgcagcctg aagcacgagg atatcaacct gcaggagatc atctctgccg caggcaagga 6960
gctgagcgag gccttcaagc agaaaaccag cgagatcctg tcccacgcac acgccgccct 7020
ggatcagcca ctgcctacaa ccctgaagaa gcaggaggag aaggagatcc tgaagtctca 7080
gctggacagc ctgctgggcc tgtaccacct gctggactgg tttgccgtgg atgagtccaa 7140
cgaggtggac cccgagttct ctgcccggct gaccggcatc aagctggaga tggagccttc 7200
tctgagcttc tacaacaagg ccagaaatta tgccaccaag aagccctact ccgtggagaa 7260
gttcaagctg aactttcaga tgcctacact ggcctctggc tgggacgtga ataaggagaa 7320
gaacaatggc gccatcctgt ttgtgaagaa cggcctgtac tatctgggca tcatgccaaa 7380
gcagaagggc aggtataagg ccctgagctt cgagcccaca gagaaaacca gcgagggctt 7440
tgataagatg tactatgact acttccctga tgccgccaag atgatcccaa agtgcagcac 7500
ccagctgaag gccgtgacag cccactttca gacccacaca acccccatcc tgctgtccaa 7560
caatttcatc gagcctctgg agatcacaaa ggagatctac gacctgaaca atcctgagaa 7620
ggagccaaag aagtttcaga cagcctacgc caagaaaacc ggcgaccaga agggctacag 7680
agaggccctg tgcaagtgga tcgacttcac aagggatttt ctgtccaagt ataccaagac 7740
aacctctatc gatctgtcta gcctgcggcc atcctctcag tataaggacc tgggcgagta 7800
ctatgccgag ctgaatcccc tgctgtacca catcagcttc cagagaatcg ccgagaagga 7860
gatcatggat gccgtggaga caggcaagct gtacctgttc cagatctata acaaggactt 7920
tgccaagggc caccacggca agcctaatct gcacacactg tattggaccg gcctgttttc 7980
tccagagaac ctggccaaga caagcatcaa gctgaatggc caggccgagc tgttctaccg 8040
ccctaagtcc aggatgaaga ggatggcaca ccggctggga gagaagatgc tgaacaagaa 8100
gctgaaggat cagaaaaccc caatccccga caccctgtac caggagctgt acgactatgt 8160
gaatcacaga ctgtcccacg acctgtctga tgaggccagg gccctgctgc ccaacgtgat 8220
caccaaggag gtgtctcacg agatcatcaa ggataggcgc tttaccagcg acaagttctt 8280
tttccacgtg cctatcacac tgaactatca ggccgccaat tccccatcta agttcaacca 8340
gagggtgaat gcctacctga aggagcaccc cgagacacct atcatcggca tcgatcgggg 8400
cgagagaaac ctgatctata tcacagtgat cgactccacc ggcaagatcc tggagcagcg 8460

```
gagcctgaac accatccagc agtttgatta ccagaagaag ctggacaaca gggagaagga   8520

gagggtggca gcaaggcagg cctggtctgt ggtgggcaca atcaaggatc tgaagcaggg   8580

ctatctgagc caggtcatcc acgagatcgt ggacctgatg atccactacc aggccgtggt   8640

ggtgctggag aacctgaatt tcggctttaa gagcaagagg accggcatcg ccgagaaggc   8700

cgtgtaccag cagttcgaga agatgctgat cgataagctg aattgcctgg tgctgaagga   8760

ctatccagca gagaaagtgg gaggcgtgct gaacccatac cagctgacag accagttcac   8820

ctcctttgcc aagatgggca cccagtctgg cttcctgttt tacgtgcctg ccccatatac   8880

atctaagatc gatcccctga ccggcttcgt ggaccccttc gtgtggaaaa ccatcaagaa   8940

tcacgagagc cgcaagcact tcctggaggg cttcgacttt ctgcactacg acgtgaaaac   9000

cggcgacttc atcctgcact ttaagatgaa cagaaatctg tccttccaga ggggcctgcc   9060

cggctttatg cctgcatggg atatcgtgtt cgagaagaac gagacacagt ttgacgccaa   9120

gggcacccct ttcatcgccg gcaagagaat cgtgccagtg atcgagaatc acagattcac   9180

cggcagatac cgggacctgt atcctgccaa cgagctgatc gccctgctgg aggagaaggg   9240

catcgtgttc agggatggct ccaacatcct gccaaagctg ctggagaatg acgattctca   9300

cgccatcgac accatggtgg ccctgatccg cagcgtgctg cagatgcgga actccaatgc   9360

cgccacaggc gaggactata tcaacagccc cgtgcgcgat ctgaatggcg tgtgcttcga   9420

ctcccggttt cagaacccag agtggcccat ggacgccgat gccaatggcg cctaccacat   9480

cgccctgaag ggccagctgc tgctgaatca cctgaaggag agcaaggatc tgaagctgca   9540

gaacggcatc tccaatcagg actggctggc ctacatccag gagctgcgca acaaaaggcc   9600

ggcggccacg aaaaaggccg gccaggcaaa aaagaaaaag                         9640
```

<210> SEQ ID NO 32
<211> LENGTH: 9403
<212> TYPE: DNA
<213> ORGANISM: Artificial Sequence
<220> FEATURE:
<223> OTHER INFORMATION: pMAL-C5XLbCpf1 vector

<400> SEQUENCE: 32

```
gaattccctg caggtaatta aataagcttc aaataaaacg aaaggctcag tcgaaagact     60

gggcctttcg ttttatctgt tgtttgtcgg tgaacgctct cctgagtagg acaaatccgc    120

cgggagcgga tttgaacgtt gcgaagcaac ggcccggagg gtggcgggca ggacgcccgc    180

cataaactgc caggcatcaa attaagcaga aggccatcct gacggatggc ctttttgcgt    240

ttctacaaac tctttcggtc cgttgtttat ttttctaaat acattcaaat atgtatccgc    300

tcatgagaca ataaccctga taaatgcttc aataatattg aaaaaggaag agtatgagta    360

ttcaacattt ccgtgtcgcc cttattccct tttttgcggc attttgcctt cctgtttttg    420

ctcacccaga aacgctggtg aaagtaaaag atgctgaaga tcagttgggt gcacgagtgg    480

gttacatcga actggatctc aacagcggta agatccttga gagttttcgc cccgaagaac    540

gtttcccaat gatgagcact tttaaagttc tgctatgtgg cgcggtatta tcccgtgttg    600

acgccgggca agagcaactc ggtcgccgca tacactattc tcagaatgac ttggttgagt    660

actcaccagt cacagaaaag catcttacgg atggcatgac agtaagagaa ttatgcagtg    720

ctgccataac catgagtgat aacactgcgg ccaacttact tctgacaacg atcggaggac    780

cgaaggagct aaccgctttt ttgcacaaca tgggggatca tgtaactcgc cttgatcgtt    840
```

-continued

```
gggaaccgga gctgaatgaa gccataccaa acgacgagcg tgacaccacg atgcctgtag    900
caatggcaac aacgttgcgc aaactattaa ctggcgaact acttactcta gcttcccggc    960
aacaattaat agactggatg gaggcggata aagttgcagg accacttctg cgctcggccc   1020
ttccggctgg ctggtttatt gctgataaat ctggagccgg tgagcgtggg tctcgcggta   1080
tcattgcagc actggggcca gatggtaagc cctcccgtat cgtagttatc tacacgacgg   1140
ggagtcaggc aactatggat gaacgaaata gacagatcgc tgagataggt gcctcactga   1200
ttaagcattg gtaactgtca gaccaagttt actcatatat actttagatt gatttcctta   1260
ggactgagcg tcaaccccgt agaaaagatc aaaggatctt cttgagatcc tttttttctg   1320
cgcgtaatct gctgcttgca aacaaaaaaa ccaccgctac cagcggtggt ttgtttgccg   1380
gatcaagagc taccaactct ttttccgaag gtaactggct tcagcagagc gcagatacca   1440
aatactgtcc ttctagtgta gccgtagtta ggccaccact tcaagaactc tgtagcaccg   1500
cctacatacc tcgctctgct aatcctgtta ccagtggctg ctgccagtgg cgataagtcg   1560
tgtcttaccg ggttggactc aagacgatag ttaccggata aggcgcagcg gtcgggctga   1620
acggggggtt cgtgcacaca gcccagcttg gagcgaacga cctacaccga actgagatac   1680
ctacagcgtg agctatgaga aagcgccacg cttcccgaag ggagaaaggc ggacaggtat   1740
ccggtaagcg gcagggtcgg aacaggagag cgcacgaggg agcttccagg gggaaacgcc   1800
tggtatcttt atagtcctgt cgggtttcgc cacctctgac ttgagcgtcg atttttgtga   1860
tgctcgtcag gggggcggag cctatggaaa aacgccagca acgcggcctt tttacggttc   1920
ctggcctttt gctggccttt tgctcacatg ttctttcctg cgttatcccc tgattctgtg   1980
gataaccgta ttaccgcctt tgagtgagct gataccgctc gccgcagccg aacgaccgag   2040
cgcagcgagt cagtgagcga ggaagcggaa gagcgcctga tgcggtattt tctccttacg   2100
catctgtgcg gtatttcaca ccgcatataa ggtgcactgt gactgggtca tggctgcgcc   2160
ccgacacccg ccaacacccg ctgacgcgcc ctgacgggct tgtctgctcc cggcatccgc   2220
ttacagacaa gctgtgaccg tctccgggag ctgcatgtgt cagaggtttt caccgtcatc   2280
accgaaacgc gcgaggcagc tgcggtaaag ctcatcagcg tggtcgtgca gcgattcaca   2340
gatgtctgcc tgttcatccg cgtccagctc gttgagtttc tccagaagcg ttaatgtctg   2400
gcttctgata aagcgggcca tgttaagggc ggtttttttcc tgtttggtca ctgatgcctc   2460
cgtgtaaggg ggatttctgt tcatgggggt aatgataccg atgaaacgag agaggatgct   2520
cacgatacgg gttactgatg atgaacatgc ccggttactg gaacgttgtg agggtaaaca   2580
actggcggta tggatgcggc gggaccagag aaaaatcact cagggtcaat gccagcgctt   2640
cgttaataca gatgtaggtg ttccacaggg tagccagcag catcctgcga tgcagatccg   2700
gaacataatg gtgcagggcg ctgacttccg cgtttccaga ctttacgaaa cacggaaacc   2760
gaagaccatt catgttgttg ctcaggtcgc agacgttttg cagcagcagt cgcttcacgt   2820
tcgctcgcgt atcggtgatt cattctgcta accagtaagg caaccccgcc agcctagccg   2880
ggtcctcaac gacaggagca cgatcatgcg cacccgtggc caggacccaa cgctgcccga   2940
aattccgaca ccatcgaatg gtgcaaaacc tttcgcggta tggcatgata gcgcccggaa   3000
gagagtcaat tcagggtggt gaatgtgaaa ccagtaacgt tatacgatgt cgcagagtat   3060
gccggtgtct cttatcagac cgtttcccgc gtggtgaacc aggccagcca cgtttctgcg   3120
aaaacgcggg aaaaagtgga agcggcgatg gcggagctga attacattcc caaccgcgtg   3180
gcacaacaac tggcgggcaa acagtcgttg ctgattggcg ttgccacctc cagtctggcc   3240
```

```
ctgcacgcgc cgtcgcaaat tgtcgcggcg attaaatctc gcgccgatca actgggtgcc   3300
agcgtggtgg tgtcgatggt agaacgaagc ggcgtcgaag cctgtaaagc ggcggtgcac   3360
aatcttctcg cgcaacgcgt cagtgggctg atcattaact atccgctgga tgaccaggat   3420
gccattgctg tggaagctgc ctgcactaat gttccggcgt tatttcttga tgtctctgac   3480
cagacaccca tcaacagtat tattttctcc catgaagacg gtacgcgact gggcgtggag   3540
catctggtcg cattgggtca ccagcaaatc gcgctgttag cgggcccatt aagttctgtc   3600
tcggcgcgtc tgcgtctggc tggctggcat aaatatctca ctcgcaatca aattcagccg   3660
atagcggaac gggaaggcga ctggagtgcc atgtccggtt ttcaacaaac catgcaaatg   3720
ctgaatgagg gcatcgttcc cactgcgatg ctggttgcca acgatcagat ggcgctgggc   3780
gcaatgcgcg ccattaccga gtccgggctg cgcgttggtg cggatatttc ggtagtggga   3840
tacgacgata ccgaagacag ctcatgttat atcccgccgt taaccaccat caaacaggat   3900
tttcgcctgc tggggcaaac cagcgtggac cgcttgctgc aactctctca gggccaggcg   3960
gtgaagggca atcagctgtt gcccgtctca ctggtgaaaa gaaaaaccac cctggcgccc   4020
aatacgcaaa ccgcctctcc ccgcgcgttg gccgattcat taatgcagct ggcacgacag   4080
gtttcccgac tggaaagcgg gcagtgagcg caacgcaatt aatgtaagtt agctcactca   4140
ttaggcacaa ttctcatgtt tgacagctta tcatcgactg cacggtgcac caatgcttct   4200
ggcgtcaggc agccatcgga agctgtggta tggctgtgca ggtcgtaaat cactgcataa   4260
ttcgtgtcgc tcaaggcgca ctcccgttct ggataatgtt ttttgcgccg acatcataac   4320
ggttctggca aatattctga aatgagctgt tgacaattaa tcatcggctc gtataatgtg   4380
tggaattgtg agcggataac aatttcacac aggaaacagc cagtccgttt aggtgttttc   4440
acgagcaatt gaccaacaag gaccatagat tatgaaaatc gaagaaggta aactggtaat   4500
ctggattaac ggcgataaag gctataacgg tctcgctgaa gtcggtaaga aattcgagaa   4560
agataccgga attaaagtca ccgttgagca tccggataaa ctggaagaga aattcccaca   4620
ggttgcggca actggcgatg gccctgacat tatcttctgg gcacacgacc gctttggtgg   4680
ctacgctcaa tctggcctgt tggctgaaat caccccggac aaagcgttcc aggacaagct   4740
gtatccgttt acctgggatg ccgtacgtta caacggcaag ctgattgctt acccgatcgc   4800
tgttgaagcg ttatcgctga tttataacaa agatctgctg ccgaacccgc caaaaacctg   4860
ggaagagatc ccggcgctgg ataaagaact gaaagcgaaa ggtaagagcg cgctgatgtt   4920
caacctgcaa gaaccgtact tcacctggcc gctgattgct gctgacgggg gttatgcgtt   4980
caagtatgaa aacggcaagt acgacattaa agacgtgggc gtggataacg ctggcgcgaa   5040
agcgggtctg accttcctgg ttgacctgat taaaaacaaa cacatgaatg cagacaccga   5100
ttactccatc gcagaagctg cctttaataa aggcgaaaca gcgatgacca tcaacggccc   5160
gtgggcatgg tccaacatcg acaccagcaa agtgaattat ggtgtaacgg tactgccgac   5220
cttcaagggt caaccatcca aaccgttcgt tggcgtgctg agcgcaggta ttaacgccgc   5280
cagtccgaac aaagagctgg caaaagagtt cctcgaaaac tatctgctga ctgatgaagg   5340
tctggaagcg gttaataaag acaaaccgct gggtgccgta gcgctgaagt cttacgagga   5400
agagttggtg aaagatccgc gtattgccgc cactatggaa aacgcccaga aaggtgaaat   5460
catgccgaac atcccgcaga tgtccgcttt ctggtatgcc gtgcgtactg cggtgatcaa   5520
cgccgccagc ggtcgtcaga ctgtcgatga agccctgaaa gacgcgcaga ctaattcgag   5580
```

-continued

```
ctcgaacaac aacaacaata acaataacaa caacctcggg atcgagggaa ggatttcaca   5640
tatgtccatg ggcggccgcg atatcgtcga catgagcaag ctggagaagt ttacaaactg   5700
ctactccctg tctaagaccc tgaggttcaa ggccatccct gtgggcaaga cccaggagaa   5760
catcgacaat aagcggctgc tggtggagga cgagaagaga gccgaggatt ataagggcgt   5820
gaagaagctg ctggatcgct actatctgtc ttttatcaac gacgtgctgc acagcatcaa   5880
gctgaagaat ctgaacaatt acatcagcct gttccggaag aaaaccagaa ccgagaagga   5940
gaataaggag ctggagaacc tggagatcaa tctgcggaag gagatcgcca aggccttcaa   6000
gggcaacgag ggctacaagt ccctgtttaa gaaggatatc atcgagacaa tcctgccaga   6060
gttcctggac gataaggacg agatcgccct ggtgaacagc ttcaatggct ttaccacagc   6120
cttcaccggc ttctttgata acagagagaa tatgttttcc gaggaggcca agagcacatc   6180
catcgccttc aggtgtatca acgagaatct gacccgctac atctctaata tggacatctt   6240
cgagaaggtg gacgccatct ttgataagca cgaggtgcag gagatcaagg agaagatcct   6300
gaacagcgac tatgatgtgg aggatttctt tgagggcgag ttctttaact ttgtgctgac   6360
acaggagggc atcgacgtgt ataacgccat catcggcggc ttcgtgaccg agagcggcga   6420
gaagatcaag ggcctgaacg agtacatcaa cctgtataat cagaaaacca agcagaagct   6480
gcctaagttt aagccactgt ataagcaggt gctgagcgat cgggagtctc tgagcttcta   6540
cggcgagggc tatacatccg atgaggaggt gctggaggtg tttagaaaca ccctgaacaa   6600
gaacagcgag atcttcagct ccatcaagaa gctggagaag ctgttcaaga attttgacga   6660
gtactctagc gccggcatct ttgtgaagaa cggccccgcc atcagcacaa tctccaagga   6720
tatcttcggc gagtggaacg tgatccggga caagtggaat gccgagtatg acgatatcca   6780
cctgaagaag aaggccgtgg tgaccgagaa gtacgaggac gatcggagaa agtccttcaa   6840
gaagatcggc tccttttctc tggagcagct gcaggagtac gccgacgccg atctgtctgt   6900
ggtggagaag ctgaaggaga tcatcatcca gaaggtggat gagatctaca aggtgtatgg   6960
ctcctctgag aagctgttcg acgccgattt tgtgctggag aagagcctga agaagaacga   7020
cgccgtggtg gccatcatga aggacctgct ggattctgtg aagagcttcg agaattacat   7080
caaggccttc tttggcgagg gcaaggagac aaacagggac gagtccttct atggcgattt   7140
tgtgctggcc tacgacatcc tgctgaaggt ggaccacatc tacgatgcca tccgcaatta   7200
tgtgacccag aagccctact ctaaggataa gttcaagctg tattttcaga accctcagtt   7260
catgggcggc tgggacaagg ataaggagac agactatcgg gccaccatcc tgagatacgg   7320
ctccaagtac tatctggcca tcatggataa gaagtacgcc aagtgcctgc agaagatcga   7380
caaggacgat gtgaacggca attacgagaa gatcaactat aagctgctgc ccggccctaa   7440
taagatgctg ccaaaggtgt tcttttctaa gaagtggatg gcctactata accccagcga   7500
ggacatccag aagatctaca agaatggcac attcaagaag ggcgatatgt ttaacctgaa   7560
tgactgtcac aagctgatcg acttctttaa ggatagcatc tcccggtatc caaagtggtc   7620
caatgcctac gatttcaact tttctgagac agagaagtat aaggacatcg ccggctttta   7680
cagagaggtg gaggagcagg gctataaggt gagcttcgag tctgccagca agaaggaggt   7740
ggataagctg gtggaggagg gcaagctgta tatgttccag atctataaca aggacttttc   7800
cgataagtct cacggcacac ccaatctgca caccatgtac ttcaagctgc tgtttgacga   7860
gaacaatcac ggacagatca ggctgagcgg aggagcagag ctgttcatga ggcgcgcctc   7920
cctgaagaag gaggagctgg tggtgcaccc agccaactcc cctatcgcca acaagaatcc   7980
```

agataatccc aagaaaacca caaccctgtc ctacgacgtg tataaggata agaggttttc 8040
tgaggaccag tacgagctgc acatcccaat cgccatcaat aagtgcccca agaacatctt 8100
caagatcaat acagaggtgc gcgtgctgct gaagcacgac gataacccct atgtgatcgg 8160
catcgatagg ggcgagcgca atctgctgta tatcgtggtg gtggacggca agggcaacat 8220
cgtggagcag tattccctga acgagatcat caacaacttc aacggcatca ggatcaagac 8280
agattaccac tctctgctgg acaagaagga gaaggagagg ttcgaggccc gccagaactg 8340
gacctccatc gagaatatca aggagctgaa ggccggctat atctctcagg tggtgcacaa 8400
gatctgcgag ctggtggaga agtacgatgc cgtgatcgcc ctggaggacc tgaactctgg 8460
ctttaagaat agccgcgtga aggtggagaa gcaggtgtat cagaagttcg agaagatgct 8520
gatcgataag ctgaactaca tggtggacaa gaagtctaat ccttgtgcaa caggcggcgc 8580
cctgaagggc tatcagatca ccaataagtt cgagagcttt aagtccatgt ctacccagaa 8640
cggcttcatc ttttacatcc ctgcctggct gacatccaag atcgatccat ctaccggctt 8700
tgtgaacctg ctgaaaacca agtataccag catcgccgat tccaagaagt tcatcagctc 8760
ctttgacagg atcatgtacg tgcccgagga ggatctgttc gagtttgccc tggactataa 8820
gaacttctct cgcacagacg ccgattacat caagaagtgg aagctgtact cctacggcaa 8880
ccggatcaga atcttccgga atcctaagaa gaacaacgtg ttcgactggg aggaggtgtg 8940
cctgaccagc gcctataagg agctgttcaa caagtacggc atcaattatc agcagggcga 9000
tatcagagcc ctgctgtgcg agcagtccga caaggccttc tactctagct ttatggccct 9060
gatgagcctg atgctgcaga tgcggaacag catcacaggc cgcaccgacg tggattttct 9120
gatcagccct gtgaagaact ccgacggcat cttctacgat agccggaact atgaggccca 9180
ggagaatgcc atcctgccaa agaacgccga cgccaatggc gcctataaca tcgccagaaa 9240
ggtgctgtgg gccatcggcc agttcaagaa ggccgaggac gagaagctgg ataaggtgaa 9300
gatcgccatc tctaacaagg agtggctgga gtacgcccag accagcgtga agcacaaaag 9360
gccggcggcc acgaaaaagg ccggccaggc aaaaaagaaa aag 9403

<210> SEQ ID NO 33
<211> LENGTH: 9619
<212> TYPE: DNA
<213> ORGANISM: Artificial Sequence
<220> FEATURE:
<223> OTHER INFORMATION: pMAL-C5X/FnCpf1 vector

<400> SEQUENCE: 33
gaattccctg caggtaatta aataagcttc aaataaaacg aaaggctcag tcgaaagact 60
gggcctttcg ttttatctgt tgtttgtcgg tgaacgctct cctgagtagg acaaatccgc 120
cgggagcgga tttgaacgtt gcgaagcaac ggcccggagg gtggcgggca ggacgcccgc 180
cataaactgc caggcatcaa attaagcaga aggccatcct gacggatggc ctttttgcgt 240
ttctacaaac tctttcggtc cgttgtttat ttttctaaat acattcaaat atgtatccgc 300
tcatgagaca ataaccctga taaatgcttc aataatattg aaaaaggaag agtatgagta 360
ttcaacattt ccgtgtcgcc cttattccct tttttgcggc attttgcctt cctgtttttg 420
ctcacccaga aacgctggtg aaagtaaaag atgctgaaga tcagttgggt gcacgagtgg 480
gttacatcga actggatctc aacagcggta agatccttga gagttttcgc cccgaagaac 540
gtttcccaat gatgagcact tttaaagttc tgctatgtgg cgcggtatta tcccgtgttg 600

```
acgccgggca agagcaactc ggtcgccgca tacactattc tcagaatgac ttggttgagt    660
actcaccagt cacagaaaag catcttacgg atggcatgac agtaagagaa ttatgcagtg    720
ctgccataac catgagtgat aacactgcgg ccaacttact tctgacaacg atcggaggac    780
cgaaggagct aaccgctttt ttgcacaaca tgggggatca tgtaactcgc cttgatcgtt    840
gggaaccgga gctgaatgaa gccataccaa acgacgagcg tgacaccacg atgcctgtag    900
caatggcaac aacgttgcgc aaactattaa ctggcgaact acttactcta gcttcccggc    960
aacaattaat agactggatg gaggcggata aagttgcagg accacttctg cgctcggccc   1020
ttccggctgg ctggtttatt gctgataaat ctggagccgg tgagcgtggg tctcgcggta   1080
tcattgcagc actggggcca gatggtaagc cctcccgtat cgtagttatc tacacgacgg   1140
ggagtcaggc aactatggat gaacgaaata gacagatcgc tgagataggt gcctcactga   1200
ttaagcattg gtaactgtca gaccaagttt actcatatat actttagatt gatttcctta   1260
ggactgagcg tcaaccccgt agaaaagatc aaaggatctt cttgagatcc tttttttctg   1320
cgcgtaatct gctgcttgca aacaaaaaaa ccaccgctac cagcggtggt ttgtttgccg   1380
gatcaagagc taccaactct ttttccgaag gtaactggct tcagcagagc gcagatacca   1440
aatactgtcc ttctagtgta gccgtagtta ggccaccact tcaagaactc tgtagcaccg   1500
cctacatacc tcgctctgct aatcctgtta ccagtggctg ctgccagtgg cgataagtcg   1560
tgtcttaccg ggttggactc aagacgatag ttaccggata aggcgcagcg gtcgggctga   1620
acggggggtt cgtgcacaca gcccagcttg gagcgaacga cctacaccga actgagatac   1680
ctacagcgtg agctatgaga aagcgccacg cttcccgaag ggagaaaggc ggacaggtat   1740
ccggtaagcg gcagggtcgg aacaggagag cgcacgaggg agcttccagg gggaaacgcc   1800
tggtatcttt atagtcctgt cgggtttcgc cacctctgac ttgagcgtcg atttttgtga   1860
tgctcgtcag gggggcggag cctatggaaa aacgccagca acgcggcctt tttacggttc   1920
ctggcctttt gctggccttt tgctcacatg ttctttcctg cgttatcccc tgattctgtg   1980
gataaccgta ttaccgcctt tgagtgagct gataccgctc gccgcagccg aacgaccgag   2040
cgcagcgagt cagtgagcga ggaagcggaa gagcgcctga tgcggtattt tctccttacg   2100
catctgtgcg gtatttcaca ccgcatataa ggtgcactgt gactgggtca tggctgcgcc   2160
ccgacacccg ccaacacccg ctgacgcgcc ctgacgggct tgtctgctcc cggcatccgc   2220
ttacagacaa gctgtgaccg tctccgggag ctgcatgtgt cagaggtttt caccgtcatc   2280
accgaaacgc gcgaggcagc tgcggtaaag ctcatcagcg tggtcgtgca gcgattcaca   2340
gatgtctgcc tgttcatccg cgtccagctc gttgagtttc tccagaagcg ttaatgtctg   2400
gcttctgata aagcgggcca tgttaagggc ggtttttttcc tgtttggtca ctgatgcctc   2460
cgtgtaaggg ggatttctgt tcatgggggt aatgataccg atgaaacgag agaggatgct   2520
cacgatacgg gttactgatg atgaacatgc ccggttactg gaacgttgtg agggtaaaca   2580
actggcggta tggatgcggc gggaccagag aaaaatcact cagggtcaat gccagcgctt   2640
cgttaataca gatgtaggtg ttccacaggg tagccagcag catcctgcga tgcagatccg   2700
gaacataatg gtgcagggcg ctgacttccg cgtttccaga ctttacgaaa cacggaaacc   2760
gaagaccatt catgttgttg ctcaggtcgc agacgttttg cagcagcagt cgcttcacgt   2820
tcgctcgcgt atcggtgatt cattctgcta accagtaagg caaccccgcc agcctagccg   2880
ggtcctcaac gacaggagca cgatcatgcg cacccgtggc caggacccaa cgctgcccga   2940
aattccgaca ccatcgaatg gtgcaaaacc tttcgcggta tggcatgata gcgcccggaa   3000
```

gagagtcaat tcagggtggt gaatgtgaaa ccagtaacgt tatacgatgt cgcagagtat 3060
gccggtgtct cttatcagac cgtttcccgc gtggtgaacc aggccagcca cgtttctgcg 3120
aaaacgcggg aaaaagtgga agcggcgatg gcggagctga attacattcc caaccgcgtg 3180
gcacaacaac tggcgggcaa acagtcgttg ctgattggcg ttgccacctc cagtctggcc 3240
ctgcacgcgc cgtcgcaaat tgtcgcggcg attaaatctc gcgccgatca actgggtgcc 3300
agcgtggtgg tgtcgatggt agaacgaagc ggcgtcgaag cctgtaaagc ggcggtgcac 3360
aatcttctcg cgcaacgcgt cagtgggctg atcattaact atccgctgga tgaccaggat 3420
gccattgctg tggaagctgc ctgcactaat gttccggcgt tatttcttga tgtctctgac 3480
cagacaccca tcaacagtat tattttctcc catgaagacg gtacgcgact gggcgtggag 3540
catctggtcg cattgggtca ccagcaaatc gcgctgttag cgggcccatt aagttctgtc 3600
tcggcgcgtc tgcgtctggc tggctggcat aaatatctca ctcgcaatca aattcagccg 3660
atagcggaac gggaaggcga ctggagtgcc atgtccggtt ttcaacaaac catgcaaatg 3720
ctgaatgagg gcatcgttcc cactgcgatg ctggttgcca acgatcagat ggcgctgggc 3780
gcaatgcgcg ccattaccga gtccgggctg cgcgttggtg cggatatttc ggtagtggga 3840
tacgacgata ccgaagacag ctcatgttat atcccgccgt taaccaccat caaacaggat 3900
tttcgcctgc tggggcaaac cagcgtggac cgcttgctgc aactctctca gggccaggcg 3960
gtgaagggca atcagctgtt gcccgtctca ctggtgaaaa gaaaaaccac cctggcgccc 4020
aatacgcaaa ccgcctctcc ccgcgcgttg gccgattcat taatgcagct ggcacgacag 4080
gtttcccgac tggaaagcgg gcagtgagcg caacgcaatt aatgtaagtt agctcactca 4140
ttaggcacaa ttctcatgtt tgacagctta tcatcgactg cacggtgcac caatgcttct 4200
ggcgtcaggc agccatcgga agctgtggta tggctgtgca ggtcgtaaat cactgcataa 4260
ttcgtgtcgc tcaaggcgca ctcccgttct ggataatgtt ttttgcgccg acatcataac 4320
ggttctggca aatattctga aatgagctgt tgacaattaa tcatcggctc gtataatgtg 4380
tggaattgtg agcggataac aatttcacac aggaaacagc cagtccgttt aggtgttttc 4440
acgagcaatt gaccaacaag gaccatagat tatgaaaatc gaagaaggta aactggtaat 4500
ctggattaac ggcgataaag gctataacgg tctcgctgaa gtcggtaaga aattcgagaa 4560
agataccgga attaaagtca ccgttgagca tccggataaa ctggaagaga aattcccaca 4620
ggttgcggca actggcgatg gccctgacat tatcttctgg gcacacgacc gctttggtgg 4680
ctacgctcaa tctggcctgt tggctgaaat caccccggac aaagcgttcc aggacaagct 4740
gtatccgttt acctgggatg ccgtacgtta caacggcaag ctgattgctt acccgatcgc 4800
tgttgaagcg ttatcgctga tttataacaa agatctgctg ccgaacccgc caaaaacctg 4860
ggaagagatc ccggcgctgg ataaagaact gaaagcgaaa ggtaagagcg cgctgatgtt 4920
caacctgcaa gaaccgtact tcacctggcc gctgattgct gctgacgggg gttatgcgtt 4980
caagtatgaa aacggcaagt acgacattaa agacgtgggc gtggataacg ctggcgcgaa 5040
agcgggtctg accttcctgg ttgacctgat taaaaacaaa cacatgaatg cagacaccga 5100
ttactccatc gcagaagctg cctttaataa aggcgaaaca gcgatgacca tcaacggccc 5160
gtgggcatgg tccaacatcg acaccagcaa agtgaattat ggtgtaacgg tactgccgac 5220
cttcaagggt caaccatcca aaccgttcgt tggcgtgctg agcgcaggta ttaacgccgc 5280
cagtccgaac aaagagctgg caaaagagtt cctcgaaaac tatctgctga ctgatgaagg 5340
tctggaagcg gttaataaag acaaaccgct gggtgccgta gcgctgaagt cttacgagga 5400
agagttggtg aaagatccgc gtattgccgc cactatggaa aacgcccaga aaggtgaaat 5460
catgccgaac atcccgcaga tgtccgcttt ctggtatgcc gtgcgtactg cggtgatcaa 5520
cgccgccagc ggtcgtcaga ctgtcgatga agccctgaaa gacgcgcaga ctaattcgag 5580
ctcgaacaac aacaacaata acaataacaa caacctcggg atcgagggaa ggatttcaca 5640
tatgtccatg ggcggccgcg atatcgtcga catgagcatc taccaggagt tcgtcaacaa 5700
gtattcactg agtaagacac tgcggttcga gctgatccca cagggcaaga cactggagaa 5760
catcaaggcc cgaggcctga ttctggacga tgagaagcgg gcaaaagact ataagaaagc 5820
caagcagatc attgataaat accaccagtt ctttatcgag gaaattctga gctccgtgtg 5880
catcagtgag gatctgctgc agaattactc agacgtgtac ttcaagctga agaagagcga 5940
cgatgacaac ctgcagaagg acttcaagtc cgccaaggac accatcaaga aacagattag 6000
cgagtacatc aaggactccg aaaagtttaa aaatctgttc aaccagaatc tgatcgatgc 6060
taagaaaggc caggagtccg acctgatcct gtggctgaaa cagtctaagg acaatgggat 6120
tgaactgttc aaggctaact ccgatatcac tgatattgac gaggcactgg aaatcatcaa 6180
gagcttcaag ggatggacca catactttaa aggcttccac gagaaccgca agaacgtgta 6240
ctccagcaac gacattccta cctccatcat ctaccgaatc gtcgatgaca atctgccaaa 6300
gttcctggag aacaaggcca aatatgaatc tctgaaggac aaagctcccg aggcaattaa 6360
ttacgaacag atcaagaaag atctggctga ggaactgaca ttcgatatcg actataagac 6420
tagcgaggtg aaccagaggg tcttttccct ggacgaggtg tttgaaatcg ccaatttcaa 6480
caattacctg aaccagtccg gcattactaa attcaatacc atcattggcg ggaagtttgt 6540
gaacggggag aataccaagc gcaagggaat taacgaatac atcaatctgt atagccagca 6600
gatcaacgac aaaactctga agaaatacaa gatgtctgtg ctgttcaaac agatcctgag 6660
tgataccgag tccaagtctt ttgtcattga taaactggaa gatgactcag acgtggtcac 6720
taccatgcag agcttttatg agcagatcgc cgctttcaag acagtggagg aaaaatctat 6780
taaggaaact ctgagtctgc tgttcgatga cctgaaagcc cagaagctgg acctgagtaa 6840
gatctacttc aaaaacgata agagtctgac agacctgtca cagcaggtgt ttgatgacta 6900
ttccgtgatt gggaccgccg tcctggagta cattacacag cagatcgctc caaagaacct 6960
ggataatccc tctaagaaag agcaggaact gatcgctaag aaaaccgaga aggcaaaata 7020
tctgagtctg gaaacaatta agctggcact ggaggagttc aacaagcaca gggatattga 7080
caaacagtgc cgctttgagg aaatcctggc caacttcgca gccatcccca tgatttttga 7140
tgagatcgcc cagaacaaag acaatctggc tcagatcagt attaagtacc agaaccaggg 7200
caagaaagac ctgctgcagg cttcagcaga agatgacgtg aaagccatca aggatctgct 7260
ggaccagacc aacaatctgc tgcacaagct gaaaatcttc catattagtc agtcagagga 7320
taaggctaat atcctggata aagacgaaca cttctacctg gtgttcgagg aatgttactt 7380
cgagctggca aacattgtcc ccctgtataa caagattagg aactacatca cacagaagcc 7440
ttactctgac gagaagttta aactgaactt cgaaaatagt accctggcca acgggtggga 7500
taagaacaag gagcctgaca acacagctat cctgttcatc aaggatgaca agtactatct 7560
gggagtgatg aataagaaaa acaataagat cttcgatgac aaagccatta aggagaacaa 7620
aggggaagga tacaagaaaa tcgtgtataa gctgctgccc ggcgcaaata agatgctgcc 7680
taaggtgttc ttcagcgcca agagtatcaa attctacaac ccatccgagg acatcctgcg 7740
gattagaaat cactcaacac atactaagaa cgggagcccc cagaagggat atgagaaatt 7800
tgagttcaac atcgaggatt gcaggaagtt tattgacttc tacaagcaga gcatctccaa 7860
acaccctgaa tggaaggatt ttggcttccg gttttccgac acacagagat ataactctat 7920
cgacgagttc taccgcgagg tggaaaatca ggggtataag ctgacttttg agaacatttc 7980
tgaaagttac atcgacagcg tggtcaatca gggaaagctg tacctgttcc agatctataa 8040
caaagatttt tcagcataca gcaagggcag accaaacctg catacactgt actggaaggc 8100
cctgttcgat gagaggaatc tgcaggacgt ggtctataaa ctgaacggag aggccgaact 8160
gttttaccgg aagcagtcta ttcctaagaa aatcactcac ccagctaagg aggccatcgc 8220
taacaagaac aaggacaatc ctaagaaaga gagcgtgttc gaatacgatc tgattaagga 8280
caagcggttc accgaagata agttcttttt ccattgtcca atcaccatta acttcaagtc 8340
aagcggcgct aacaagttca acgacgagat caatctgctg ctgaaggaaa aagcaaacga 8400
tgtgcacatc ctgagcattg accgaggaga gcggcatctg gcctactata ccctggtgga 8460
tggcaaaggg aatatcatta agcaggatac attcaacatc attggcaatg accggatgaa 8520
aaccaactac cacgataaac tggctgcaat cgagaaggat agagactcag ctaggaagga 8580
ctggaagaaa atcaacaaca ttaaggagat gaaggaaggc tatctgagcc aggtggtcca 8640
tgagattgca aagctggtca tcgaatacaa tgccattgtg gtgttcgagg atctgaactt 8700
cggctttaag agggggcgct ttaaggtgga aaaacaggtc tatcagaagc tggagaaaat 8760
gctgatcgaa aagctgaatt acctggtgtt taaagataac gagttcgaca agaccggagg 8820
cgtcctgaga gcctaccagc tgacagctcc ctttgaaact ttcaagaaaa tgggaaaaca 8880
gacaggcatc atctactatg tgccagccgg attcacttcc aagatctgcc ccgtgaccgg 8940
ctttgtcaac cagctgtacc ctaaatatga gtcagtgagc aagtcccagg aatttttcag 9000
caagttcgat aagatctgtt ataatctgga caaggggtac ttcgagtttt ccttcgatta 9060
caagaacttc ggcgacaagg ccgctaaggg gaaatggacc attgcctcct tcggatctcg 9120
cctgatcaac tttcgaaatt ccgataaaaa ccacaattgg gacactaggg aggtgtaccc 9180
aaccaaggag ctggaaaagc tgctgaaaga ctactctatc gagtatggac atggcgaatg 9240
catcaaggca gccatctgtg gcgagagtga taagaaattt ttcgccaagc tgacctcagt 9300
gctgaataca atcctgcaga tgcggaactc aaagaccggg acagaactgg actatctgat 9360
tagccccgtg gctgatgtca acggaaactt cttcgacagc agacaggcac ccaaaaatat 9420
gcctcaggat gcagacgcca acggggccta ccacatcggg ctgaagggac tgatgctgct 9480
gggccggatc aagaacaatc aggaggggaa gaagctgaac ctggtcatta agaacgagga 9540
atacttcgag tttgtccaga atagaaataa caaaaggccg gcggccacga aaaaggccgg 9600
ccaggcaaaa aagaaaaag 9619

<210> SEQ ID NO 34
<211> LENGTH: 1100
<212> TYPE: DNA
<213> ORGANISM: Citrus sinensis

<400> SEQUENCE: 34
tcctcatccc ttactgtctt tgctttctca ctaactacta caacccaaca gttttcttct 60
ctcaaaaatg gaatgcaaac acaaaattaa tgtagcaatc ccaatcacta atatgaagaa 120
cactcaattc tcatctccat ctactttctc tacttctcct ccttctcaat cttctccacg 180

```
cttcccttct cctaatcatc aacaattgtc ttctccagaa tcttctccaa gctttaaagc    240

ttctccttca caatcctctc caaatcttgc agctcccctc tctccgccgc ctatagttct    300

tagcccttgt gctgcttgca aaatcctccg ccgcagatgc gtcgagaaat gtgttttagc    360

tccatatttt ccaccaaccg aaccatacaa gttcaccatt gctcatagag tcttcggtgc    420

tagcaatatc atcaagttct tgcaggaact gccagaatct caacgagcag atgcagtgag    480

cagcatggtc tatgaagcaa gtgccagaat ccgggatcct gtttacggct gcgccggggc    540

tatttgccat ctccagaaac aagtcagtga gcttcaggct cagttagcca aggcacaggc    600

tgagcttgtc accatggaaa gccagcaacg caatttaata actctaattt gcatggaaat    660

ggcacaatct caagaacaag tcttgcagca gcagcagcag cagcagcaac agttcatgga    720

tactagctgt tttttggatg acaatggtat tggatcagct tgggagcctc tgtggacatg    780

atcaagagaa attaaagcaa gattgttgaa attttaacct tttaagagat tatttacata    840

aagctaaaca tacttaatta taaaagtttc tgatcaataa ttaaagttat ttgctgcgcg    900

gtagatggga gtgattatta tgtgctttaa ttttcattag tcttgttgac aaaaaggaat    960

ctttgaacca tctggagaag tcctttgtta acggttcgag attaattatt agtttatctt   1020

tatttacatt tagtgaaatt ttgtttttaa ctaattttat agacataaat aacccaacca   1080

agatgggaat tcagtgctga                                                1100


<210> SEQ ID NO 35
<211> LENGTH: 62
<212> TYPE: DNA
<213> ORGANISM: Artificial Sequence
<220> FEATURE:
<223> OTHER INFORMATION: PDS-349

<400> SEQUENCE: 35

ggtgctgttt tgtcagggaa gctttgtgca caagcaattg tacaggtaca ttatagttct     60

gg                                                                    62


<210> SEQ ID NO 36
<211> LENGTH: 54
<212> TYPE: DNA
<213> ORGANISM: Artificial Sequence
<220> FEATURE:
<223> OTHER INFORMATION: PDS-349 2g

<400> SEQUENCE: 36

aaggagctgt tttgtcaggg acgaatgcca aaggacagga cattatagtt ctgg           54


<210> SEQ ID NO 37
<211> LENGTH: 62
<212> TYPE: DNA
<213> ORGANISM: Artificial Sequence
<220> FEATURE:
<223> OTHER INFORMATION: PDS-349 3g

<400> SEQUENCE: 37

ggtgctgttg tgtctggggg gctttgtggc acgacaattg tacaggtgca ttatagttct     60

gg                                                                    62


<210> SEQ ID NO 38
<211> LENGTH: 61
<212> TYPE: DNA
<213> ORGANISM: Artificial Sequence
<220> FEATURE:
<223> OTHER INFORMATION: PDS-349 3b
```

<400> SEQUENCE: 38
ggtgctgttt tgtcagggaa ttttagtgcc aaacaattgt acaggtacat tatagttctg 60
g 61

<210> SEQ ID NO 39
<211> LENGTH: 69
<212> TYPE: DNA
<213> ORGANISM: Artificial Sequence
<220> FEATURE:
<223> OTHER INFORMATION: PDS-349 1J

<400> SEQUENCE: 39
tggaaggtgc tgttttgtca gggaagcttt gtgctaagca attgtacagg tacattatag 60
ttctggtgt 69

<210> SEQ ID NO 40
<211> LENGTH: 70
<212> TYPE: DNA
<213> ORGANISM: Artificial Sequence
<220> FEATURE:
<223> OTHER INFORMATION: PDS-349 3J

<400> SEQUENCE: 40
tggaaggtcg cgggtcttgt cagggaagct ttgggccccg gtattggaca ggtacattat 60
agttctggtg 70

<210> SEQ ID NO 41
<211> LENGTH: 65
<212> TYPE: DNA
<213> ORGANISM: Artificial Sequence
<220> FEATURE:
<223> OTHER INFORMATION: PDS-349 7J

<400> SEQUENCE: 41
tgttgggtgc ggttctgtcg ggaactttgt gccaagcaac tgacaggtac attatagttc 60
tggtg 65

<210> SEQ ID NO 42
<211> LENGTH: 58
<212> TYPE: DNA
<213> ORGANISM: Artificial Sequence
<220> FEATURE:
<223> OTHER INFORMATION: PDS349 9J

<400> SEQUENCE: 42
tgttttgtca gggaagcttt gtgccaagca attggacagg tacattatag ttctggtg 58

<210> SEQ ID NO 43
<211> LENGTH: 23
<212> TYPE: DNA
<213> ORGANISM: Artificial Sequence
<220> FEATURE:
<223> OTHER INFORMATION: CsLOB1-sgRNA6

<400> SEQUENCE: 43
cctatagttc ttagcccttg tgc 23

<210> SEQ ID NO 44
<211> LENGTH: 23
<212> TYPE: DNA
<213> ORGANISM: Artificial Sequence
<220> FEATURE:

<223> OTHER INFORMATION: csLOB1 target site

<400> SEQUENCE: 44
gcacaagggc taagaactat agg 23

<210> SEQ ID NO 45
<211> LENGTH: 24
<212> TYPE: DNA
<213> ORGANISM: Artificial Sequence
<220> FEATURE:
<223> OTHER INFORMATION: CsLOB1 target site mutant M1

<400> SEQUENCE: 45
gcacaagggc taagaacata tagg 24

<210> SEQ ID NO 46
<211> LENGTH: 21
<212> TYPE: DNA
<213> ORGANISM: Artificial Sequence
<220> FEATURE:
<223> OTHER INFORMATION: CsLOB1 target site mutant M2

<400> SEQUENCE: 46
gcacaagggc taagatatag g 21

<210> SEQ ID NO 47
<211> LENGTH: 7
<212> TYPE: DNA
<213> ORGANISM: Artificial Sequence
<220> FEATURE:
<223> OTHER INFORMATION: CsLOB1 target site mutant M3

<400> SEQUENCE: 47 gcacagg 7

<210> SEQ ID NO 48
<211> LENGTH: 22
<212> TYPE: DNA
<213> ORGANISM: Artificial Sequence
<220> FEATURE:
<223> OTHER INFORMATION: CsLOB1 target site mutant M4

<400> SEQUENCE: 48
gcacaagggc taagaatata gg 22

<210> SEQ ID NO 49
<211> LENGTH: 19
<212> TYPE: DNA
<213> ORGANISM: Artificial Sequence
<220> FEATURE:
<223> OTHER INFORMATION: CsLOB1 target site mutant M5

<400> SEQUENCE: 49
gcacaagggc taatatagg 19

<210> SEQ ID NO 50
<211> LENGTH: 28
<212> TYPE: DNA
<213> ORGANISM: Artificial Sequence
<220> FEATURE:
<223> OTHER INFORMATION: target site

<400> SEQUENCE: 50
gcacaagggc taagaactat aggcggcg 28

<210> SEQ ID NO 51
<211> LENGTH: 29
<212> TYPE: DNA
<213> ORGANISM: Artificial Sequence
<220> FEATURE:
<223> OTHER INFORMATION: type 1 insertion +1 G

<400> SEQUENCE: 51
gcacaagggc taagaacgta taggcggcg 29

<210> SEQ ID NO 52
<211> LENGTH: 29
<212> TYPE: DNA
<213> ORGANISM: Artificial Sequence
<220> FEATURE:
<223> OTHER INFORMATION: Type 1 insertion +1T

<400> SEQUENCE: 52
gcacaagggc taagaactta taggcggcg 29

<210> SEQ ID NO 53
<211> LENGTH: 29
<212> TYPE: DNA
<213> ORGANISM: Artificial Sequence
<220> FEATURE:
<223> OTHER INFORMATION: type 1 Insertion +1A

<400> SEQUENCE: 53
gcacaagggc taagaacata taggcggcg 29

<210> SEQ ID NO 54
<211> LENGTH: 27
<212> TYPE: DNA
<213> ORGANISM: Artificial Sequence
<220> FEATURE:
<223> OTHER INFORMATION: Type II deletion -1T

<400> SEQUENCE: 54
gcacaagggc taagaacata ggcggcg 27

<210> SEQ ID NO 55
<211> LENGTH: 27
<212> TYPE: DNA
<213> ORGANISM: Artificial Sequence
<220> FEATURE:
<223> OTHER INFORMATION: Type II deletion -1 C

<400> SEQUENCE: 55
gcacaagggc taagaatata ggcggcg 27

<210> SEQ ID NO 56
<211> LENGTH: 26
<212> TYPE: DNA
<213> ORGANISM: Artificial Sequence
<220> FEATURE:
<223> OTHER INFORMATION: Type II delection -2 CT

<400> SEQUENCE: 56
gcacaagggc taagaaatag gcggcg 26

<210> SEQ ID NO 57
<211> LENGTH: 26
<212> TYPE: DNA
<213> ORGANISM: Artificial Sequence
<220> FEATURE:
<223> OTHER INFORMATION: Type II delection -2 AC

<400> SEQUENCE: 57
gcacaagggc taagatatag gcggcg 26

<210> SEQ ID NO 58
<211> LENGTH: 26
<212> TYPE: DNA
<213> ORGANISM: Artificial Sequence
<220> FEATURE:
<223> OTHER INFORMATION: Type II Delection -TA

<400> SEQUENCE: 58
gcacaagggc taagaactag gcggcg 26

<210> SEQ ID NO 59
<211> LENGTH: 25
<212> TYPE: DNA
<213> ORGANISM: Artificial Sequence
<220> FEATURE:
<223> OTHER INFORMATION: Type II delection -3 ACT

<400> SEQUENCE: 59
gcacaagggc taagaatagg cggcg 25

<210> SEQ ID NO 60
<211> LENGTH: 25
<212> TYPE: DNA
<213> ORGANISM: Artificial Sequence
<220> FEATURE:
<223> OTHER INFORMATION: Type II deletion -3 GAA, C

<400> SEQUENCE: 60
gcacaagggc taaatatagg cggcg 25

<210> SEQ ID NO 61
<211> LENGTH: 25
<212> TYPE: DNA
<213> ORGANISM: Artificial Sequence
<220> FEATURE:
<223> OTHER INFORMATION: Typye II deletion -3 CTA

<400> SEQUENCE: 61
gcacaagggc taagaatagg cggcg 25

<210> SEQ ID NO 62
<211> LENGTH: 25
<212> TYPE: DNA
<213> ORGANISM: Artificial Sequence
<220> FEATURE:
<223> OTHER INFORMATION: Type II delection -3 AAC

<400> SEQUENCE: 62
gcacaagggc taagtatagg cggcg 25

<210> SEQ ID NO 63
<211> LENGTH: 24
<212> TYPE: DNA
<213> ORGANISM: Artificial Sequence
<220> FEATURE:
<223> OTHER INFORMATION: Type II deletion -4 GACC

<400> SEQUENCE: 63
gcacaagggc taatataggc ggcg 24

<210> SEQ ID NO 64
<211> LENGTH: 23

<212> TYPE: DNA
<213> ORGANISM: Artificial Sequence
<220> FEATURE:
<223> OTHER INFORMATION: Type II deletion -5 AGAAC

<400> SEQUENCE: 64
gcacaagggc tatataggcg gcg 23

<210> SEQ ID NO 65
<211> LENGTH: 23
<212> TYPE: DNA
<213> ORGANISM: Artificial Sequence
<220> FEATURE:
<223> OTHER INFORMATION: Type II deletion -5 GAACT

<400> SEQUENCE: 65
gcacaagggc taaataggcg gcg 23

<210> SEQ ID NO 66
<211> LENGTH: 22
<212> TYPE: DNA
<213> ORGANISM: Artificial Sequence
<220> FEATURE:
<223> OTHER INFORMATION: Type II deletion, -6 AGAACT

<400> SEQUENCE: 66
gcacaagggc taataggcgg cg 22

<210> SEQ ID NO 67
<211> LENGTH: 22
<212> TYPE: DNA
<213> ORGANISM: Artificial Sequence
<220> FEATURE:
<223> OTHER INFORMATION: Type II deletion, -6 AAGAAC

<400> SEQUENCE: 67
gcacaagggc ttataggcgg cg 22

<210> SEQ ID NO 68
<211> LENGTH: 20
<212> TYPE: DNA
<213> ORGANISM: Artificial Sequence
<220> FEATURE:
<223> OTHER INFORMATION: Type II deletion, -8 TAAGAACT

<400> SEQUENCE: 68
gcacaagggc ataggcggcg 20

<210> SEQ ID NO 69
<211> LENGTH: 12
<212> TYPE: DNA
<213> ORGANISM: Artificial Sequence
<220> FEATURE:
<223> OTHER INFORMATION: Type II deletion, -16 AGGGCTAAGAACTATA

<400> SEQUENCE: 69
gcacaggcgg cg 12

<210> SEQ ID NO 70
<211> LENGTH: 28
<212> TYPE: DNA
<213> ORGANISM: Artificial Sequence
<220> FEATURE:
<223> OTHER INFORMATION: Type III change, A G

<400> SEQUENCE: 70
gcacaagggc taagaactgt aggcggcg 28

<210> SEQ ID NO 71
<211> LENGTH: 28
<212> TYPE: DNA
<213> ORGANISM: Artificial Sequence
<220> FEATURE:
<223> OTHER INFORMATION: Type III change, T C

<400> SEQUENCE: 71
gcacaagggc taagaactac aggcggcg 28

<210> SEQ ID NO 72
<211> LENGTH: 27
<212> TYPE: DNA
<213> ORGANISM: Artificial Sequence
<220> FEATURE:
<223> OTHER INFORMATION: CsPDS

<400> SEQUENCE: 72
tttcaggtaa ctgaagcttg aggatat 27

<210> SEQ ID NO 73
<211> LENGTH: 27
<212> TYPE: DNA
<213> ORGANISM: Artificial Sequence
<220> FEATURE:
<223> OTHER INFORMATION: EBE-pthA4

<400> SEQUENCE: 73
tttcctttct ctatataaac ccctttt 27

<210> SEQ ID NO 74
<211> LENGTH: 47
<212> TYPE: DNA
<213> ORGANISM: Artificial Sequence
<220> FEATURE:
<223> OTHER INFORMATION: LbCas-12a-crRNA-cspds indel (wild type)

<400> SEQUENCE: 74
tctttccagt tttcaggtaa ctgaagcttg aggatatcaa ctgaagg 47

<210> SEQ ID NO 75
<211> LENGTH: 39
<212> TYPE: DNA
<213> ORGANISM: Artificial Sequence
<220> FEATURE:
<223> OTHER INFORMATION: LbCas12a-crRNA-cspds indel

<400> SEQUENCE: 75
tctttccagt tttcaggtaa ctgaagcatc aactgaagg 39

<210> SEQ ID NO 76
<211> LENGTH: 38
<212> TYPE: DNA
<213> ORGANISM: Artificial Sequence
<220> FEATURE:
<223> OTHER INFORMATION: LbCas12a-crRNA-cspds indel

<400> SEQUENCE: 76
tctttccagt tttcaggtaa ctgaagctca actgaagg 38

<210> SEQ ID NO 77

<211> LENGTH: 288
<212> TYPE: DNA
<213> ORGANISM: Citrus sinensis

<400> SEQUENCE: 77
cgtcattcaa ttaaaattaa tgacgtcatc tagtggctcg gtgacatacg ctttagatac 60
aattgtcatt cttgcctttt cctttctcta tataaacccc ttttgccttg aactttgttt 120
caactaaagc agctcctcct catcccttac tgtctttgct ttctcactaa ctactacaac 180
ccaacagttt tcttctctca aaaatggaat gcaaacacaa aattaatgta gcaatcccaa 240
tcactaatat gaagaacact caattctcat ctccatctac tttctcta 288

<210> SEQ ID NO 78
<211> LENGTH: 287
<212> TYPE: DNA
<213> ORGANISM: Citrus sinensis

<400> SEQUENCE: 78
cgtcattcaa ttaaaattaa tgacgtcatc tagtggcttg gtgacatacg ctttagatac 60
aattgtcatt cttgcctttt cctttctcta tataaacccc ttttgcctta actttgtttc 120
aactaaagca gctcctcctc atcccttact gtcttcgctt tctcactaac tactacaacc 180
caacagtttt cttctctcaa aaatggaatg cagacacaaa attaatgtag caatcccaat 240
cactaatatg aagaatactc aattctcatc tccatctact ttctcta 287

<210> SEQ ID NO 79
<211> LENGTH: 47
<212> TYPE: DNA
<213> ORGANISM: Artificial Sequence
<220> FEATURE:
<223> OTHER INFORMATION: chromatogram

<400> SEQUENCE: 79
attcttgcct tttcctttct ctatataaac cccttttgcc ttgactt 47

<210> SEQ ID NO 80
<211> LENGTH: 47
<212> TYPE: DNA
<213> ORGANISM: Artificial Sequence
<220> FEATURE:
<223> OTHER INFORMATION: chromotogram

<400> SEQUENCE: 80
attcttgcct tttcctttct ctatataaac ccctttggct ttgaact 47

<210> SEQ ID NO 81
<211> LENGTH: 47
<212> TYPE: DNA
<213> ORGANISM: Artificial Sequence
<220> FEATURE:
<223> OTHER INFORMATION: CsLOBP target site wild-type

<400> SEQUENCE: 81
attcttgcct tttcctttct ctatataaac cccttttgcc ttgaact 47

<210> SEQ ID NO 82
<211> LENGTH: 46
<212> TYPE: DNA
<213> ORGANISM: Artificial Sequence
<220> FEATURE:
<223> OTHER INFORMATION: CsLOBP mutation

<400> SEQUENCE: 82
attcttgcct tttcctttct ctatataaac cccttttgcc ttaact 46

<210> SEQ ID NO 83
<211> LENGTH: 38
<212> TYPE: DNA
<213> ORGANISM: Artificial Sequence
<220> FEATURE:
<223> OTHER INFORMATION: CsLOBP mutation

<400> SEQUENCE: 83
attcttgcct tttcctttct ctatataaac cttgaact 38

<210> SEQ ID NO 84
<211> LENGTH: 45
<212> TYPE: DNA
<213> ORGANISM: Artificial Sequence
<220> FEATURE:
<223> OTHER INFORMATION: csLOBP mutation

<400> SEQUENCE: 84
attcttgcct tttcctttct ctatataaac ccctttgcct taact 45

<210> SEQ ID NO 85
<211> LENGTH: 47
<212> TYPE: DNA
<213> ORGANISM: Artificial Sequence
<220> FEATURE:
<223> OTHER INFORMATION: CsLOBP indels in transgenic Duncan #D35s1

<400> SEQUENCE: 85
attcttgcct tttcctttct ctatataaac cccttttgcc ttgaact 47

<210> SEQ ID NO 86
<211> LENGTH: 46
<212> TYPE: DNA
<213> ORGANISM: Artificial Sequence
<220> FEATURE:
<223> OTHER INFORMATION: CsLOBP indels in transgenic Duncan #D35s1

<400> SEQUENCE: 86
attcttgcct tttcctttct ctatataaac cccttttgcc ttaact 46

<210> SEQ ID NO 87
<211> LENGTH: 45
<212> TYPE: DNA
<213> ORGANISM: Artificial Sequence
<220> FEATURE:
<223> OTHER INFORMATION: CsLOBP indels in transgenic Duncan #D35s1

<400> SEQUENCE: 87
attcttgcct tttcctttct ctatataaac cttttgcctt gaact 45

<210> SEQ ID NO 88
<211> LENGTH: 45
<212> TYPE: DNA
<213> ORGANISM: Artificial Sequence
<220> FEATURE:
<223> OTHER INFORMATION: CsLOBP indels in transgenic Duncan #D35s1

<400> SEQUENCE: 88
attcttgcct tttcctttct ctatataaac ccctttgcct taact 45

<210> SEQ ID NO 89

<211> LENGTH: 47
<212> TYPE: DNA
<213> ORGANISM: Artificial Sequence
<220> FEATURE:
<223> OTHER INFORMATION: CsLOBP indels in transgenic Duncan #D35s1

<400> SEQUENCE: 89
attcttgcct tttcctttct ctatataaac cccttttgcc ttgaact 47

<210> SEQ ID NO 90
<211> LENGTH: 46
<212> TYPE: DNA
<213> ORGANISM: Artificial Sequence
<220> FEATURE:
<223> OTHER INFORMATION: CsLOBP indels in transgenic Duncan #D35s1

<400> SEQUENCE: 90
attcttgcct tttcctttct ctatataaac cccttttgcc ttaact 46

<210> SEQ ID NO 91
<211> LENGTH: 34
<212> TYPE: DNA
<213> ORGANISM: Artificial Sequence
<220> FEATURE:
<223> OTHER INFORMATION: CsLOBP indels in transgenic Duncan #D35s1

<400> SEQUENCE: 91
attcttgcct tttcctttct ctatatattg aact 34

<210> SEQ ID NO 92
<211> LENGTH: 40
<212> TYPE: DNA
<213> ORGANISM: Artificial Sequence
<220> FEATURE:
<223> OTHER INFORMATION: CsLOBP indels in transgenic Duncan #D35s1

<400> SEQUENCE: 92
attcttgcct tttcctttct ctatataaag gccttgaact 40

<210> SEQ ID NO 93
<211> LENGTH: 32
<212> TYPE: DNA
<213> ORGANISM: Artificial Sequence
<220> FEATURE:
<223> OTHER INFORMATION: CsLOBP indels in transgenic Duncan #D35s1

<400> SEQUENCE: 93
attcttgcct tttcctttct gtaccttgaa ct 32

<210> SEQ ID NO 94
<211> LENGTH: 38
<212> TYPE: DNA
<213> ORGANISM: Artificial Sequence
<220> FEATURE:
<223> OTHER INFORMATION: artificial dTALE dCsLOB1.4

<400> SEQUENCE: 94
tttctctata taaacccctt ttgccttaac tttgtatg 38

<210> SEQ ID NO 95
<211> LENGTH: 21
<212> TYPE: DNA
<213> ORGANISM: Artificial Sequence
<220> FEATURE:
<223> OTHER INFORMATION: artificial dTALE dCsLOB1.4

<400> SEQUENCE: 95
aaaccccttt tgccttaact t 21

<210> SEQ ID NO 96
<211> LENGTH: 25
<212> TYPE: DNA
<213> ORGANISM: Artificial Sequence
<220> FEATURE:
<223> OTHER INFORMATION: crRNA spacer

<400> SEQUENCE: 96
cagcagcagc agcagcagca gcaac 25

<210> SEQ ID NO 97
<211> LENGTH: 24
<212> TYPE: DNA
<213> ORGANISM: Artificial Sequence
<220> FEATURE:
<223> OTHER INFORMATION: crRNA spacer

<400> SEQUENCE: 97
cggctgcgcc ggggctattt gcca 24

<210> SEQ ID NO 98
<211> LENGTH: 24
<212> TYPE: DNA
<213> ORGANISM: Artificial Sequence
<220> FEATURE:
<223> OTHER INFORMATION: primer

<400> SEQUENCE: 98
tggcaatgtg attgacggag atgc 24

<210> SEQ ID NO 99
<211> LENGTH: 24
<212> TYPE: DNA
<213> ORGANISM: Artificial Sequence
<220> FEATURE:
<223> OTHER INFORMATION: primer

<400> SEQUENCE: 99
atgagtcctc cttgttactt cagt 24

<210> SEQ ID NO 100
<211> LENGTH: 35
<212> TYPE: DNA
<213> ORGANISM: Artificial Sequence
<220> FEATURE:
<223> OTHER INFORMATION: primer

<400> SEQUENCE: 100
aggtaagctt attcatatta acgttatcaa tgatt 35

<210> SEQ ID NO 101
<211> LENGTH: 35
<212> TYPE: DNA
<213> ORGANISM: Artificial Sequence
<220> FEATURE:
<223> OTHER INFORMATION: primer

<400> SEQUENCE: 101
acctggatcc ttttgagaga agaaaactgt tgggt 35

<210> SEQ ID NO 102

<211> LENGTH: 24
<212> TYPE: DNA
<213> ORGANISM: Artificial Sequence
<220> FEATURE:
<223> OTHER INFORMATION: primer

<400> SEQUENCE: 102
cgtcattcaa ttaaaattaa tgac 24

<210> SEQ ID NO 103
<211> LENGTH: 25
<212> TYPE: DNA
<213> ORGANISM: Artificial Sequence
<220> FEATURE:
<223> OTHER INFORMATION: primer

<400> SEQUENCE: 103
cagcagcagc agcagcagca gcaac 25

<210> SEQ ID NO 104
<211> LENGTH: 24
<212> TYPE: DNA
<213> ORGANISM: Artificial Sequence
<220> FEATURE:
<223> OTHER INFORMATION: primer

<400> SEQUENCE: 104
cggctgcgcc ggggctattt gcca 24

<210> SEQ ID NO 105
<211> LENGTH: 36
<212> TYPE: DNA
<213> ORGANISM: Artificial Sequence
<220> FEATURE:
<223> OTHER INFORMATION: primer

<400> SEQUENCE: 105
aggtcctgca ggtccccaga ttagcctttt caattt 36

<210> SEQ ID NO 106
<211> LENGTH: 40
<212> TYPE: DNA
<213> ORGANISM: Artificial Sequence
<220> FEATURE:
<223> OTHER INFORMATION: primer

<400> SEQUENCE: 106
aggtggatcc ggtacctatc gttcgtaaat ggtgaaaatt 40

<210> SEQ ID NO 107
<211> LENGTH: 35
<212> TYPE: DNA
<213> ORGANISM: Artificial Sequence
<220> FEATURE:
<223> OTHER INFORMATION: primer

<400> SEQUENCE: 107
aggtcctgca ggatgggaaa ttcattgaaa accct 35

<210> SEQ ID NO 108
<211> LENGTH: 43
<212> TYPE: DNA
<213> ORGANISM: Artificial Sequence
<220> FEATURE:
<223> OTHER INFORMATION: primer

<400> SEQUENCE: 108
aggtggtacc ggatcctttc ttcttctcgt tgttgtactt cat 43

<210> SEQ ID NO 109
<211> LENGTH: 44
<212> TYPE: DNA
<213> ORGANISM: Artificial Sequence
<220> FEATURE:
<223> OTHER INFORMATION: primer

<400> SEQUENCE: 109
aggatccacc ggtgcacgaa ttccgaattt ccccgatcgt tcaa 44

<210> SEQ ID NO 110
<211> LENGTH: 64
<212> TYPE: DNA
<213> ORGANISM: Artificial Sequence
<220> FEATURE:
<223> OTHER INFORMATION: primer

<400> SEQUENCE: 110
agtttaaact ctagacaagg cgcgccattt aaatctcgag ccgatctagt aacatagatg 60
acac 64

<210> SEQ ID NO 111
<211> LENGTH: 34
<212> TYPE: DNA
<213> ORGANISM: Artificial Sequence
<220> FEATURE:
<223> OTHER INFORMATION: primer

<400> SEQUENCE: 111
actcgagact agtaccatgg tggactcctc ttaa 34

<210> SEQ ID NO 112
<211> LENGTH: 43
<212> TYPE: DNA
<213> ORGANISM: Artificial Sequence
<220> FEATURE:
<223> OTHER INFORMATION: 113

<400> SEQUENCE: 112
ctacacttag tagaaattcc tctccaaatg aaatgaactt cct 43

<210> SEQ ID NO 113
<211> LENGTH: 52
<212> TYPE: DNA
<213> ORGANISM: Artificial Sequence
<220> FEATURE:
<223> OTHER INFORMATION: primer

<400> SEQUENCE: 113
ataggtaact gaagcttgag gatatgaatt tccccgatcg ttcaaacatt tg 52

<210> SEQ ID NO 114
<211> LENGTH: 37
<212> TYPE: DNA
<213> ORGANISM: Artificial Sequence
<220> FEATURE:
<223> OTHER INFORMATION: primer

<400> SEQUENCE: 114
acctgggccc ggcgcgccga tctagtaaca tagatga 37

<210> SEQ ID NO 115
<211> LENGTH: 52
<212> TYPE: DNA
<213> ORGANISM: Artificial Sequence
<220> FEATURE:
<223> OTHER INFORMATION: primer

<400> SEQUENCE: 115
atctttctct atataaaccc cttttgaatt tccccgatcg ttcaaacatt tg 52

<210> SEQ ID NO 116
<211> LENGTH: 35
<212> TYPE: DNA
<213> ORGANISM: Artificial Sequence
<220> FEATURE:
<223> OTHER INFORMATION: primer

<400> SEQUENCE: 116
aggtggcgcg cctcttacag cttagaaatc tcaaa 35

<210> SEQ ID NO 117
<211> LENGTH: 46
<212> TYPE: DNA
<213> ORGANISM: Artificial Sequence
<220> FEATURE:
<223> OTHER INFORMATION: primer

<400> SEQUENCE: 117
ctacacttag tagaaattca atcactactt cgtctctaac catata 46

<210> SEQ ID NO 118
<211> LENGTH: 33
<212> TYPE: DNA
<213> ORGANISM: Artificial Sequence
<220> FEATURE:
<223> OTHER INFORMATION: primer

<400> SEQUENCE: 118
aggtactagt ccgatctagt aacatagatg aca 33

<210> SEQ ID NO 119
<211> LENGTH: 24
<212> TYPE: DNA
<213> ORGANISM: Artificial Sequence
<220> FEATURE:
<223> OTHER INFORMATION: primer

<400> SEQUENCE: 119
tgtgctcgac gttgtcactg aagc 24

<210> SEQ ID NO 120
<211> LENGTH: 24
<212> TYPE: DNA
<213> ORGANISM: Artificial Sequence
<220> FEATURE:
<223> OTHER INFORMATION: primer

<400> SEQUENCE: 120
ttcgggggat ctggatttta gtac 24

<210> SEQ ID NO 121
<211> LENGTH: 17
<212> TYPE: DNA
<213> ORGANISM: Artificial Sequence
<220> FEATURE:
<223> OTHER INFORMATION: CsLOB1.1 binding site

<400> SEQUENCE: 121
taaagcagct cctcctc 17

<210> SEQ ID NO 122
<211> LENGTH: 19
<212> TYPE: DNA
<213> ORGANISM: Artificial Sequence
<220> FEATURE:
<223> OTHER INFORMATION: dCsLOB1.2 recognition sequence

<400> SEQUENCE: 122
tataaacccc ttttgcctt 19

<210> SEQ ID NO 123
<211> LENGTH: 18
<212> TYPE: DNA
<213> ORGANISM: Artificial Sequence
<220> FEATURE:
<223> OTHER INFORMATION: dCsLOB1.3 binding sequence

<400> SEQUENCE: 123
ccttttgcct tgaacttt 18

<210> SEQ ID NO 124
<211> LENGTH: 34
<212> TYPE: DNA
<213> ORGANISM: Artificial Sequence
<220> FEATURE:
<223> OTHER INFORMATION: CsLOBP binding sequence

<400> SEQUENCE: 124
ccgcgatatc gtcgacatga cacagttcga gggc 34

<210> SEQ ID NO 125
<211> LENGTH: 36
<212> TYPE: DNA
<213> ORGANISM: Artificial Sequence
<220> FEATURE:
<223> OTHER INFORMATION: AtU6-26 promoter

<400> SEQUENCE: 125
tacctgcagg gaattccttt ttcttttttg cctggc 36

<210> SEQ ID NO 126
<211> LENGTH: 35
<212> TYPE: DNA
<213> ORGANISM: Artificial Sequence
<220> FEATURE:
<223> OTHER INFORMATION: CsU6-2 promoter

<400> SEQUENCE: 126
ccgcgatatc gtcgacatga gcaagctgga gaagt 35

<210> SEQ ID NO 127
<211> LENGTH: 36
<212> TYPE: DNA
<213> ORGANISM: Artificial Sequence
<220> FEATURE:
<223> OTHER INFORMATION: CsUg-7 promoter

<400> SEQUENCE: 127
tacctgcagg gaattccttt ttcttttttg cctggc 36

<210> SEQ ID NO 128

<211> LENGTH: 35
<212> TYPE: DNA
<213> ORGANISM: Artificial Sequence
<220> FEATURE:
<223> OTHER INFORMATION: primer

<400> SEQUENCE: 128
ccgcgatatc gtcgacatga gcatctacca ggagt 35

<210> SEQ ID NO 129
<211> LENGTH: 36
<212> TYPE: DNA
<213> ORGANISM: Artificial Sequence
<220> FEATURE:
<223> OTHER INFORMATION: primer

<400> SEQUENCE: 129
tacctgcagg gaattccttt ttcttttttg cctggc 36

<210> SEQ ID NO 130
<211> LENGTH: 20
<212> TYPE: DNA
<213> ORGANISM: Artificial Sequence
<220> FEATURE:
<223> OTHER INFORMATION: primer

<400> SEQUENCE: 130
cgcagatgcg tcgagaaatg 20

<210> SEQ ID NO 131
<211> LENGTH: 20
<212> TYPE: DNA
<213> ORGANISM: Artificial Sequence
<220> FEATURE:
<223> OTHER INFORMATION: primer

<400> SEQUENCE: 131
ggctcccaag ctgatccaat 20

<210> SEQ ID NO 132
<211> LENGTH: 20
<212> TYPE: DNA
<213> ORGANISM: Artificial Sequence
<220> FEATURE:
<223> OTHER INFORMATION: primer

<400> SEQUENCE: 132
gcagtgagca gcatggtcta 20

<210> SEQ ID NO 133
<211> LENGTH: 20
<212> TYPE: DNA
<213> ORGANISM: Artificial Sequence
<220> FEATURE:
<223> OTHER INFORMATION: primer

<400> SEQUENCE: 133
accgcgcagc aaataacttt 20

<210> SEQ ID NO 134
<211> LENGTH: 20
<212> TYPE: DNA
<213> ORGANISM: Artificial Sequence
<220> FEATURE:
<223> OTHER INFORMATION: primer

<400> SEQUENCE: 134
tctccgccgc ctatagttct 20

<210> SEQ ID NO 135
<211> LENGTH: 20
<212> TYPE: DNA
<213> ORGANISM: Artificial Sequence
<220> FEATURE:
<223> OTHER INFORMATION: primer

<400> SEQUENCE: 135
atcatgtcca cagaggctcc 20

<210> SEQ ID NO 136
<211> LENGTH: 20
<212> TYPE: DNA
<213> ORGANISM: Artificial Sequence
<220> FEATURE:
<223> OTHER INFORMATION: primer

<400> SEQUENCE: 136
tctctccgcc gcctatagtt 20

<210> SEQ ID NO 137
<211> LENGTH: 20
<212> TYPE: DNA
<213> ORGANISM: Artificial Sequence
<220> FEATURE:
<223> OTHER INFORMATION: primer

<400> SEQUENCE: 137
atgtccacag aggctcccaa 20

<210> SEQ ID NO 138
<211> LENGTH: 24
<212> TYPE: DNA
<213> ORGANISM: Artificial Sequence
<220> FEATURE:
<223> OTHER INFORMATION: primer

<400> SEQUENCE: 138
gaagaacact caattctcat ctcc 24

<210> SEQ ID NO 139
<211> LENGTH: 19
<212> TYPE: DNA
<213> ORGANISM: Artificial Sequence
<220> FEATURE:
<223> OTHER INFORMATION: primer

<400> SEQUENCE: 139
gtccacagag gctcccaag 19

<210> SEQ ID NO 140
<211> LENGTH: 23
<212> TYPE: DNA
<213> ORGANISM: Artificial Sequence
<220> FEATURE:
<223> OTHER INFORMATION: cs7g27620

<400> SEQUENCE: 140
gcgcatggac taagaacaat agg 23

<210> SEQ ID NO 141

<211> LENGTH: 23
<212> TYPE: DNA
<213> ORGANISM: Artificial Sequence
<220> FEATURE:
<223> OTHER INFORMATION: Cs7g27620

<400> SEQUENCE: 141
gcgcatggac taagaacaat aag 23

<210> SEQ ID NO 142
<211> LENGTH: 23
<212> TYPE: DNA
<213> ORGANISM: Artificial Sequence
<220> FEATURE:
<223> OTHER INFORMATION: Cs7g27620

<400> SEQUENCE: 142
gcgcatggac caagaacaat aag 23

<210> SEQ ID NO 143
<211> LENGTH: 23
<212> TYPE: DNA
<213> ORGANISM: Artificial Sequence
<220> FEATURE:
<223> OTHER INFORMATION: Cs7g27620

<400> SEQUENCE: 143
gcgcgtggac taagaacaat agg 23

<210> SEQ ID NO 144
<211> LENGTH: 23
<212> TYPE: DNA
<213> ORGANISM: Artificial Sequence
<220> FEATURE:
<223> OTHER INFORMATION: Cs7g02090

<400> SEQUENCE: 144
gcacaagatc taagaacatt aag 23

<210> SEQ ID NO 145
<211> LENGTH: 23
<212> TYPE: DNA
<213> ORGANISM: Artificial Sequence
<220> FEATURE:
<223> OTHER INFORMATION: orange1.1t01786

<400> SEQUENCE: 145
tcacaaggac caagaagtat tgg 23

<210> SEQ ID NO 146
<211> LENGTH: 23
<212> TYPE: DNA
<213> ORGANISM: Artificial Sequence
<220> FEATURE:
<223> OTHER INFORMATION: Cs2g10860

<400> SEQUENCE: 146
gcagaaaggg taagagctat aag 23

<210> SEQ ID NO 147
<211> LENGTH: 23
<212> TYPE: DNA
<213> ORGANISM: Artificial Sequence
<220> FEATURE:
<223> OTHER INFORMATION: Cs2610860 Off-target No.

<400> SEQUENCE: 147
acagaaaggg taagagctat aag 23

<210> SEQ ID NO 148
<211> LENGTH: 184
<212> TYPE: DNA
<213> ORGANISM: Arabidopsis thaliana

<400> SEQUENCE: 148
caatcttcaa aagtcccaca tcgcttagat aagaaaacga agctgagttt atatacagct 60
agagtcgaag tagtgattgt cccttagggg acatccgata aaattggaac gatacagaga 120
agattagcat ggcccctgcg caaggatgac acgcataaat cgagaaatgg tccaaatttt 180
tttt 184

<210> SEQ ID NO 149
<211> LENGTH: 183
<212> TYPE: DNA
<213> ORGANISM: Citrus sinensis

<400> SEQUENCE: 149
ccgttgaaga aaatcccaca tcgaaagaaa aaactgaata aacatggtct atatatacaa 60
ggactcccag gttggttgtc tcttcggaga catccgataa aattggaacg atacagagaa 120
gattagcatg gcccctgcgc aaggatgaca cgcacaaatc gagaaatggt ccaaattttt 180
ttt 183

<210> SEQ ID NO 150
<211> LENGTH: 183
<212> TYPE: DNA
<213> ORGANISM: Citrus sinensis

<400> SEQUENCE: 150
aaattgaact aaatcccaca tcgtctagtt gcgcttcgtt gagagtctta atataatcat 60
aaccaaccag tgcgattgtc tcttcggaga catccgataa aattggaacg atacagagaa 120
gattagcatg gcccctgcgc aaggatgaca cgcacaaatc gagaaatggt ccaaattttt 180
ttt 183

<210> SEQ ID NO 151
<211> LENGTH: 22
<212> TYPE: DNA
<213> ORGANISM: Artificial Sequence
<220> FEATURE:
<223> OTHER INFORMATION: Type II CsLOBP repeat variable di-residues

<400> SEQUENCE: 151
taaacccctt ttgccttaac tt 22

<210> SEQ ID NO 152
<211> LENGTH: 21
<212> TYPE: DNA
<213> ORGANISM: Artificial Sequence
<220> FEATURE:
<223> OTHER INFORMATION: primer

<400> SEQUENCE: 152
cagctcctcc tcatccctta c 21

<210> SEQ ID NO 153

<211> LENGTH: 23
<212> TYPE: DNA
<213> ORGANISM: Artificial Sequence
<220> FEATURE:
<223> OTHER INFORMATION: primer

<400> SEQUENCE: 153
agtggaacaa tcaaccactc caa 23

<210> SEQ ID NO 154
<211> LENGTH: 20
<212> TYPE: DNA
<213> ORGANISM: Artificial Sequence
<220> FEATURE:
<223> OTHER INFORMATION: primer

<400> SEQUENCE: 154
agctcctcct catcccttac 20

<210> SEQ ID NO 155
<211> LENGTH: 24
<212> TYPE: DNA
<213> ORGANISM: Artificial Sequence
<220> FEATURE:
<223> OTHER INFORMATION: primer

<400> SEQUENCE: 155
accactccaa agtctaatca caca 24

<210> SEQ ID NO 156
<211> LENGTH: 20
<212> TYPE: DNA
<213> ORGANISM: Artificial Sequence
<220> FEATURE:
<223> OTHER INFORMATION: primer

<400> SEQUENCE: 156
agcgtttgct tcgtagacca 20

<210> SEQ ID NO 157
<211> LENGTH: 20
<212> TYPE: DNA
<213> ORGANISM: Artificial Sequence
<220> FEATURE:
<223> OTHER INFORMATION: primer

<400> SEQUENCE: 157
tatggggcta gccaatcacg 20

<210> SEQ ID NO 158
<211> LENGTH: 20
<212> TYPE: DNA
<213> ORGANISM: Artificial Sequence
<220> FEATURE:
<223> OTHER INFORMATION: primer

<400> SEQUENCE: 158
tcagaatcac gtctgcacca 20

<210> SEQ ID NO 159
<211> LENGTH: 19
<212> TYPE: DNA
<213> ORGANISM: Artificial Sequence
<220> FEATURE:
<223> OTHER INFORMATION: primer -continued

<400> SEQUENCE: 159
gtgaaaaccc acaacccgc 19

<210> SEQ ID NO 160
<211> LENGTH: 20
<212> TYPE: DNA
<213> ORGANISM: Artificial Sequence
<220> FEATURE:
<223> OTHER INFORMATION: primer

<400> SEQUENCE: 160
aaacgtgcat aaccacccct 20

<210> SEQ ID NO 161
<211> LENGTH: 20
<212> TYPE: DNA
<213> ORGANISM: Artificial Sequence
<220> FEATURE:
<223> OTHER INFORMATION: primer

<400> SEQUENCE: 161
atctggttga tcgcatggct 20

<210> SEQ ID NO 162
<211> LENGTH: 20
<212> TYPE: DNA
<213> ORGANISM: Artificial Sequence
<220> FEATURE:
<223> OTHER INFORMATION: primer

<400> SEQUENCE: 162
atggatgcgt tcaggggaag 20

<210> SEQ ID NO 163
<211> LENGTH: 20
<212> TYPE: DNA
<213> ORGANISM: Artificial Sequence
<220> FEATURE:
<223> OTHER INFORMATION: primer

<400> SEQUENCE: 163
ataggcccaa gaatgtgcaa 20